(12) United States Patent
Li et al.

(10) Patent No.: US 10,158,091 B2
(45) Date of Patent: Dec. 18, 2018

(54) TETRADENTATE PLATINUM (II) AND PALLADIUM (II) COMPLEXES, DEVICES, AND USES THEREOF

(71) Applicant: ARIZONA BOARD OF REGENTS ON BEHALF OF ARIZONA STATE UNIVERSITY, Scottsdale, AZ (US)

(72) Inventors: Jian Li, Tempe, AZ (US); Zhi-Qiang Zhu, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/228,401

(22) Filed: Aug. 4, 2016

(65) Prior Publication Data

US 2017/0040555 A1 Feb. 9, 2017

Related U.S. Application Data

(60) Provisional application No. 62/200,960, filed on Aug. 4, 2015.

(51) Int. Cl.
| | | |
|---|---|---|
| H01L 51/54 | (2006.01) | |
| H01L 51/00 | (2006.01) | |
| C07F 15/00 | (2006.01) | |
| C09K 11/06 | (2006.01) | |
| H01L 51/50 | (2006.01) | |

(52) U.S. Cl.
CPC ...... *H01L 51/0087* (2013.01); *C07F 15/0086* (2013.01); *C09K 11/06* (2013.01); *H01L 51/0093* (2013.01); *C09K 2211/1022* (2013.01); *C09K 2211/1029* (2013.01); *C09K 2211/185* (2013.01); *H01L 51/5016* (2013.01)

(58) Field of Classification Search
CPC ...... C07F 15/00; C07F 15/0086; H01L 51/50; H01L 51/0087; H01L 51/0093; H01L 51/5016; C09K 11/06
See application file for complete search history.

(56) References Cited

U.S. PATENT DOCUMENTS

| | | | |
|---|---|---|---|
| 4,769,292 A | 9/1988 | Tang et al. | |
| 5,707,745 A | 1/1998 | Forrest et al. | |
| 5,844,363 A | 12/1998 | Gu et al. | |
| 6,200,695 B1 | 3/2001 | Arai | |
| 6,303,238 B1 | 10/2001 | Thompson et al. | |
| 6,780,528 B2 | 8/2004 | Tsuboyama et al. | |
| 7,002,013 B1 | 2/2006 | Chi et al. | |
| 7,037,599 B2 | 5/2006 | Culligan et al. | |
| 7,064,228 B1 | 6/2006 | Yu et al. | |
| 7,268,485 B2 | 9/2007 | Tyan et al. | |
| 7,279,704 B2 | 10/2007 | Walters et al. | |
| 7,332,232 B2 | 2/2008 | Ma et al. | |
| 7,442,797 B2 | 10/2008 | Itoh et al. | |
| 7,501,190 B2 | 3/2009 | Ise | |
| 7,655,322 B2 | 2/2010 | Forrest et al. | |
| 7,854,513 B2 | 12/2010 | Quach | |
| 7,947,383 B2 | 5/2011 | Ise et al. | |
| 8,133,597 B2 | 3/2012 | Yasukawa et al. | |
| 8,389,725 B2 | 3/2013 | Li et al. | |
| 8,617,723 B2 | 12/2013 | Stoessel | |
| 8,816,080 B2 | 8/2014 | Li et al. | |
| 8,871,361 B2 | 10/2014 | Xia et al. | |
| 8,927,713 B2 | 1/2015 | Li et al. | |
| 8,946,417 B2 | 2/2015 | Li et al. | |
| 9,059,412 B2 | 6/2015 | Zeng et al. | |
| 9,221,857 B2 | 12/2015 | Li et al. | |
| 9,224,963 B2 | 12/2015 | Li et al. | |
| 9,238,668 B2 | 1/2016 | Li et al. | |
| 9,312,502 B2 | 4/2016 | Li et al. | |
| 9,312,505 B2 | 4/2016 | Brooks et al. | |
| 9,318,725 B2 | 4/2016 | Li | |
| 9,324,957 B2 | 4/2016 | Li et al. | |
| 9,382,273 B2 | 7/2016 | Li | |
| 9,385,329 B2 | 7/2016 | Li et al. | |
| 9,425,415 B2 | 8/2016 | Li et al. | |
| 9,461,254 B2 | 10/2016 | Tsai | |
| 9,550,801 B2 | 1/2017 | Li et al. | |
| 9,617,291 B2 | 4/2017 | Li et al. | |
| 9,673,409 B2 | 6/2017 | Li | |
| 9,698,359 B2 | 7/2017 | Li et al. | |
| 9,711,739 B2 | 7/2017 | Li | |
| 9,711,742 B2 | 7/2017 | Li et al. | |
| 9,755,163 B2 | 9/2017 | Li et al. | |
| 9,818,959 B2 | 11/2017 | Li | |
| 9,879,039 B2 | 1/2018 | Li et al. | |
| 9,882,150 B2 | 1/2018 | Li et al. | |
| 9,899,614 B2 | 2/2018 | Li et al. | |
| 9,920,242 B2 | 3/2018 | Li | |
| 9,923,155 B2 | 3/2018 | Li et al. | |

(Continued)

FOREIGN PATENT DOCUMENTS

| | | |
|---|---|---|
| CN | 1680366 A | 10/2005 |
| CN | 1777663 | 5/2006 |

(Continued)

OTHER PUBLICATIONS

Li, Inorg Chem, vol. 56, 8244-8256, 2017. (Year: 2017).*

(Continued)

*Primary Examiner* — D Margaret M Seaman
(74) *Attorney, Agent, or Firm* — Fish & Richardson P.C.

(57) ABSTRACT

The complexes disclosed herein are cyclometalated metal complexes of Formula (I) that are useful for full color displays and lighting applications.

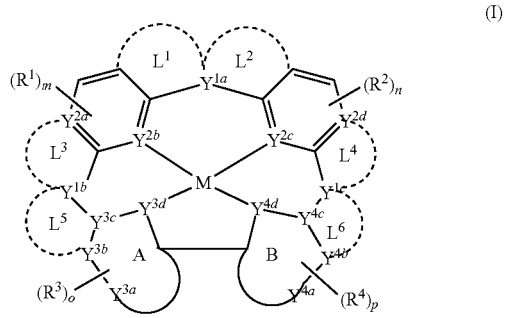

(I)

15 Claims, 2 Drawing Sheets

(56) References Cited

U.S. PATENT DOCUMENTS

| | | |
|---|---|---|
| 2001/0019782 A1 | 9/2001 | Igarashi et al. |
| 2002/0068190 A1 | 6/2002 | Tsuboyama et al. |
| 2003/0062519 A1 | 4/2003 | Yamazaki et al. |
| 2003/0186077 A1 | 10/2003 | Chen |
| 2004/0230061 A1 | 11/2004 | Seo et al. |
| 2005/0170207 A1 | 8/2005 | Ma et al. |
| 2005/0260446 A1 | 11/2005 | Mackenzie et al. |
| 2006/0024522 A1 | 2/2006 | Thompson |
| 2006/0073359 A1 | 4/2006 | Ise et al. |
| 2006/0094875 A1 | 5/2006 | Itoh et al. |
| 2006/0127696 A1 | 6/2006 | Stossel et al. |
| 2006/0182992 A1 | 8/2006 | Nii et al. |
| 2006/0202197 A1 | 9/2006 | Nakayama et al. |
| 2006/0210831 A1 | 9/2006 | Sano et al. |
| 2006/0255721 A1 | 11/2006 | Igarashi et al. |
| 2006/0263635 A1 | 11/2006 | Ise |
| 2006/0286406 A1 | 12/2006 | Tatsuya et al. |
| 2007/0057630 A1 | 3/2007 | Nishita et al. |
| 2007/0059551 A1 | 3/2007 | Yamazaki |
| 2007/0082284 A1 | 4/2007 | Stoessel et al. |
| 2007/0103060 A1 | 5/2007 | Itoh et al. |
| 2008/0001530 A1 | 1/2008 | Ise et al. |
| 2008/0036373 A1 | 2/2008 | Itoh et al. |
| 2008/0054799 A1 | 3/2008 | Satou |
| 2008/0079358 A1 | 4/2008 | Satou |
| 2008/0111476 A1 | 5/2008 | Choi et al. |
| 2008/0241518 A1 | 10/2008 | Satou et al. |
| 2008/0241589 A1 | 10/2008 | Fukunaga et al. |
| 2009/0026936 A1 | 1/2009 | Satou et al. |
| 2009/0026939 A1 | 1/2009 | Kinoshita et al. |
| 2009/0032989 A1 | 2/2009 | Karim et al. |
| 2009/0039768 A1 | 2/2009 | Igarashi et al. |
| 2009/0079340 A1 | 3/2009 | Kinoshita et al. |
| 2009/0128008 A1 | 5/2009 | Ise et al. |
| 2009/0218561 A1 | 9/2009 | Kitamura et al. |
| 2009/0261721 A1 | 10/2009 | Murakami et al. |
| 2009/0267500 A1 | 10/2009 | Kinoshita et al. |
| 2010/0000606 A1 | 1/2010 | Thompson et al. |
| 2010/0013386 A1 | 1/2010 | Thompson et al. |
| 2010/0141127 A1 | 6/2010 | Xia et al. |
| 2010/0171111 A1 | 7/2010 | Takada et al. |
| 2010/0171418 A1 | 7/2010 | Kinoshita et al. |
| 2010/0270540 A1 | 10/2010 | Chung et al. |
| 2011/0049496 A1 | 3/2011 | Fukuzaki |
| 2011/0062858 A1 | 3/2011 | Yersin et al. |
| 2012/0095232 A1 | 4/2012 | Li et al. |
| 2012/0181528 A1 | 7/2012 | Takada et al. |
| 2012/0199823 A1 | 8/2012 | Molt et al. |
| 2012/0215001 A1 | 8/2012 | Li et al. |
| 2012/0223634 A1 | 9/2012 | Xia et al. |
| 2012/0264938 A1 | 10/2012 | Li et al. |
| 2012/0273736 A1 | 11/2012 | James et al. |
| 2012/0302753 A1 | 11/2012 | Li |
| 2013/0048963 A1 | 2/2013 | Beers et al. |
| 2013/0168656 A1 | 7/2013 | Tsai et al. |
| 2013/0203996 A1 | 8/2013 | Li et al. |
| 2013/0237706 A1 | 9/2013 | Li |
| 2013/0341600 A1 | 12/2013 | Lin et al. |
| 2014/0014922 A1 | 1/2014 | Lin et al. |
| 2014/0027733 A1 | 1/2014 | Zeng et al. |
| 2014/0084261 A1 | 3/2014 | Brooks et al. |
| 2014/0114072 A1 | 4/2014 | Li et al. |
| 2014/0191206 A1 | 7/2014 | Cho |
| 2014/0203248 A1 | 7/2014 | Zhou et al. |
| 2014/0326960 A1 | 11/2014 | Kim et al. |
| 2014/0330019 A1 | 11/2014 | Li et al. |
| 2014/0364605 A1 | 12/2014 | Li et al. |
| 2015/0008419 A1 | 1/2015 | Li |
| 2015/0028323 A1 | 1/2015 | Xia et al. |
| 2015/0069334 A1 | 3/2015 | Xia et al. |
| 2015/0105556 A1 | 4/2015 | Li et al. |
| 2015/0162552 A1 | 6/2015 | Li et al. |
| 2015/0194616 A1 | 7/2015 | Li et al. |
| 2015/0207086 A1 | 7/2015 | Li et al. |
| 2015/0228914 A1 | 8/2015 | Li et al. |
| 2015/0274762 A1 | 10/2015 | Li et al. |
| 2015/0287938 A1 | 10/2015 | Li et al. |
| 2015/0318500 A1 | 11/2015 | Li |
| 2015/0349279 A1 | 12/2015 | Li et al. |
| 2016/0028028 A1 | 1/2016 | Li et al. |
| 2016/0043331 A1 | 2/2016 | Li et al. |
| 2016/0072082 A1 | 3/2016 | Brooks et al. |
| 2016/0133862 A1 | 5/2016 | Li et al. |
| 2016/0197285 A1 | 7/2016 | Zeng et al. |
| 2016/0197291 A1 | 7/2016 | Li et al. |
| 2016/0285015 A1 | 9/2016 | Li et al. |
| 2016/0359120 A1 | 12/2016 | Li |
| 2016/0359125 A1 | 12/2016 | Li |
| 2017/0005278 A1 | 1/2017 | Li et al. |
| 2017/0012224 A1 | 1/2017 | Li et al. |
| 2017/0040555 A1 | 2/2017 | Li et al. |
| 2017/0047533 A1 | 2/2017 | Li et al. |
| 2017/0066792 A1 | 3/2017 | Li et al. |
| 2017/0069855 A1 | 3/2017 | Li et al. |
| 2017/0267923 A1 | 9/2017 | Li |
| 2017/0271611 A1 | 9/2017 | Li et al. |
| 2017/0301871 A1 | 10/2017 | Li |
| 2017/0305881 A1 | 10/2017 | Li et al. |
| 2017/0331056 A1 | 11/2017 | Li et al. |
| 2017/0373260 A1 | 12/2017 | Li et al. |
| 2018/0006246 A1 | 1/2018 | Li |
| 2018/0053904 A1 | 2/2018 | Li et al. |

FOREIGN PATENT DOCUMENTS

| | | |
|---|---|---|
| CN | 1894269 | 1/2007 |
| CN | 101667626 | 3/2010 |
| CN | 102449108 A | 5/2012 |
| CN | 102892860 | 1/2013 |
| CN | 102971396 | 3/2013 |
| CN | 103102372 A1 | 5/2013 |
| CN | 104232076 | 12/2014 |
| CN | 104377231 | 2/2015 |
| CN | 104649243 | 6/2015 |
| CN | 105367605 | 3/2016 |
| CN | 105418591 | 3/2016 |
| EP | 1874893 | 1/2008 |
| EP | 1874894 | 1/2008 |
| EP | 1919928 | 5/2008 |
| EP | 2036907 | 3/2009 |
| EP | 2096690 A2 | 9/2009 |
| EP | 2417217 | 2/2012 |
| EP | 2112213 | 7/2012 |
| EP | 2711999 | 3/2014 |
| JP | 2002105055 A | 4/2002 |
| JP | 2005267557 | 9/2005 |
| JP | 2005310733 | 11/2005 |
| JP | 2006047240 | 2/2006 |
| JP | 2006232784 | 9/2006 |
| JP | 2006242080 | 9/2006 |
| JP | 2006242081 | 9/2006 |
| JP | 2006256999 | 9/2006 |
| JP | 2006257238 | 9/2006 |
| JP | 2006261623 | 9/2006 |
| JP | 2006290988 | 10/2006 |
| JP | 2006313796 | 11/2006 |
| JP | 2006332622 | 12/2006 |
| JP | 2006351638 | 12/2006 |
| JP | 2007019462 | 1/2007 |
| JP | 2007031678 A | 2/2007 |
| JP | 2007042875 | 2/2007 |
| JP | 2007053132 | 3/2007 |
| JP | 2007066581 | 3/2007 |
| JP | 2007073620 | 3/2007 |
| JP | 2007073845 | 3/2007 |
| JP | 2007073900 | 3/2007 |
| JP | 2007080593 | 3/2007 |
| JP | 2007080677 | 3/2007 |
| JP | 2007088105 | 4/2007 |
| JP | 2007088164 | 4/2007 |
| JP | 2007096259 | 4/2007 |
| JP | 2007099765 A | 4/2007 |
| JP | 2007110067 | 4/2007 |

(56) References Cited

FOREIGN PATENT DOCUMENTS

| | | |
|---|---|---|
| JP | 2007110102 | 4/2007 |
| JP | 2007258550 | 10/2007 |
| JP | 2007324309 | 12/2007 |
| JP | 2008010353 | 1/2008 |
| JP | 2008091860 | 4/2008 |
| JP | 2008103535 | 5/2008 |
| JP | 2008109103 | 5/2008 |
| JP | 20081090085 | 5/2008 |
| JP | 2008160087 | 7/2008 |
| JP | 2008198801 | 8/2008 |
| JP | 2008270729 | 11/2008 |
| JP | 2008270736 | 11/2008 |
| JP | 2009016184 | 1/2009 |
| JP | 2009016579 | 1/2009 |
| JP | 2009032977 | 2/2009 |
| JP | 2009032988 | 2/2009 |
| JP | 2009076509 A | 4/2009 |
| JP | 2009266943 | 11/2009 |
| JP | 2009267171 | 11/2009 |
| JP | 2009267244 | 11/2009 |
| JP | 2009272339 | 11/2009 |
| JP | 2009283891 | 12/2009 |
| JP | 2010135689 | 6/2010 |
| JP | 2012222255 | 11/2012 |
| JP | 2013525436 | 6/2013 |
| JP | 5604505 | 10/2014 |
| JP | 2014221807 | 11/2014 |
| JP | 2015081257 | 4/2015 |
| KR | 1020060115371 | 11/2006 |
| KR | 2007061830 | 6/2007 |
| KR | 2007112465 | 11/2007 |
| KR | 1020130043460 | 4/2013 |
| KR | 101338250 | 12/2013 |
| TW | 200701835 | 1/2007 |
| TW | 201307365 | 2/2013 |
| TW | 201710277 | 3/2017 |
| WO | WO2008054578 | 5/2000 |
| WO | WO2000070655 | 11/2000 |
| WO | WO2004003108 | 1/2004 |
| WO | WO2004085450 | 10/2004 |
| WO | WO2004108857 | 12/2004 |
| WO | WO2005042444 | 5/2005 |
| WO | WO2005042550 | 5/2005 |
| WO | WO2005113704 | 12/2005 |
| WO | WO2006033440 | 3/2006 |
| WO | WO2006067074 | 6/2006 |
| WO | WO2006098505 | 9/2006 |
| WO | WO2006113106 | 10/2006 |
| WO | WO2006115299 | 11/2006 |
| WO | WO2006115301 | 11/2006 |
| WO | WO2007034985 | 3/2007 |
| WO | WO2007069498 | 6/2007 |
| WO | WO2008066192 | 6/2008 |
| WO | WO2008066195 | 6/2008 |
| WO | WO2008066196 | 6/2008 |
| WO | WO2008101842 | 8/2008 |
| WO | WO2008117889 | 10/2008 |
| WO | WO2008123540 | 10/2008 |
| WO | WO2009017211 | 2/2009 |
| WO | WO2009023667 | 2/2009 |
| WO | WO2010007098 | 1/2010 |
| WO | WO2010056669 | 5/2010 |
| WO | WO2010093176 | 8/2010 |
| WO | WO2010118026 | 10/2010 |
| WO | WO2011064335 | 6/2011 |
| WO | WO2011070989 | 6/2011 |
| WO | WO2011089163 | 7/2011 |
| WO | WO2011137429 | 11/2011 |
| WO | WO2011137431 | 11/2011 |
| WO | WO2012112853 | 8/2012 |
| WO | WO2012116231 A1 | 8/2012 |
| WO | WO2012142387 | 10/2012 |
| WO | WO2012162488 | 11/2012 |
| WO | WO201263471 | 12/2012 |
| WO | WO2013130483 | 9/2013 |
| WO | WO2014016611 | 1/2014 |
| WO | WO2014031977 | 2/2014 |
| WO | WO2014047616 | 3/2014 |
| WO | WO2014109814 | 7/2014 |
| WO | WO2014208271 | 12/2014 |
| WO | WO2015027060 | 2/2015 |
| WO | WO2015131158 | 9/2015 |
| WO | WO2016025921 | 2/2016 |
| WO | WO2016029137 | 2/2016 |
| WO | WO2016029186 | 2/2016 |
| WO | WO2016197019 | 12/2016 |

OTHER PUBLICATIONS

Zhu, Adv Mater, vol. 27, 2533-2537, 2015. (Year: 2015).*
Zhu, Adv Mater, vol. 29, 1605002, pp. 1-5, 2017 (Year: 2017).*
Chew, Applied Phys Letters, vol. 88, 093510-1-093510-3, 2006 (Year: 2006).*
Li, J Physical Chem C, vol. 115(42), 20722-20731, 2011. (Year: 2011).*
Bettington, Chem: a Eru J, vol. 13, 1423-1431, 2007. (Year: 2007).*
Tang, Cyes and Pigments, vol. 91, 413-421, 2011. (Year: 2011).*
Wong; Challenges in organometallic research—Great opportunity for solar cells and OLEDs, Journal of Organometallic Chemistry, 2009, 694, 2644-2647.
JP2009267244, English Translation from EPO, Nov. 2009, 80 pages.
JP2010135689, English translation from EPO, Jun. 2010, 95 pages.
Chi et al.; Transition-metal phosphors with cyclometalating ligands: fundamentals and applications, Chemical Society Reviews, vol. 39, No. 2, Feb. 2010, pp. 638-655.
Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.
Ayan Maity et al., "Room-temperature synthesis of cyclometalated iridium(III) complexes; kinetic isomers and reactive functionalities" Chem. Sci., vol. 4, pp. 1175-1181 (2013).
Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Barry O'Brien et al.: White organic light emitting diodes using Pt-based red, green and blue phosphorescent dopants. Proc. SPIE, vol. 8829, pp. 1-6, Aug. 25, 2013.
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Vanessa Wood et al., "Colloidal quantum dot light-emitting devices," Nano Reviews, vol. 1, 2010, 8 pages.
Glauco Ponterini et al., "Comparison of Radiationless Decay Processes in Osmium and Platinum Porphyrins," J. Am. Chem. Soc., vol. 105, No. 14, 1983, pp. 4639-4645.
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.

(56) References Cited

OTHER PUBLICATIONS

Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Shih-Chun Lo et al., "High-Triplet-Energy Dendrons: Enhancing the Luminescence of Deep Blue Phosphorescent Iridium(III) Complexes," J. Am. Chem. Soc., vol. 131, 2009, pp. 16681-16688.
Jan Kalinowski et al., "Light-emitting devices based on organometallic platinum complexes as emitters," Coordination Chemistry Reviews, vol. 255, 2011, pp. 2401-2425.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Chi-Ming Che et al., "Photophysical Properties and OLED Applications of Phosphorescent Platinum(II) Schiff Base Complexes," Chem. Eur. J., vol. 16, 2010, pp. 233-247.
Stephen R. Forrest, "The path to ubiquitous and low-cost organic electronic appliances on plastic," Nature, vol. 428, Apr. 29, 2004, pp. 911-918.
Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.
Xiaofan Ren et al., "Ultrahigh Energy Gap Hosts in Deep Blue Organic Electrophosphorescent Devices," Chem. Mater., vol. 16, 2004, pp. 4743-4747.
Jeonghun Kwak et al., "Bright and Efficient Full-Color Colloidal Quantum Dot Light-Emitting Diodes Using an Inverted Device Structure," Nano Lett., 2012, Vo. 12, pp. 2362-2366.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Eric Turner et al., "Cyclometalated Platinum Complexes with Luminescent Quantum Yields Approaching 100%," Inorg. Chem., 2013, vol. 52, pp. 7344-7351.
Steven C. F. Kui et al., "Robust Phosphorescent Platinum(II) Complexes Containing Tetradentate O ,N ,C ,N Ligands: Excimeric Excited State and Application in Organic White-Light-Emitting Diodes," Chem. Eur. J., 2013, vol. 19, pp. 69-73.
Steven C. F. Kui et al., "Robust phosphorescent platinum(II) complexes with tetradentate O ,N ,C ,N ligands: high efficiency OLEDs with excellent efficiency stability," Chem. Commun., 2013, vol. 49, pp. 1497-1499.
Guijie Li et al., "Efficient and stable red organic light emitting devices from a tetradentate cyclometalated platinum complex," Organic Electronics, 2014, vol. 15 pp. 1862-1867.
Guijie Li et al., Efficient and Stable White Organic Light-Emitting Diodes Employing a Single Emitter, Adv. Mater., 2014, vol. 26, pp. 2931-2936.
Barry O'Brien et al., "High efficiency white organic light emitting diodes employing blue and red platinum emitters," Journal of Photonics for Energy, vol. 4, 2014, pp. 043597-1-043597-8.
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Dorwald; "Side Reactions in Organic Synthesis: A Guide to Successful Synthesis Design," Chapter 1, 2005 Wiley-VCH Verlag GmbH & Co. KGaA, Wienheim, 32 pages.
Murakami; JP 2007258550, English machine translation from EPO, Oct. 4, 2007. 80 pages.
Murakami; JP 2007324309, English machine translation from EPO, Dec. 13, 2007, 89 pages.

Marc Lepeltier et al., "Efficient blue green organic light-emitting devices based on a monofluorinated heteroleptic iridium(III) complex," Synthetic Metals, vol. 199, 2015, pp. 139-146.
Stefan Bernhard, "The First Six Years: A Report," Department of Chemistry, Princeton University, May 2008, 11 pages.
Ivaylo Ivanov et al., "Comparison of the INDO band structures of polyacetylene, polythiophene, polyfuran, and polypyrrole," Synthetic Metals, vol. 116, Issues 1-3, Jan. 1, 2001, pp. 111-114.
Zhi-Qiang Zhu et.al., "Harvesting All Electrogenerated Excitons through Metal Assisted Delayed Fluorescent Materials," Adv. Mater. 27 (2015) 2533-2537.
Zhi-Qiang Zhu et. al.. "Efficient Cyclometalated Platinum(II) Complex with Superior Operational Stability," Adv. Mater. 29 (2017) 1605002.
Chew, S. et al.: Photoluminescence and electroluminescence of a new blue-emitting homoleptic iridium complex. Applied Phys. Letters; 2006, vol. 88, pp. 093510-1-093510-3.
Xin Li et al., "Density functional theory study of photophysical properties of iridium (III) complexes with phenylisoquinoline and phenylpyridine ligands", The Journal of Physical Chemistry C, 2011, vol. 115, No. 42, pp. 20722-20731.
Sylvia Bettington et al. "Tris-Cyclometalated Iridium(III) Complexes of Carbazole(fluorenyl)pyridine Ligands: Synthesis, Redox and Photophysical Properties, and Electrophosphorescent Light-Emitting Diodes" Chemistry: A European Journal, 2007, vol. 13, pp. 1423-1431.
Christoph Ulbricht et al., "Synthesis and Characterization of Oxetane—Functionalized Phosphorescent Ir(III)—Complexes", Macromol. Chem. Phys. 2009, 210, pp. 531-541.
Dan Wang et al., "Carbazole and arylamine functionalized iridium complexes for efficient electro-phosphorescent light-emitting diodes", Inorganica Chimica Acta 370 (2011) pp. 340-345.
Huaijun Tang et al., "Novel yellow phosphorescent iridium complexes containing a carbazoleeoxadiazole unit used in polymeric light-emitting diodes", Dyes and Pigments 91 (2011) pp. 413-421.
Hoe-Joo Seo et al., "Blue phosphorescent iridium(III) complexes containing carbazole-functionalized phenyl pyridine for organic light-emitting diodes: energy transfer from carbazolyl moieties to iridium(III) cores", RSC Advances, 2011, 1, pp. 755-757.
Jack W. Levell et al., "Carbazole/iridium dendrimer side-chain phosphorescent copolymers for efficient light emitting devices", New J. Chem., 2012, 36, pp. 407-413.
Z Liu et al., "Green and blue-green phosphorescent heteroleptic iridium complexes containing carbazole-functionalized beta-diketonate for non-doped organic light-emitting diodes", Organic Electronics 9 (2008) pp. 171-182.
Zhaowu Xu et al., "Synthesis and properties of iridium complexes based 1,3,4-oxadiazoles derivatives", Tetrahedron 64 (2008) pp. 1860-1867.
D.F. O'Brien et al., "Improved energy transfer in electrophosphorescent devices," Appl. Phys. Lett., vol. 74, No. 3, Jan. 18, 1999, pp. 442-444.
Vadim Adamovich et al., "High efficiency single dopant white electrophosphorescent light emitting diodes," New J. Chem., 2002, 26, pp. 1171-1178.
Kwon-Hyeon Kim et al., "Controlling Emitting Dipole Orientation with Methyl Substituents on Main Ligand of Iridium Complexes for Highly Efficient Phosphorescent Organic Light-Emitting Diodes", Adv. Optical Mater. 2015, 3, pp. 1191-1196.
Matthew J. Jurow et al., "Understanding and predicting the orientation of heteroleptic phosphors in organic light-emitting materials", Nature Materials, vol. 15, Jan. 2016, pp. 85-93.
Kwon-Hyeon Kim et al., "Crystal Organic Light-Emitting Diodes with Perfectly Oriented Non-Doped Pt-Based Emitting Layer", Adv. Mater. 2016, 28, pp. 2526-2532.
Maestri et al., "Absorption Spectra and Luminescence Properties of Isomeric Platinum (II) and Palladium (II) Complexes Containing 1,1'-Biphenyldiyl, 2-Phenylpyridine, and 2,2'-Bipyridine as Ligands," Helvetica Chimica Acta, vol. 71, Issue 5, Aug. 10, 1988, pp. 1053-1059.
Guijie Li et al., "Modifying Emission Spectral Bandwidth of Phosphorescent Platinum(II) Complexes Through Synthetic Control," Inorg. Chem. 2017, 56, 8244-8256.

(56) References Cited

OTHER PUBLICATIONS

Tyler Fleetham et al., "Efficient Red-Emitting Platinum Complex with Long Operational Stability," ACS Appl. Mater. Interfaces 2015, 7, 16240-16246.
U.S. Appl. No. 61/945,940, filed Feb. 28, 2014, Chiral Metal Complexes as Emitters for Organic Polarized Electroluminescent Devices, Jian Li.
U.S. Appl. No. 15/119,961, filed Aug. 18, 2016, Chiral Metal Complexes as Emitters for Organic Polarized Electroluminescent Devices, Jian Li.
U.S. Appl. No. 62/037,802, filed Aug. 15, 2014, Non-Platinum Metal Complexes for Excimer Based Single Dopant White Organic Light Emitting Diodes, Jian Li, Liang Huang, Tyler Fleetham.
U.S. Appl. No. 15/503,690, filed Feb. 13, 2017, Non-Platinum Metal Complexes for Excimer Based Single Dopant White Organic Light Emitting Diodes, Jian Li, Liang Huang, Tyler Fleetham.
U.S. Appl. No. 62/040,470, filed Aug. 22, 2014, Organic Light-Emitting Diodes With Fluorescent and Phosphorescent Emitters, Jian Li, Tyler Fleetham.
U.S. Appl. No. 15/505,527, filed Feb. 21, 2017, Organic Light-Emitting Diodes With Fluorescent and Phosphorescent Emitters, Jian Li, Tyler Fleetham.
U.S. Appl. No. 62/040,727, filed Aug. 22, 2014, Metal-Assisted Delayed Fluorescent Materials as Co-Host Materials for Fluorescent OLEDs, Jian Li.
U.S. Appl. No. 15/505,544, filed Feb. 21, 2017 Metal-Assisted Delayed Fluorescent Materials as Co-Host Materials for Fluorescent OLEDs, Jian Li.
U.S. Appl. No. 62/050,243, filed Sep. 15, 2014, Ionic Liquid Catholyte, C. Austen Angell, Leigang Xue.
U.S. Appl. No. 62/138,710, filed Mar. 26, 2015, Ionic Liquid Catholytes and Electrochemical Devices Containing Same, Charles Austen Angell, Leigang Xue.
U.S. Appl. No. 15/508,032, filed Mar. 1, 2017, Ionic Liquid Catholytes and Electrochemical Devices Containing Same, Charles Austen Angell, Leigang Xue.
U.S. Appl. No. 62/170,809, filed Jun. 4, 2015, Transparent Electroluminescent Devices With Controlled One-Side Emissive Displays, Jian Li.
U.S. Appl. No. 15/577,655, filed Nov. 28, 2017, Transparent Electroluminescent Devices With Controlled One-Side Emissive Displays, Jian Li.
U.S. Appl. No. 62/323,383, filed Apr. 15, 2016, OLED With Doped Electron Blocking Layer, Jian Li.
U.S. Appl. No. 62/377,747, filed Aug. 22, 2016, OLED With Multi-Emissive Material Layer, Jian Li.
U.S. Appl. No. 62/407,020, filed Oct. 12, 2016, Narrow Band Red Phosphorescent Tetradentate Platinum (II) Complexes, Jian Li, Qunbo Mei.
U.S. Appl. No. 62/435,455, filed Dec. 16, 2016, Organic Light Emitting Diode With Split Emissive Layer, Jian Li, Kody George Klimes.
U.S. Appl. No. 14/437,963, filed Apr. 23, 2015 Metal Complexes, Methods, and Uses Thereof, Eric Turner, Jian Li.
U.S. Appl. No. 15/905,385, filed Feb. 26, 2018, Metal Complexes, Methods, and Uses Thereof, Eric Turner, Jian Li.
U.S. Appl. No. 61/166,901, filed Apr. 6, 2009, Synthesis of Four Coordinated Platinum Complexes and Their Applications in Light Emitting Devices Thereof, Eric Turner, Jian Li, Zixing Wang.
U.S. Appl. No. 13/263,096, filed Jan. 3, 2014, Synthesis of Four Coordinated Platinum Complexes and Their Applications in Light Emitting Devices Thereof, Eric Turner, Jian Li, Zixing Wang.
U.S. Appl. No. 14/611,654, filed Feb. 2, 2015, Eric Turner, Jian Li, Zixing Wang.
U.S. Appl. No. 61/329,687, filed Apr. 30, 2010, Synthesis of Four Coordinated Gold Complexes and Their Applications in Light Emitting Devices Thereof, Eric Turner, Jian Li.
U.S. Appl. No. 13/695,338, filed May 16, 2013, Synthesis of Four Coordinated Gold Complexes and Their Applications in Light Emitting Devices Thereof, Eric Turner, Jian Li.
U.S. Appl. No. 61/913,552, filed Dec. 9, 2013, Stable Emitters, Jian Li, Guijie Li.
U.S. Appl. No. 61/969,729, filed Mar. 24, 2014, Efficient Pure Blue OLEDs Employing Tetradentate Pt Complexes with Narrow Spectral Bandwidth, Jian Li, Guijie Li.
U.S. Appl. No. 62/021,488, filed Jul. 7, 2014, Stable and Efficient Platinum Complexes as Red Phosphorescent Emitters, Jian Li, Guijie Li.
U.S. Appl. No. 14/562,195, filed Dec. 5, 2014, Stable Emitters, Jian Li, Guijie Li.
U.S. Appl. No. 61/329,684, filed Apr. 30, 2010, Synthesis of Four Coordinated Palladium complexes and Their Applications in Light Emitting Devices Thereof, Eric Turner, Jian Li.
U.S. Appl. No. 13/695,337, filed Mar. 13, 2013, Synthesis of Four Coordinated Palladium Complexes and Their Applications in Light Emitting Devices Thereof, Eric Turner, Jian Li.
U.S. Appl. No. 14/145,461, filed Dec. 31, 2013, Synthesis of Four Coordinated Palladium Complexes and Their Applications in Light Emitting Devices Thereof, Jian Li.
U.S. Appl. No. 15/202,058, filed Jul. 5, 2016, Synthesis of Four Coordinated Palladium Complexes and Their Applications in Light Emitting Devices Thereof, Eric Turner, Jian Li.
U.S. Appl. No. 15/692,660, filed Aug. 31, 2017, Synthesis of Four Coordinated Palladium Complexes and Their Applications in Light Emitting Devices Thereof, Eric Turner, Jian Li.
U.S. Appl. No. 61/444,387, filed Feb. 18, 2011, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 13/399,252, filed Feb. 17, 2012, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 14/332,610, filed Jul. 16, 2014, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 14/589,599, filed Jan. 5, 2015, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 15/243,801, filed Aug. 22, 2016, Four Coordinated Platinum and Palladium Complexes With Geometrically Distorted Charge Transfer State and Their Applications in Light Emitting Devices, Eric Turner, Jian Li, Xiaochun Hang.
U.S. Appl. No. 61/490,111, filed May 26, 2011, Synthesis of Platinum and Palladium Complexes as Narrow-Band Phosphorescent Emitters for Full Color Displays, Eric Turner, Jain Li.
U.S. Appl. No. 13/479,921, filed May 24, 2012, Synthesis of Platinum and Palladium Complexes as Narrow-Band Phosphorescent Emitters for Full Color Displays, Eric Turner, Jian Li.
U.S. Appl. No. 14/996,522, filed Jan. 15, 2016, Synthesis of Platinum and Palladium Complexes as Narrow-Band Phosphorescent Emitters for Full Color Displays, Eric Turner, Jian Li.
U.S. Appl. No. 15/640,686, filed Jul. 3, 2017, Synthesis of Platinum and Palladium Complexes as Narrow-Band Phosphorescent Emitters for Full Color Displays, Eric Turner, Jian Li.
U.S. Appl. No. 61/704,880, filed Sep. 24, 2012, Terradentate Cyclometalated Metal Complexes, Guijie Li, Jian Li.
U.S. Appl. No. 14/430,454, filed Mar. 23, 2015, Metal Compounds, Methods, and Uses Thereof, Guijie Li, Jian Li.
U.S. Appl. No. 15/882,358, filed Jan. 29, 2018, Metal Compounds, Methods, and Uses Thereof, Guijie Li, Jian Li.
U.S. Appl. No. 61/833,091, filed Jun. 10, 2013, Phosphorescent Tetradentate Metal Complexes Having Modified Emission Spectra, Guijie Li, Jason Brooks, Jian Li.
U.S. Appl. No. 61/868,411, filed Aug. 21, 2013, Highly Efficient Organic Electrophosphorescent Devices With "Quantum Dot" Like Emission, Jian Li.
U.S. Appl. No. 14/913,306, filed Feb. 19, 2016, Phosphorescent Tetradentate Metal Complexes Having Modified Emission Spectra, Guijie Li, Jason Brooks, Jian Li.

(56) References Cited

OTHER PUBLICATIONS

U.S. Appl. No. 14/513,506, filed Oct. 14, 2014, Platinum Complexes and Devices, Guijie Li, Jason Brooks, Jian Li.
U.S. Appl. No. 15/202,111, filed Jul. 5, 2016, Platinum Complexes and Devices, Guijie Li, Jason Brooks, Jian Li.
U.S. Appl. No. 15/615,566, filed Jun. 6, 2017, Phosphorescent Tetradentate Metal Complexes Having Modified Emission Spectra, Guiji Li, Jason Brooks, Jian Li, Jason Brooks.
U.S. Appl. No. 15/900,260, filed Feb. 20, 2018, Phosphorescent Tetradentate Metal Complexes Having Modified Emission Spectra, Guijie Li, Jason Brooks, Jian Li, Jason Brooks.
U.S. Appl. No. 61/890,545, filed Oct. 14, 2013, Platinum Complexes, Devices, and Uses Thereof, Guijie Li, Jason Brooks, Jian Li.
U.S. Appl. No. 61/890,580, filed Oct. 14, 2013, Platinum Complexes, Devices, and Uses Thereof, Guijie Li, Jason Brooks, Jian Li.
U.S. Appl. No. 61/924,462, filed Jan. 7, 2014, Delayed Fluorescent Emitters Containing Phenyl-Pyrazole and its Analogues, Guijie Li, Jian Li.
U.S. Appl. No. 14/591,188, filed Jan. 7, 2015, Tetradentate Platinum and Palladium Complex Emitters Containing Phenyl-Pyrazole and Its Analogues, Guijie Li, Jian Li.
U.S. Appl. No. 61/897,065, filed Oct. 29, 2013, Efficient and Stable Blue and White Organic Light Emitting Diodes, Guijie Li, Jian Li.
U.S. Appl. No. 62/006,509, filed Jun. 2, 2014, Tetradentate Cyclometalated Platinum Complexes Containing 9,10-Dihydroacridine and its Analogues, Guijie Li, Jian Li, Zhi-Qiang Zhu.
U.S. Appl. No. 14/728,848, filed Jun. 2, 2015, Tetradentate Cyclometalated Platinum Complexes Containing 9,10-Dihydroacridine and Its Analogues, Guijie Li, Jian Li, Zhi-Qiang Zhu.
U.S. Appl. No. 62/030,235, filed Jul. 29, 2014, Metal-Assisted Delayed Fluorescent Emitters Containing Tridentated Ligands, Guijie Li, Jian Li.
U.S. Appl. No. 14/809,981, filed Jul. 27, 2015, Metal-Assisted Delayed Fluorescent Emitters Containing Tridentated Ligands, Guijie Li, Jian Li.
U.S. Appl. No. 15/711,525, filed Sep. 21, 2017, Metal-Assisted Delayed Fluorescent Emitters Containing Tridentate Ligands, Guijie Li, Jian Li.
U.S. Appl. No. 62/028,562, filed Jul. 24, 2014, Tetradentate Platinum (II) Complexes Cyclometalated With Functionalized Phenyl Carbene Ligands and Their Analogues, Jian Li, Zhi-Qiang Zhu.
U.S. Appl. No. 14/805,691, filed Jul. 22, 2015, Tetradentate Platinum (II) Complexes Cyclometalated With Functionalized Phenyl Carbene Ligands and Their Analogues, Jian Li, Zhi-Qiang Zhu.
U.S. Appl. No. 62/040,133, filed Aug. 21, 2014, Efficient Cyclometalated Platinum Complexes for Displays and Lighting Applications, Jian Li.
U.S. Appl. No. 62/077,431, filed Nov. 10, 2014, Tetradentate Metal Complexes With Carbon Group Bridging Ligands, Guijie Li, Jian Li.
U.S. Appl. No. 14/937,318, filed Nov. 10, 2015, Tetradentate Metal Complexes With Carbon Group Bridging Ligands, Guijie Li, Jian Li.
U.S. Appl. No. 62/170,283, filed Jun. 3, 2015, Tetradentate Metal Complexes Containing Napthyridinocarbazole and Its Analogues, Guijie Li, Jian Li.
U.S. Appl. No. 62/254,011, filed Nov. 11, 2015, Tetradentate and Octahedral Metal Complexes Containing Naphthyridinocarbazole and Its Analogues, Guijie Li, Jian Li.
U.S. Appl. No. 15/168,942, filed May 31, 2016, Tetradentate and Octahedral Metal Complexes Containing Naphthyridinocarbazole and Its Analogues, Guijie Li, Jian Li.
U.S. Appl. No. 15/354,280, filed Nov. 17, 2016, Tetradentate and Octahedral Metal Complexes Containing Naphthyridinocarbazole and Its Analogues, Guijie Li, Jian Li.
U.S. Appl. No. 15/882,267, filed Jan. 29, 2018, Tetradentate and Octahedral Metal Complexes Containing Naphthyridinocarbazole and Its Analogues, Guijie Li, Jian Li.
U.S. Appl. No. 62/170,049, filed Jun. 2, 2015, Tetradentate Metal Complexes Containing Indoloacridine and Its Analogues, Jian Li.
U.S. Appl. No. 62/274,456, filed Jan. 4, 2016, Tetradentate Metal Complexes Containing Indoloacridine and Its Analogues, Jian Li.
U.S. Appl. No. 15/168,910, filed May 31, 2016, Tetradentate Metal Complexes Containing Indoloacridine and Its Analogues, Jian Li.
U.S. Appl. No. 15/651,972, filed Jul. 17, 2017, Tetradentate Metal Complexes Containing Indoloacridine and Its Analogues, Jian Li.
U.S. Appl. No. 62/200,960, filed Aug. 4, 2015, Novel Cyclic Tetradentate Platinum (II) and Palladium (II) Complexes, Jian Li, Zhi-Qiang Zhu.
U.S. Appl. No. 62/377,883, filed Aug. 22, 2016, Octahedral Iridium (III) Complexes Employing Azepine Functional Group and Their Analogues, Jian Li, Zhi-Qiang Zhu.
U.S. Appl. No. 15/625,082, filed Jun. 16, 2017, Tetradentate Platinum (II) and Palladium (II) Complexes and Octahedral Iridium Complexes Employing Azepine Functional Groups and Their Analogues, Jian Li, Zhi-Qiang Zhu.
U.S. Appl. No. 62/377,884, filed Aug. 22, 2016, Tetradentate Platinum (II) and Palladium (II) Complexes Employing Azepine Functional Group and Their Analogues, Jian Li, Zhi-Qiang Zhu.
U.S. Appl. No. 62/451,574, filed Jan. 27, 2017, Metal-Assisted Delayed Fluorescent Emitters Employing Pyrido-Pyrrolo-Acridine and Analogues, Jian Li, Yunlong Ji.
U.S. Appl. No. 15/487,476, filed Apr. 14, 2017, OLED With Multi-Emissive Material Layer, Jian Li.
U.S. Appl. No. 62/508,560, filed May 19, 2017, Metal-Assisted Delayed Fluorescent Emttters Employing Benzo-Imidazo-Phenanthridine and Analogues, Jian Li, Yunlong Ji.
U.S. Appl. No. 62/508,849, filed May 19, 2017, Tetradentate Platinum and Palladium Complexes Based on Biscarbazole and Analogues, Jian Li, Zhiqiang Zhu.
U.S. Appl. No. 62/573,596, filed Oct. 17, 2017, Hole-Blocking Materials for Organic Light Emitting Diodes, Jian Li.
U.S. Appl. No. 62/573,472, filed Oct. 17, 2017, Phosphorescent Excimers With Preferred Molecular Orientation as Monochromatic Emitters for Display and Lighting Applications, Jian Li.
U.S. Appl. No. 62/573,639, filed Oct. 17, 2017, Phosphorescent Excimers With Preferred Molecular Orientation as Monochromatic Emitters for Display and Lighting Applications, Jian Li.
U.S. Appl. No. 62/573,462, filed Oct. 17, 2017, Single-Doped White OLED With Extraction Layer Doped With Down-Conversion Red Phosphors, Jian Li.
U.S. Appl. No. 15/845,575, filed Dec. 18, 2017, Organic Light Emitting Diode With Split Emissive Layer, Jian Li, Kody George Klimes.

* cited by examiner

TETRADENTATE PLATINUM (II) AND PALLADIUM (II) COMPLEXES, DEVICES, AND USES THEREOF

CROSS-REFERENCE TO RELATED APPLICATIONS

This application claims priority to U.S. Provisional Patent Application No. 62/200,960 entitled "Novel Cyclic Tetradentate Platinum (II) and Palladium (II) Complexes" filed on Aug. 4, 2015, which is hereby incorporated by reference in its entirety.

TECHNICAL FIELD

The present disclosure relates to cyclometalated metal complexes as emitters for organic light emitting diodes (OLEDs).

BACKGROUND

Compounds capable of absorbing and/or emitting light can be ideally suited for use in a wide variety of optical and electroluminescent devices, including, for example, photo-absorbing devices such as solar- and photo-sensitive devices, OLEDs, and photo-emitting devices. Much research has been devoted to the discovery and optimization of organic and organometallic materials for using in optical and electroluminescent devices. Generally, research in this area aims to accomplish a number of goals, including improvements in absorption and emission efficiency and improvements in the stability of devices, as well as improvements in processing ability.

Despite significant advances in research devoted to optical and electro-optical materials (e.g., red and green phosphorescent organometallic materials are commercially available and have been used as phosphors in OLEDs, lighting and advanced displays), many currently available materials exhibit a number of disadvantages, including poor processing ability, inefficient emission or absorption, and less than ideal stability, among others.

Good blue emitters are particularly scarce, with one challenge being the stability of the blue devices. The choice of the host materials has an impact on the stability and the efficiency of the devices. The lowest triplet excited state energy of the blue phosphors is very high compared with that of the red and green phosphors, which means that the lowest triplet excited state energy of host materials for the blue devices should be even higher. Thus, one of the problems is that there are limited host materials to be used for the blue devices.

Cyclometalated metal complexes have found wide applications as emitters for OLEDs in recent decades. Much attention has been paid to the development of new improved materials for both display and solid state lighting applications. So far, most of the reported platinum (II) and palladium (II) emitters are acyclic, cyclic platinum (II) and palladium (II) emitters have been rarely reported even if cyclic ones are potentially more stable compared with acyclic ones. A need exists for new materials an improved the color purity, enhanced operational stability as well as elimination of the potential intermolecular interaction. The present application addresses these needs.

SUMMARY

The compounds disclosed herein are a series of cyclic platinum (II) and palladium (II) complexes that are useful for full color displays and lighting applications.

Provided herein is a complex of Formula I:

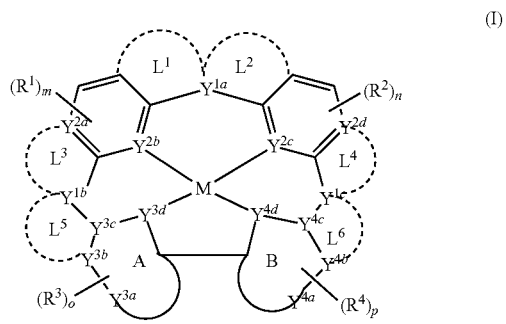

wherein:
M is Pt or Pd;
ring A and ring B each independently represents substituted or unsubstituted 5 or 6-membered aryl, or substituted or unsubstituted 5 or 6-membered heteroaryl having one or more U heteroatoms or one or more U1 heteroatoms, wherein U and U1 are each independently selected from N, P, As, O, S, and Se;
$Y^{1a}$, $Y^{1b}$ and $Y^{1c}$ each independently represents O, S, S(O), S(O)$_2$, Se, Se(O), Se(O)$_2$, N, NR$^{5a}$, P, PR$^{5a}$, As, AsR$^{5a}$, O=NR$^{5a}$, O=PR$^{5a}$, O=AsR$^{5a}$, B, BR$^{5a}$, SiR$^{5a}$, SiR$^{5b}$R$^{5c}$, CR$^{5a}$, or CR$^{5b}$R$^{5c}$;
$Y^{2a}$, $Y^{2b}$, $Y^{2c}$ and $Y^{2d}$ each independently represents C or N;
$Y^{3a}$, $Y^{3b}$, $Y^{3c}$, $Y^{3d}$ $Y^{4a}$, $Y^{4b}$, $Y^{4c}$, and $Y^{4d}$ each independently represents C, N, Si, O, or S;
$R^1$, $R^2$, $R^3$, and $R^4$ each independently represents hydrogen, halogen, hydroxy, amino, nitro, thiol, Si(C$_1$-C$_4$ alkyl)$_3$, substituted or unsubstituted C$_1$-C$_4$ alkyl, substituted or unsubstituted alkoxy, substituted or unsubstituted aryl, substituted or unsubstituted cycloalkyl, substituted or unsubstituted heteroaryl, or substituted or unsubstituted heterocycloalkyl;
$R^{5a}$, $R^{5b}$, and $R^{5c}$ each independently represents hydrogen, substituted or unsubstituted C$_1$-C$_4$ alkyl, or substituted or unsubstituted aryl;
each of L$^1$, L$^2$, L$^3$, L$^4$, L$^5$ and L$^6$ independently is absent, substituted or unsubstituted aryl, substituted or unsubstituted cycloalkyl, substituted or unsubstituted heteroaryl, substituted or unsubstituted heterocycloalkyl,

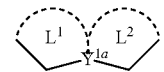

is independently

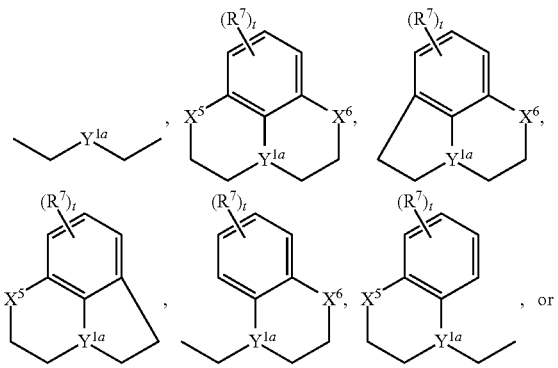

, or

-continued

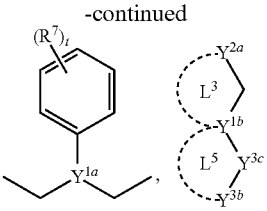

is independently

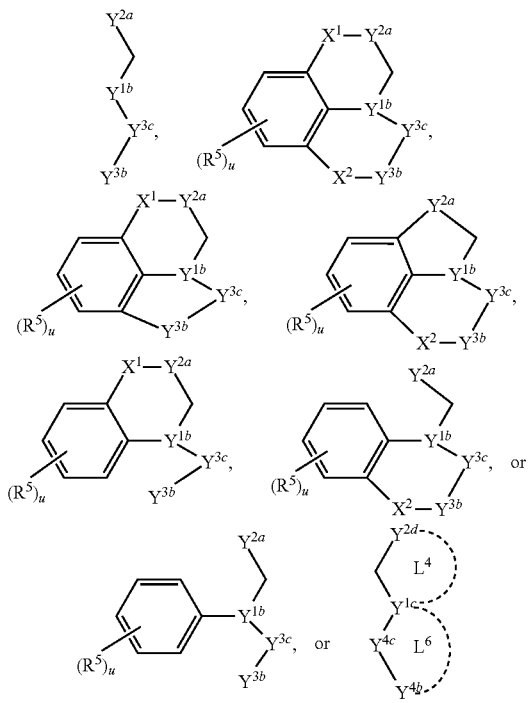

is independently

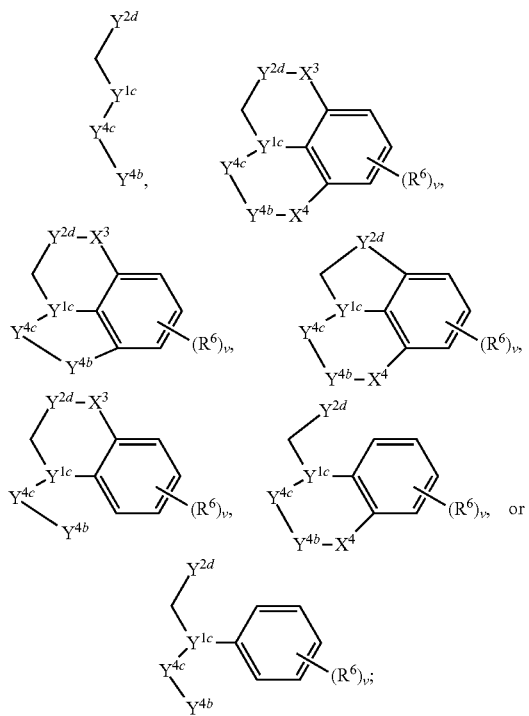

wherein $X^1$, $X^2$, $X^3$, $X^4$, $X^5$ and $X^6$ each independently is absent or represents a bond, O, S, S(O), S(O)$_2$, Se, Se(O), Se(O)$_2$, NR$^{7a}$, P, PR$^{7a}$, As, AsR$^{7a}$, O=NR$^{7a}$, O=PR$^{7a}$, O=AsR$^{7a}$, B, BR$^{7a}$, SiR$^{7a}$R$^{7b}$, or CR$^{7a}$R$^{7b}$;

$R^{7a}$ and $R^{7b}$ each independently represents hydrogen, substituted or unsubstituted C$_1$-C$_4$ alkyl, or substituted or unsubstituted aryl;

$R^5$, $R^6$ and $R^7$ each independently represents hydrogen, halogen, hydroxy, amino, nitro, thiol, Si(C$_1$-C$_4$ alkyl)$_3$, substituted or unsubstituted C$_1$-C$_4$ alkyl, substituted or unsubstituted alkoxy, substituted or unsubstituted aryl, substituted or unsubstituted cycloalkyl, substituted or unsubstituted heteroaryl, or substituted or unsubstituted heterocycloalkyl;

m, n, o, and p each independently represents 1, 2, or 3; and t, u, and v each independently represents 1, 2, 3, 4, or 5.

Provided herein is also a complex which is:

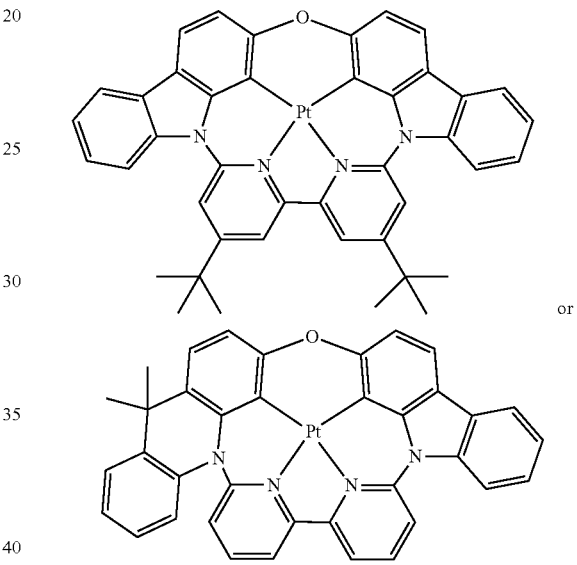

Provided herein is a light emitting device comprising a complex described herein. Examples of light emitting devices include OLEDs (e.g., phosphorescent OLED devices), photovoltaic devices, luminescent display devices, and the like.

Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

DETAILED DESCRIPTION

Figure 1:
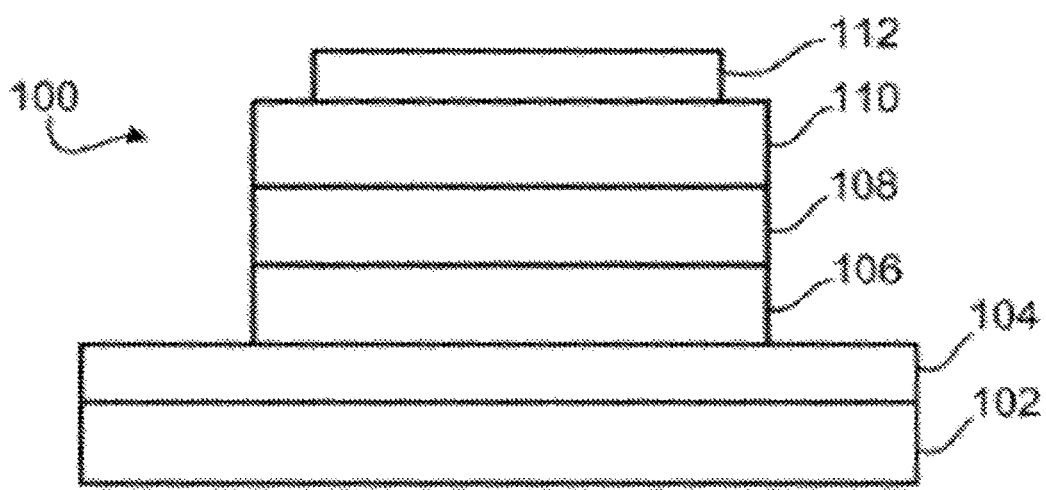
FIG. 1 depicts a cross section of an exemplary OLED.
Figure 2:
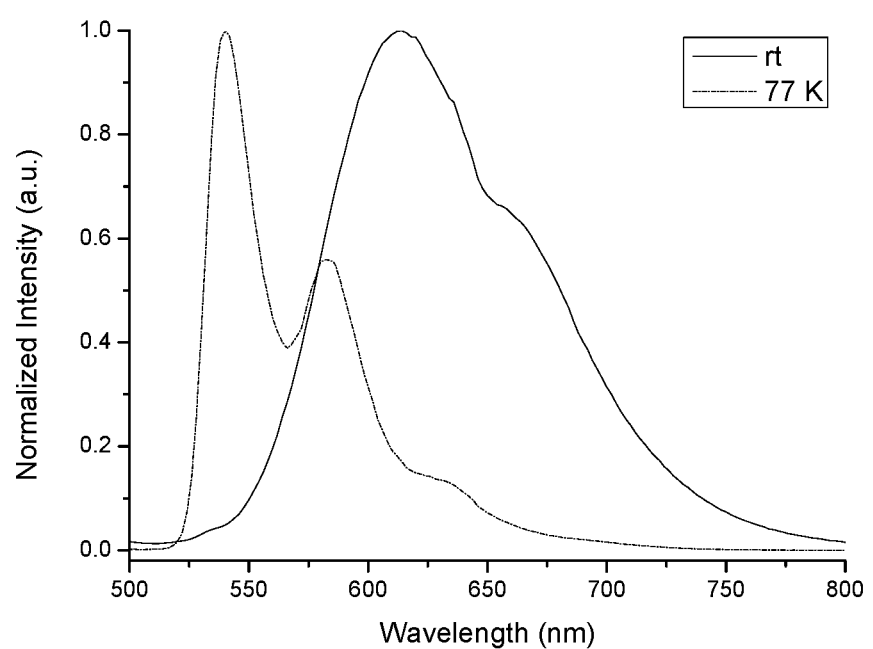
FIG. 2 shows representative photoluminescence spectra of PtNON$_C$-dtb at room temperature and at 77 K.

This disclosure relates to the complexes represented by Formula I:

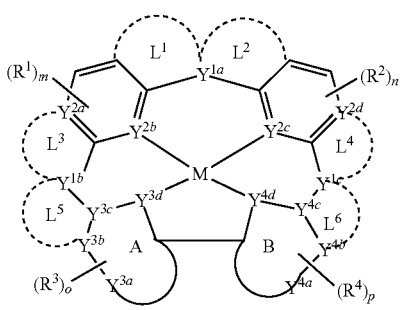

(I)

wherein:

M is Pt or Pd;

ring A and ring B each independently represents substituted or unsubstituted 5 or 6-membered aryl, or substituted or unsubstituted 5 or 6-membered heteroaryl having one or more U heteroatoms or one or more U1 heteroatoms, wherein U and U1 are each independently selected from N, P, As, O, S, and Se;

$Y^{1a}$, $Y^{1b}$ and $Y^{1c}$ each independently represents O, S, S(O), S(O)$_2$, Se, Se(O), Se(O)$_2$, N, NR$^{5a}$, P, PR$^{5a}$, As, AsR$^{5a}$, O=NR$^{5a}$, O=PR$^{5a}$, O=AsR$^{5a}$, B, BR$^{5a}$, SiR$^{5a}$, SiR$^{5b}$R$^{5c}$, CR$^{5a}$, or CR$^{5b}$R$^{5c}$;

$Y^{2a}$, $Y^{2b}$, $Y^{2c}$ and $Y^{2d}$ each independently represents C or N;

$Y^{3a}$, $Y^{3b}$, $Y^{3c}$, $Y^{3d}$ $Y^{4a}$, $Y^{4b}$, $Y^{4c}$, and $Y^{4d}$ each independently represents C, N, Si, O, or S;

$R^1$, $R^2$, $R^3$, and $R^4$ each independently represents hydrogen, halogen, hydroxy, amino, nitro, thiol, Si(C$_{1-4}$ alkyl)$_3$, substituted or unsubstituted C$_1$-C$_4$ alkyl, substituted or unsubstituted alkoxy, substituted or unsubstituted aryl, substituted or unsubstituted cycloalkyl, substituted or unsubstituted heteroaryl, or substituted or unsubstituted heterocycloalkyl;

$R^{5a}$, $R^{5b}$, and $R^{5c}$ each independently represents hydrogen, substituted or unsubstituted C$_1$-C$_4$ alkyl, or substituted or unsubstituted aryl;

each of $L^1$, $L^2$, $L^3$, $L^4$, $L^5$ and $L^6$ independently is absent, substituted or unsubstituted aryl, substituted or unsubstituted cycloalkyl, substituted or unsubstituted heteroaryl, substituted or unsubstituted heterocycloalkyl,

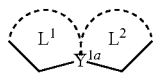

is independently

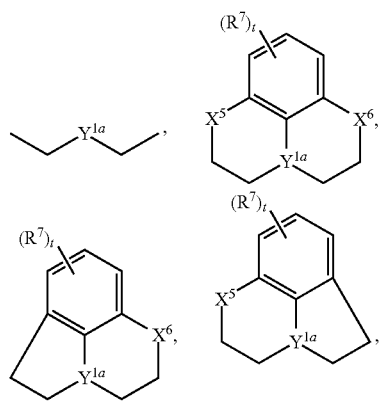

is independently

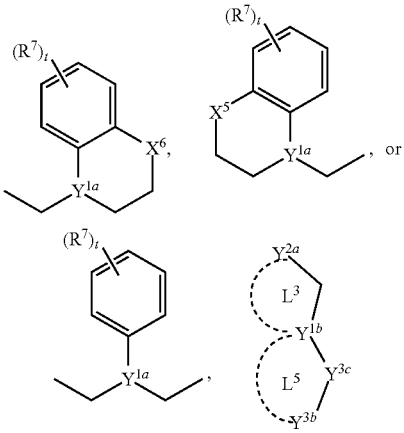

is independently

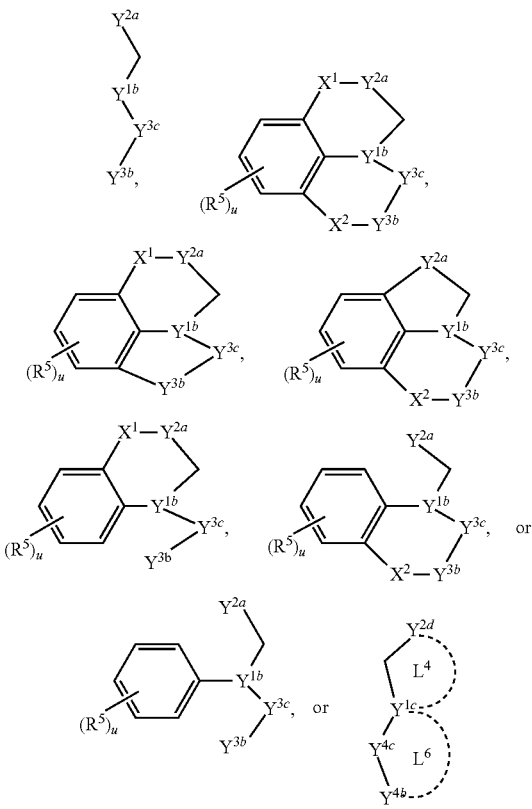

is independently

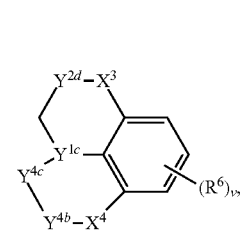

-continued

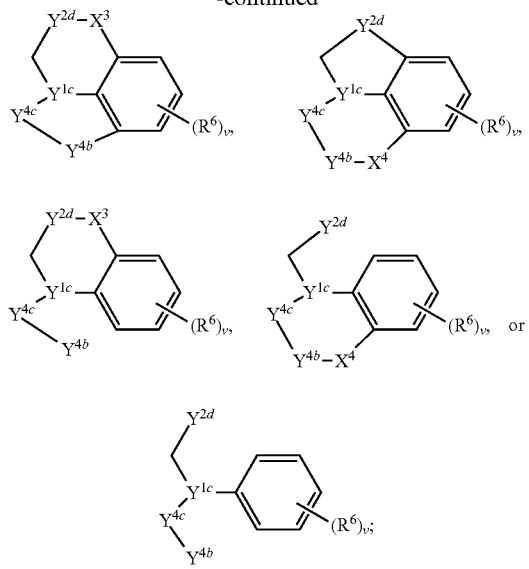
or

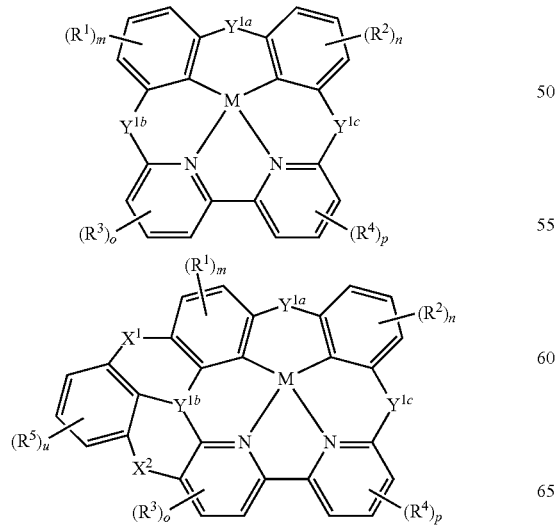

wherein $X^1$, $X^2$, $X^3$, $X^4$, $X^5$ and $X^6$ each independently is absent or represents a bond, O, S, S(O), S(O)$_2$, Se, Se(O), Se(O)$_2$, NR$^{7a}$, P, PR$^{7a}$, As, AsR$^{7a}$, O=NR$^{7a}$, O=PR$^{7a}$, O=AsR$^{7a}$, B, BR$^{7a}$, SiR$^{7a}$R$^{7b}$, or CR$^{7a}$R$^{7b}$;

$R^{7a}$ and $R^{7b}$ each independently represents hydrogen, substituted or unsubstituted C$_1$-C$_4$ alkyl, or substituted or unsubstituted aryl;

$R^5$, $R^6$ and $R^7$ each independently represents hydrogen, halogen, hydroxy, amino, nitro, thiol, Si(C$_{1-4}$ alkyl)$_3$, substituted or unsubstituted C$_1$-C$_4$ alkyl, substituted or unsubstituted alkoxy, or substituted or unsubstituted aryl, substituted or unsubstituted cycloalkyl, substituted or unsubstituted heteroaryl, or substituted or unsubstituted heterocycloalkyl;

m, n, o, and p each independently represents 1, 2, or 3; and t, u, and v each independently represents 1, 2, 3, 4, or 5.

In certain implementations, the present disclosure provides a formula selected from:

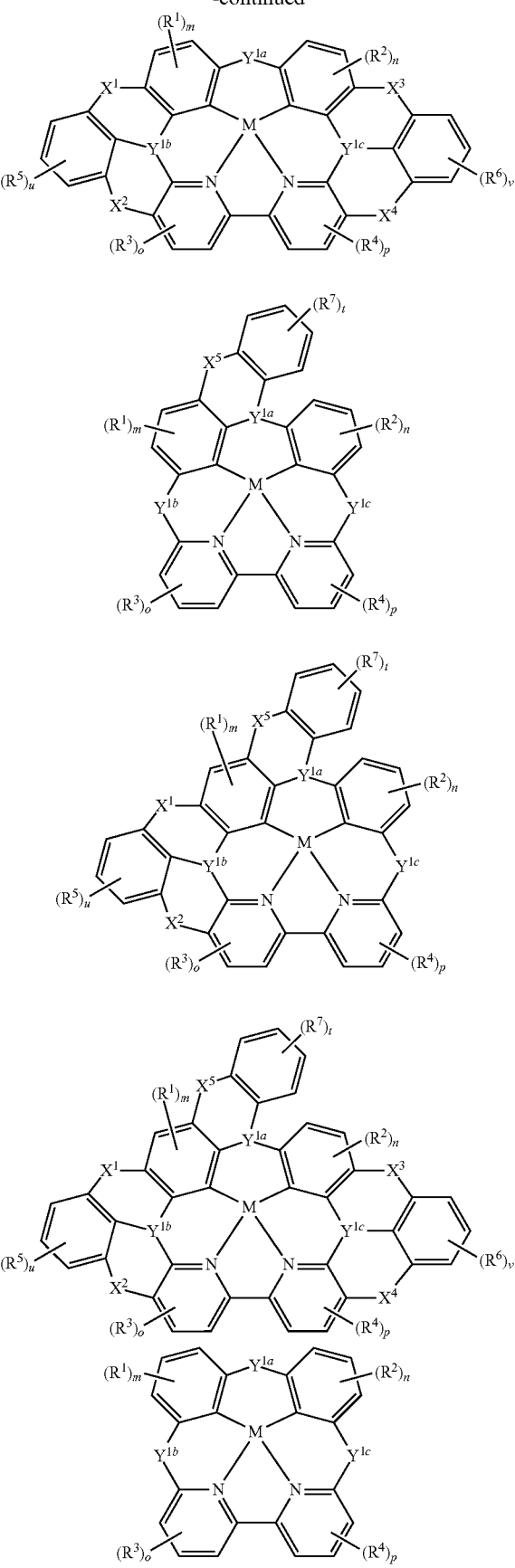

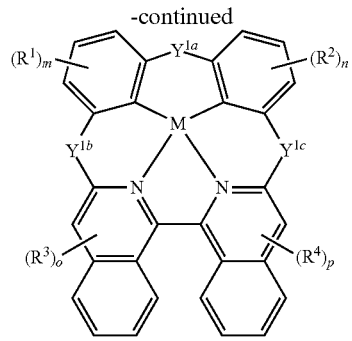
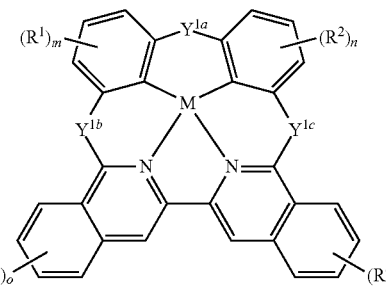
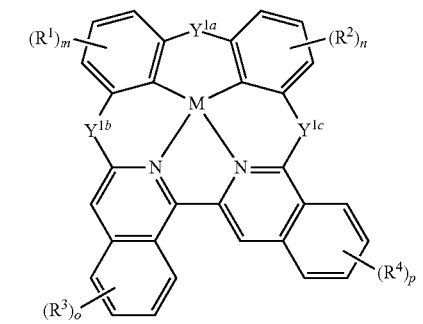
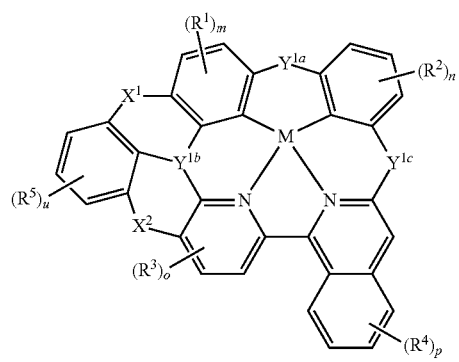
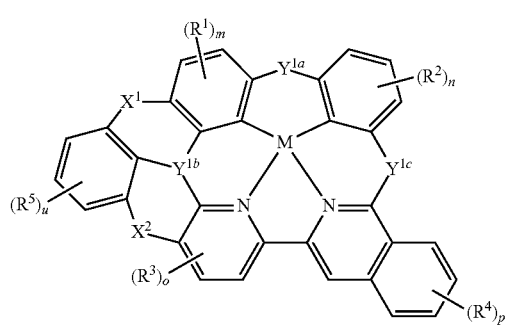
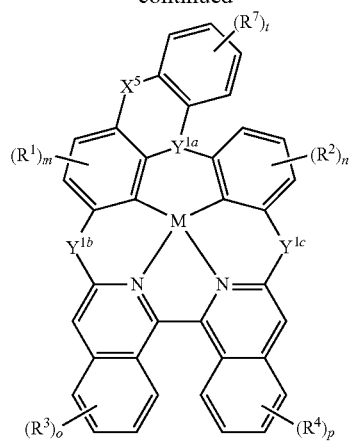
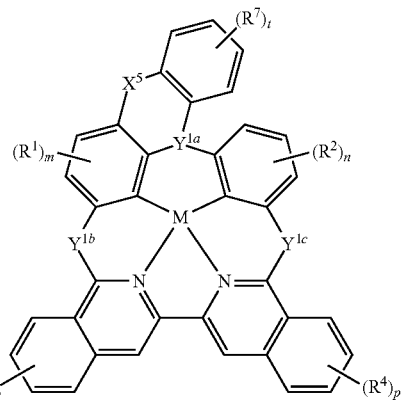
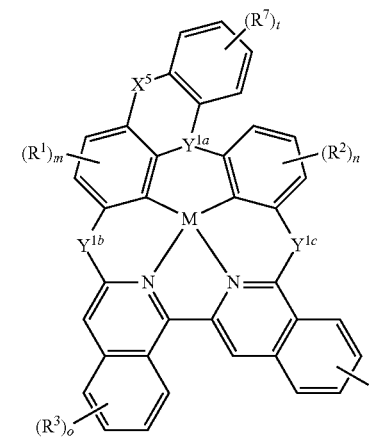
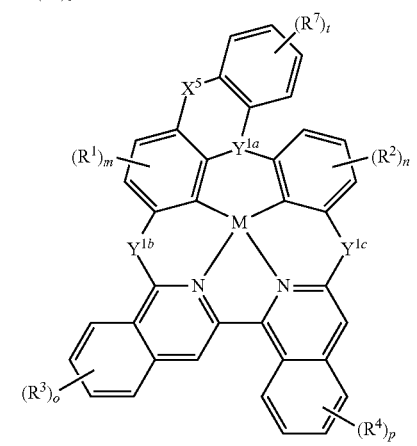

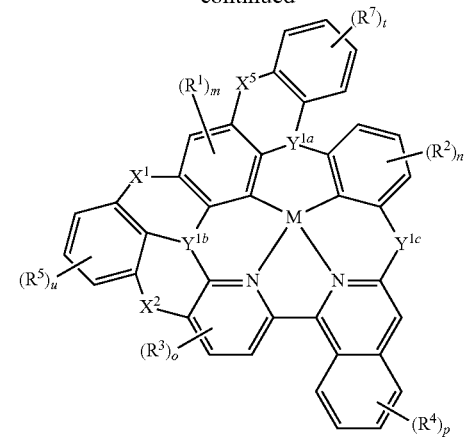
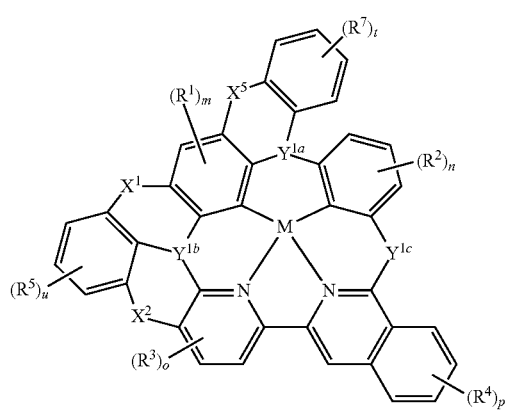
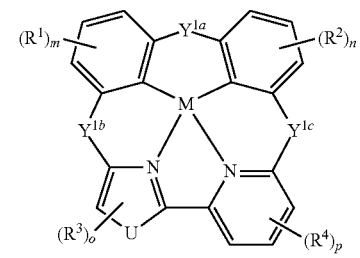
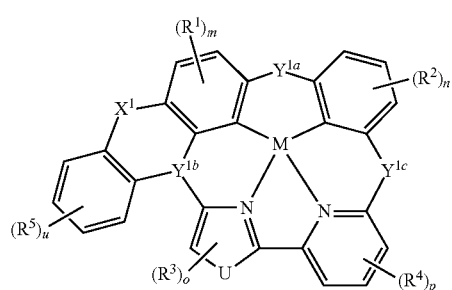
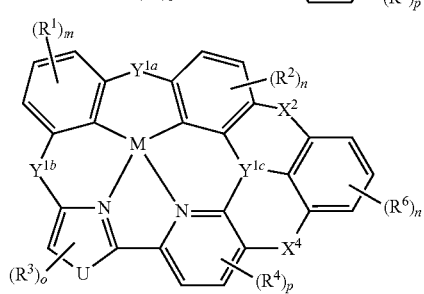
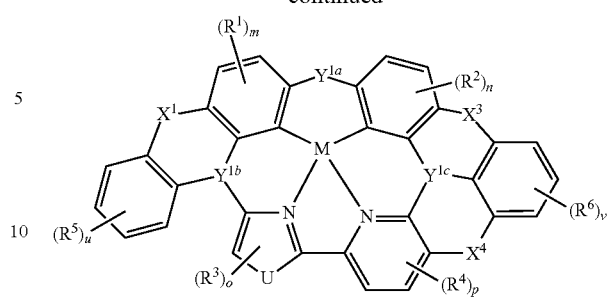
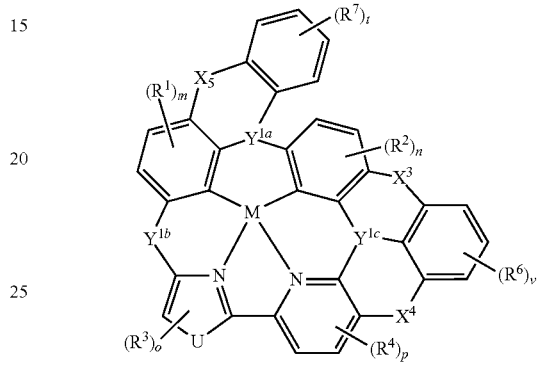
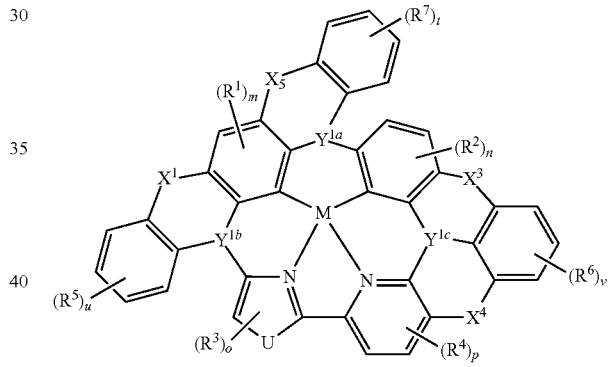
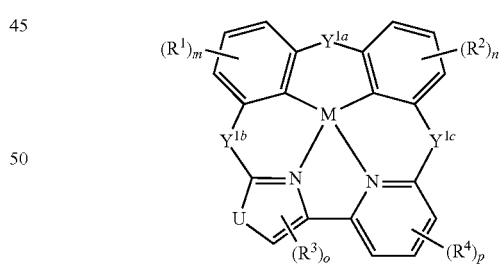
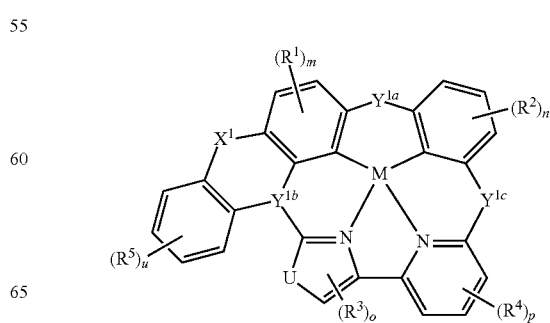

-continued
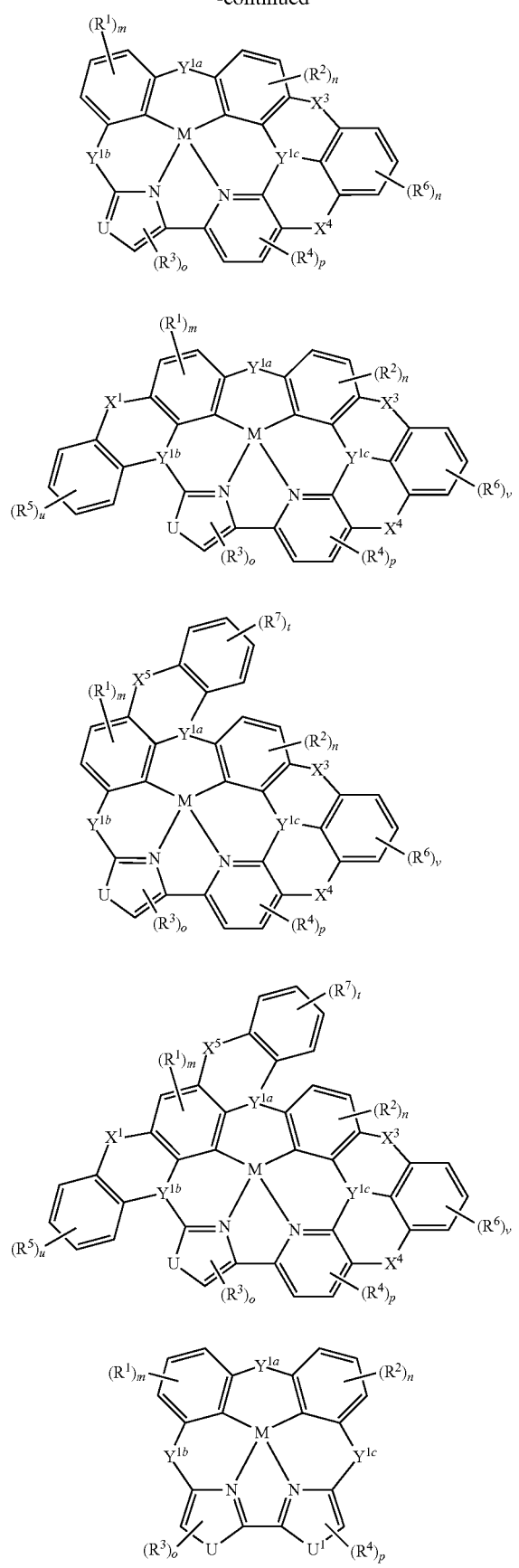
-continued
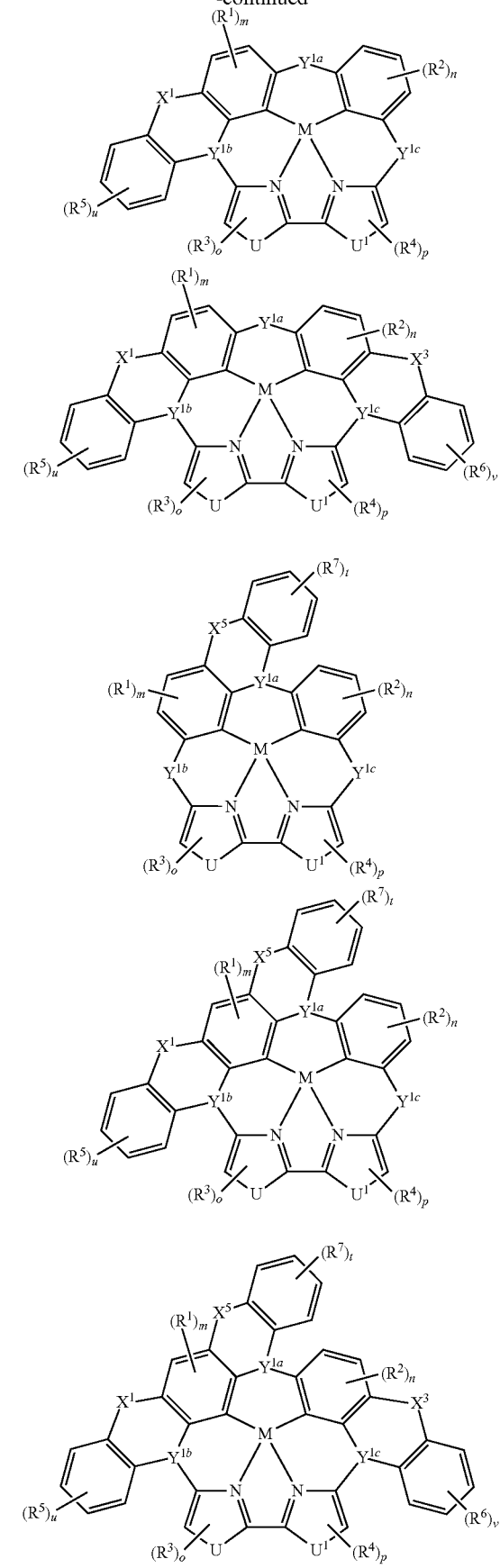

In certain implementations, each of $L^1$, $L^2$, $L^3$, $L^4$, $L^5$ and $L^6$ independently is absent, substituted or unsubstituted aryl, substituted or unsubstituted cycloalkyl, substituted or unsubstituted heteroaryl, or substituted or unsubstituted heterocycloalkyl.

In certain implementations, the moiety

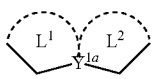

is independently

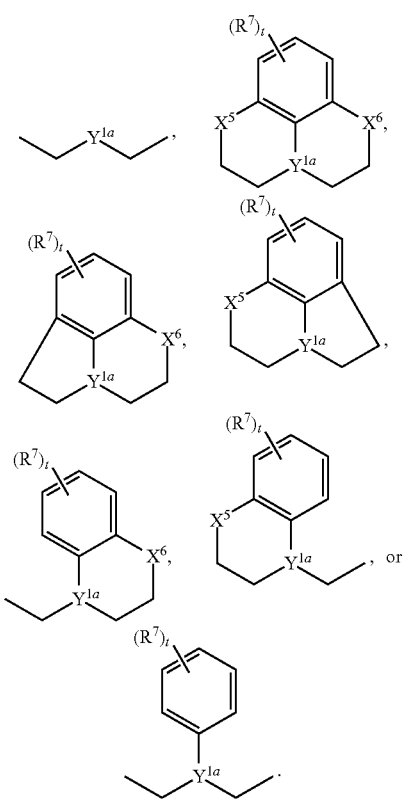

For example, one of $L^1$ and $L^2$ is absent or both $L^1$ and $L^2$ are absent. The moiety

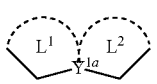

can be

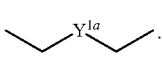

In certain implementations, the moiety

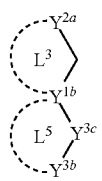

is independently

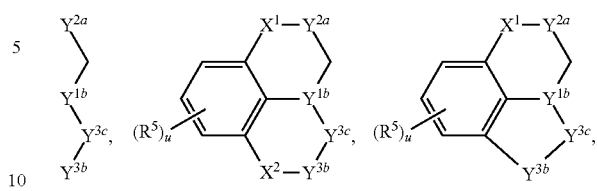

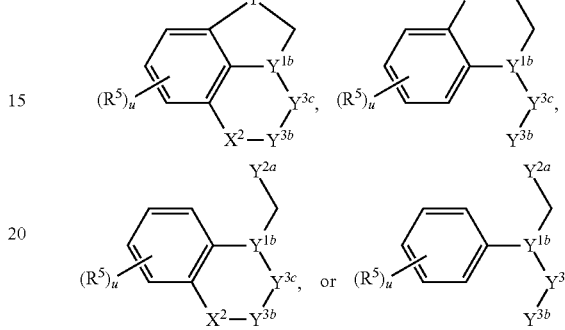

For example, one of $L^3$ and $L^5$ is absent or both $L^3$ and $L^5$ are absent. The moiety

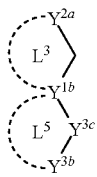

can be

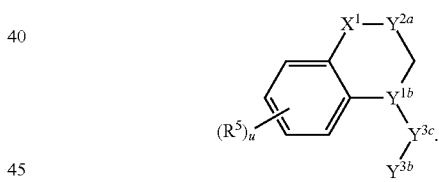

In certain implementations, the moiety

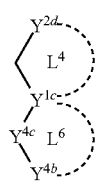

is independently

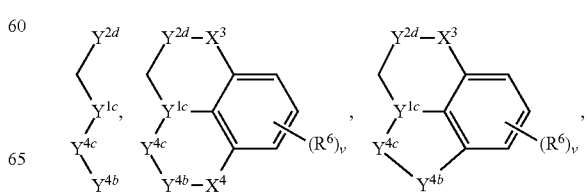

-continued

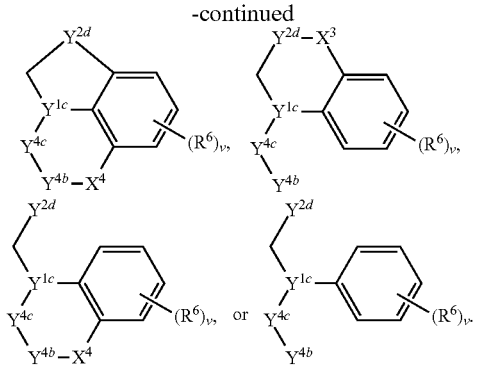

For example, one of L⁴ and L⁶ is absent or both L⁴ and L⁶ are absent. The moiety

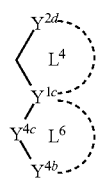

can be

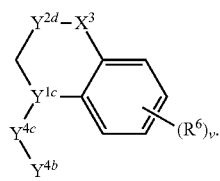

In certain implementations, the complex is a complex of Formula IIa:

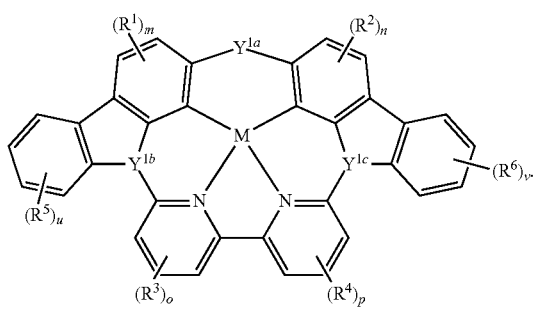

(IIa)

For example, the complex can be a complex of Formula IIIa:

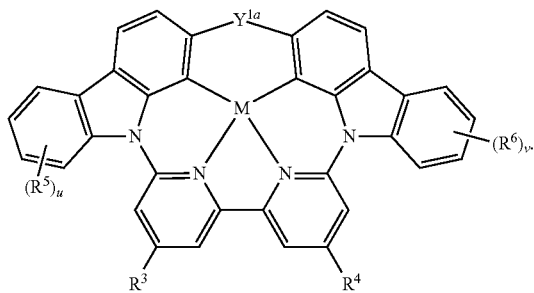

(IIIa)

In certain implementations, the complex is a complex of Formula IIb:

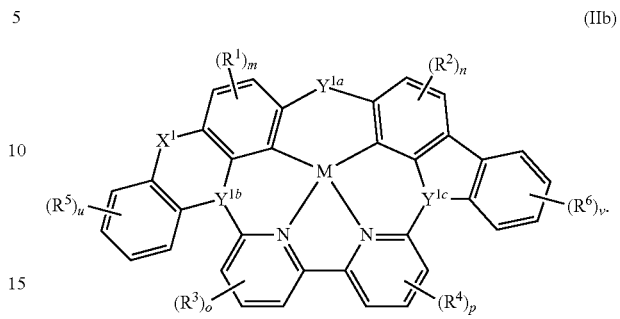

(IIb)

For example, the complex can be a complex of Formula IIIb:

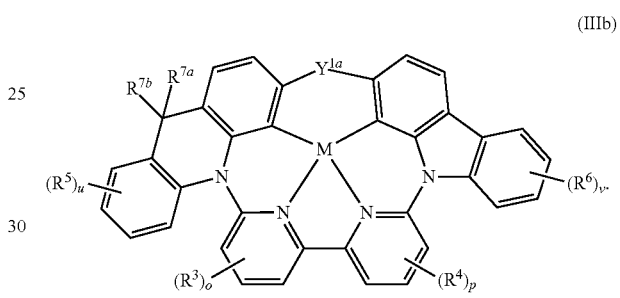

(IIIb)

The complex can also be a complex of Formula IVb:

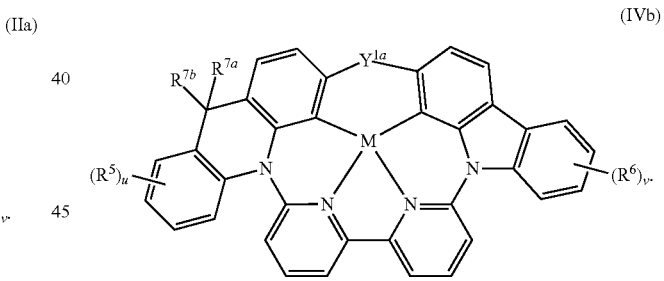

(IVb)

M is a transition metal such as Pt and Pd. In certain implementations, M is Pt. M can be Pd.

In certain implementations, $R^1$, $R^2$, $R^3$ and $R^4$ each independently represents hydrogen, halogen, hydroxy, amino, substituted or unsubstituted $C_1$-$C_4$ alkyl, or substituted or unsubstituted alkoxy. For example, $R^1$, $R^2$, $R^3$ and $R^4$ each independently represents hydrogen, halogen, or substituted or unsubstituted $C_1$-$C_4$ alkyl. In some examples, $R^1$, $R^2$, $R^3$ and $R^4$ each independently represents hydrogen or substituted or unsubstituted $C_1$-$C_4$ alkyl. $R^3$ and $R^4$ each independently can be substituted or unsubstituted $C_1$-$C_4$ alkyl, for example, unsubstituted $C_1$-$C_4$ alkyl such as methyl, ethyl, propyl, isopropyl, and n-butyl. In some implementations, $R^1$ and $R^2$ are hydrogen.

In some implementations, $R^5$, $R^6$, and $R^7$ each independently represents hydrogen, halogen, hydroxy, amino, substituted or unsubstituted $C_1$-$C_4$ alkyl, or substituted or unsubstituted alkoxy. For example, $R^5$, $R^6$, and $R^7$ each independently represents hydrogen, halogen, or substituted or unsubstituted $C_1$-$C_4$ alkyl. In some examples, $R^5$, $R^6$, and $R^7$ each independently represents hydrogen or substituted or unsubstituted $C_1$-$C_4$ alkyl. $R^5$, $R^6$, and $R^7$ can be substituted or unsubstituted $C_1$-$C_4$ alkyl, for example, unsubstituted $C_1$-$C_4$ alkyl such as methyl, ethyl, propyl, isopropyl, and n-butyl. In certain implementations, $R^5$, $R^6$, and $R^7$ are hydrogen.

In some implementations, $Y^{1a}$ is O or S. For example, $Y^{1a}$ is O. For example, $Y^{1a}$ is $NR^{5a}$.

In some implementations, $Y^{1b}$ is N. $Y^{1b}$ can also be O or S. In some examples, $Y^{1b}$ is $SiR^{5b}R^{5c}$ or $CR^{5b}R^{5c}$.

In some implementations, $Y^{1c}$ is N. $Y^{1c}$ can also be O or S. In some examples, $Y^{1c}$ is $SiR^{5b}R^{5c}$ or $CR^{5b}R^{5c}$.

In some implementations, $Y^{2a}$, $Y^{2c}$, $Y^{2b}$, and $Y^{2d}$ are C.

In some implementations, $Y^{3d}$ and $Y^{4d}$ are N, and $Y^{3c}$ and $Y^{4c}$ are C.

In some implementations, the complex provided herein is a complex of Formula (IIa), wherein:
M is Pt or Pd;
$R^1$, $R^2$, $R^3$ and $R^4$ each independently represents hydrogen, halogen, hydroxy, amino, or substituted or unsubstituted $C_1$-$C_4$ alkyl;
$Y^{1a}$ represents O or $NR^{5a}$;
$R^{5a}$ is hydrogen, or substituted or unsubstituted $C_1$-$C_4$ alkyl;
$Y^{1b}$ and $Y^{1c}$ are C;
$R^5$ and $R^6$ each independently represents hydrogen, halogen, hydroxy, amino, or substituted or unsubstituted $C_1$-$C_4$ alkyl;
m, n, o, and p each independently represents 1 or 2; and
t, u, and v each independently represents 1, 2, or 3.

In some implementations, the complex provided herein is a complex of Formula IIb, wherein
M is Pt or Pd;
$R^1$, $R^2$, $R^3$ and $R^4$ each independently represents hydrogen, halogen, hydroxy, amino, or substituted or unsubstituted $C_1$-$C_4$ alkyl;
$Y^{1a}$ represents O or $NR^{5a}$;
$R^{5a}$ is hydrogen, or substituted or unsubstituted $C_1$-$C_4$ alkyl;
$Y^{1b}$ and $Y^{1c}$ are C;
$R^5$ and $R^6$ each independently represents hydrogen, halogen, hydroxy, amino, or substituted or unsubstituted $C_1$-$C_4$ alkyl;
$X^1$ is $CR^{7a}R^{7b}$;
$R^{7a}$ and $R^{7b}$ each independently represents hydrogen or substituted or unsubstituted $C_1$-$C_4$ alkyl,
m, n, o, and p each independently represents 1 or 2; and
t, u, and v each independently represents 1, 2, or 3.

In some examples, provided herein is a complex which is:

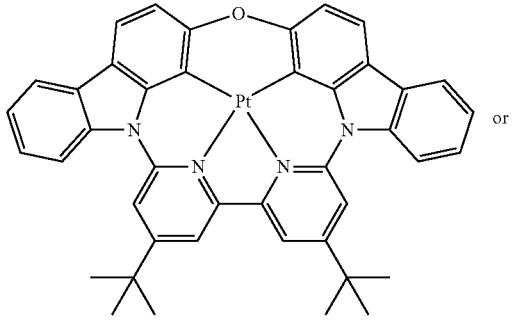

or

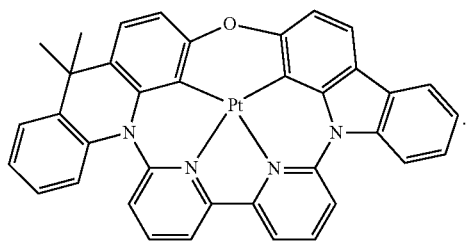

In certain implementations, the complexes are represented by the following structures:

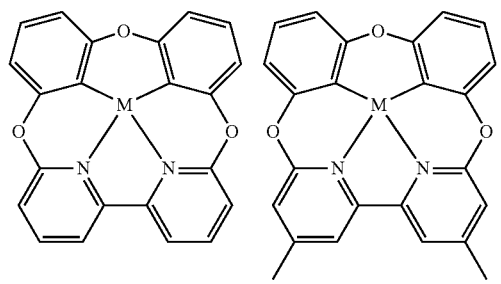

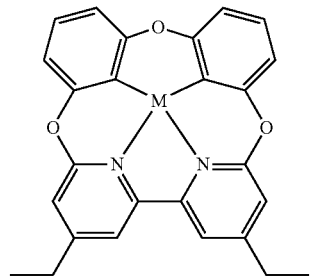

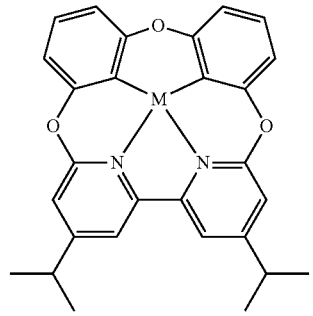

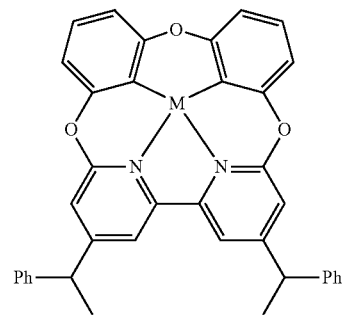

-continued
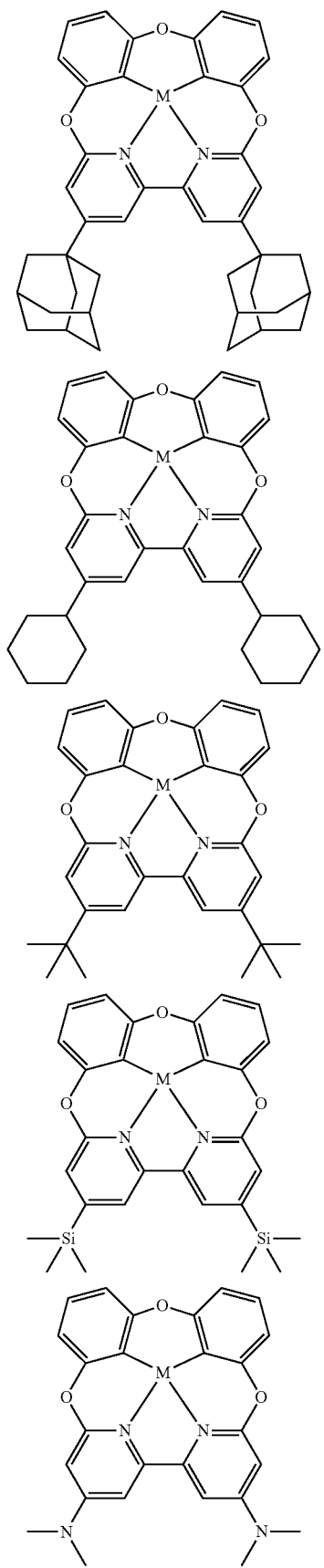
-continued
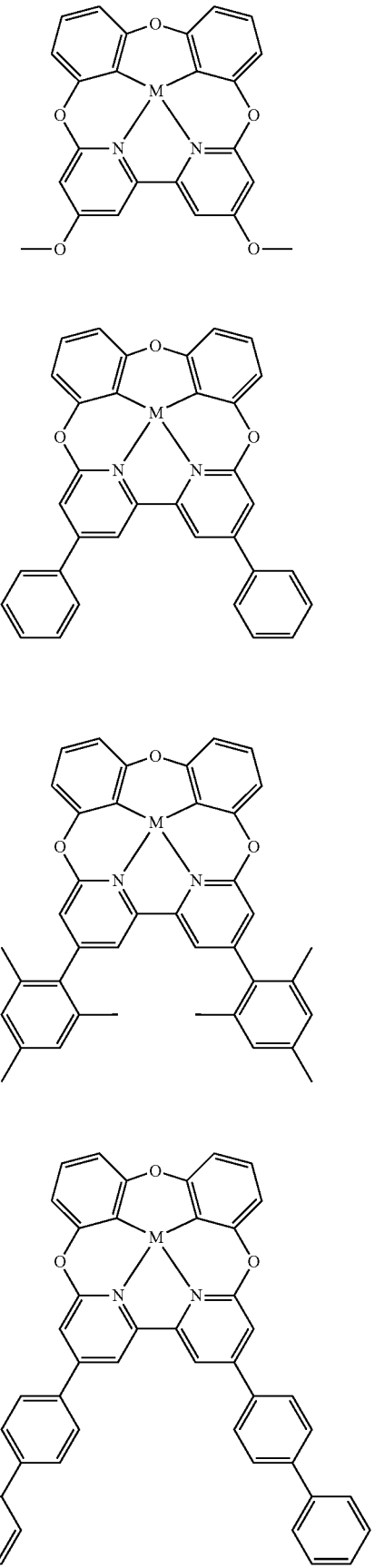

-continued
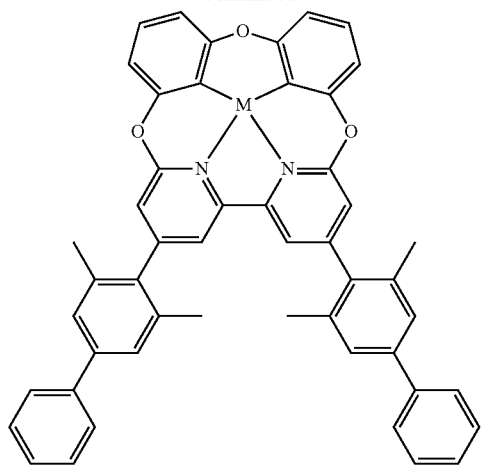
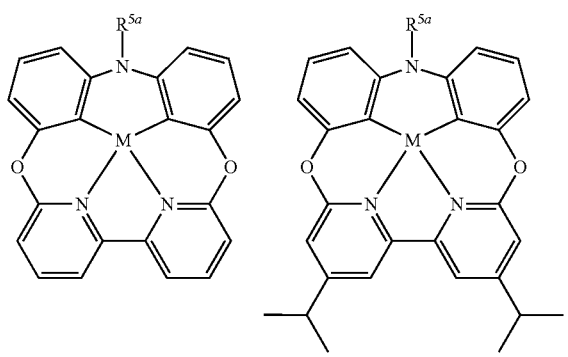
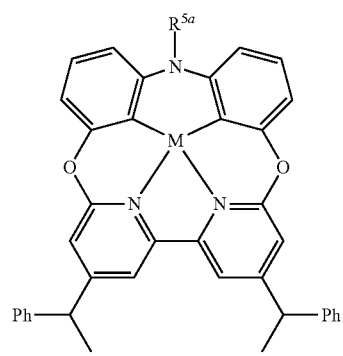
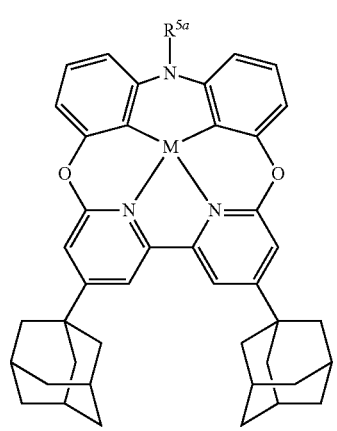
-continued
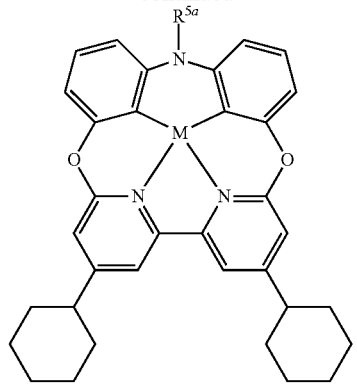
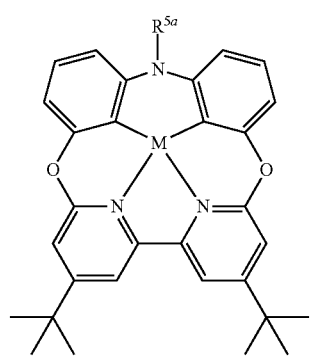
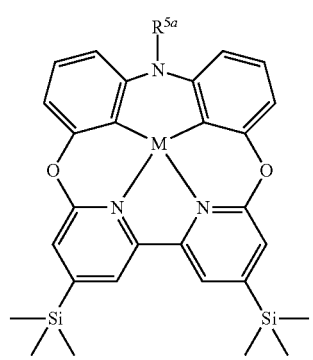
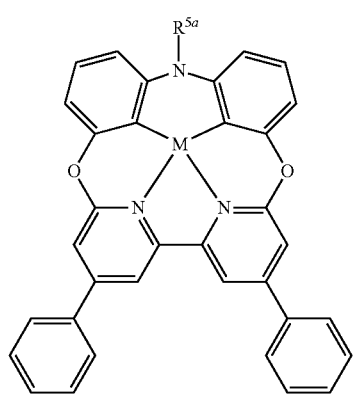

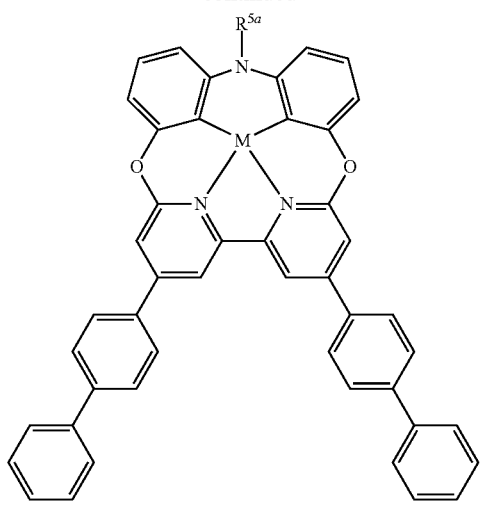
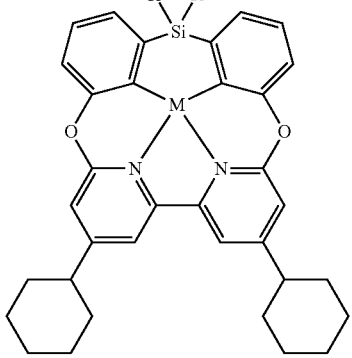
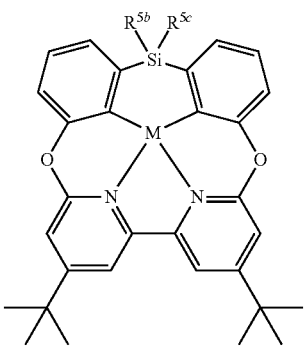
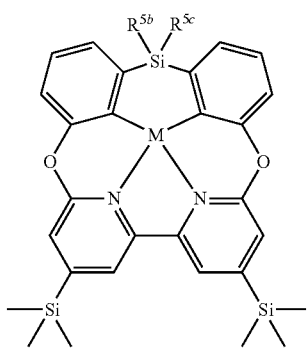
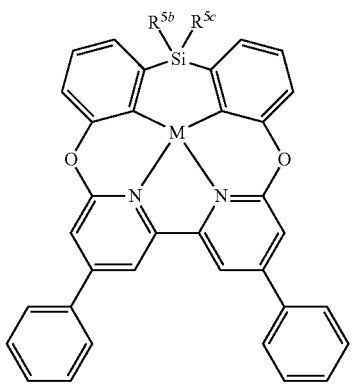

27
-continued
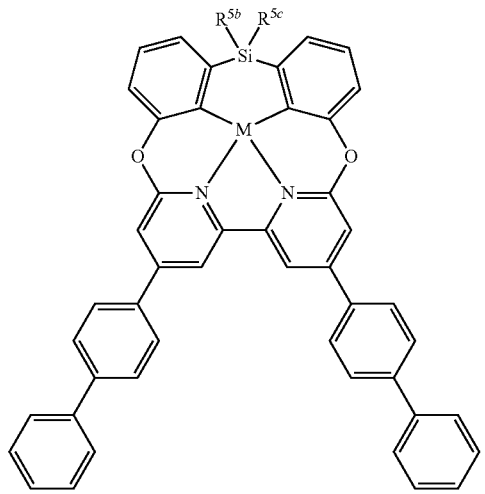
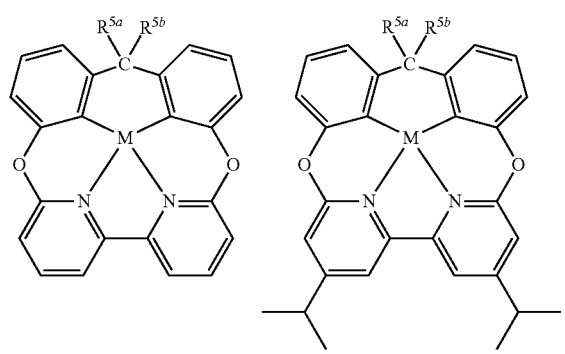
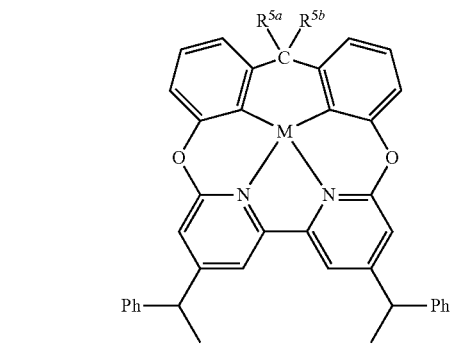
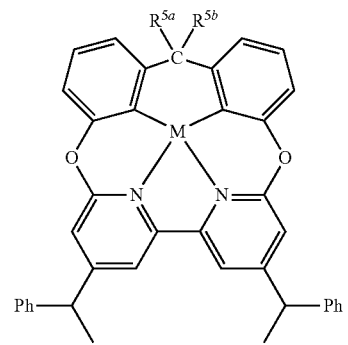
28
-continued
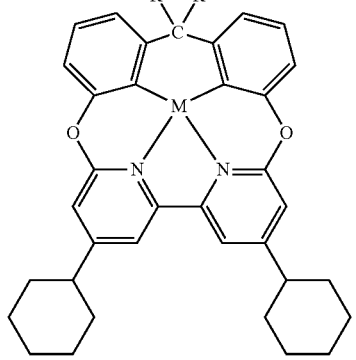
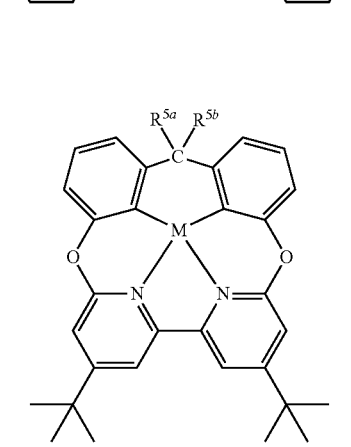
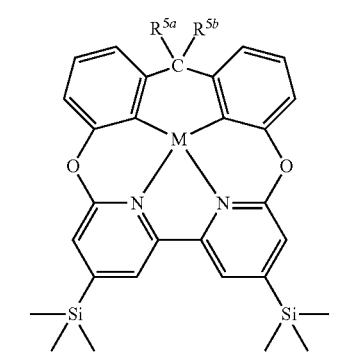
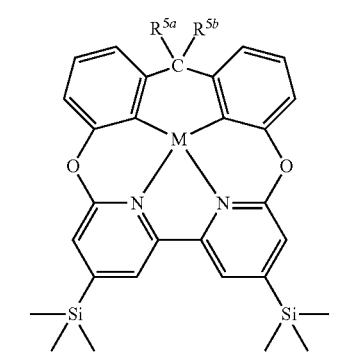
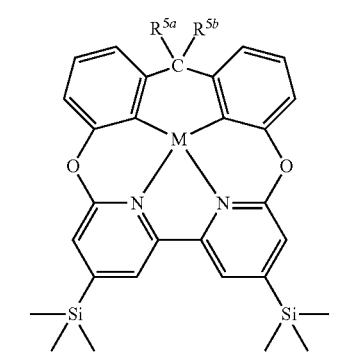

-continued
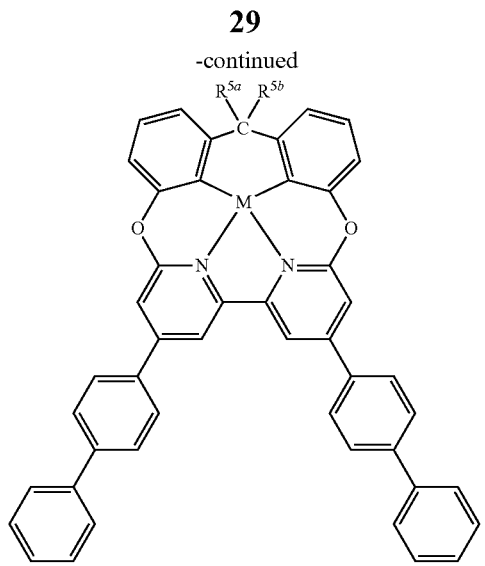
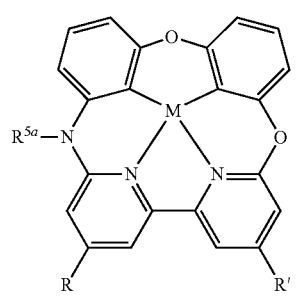
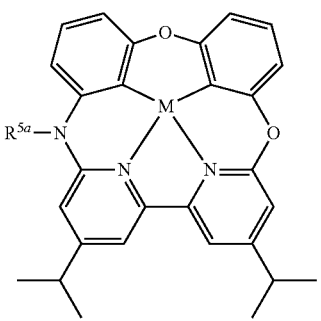
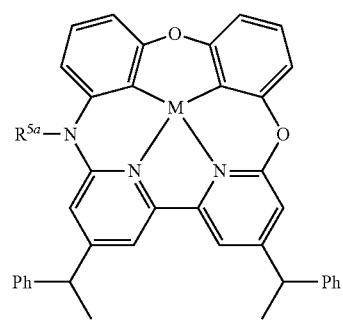
-continued
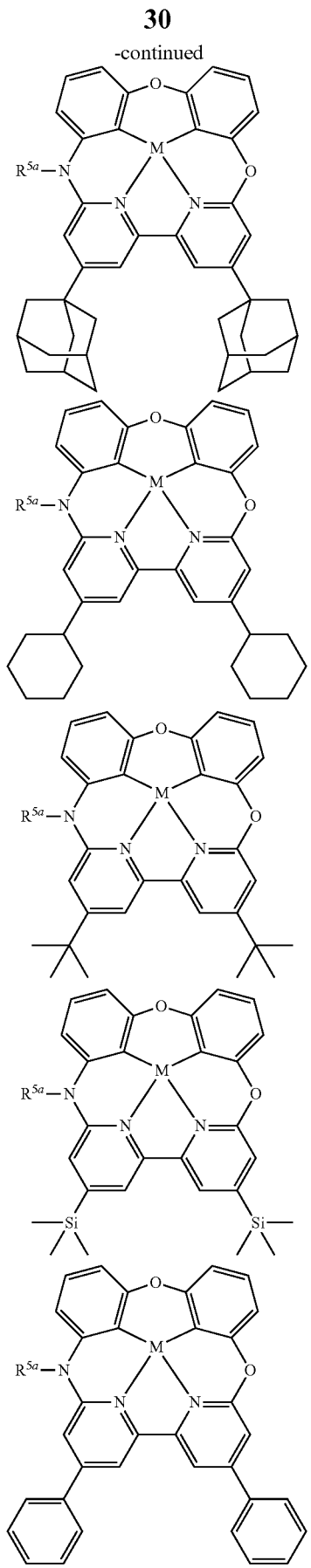

31
-continued
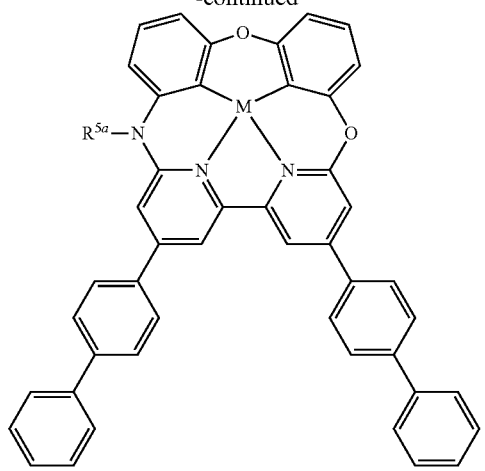
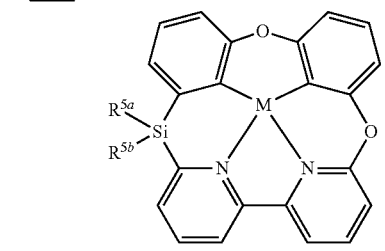
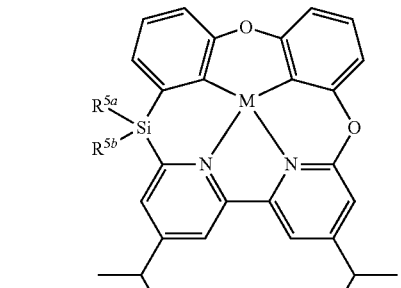
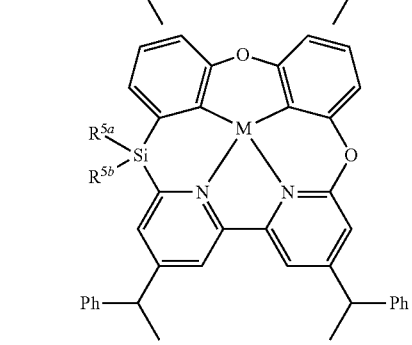
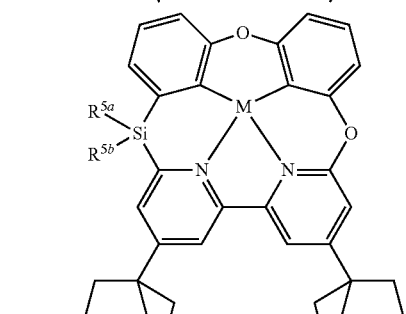
32
-continued
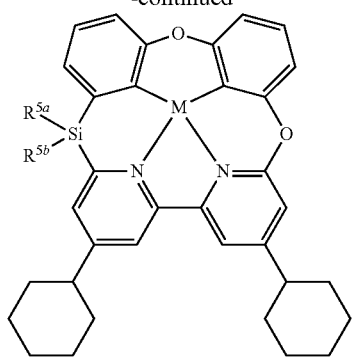
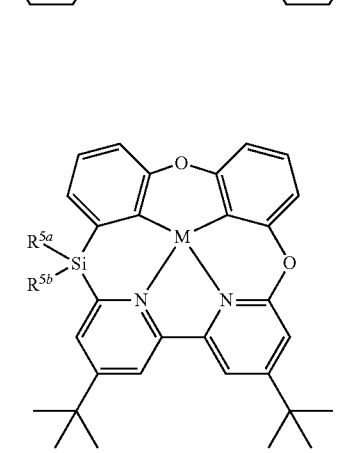
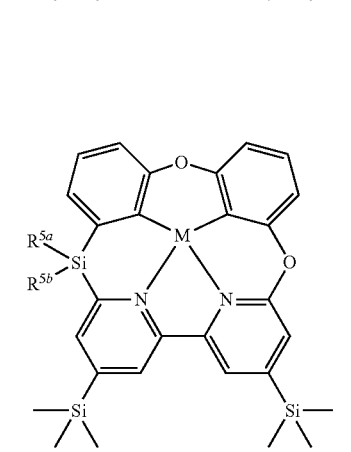
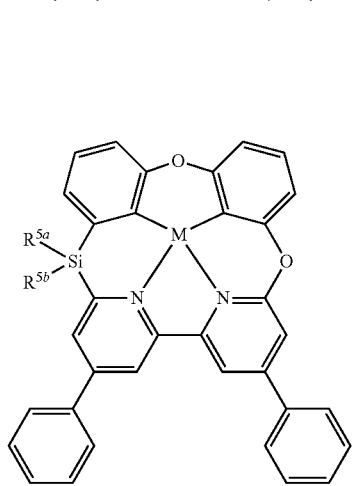

33
-continued

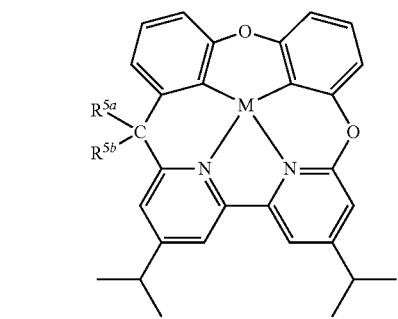
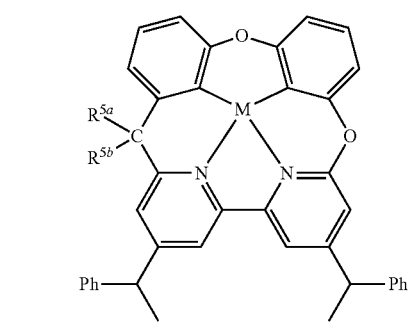
34
-continued
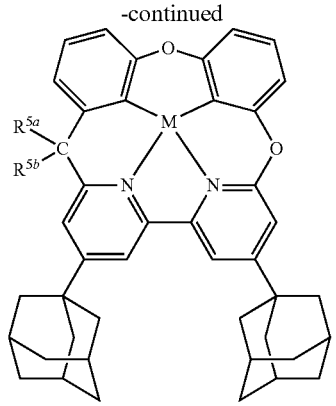
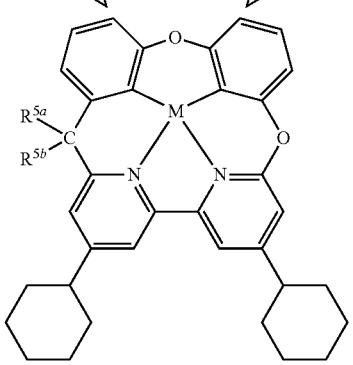
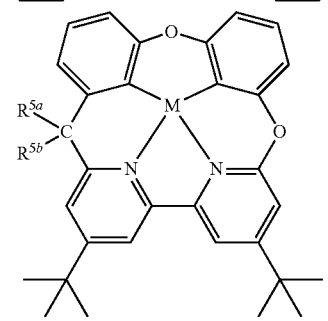
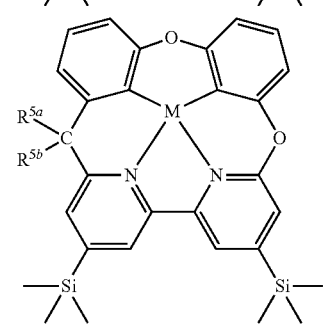
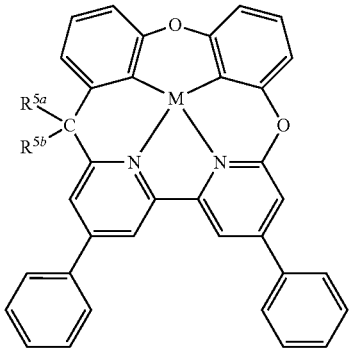

-continued
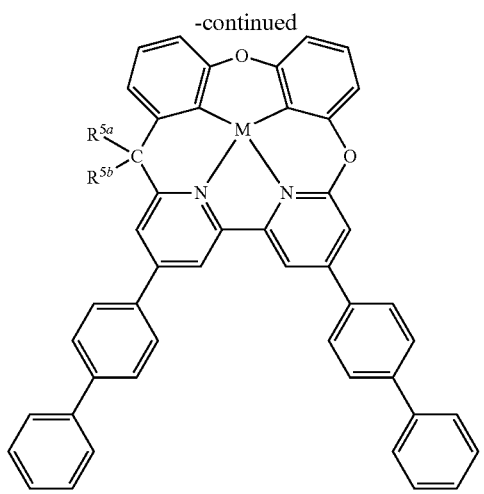
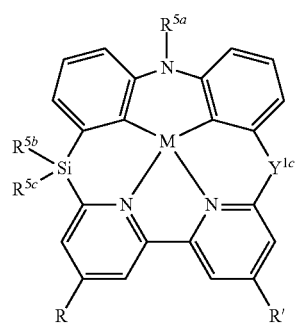
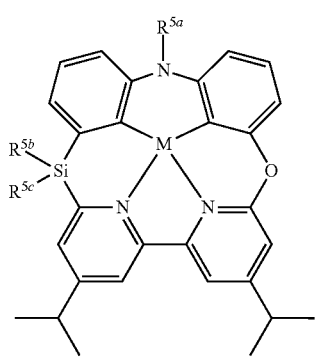
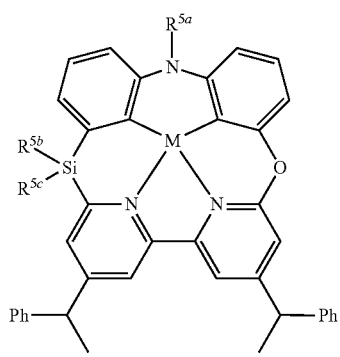
-continued
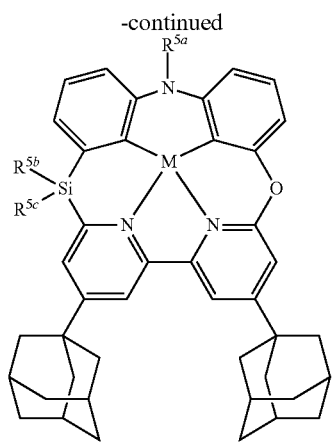
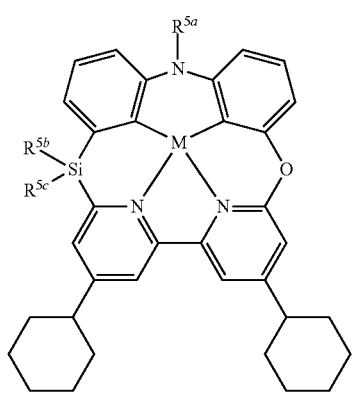
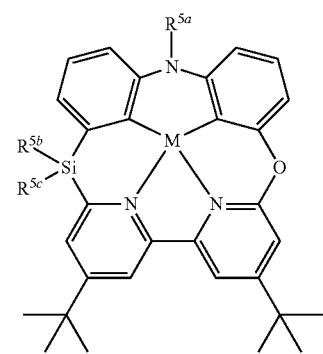
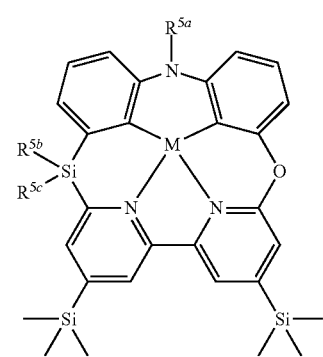

-continued
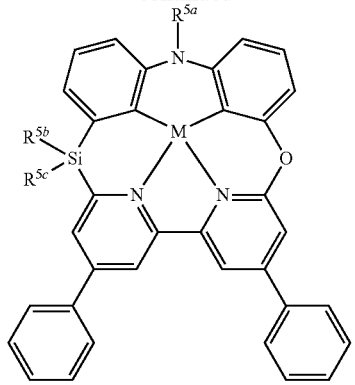
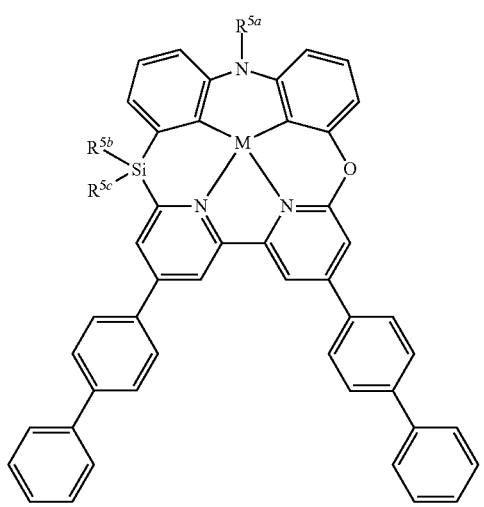
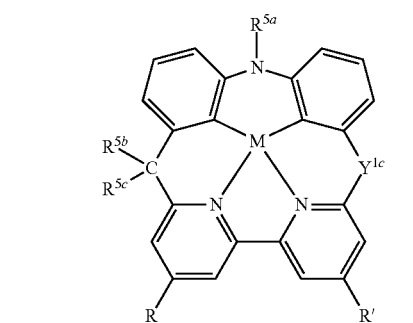
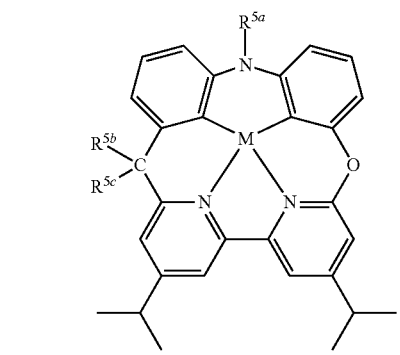
-continued
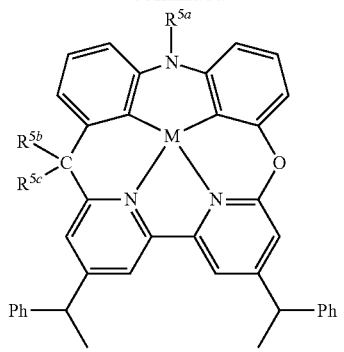
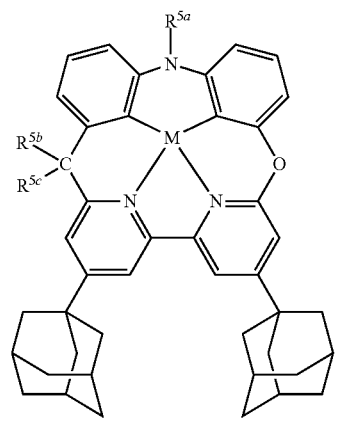
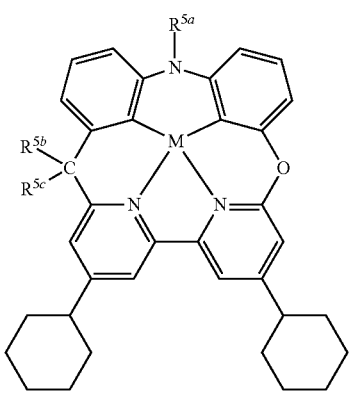
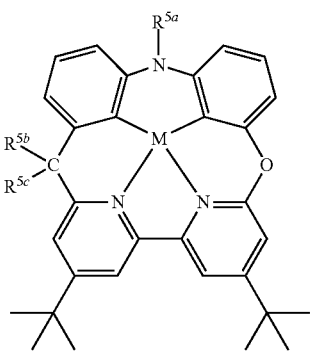

-continued
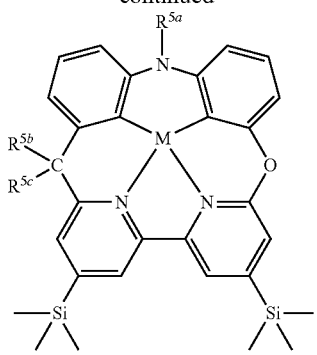
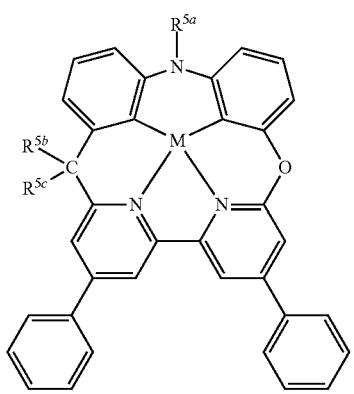
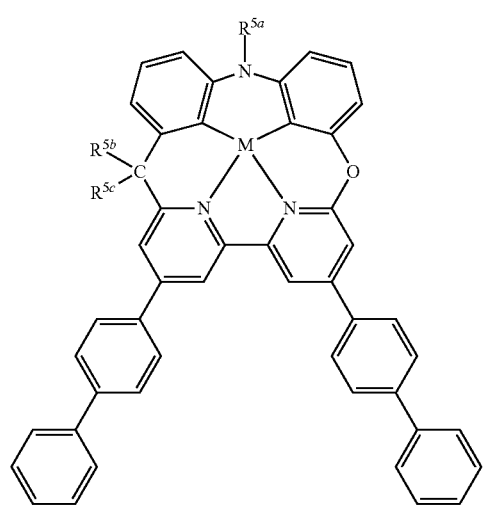
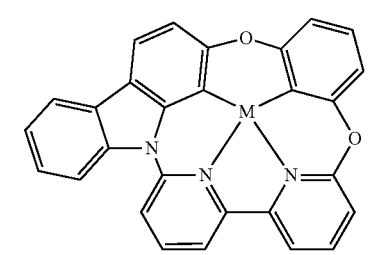
-continued
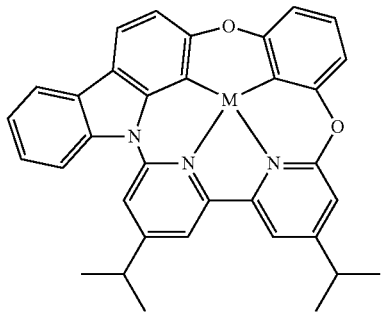
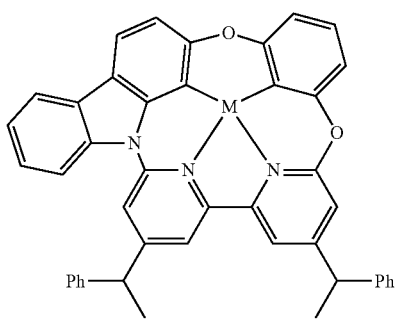
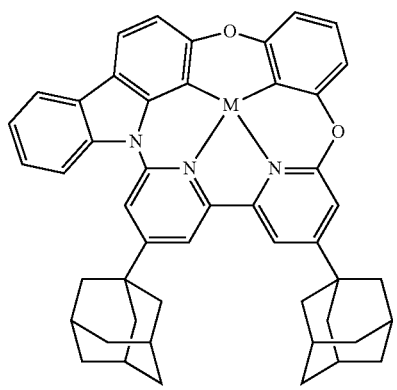
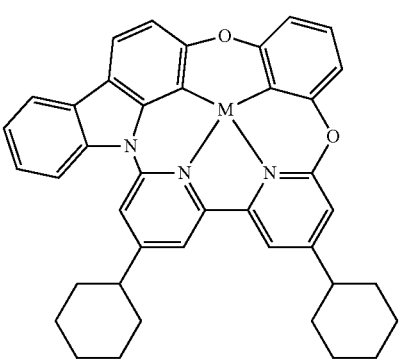
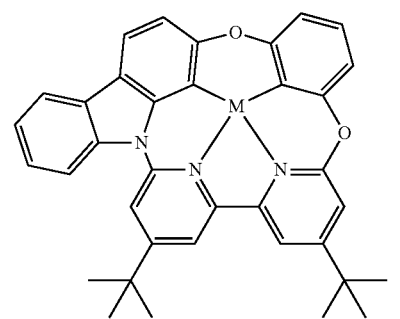

41
-continued
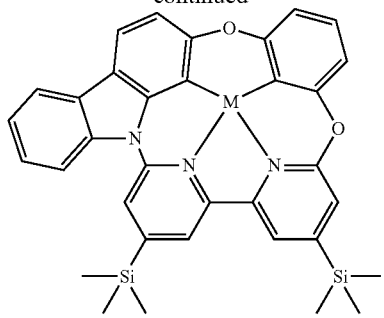
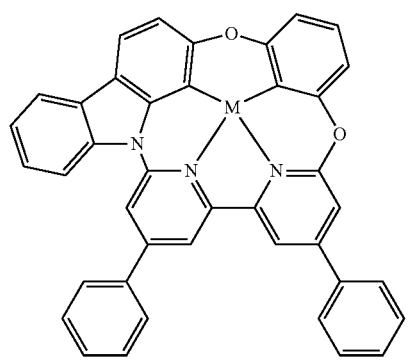
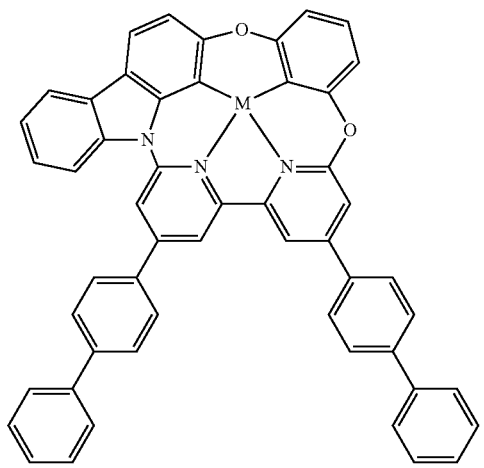
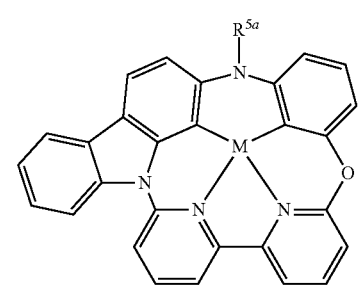
42
-continued
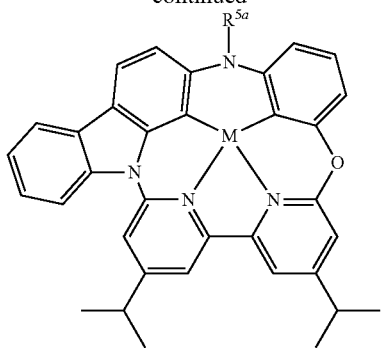
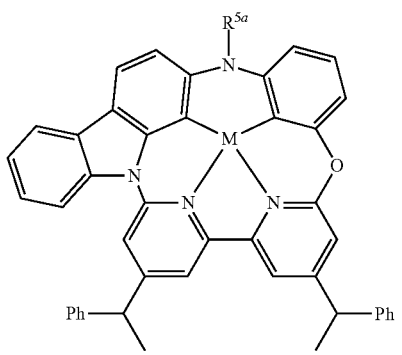
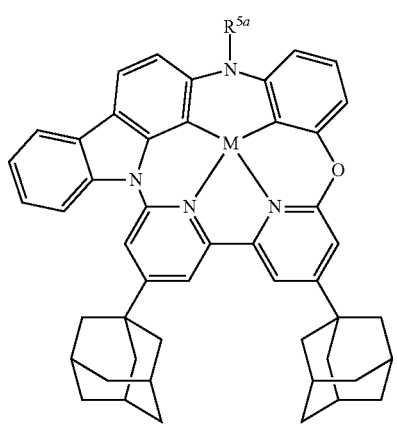
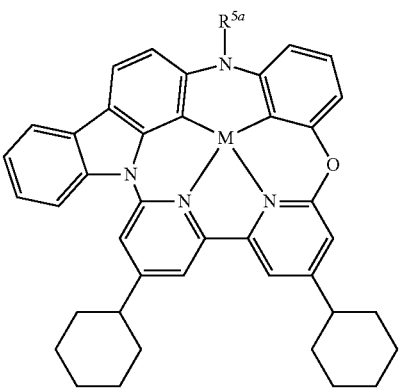

-continued
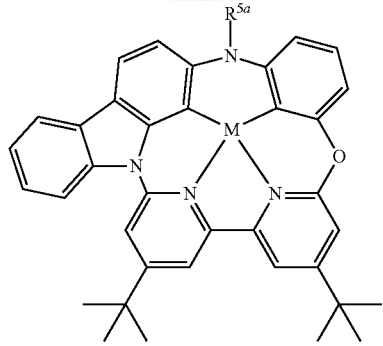
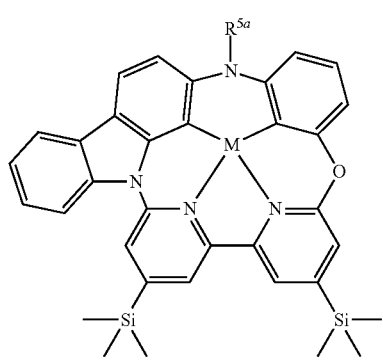
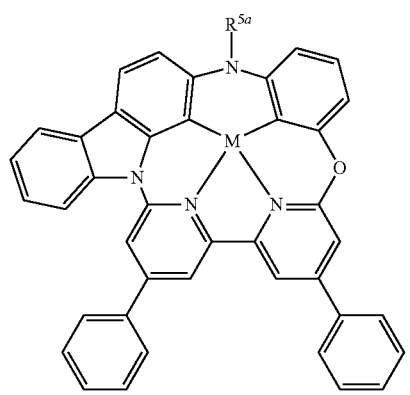
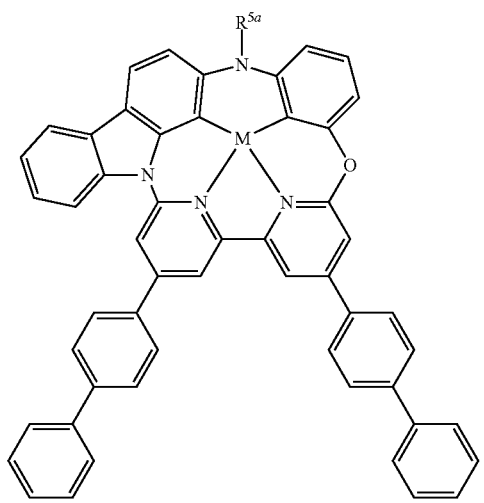
-continued
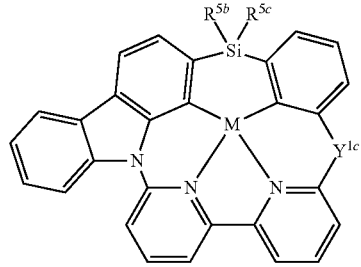
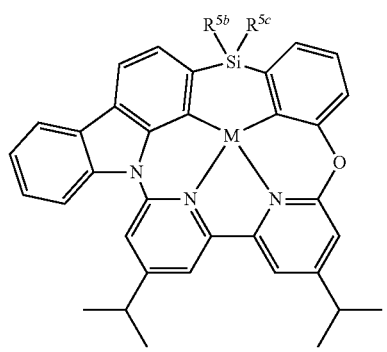
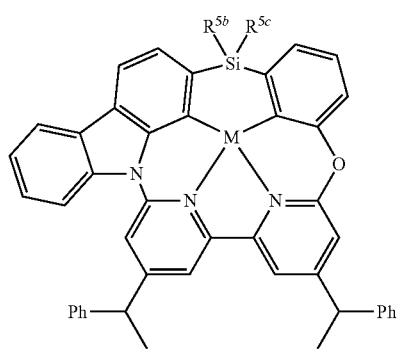
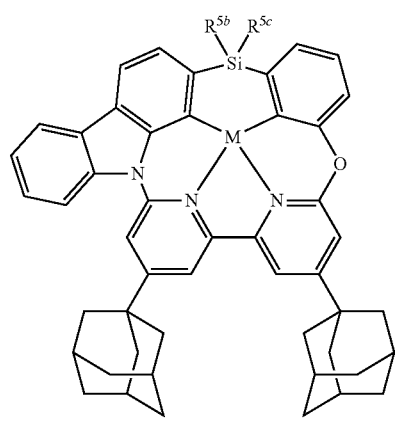

-continued
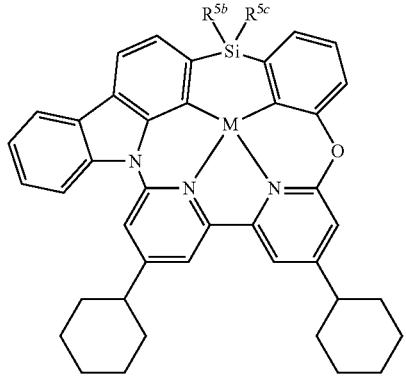
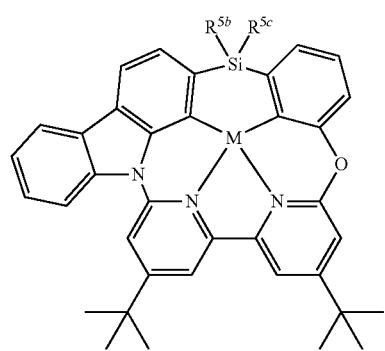
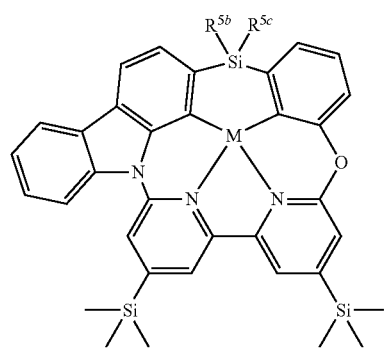
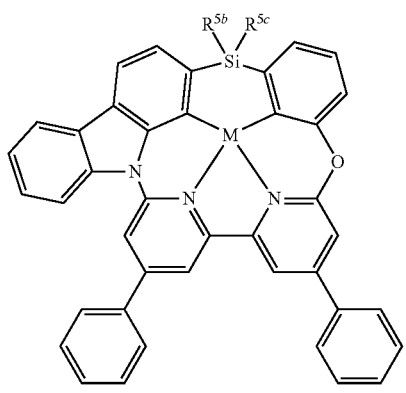
-continued
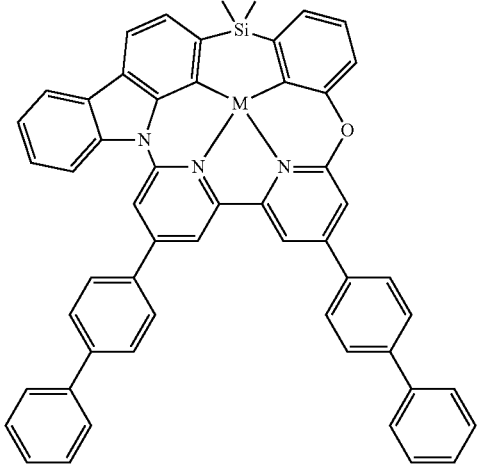
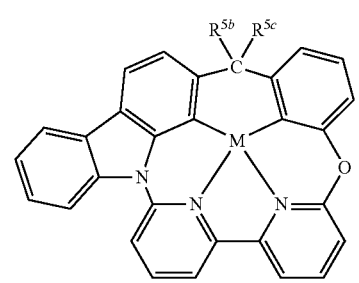
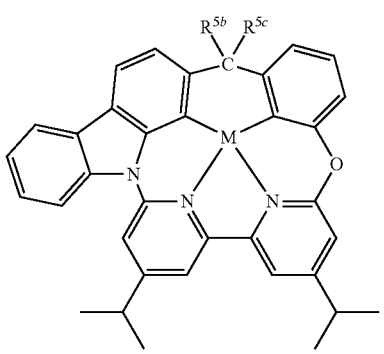
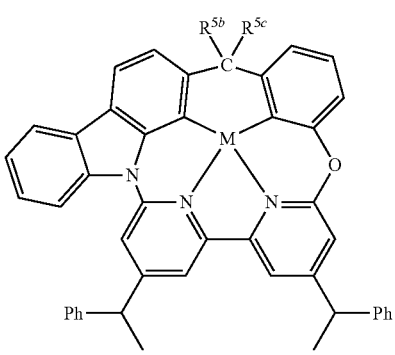

-continued
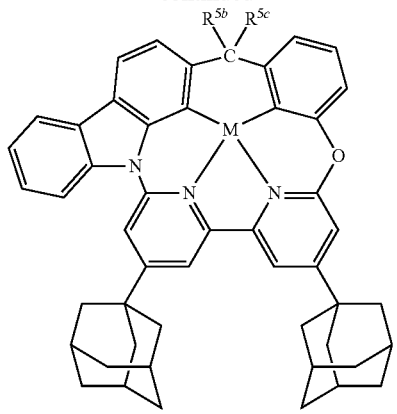
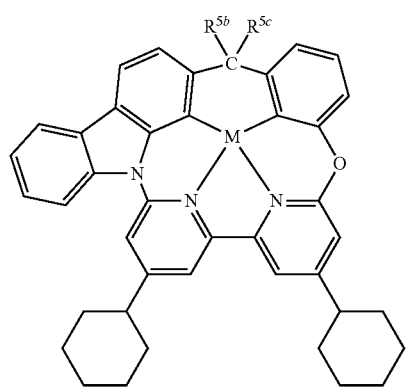
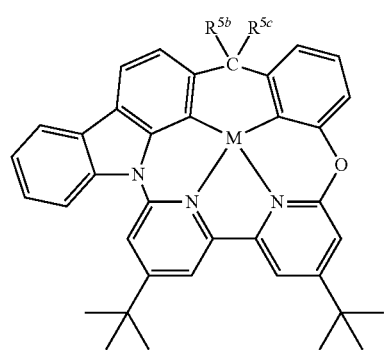
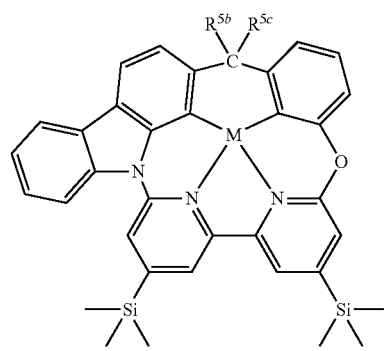
-continued
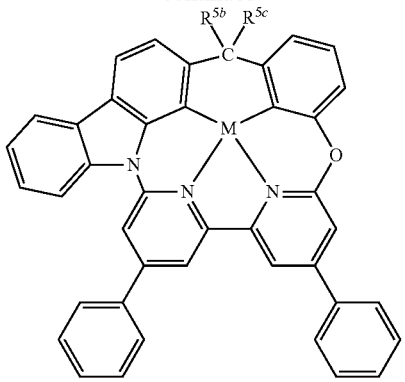
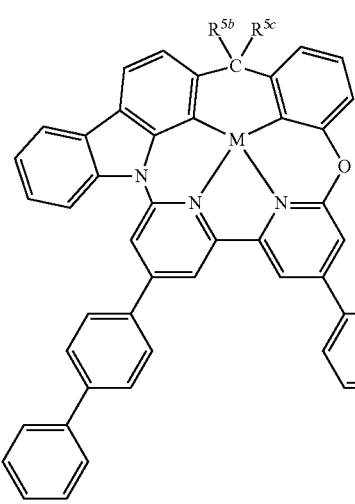
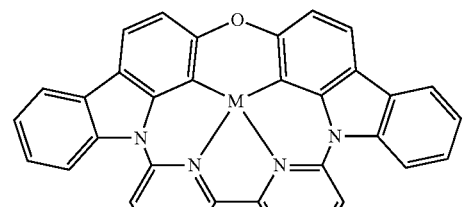
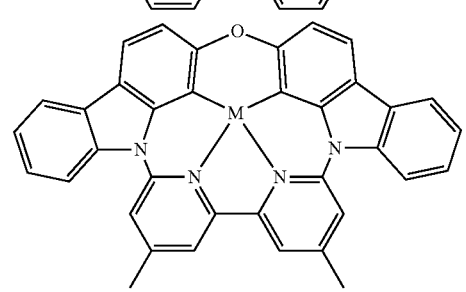
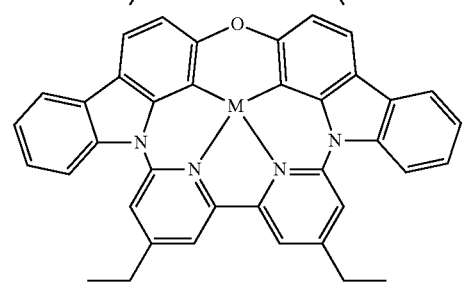

49
-continued
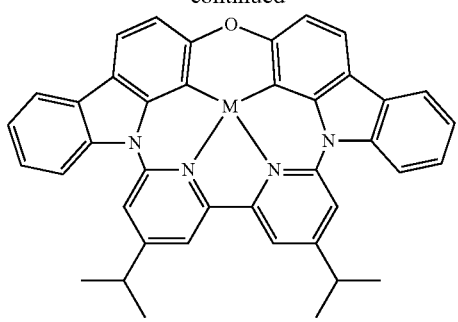
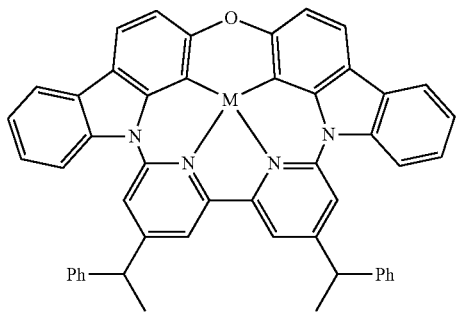
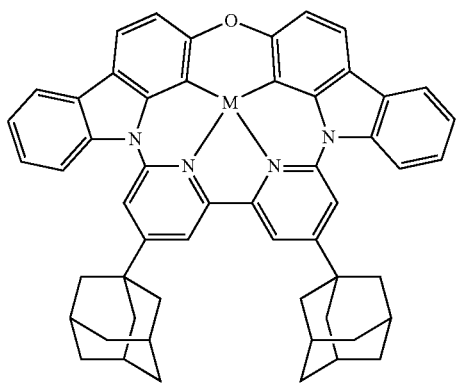
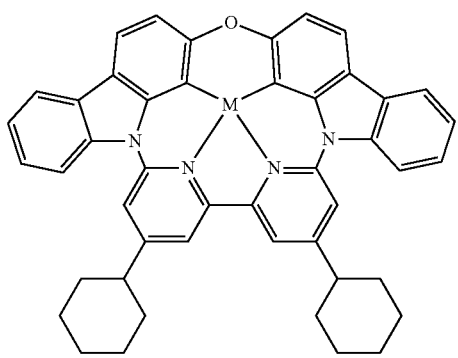
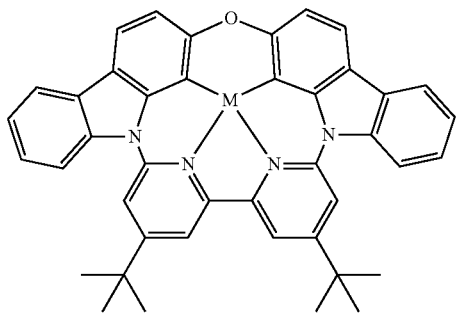
50
-continued
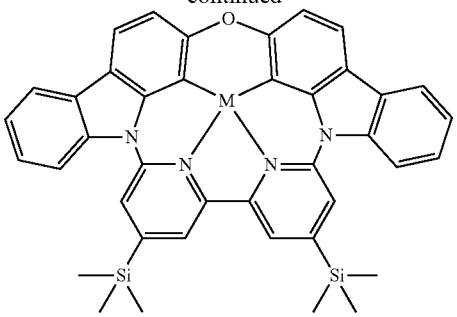
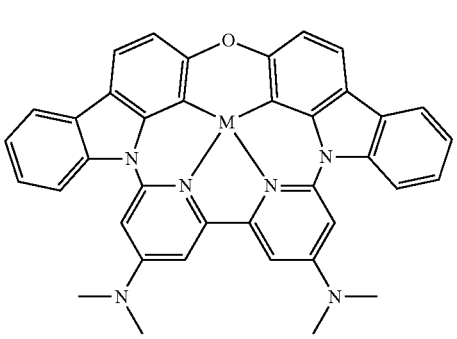
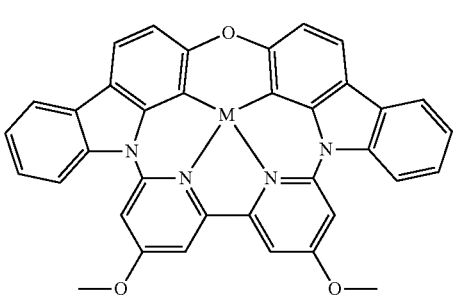
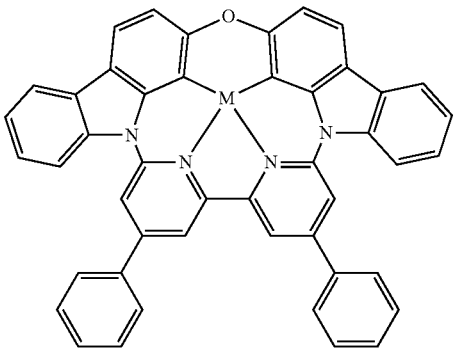
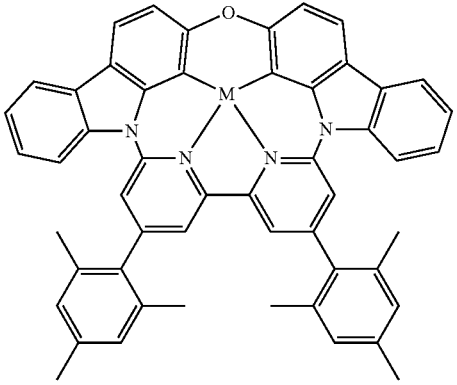

51
-continued
52
-continued
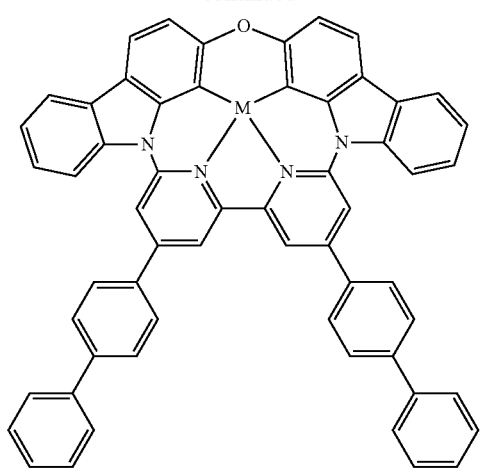
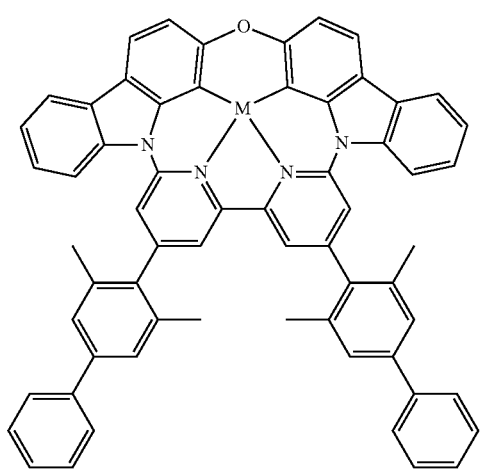
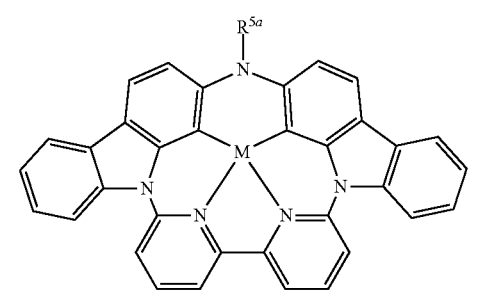
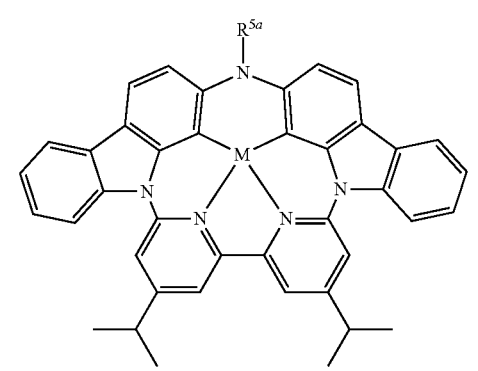
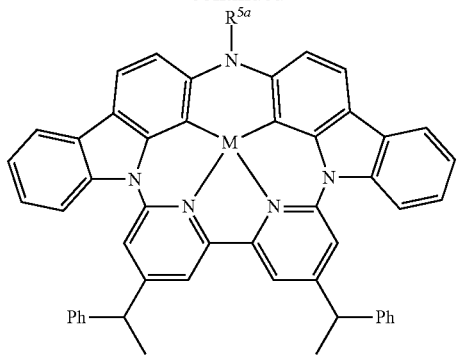
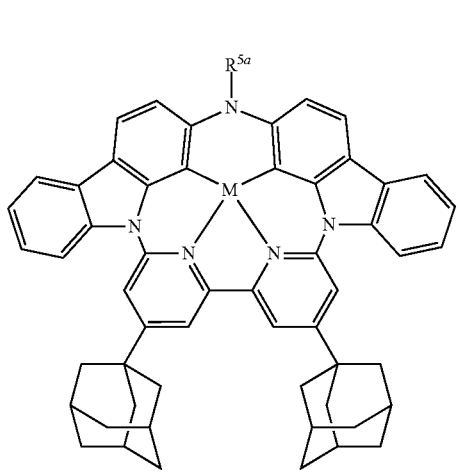
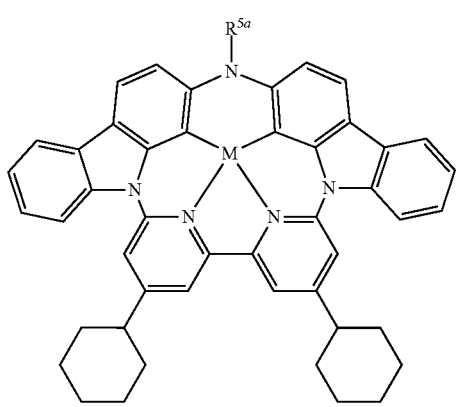
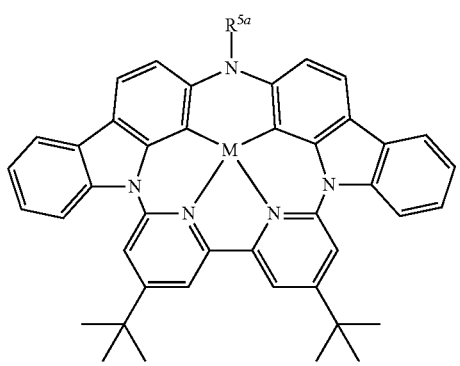

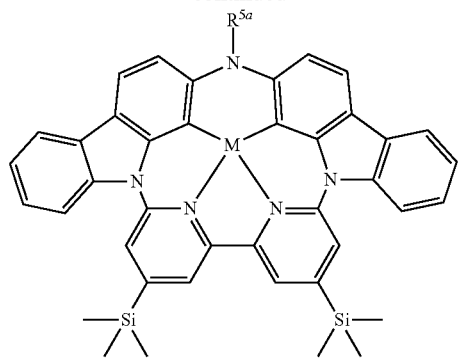
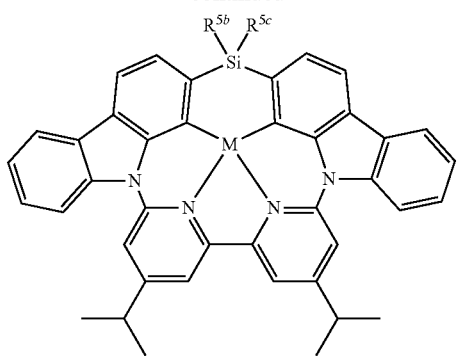
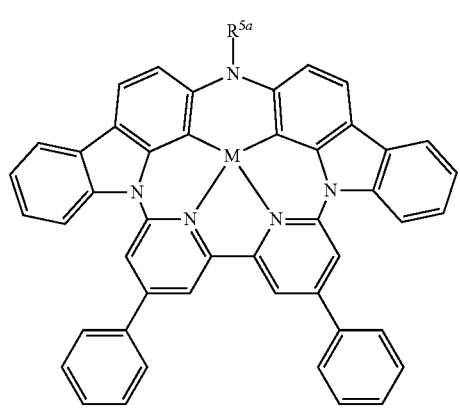
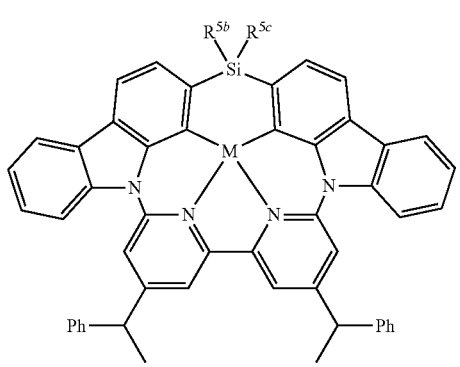
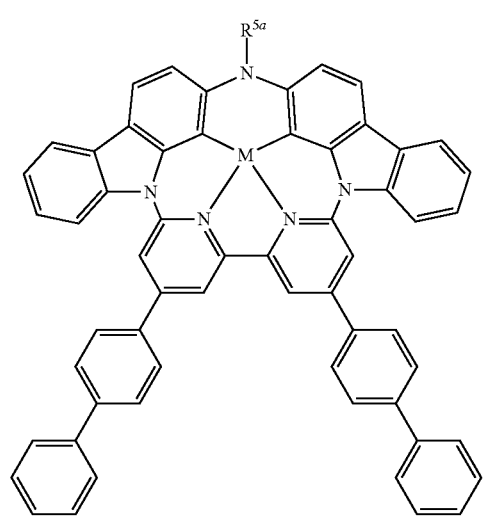
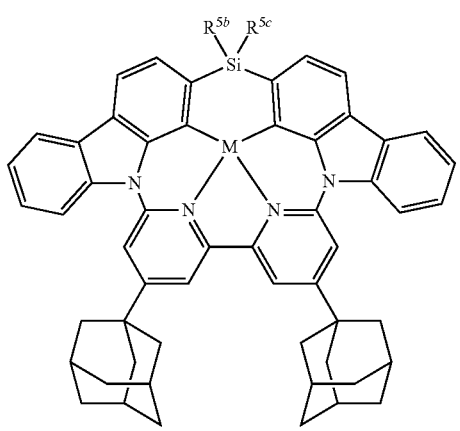
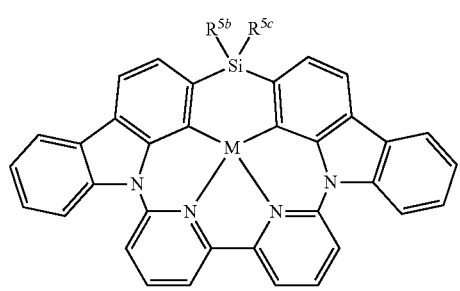
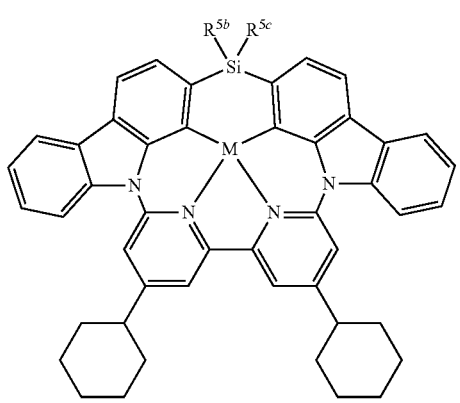

-continued
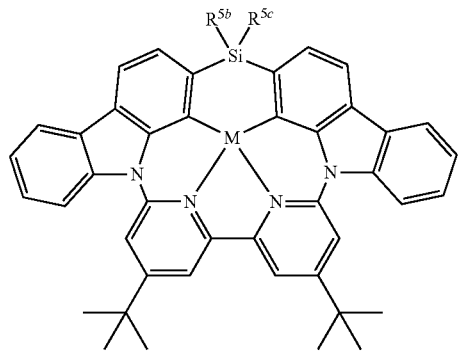
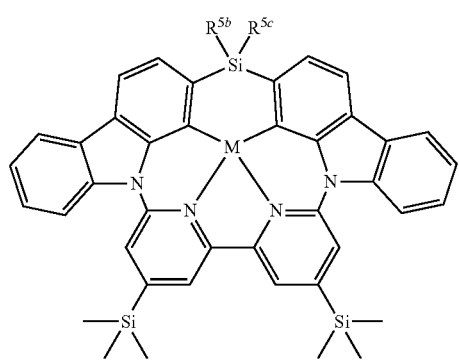
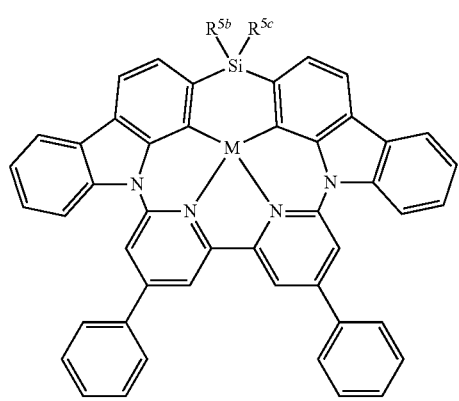
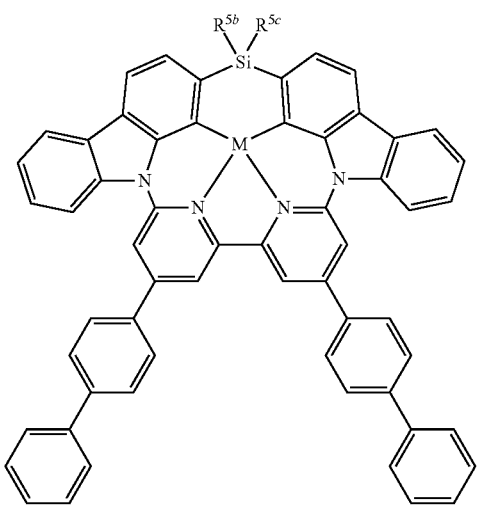
-continued
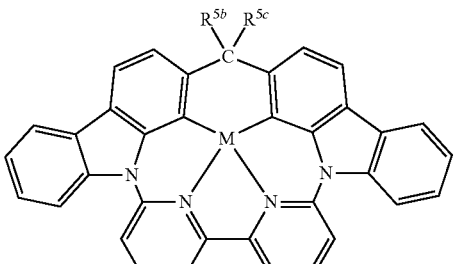
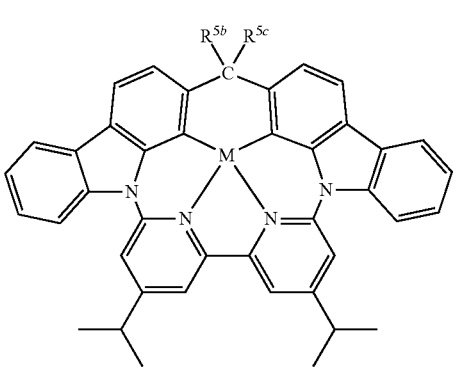
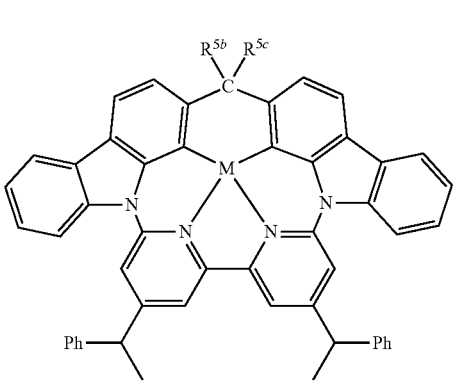
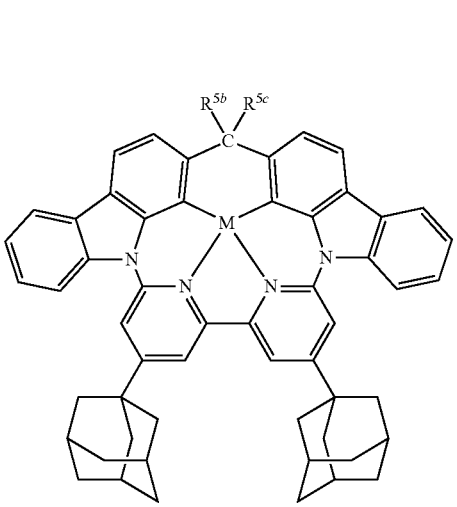

57
-continued
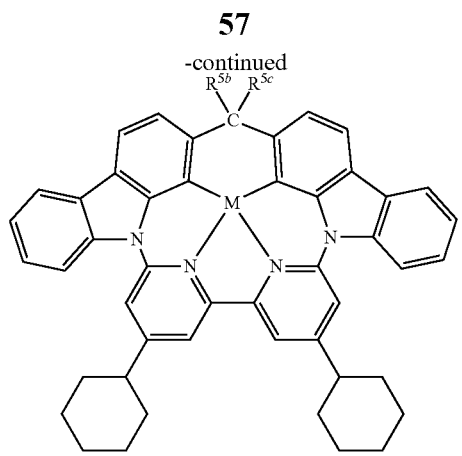
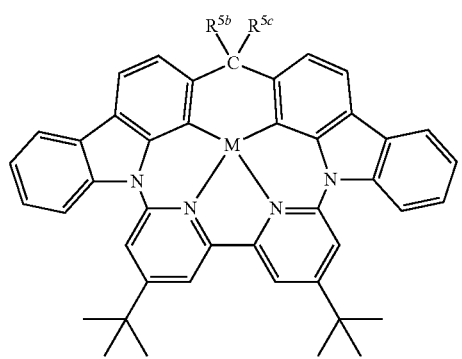
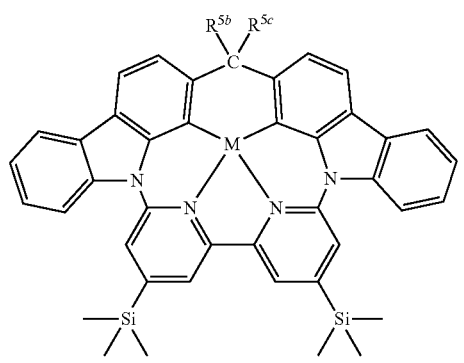
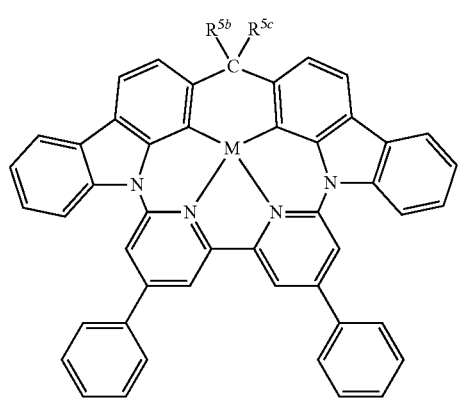
58
-continued
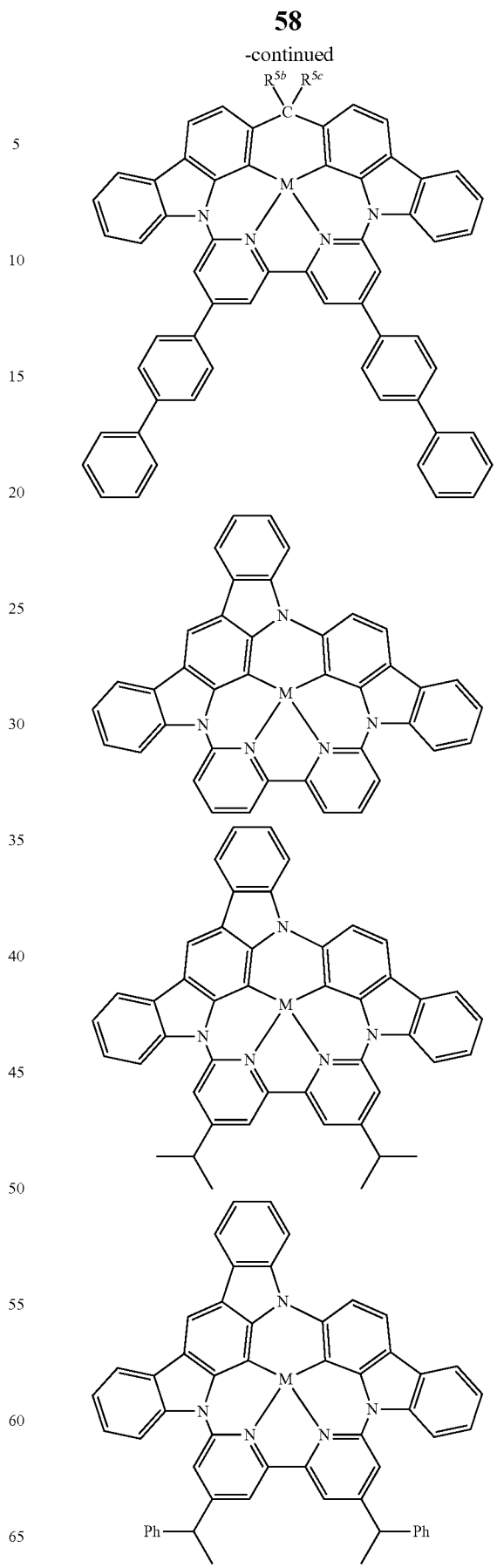

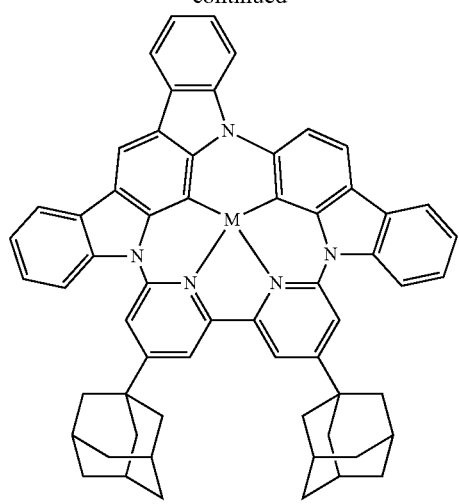
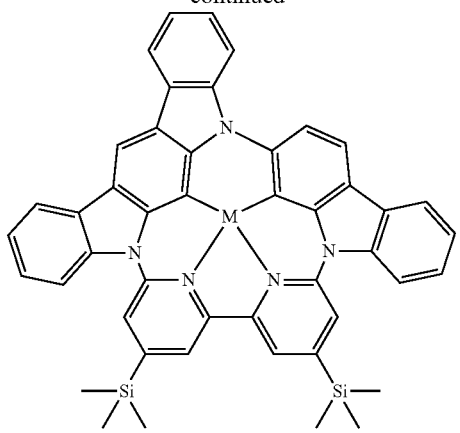
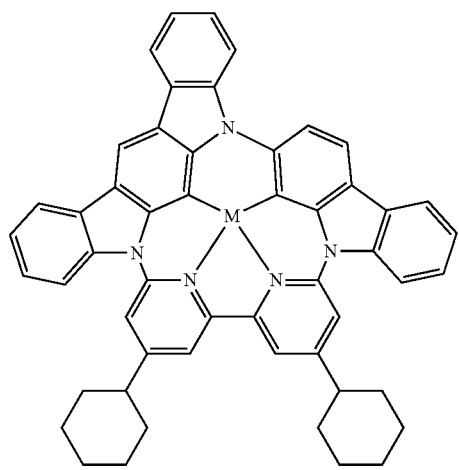
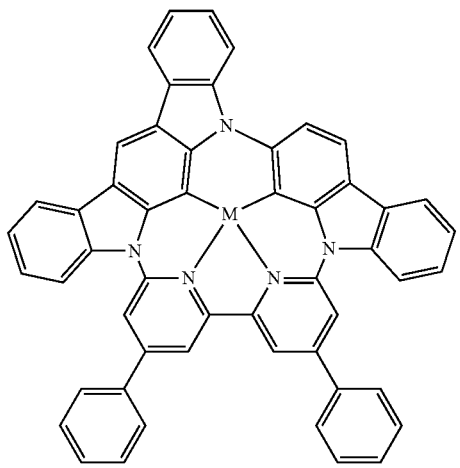
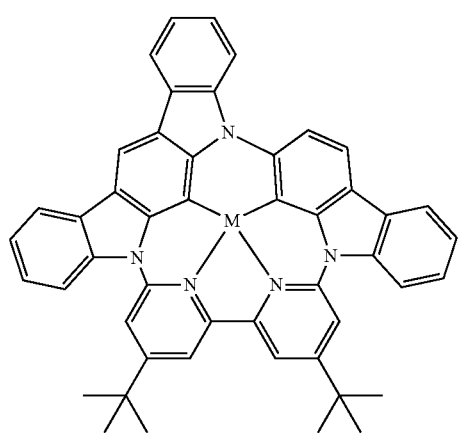
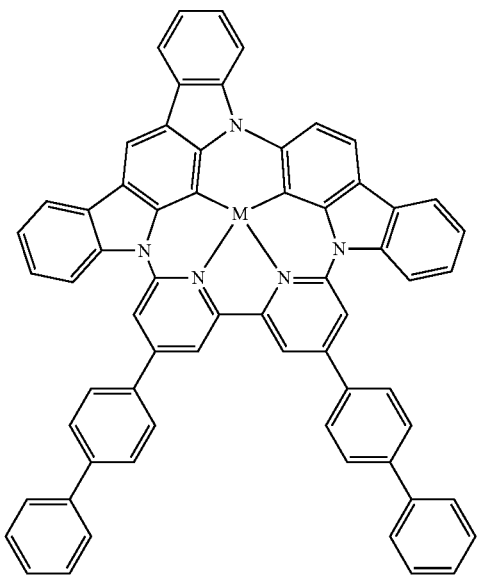

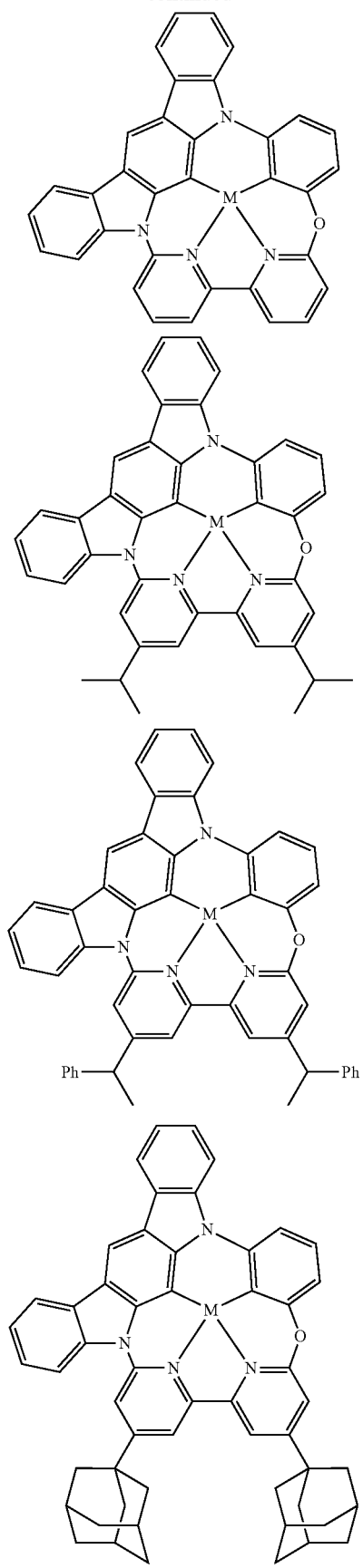

63
-continued
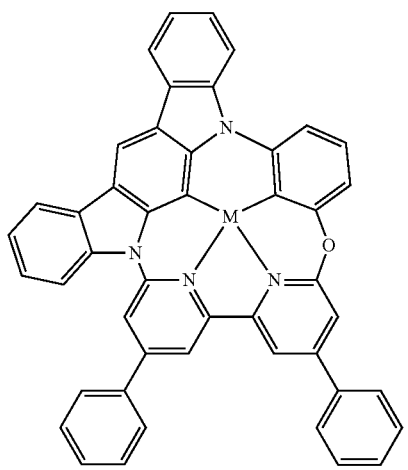
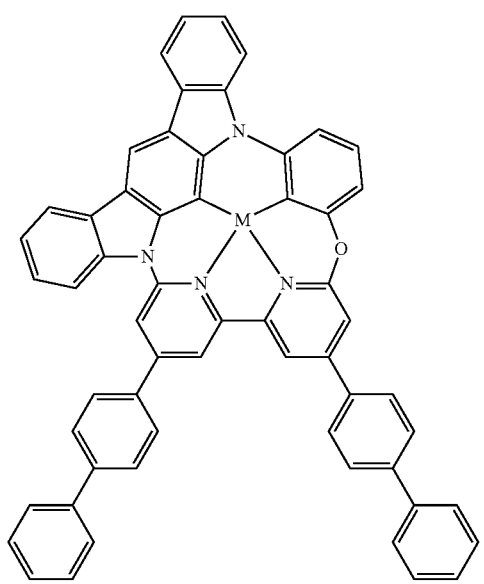
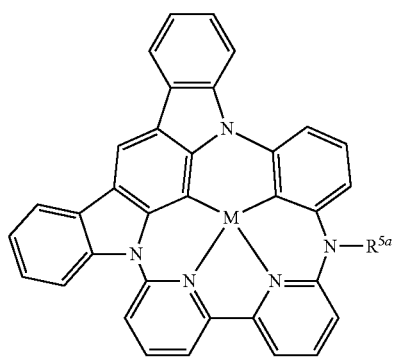
64
-continued
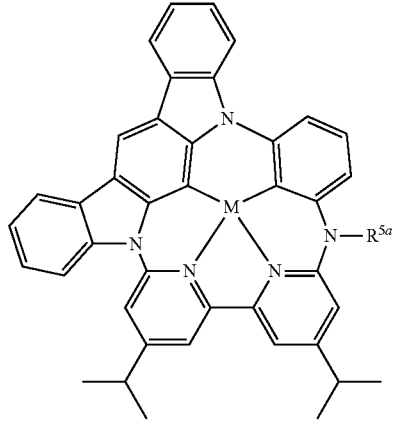
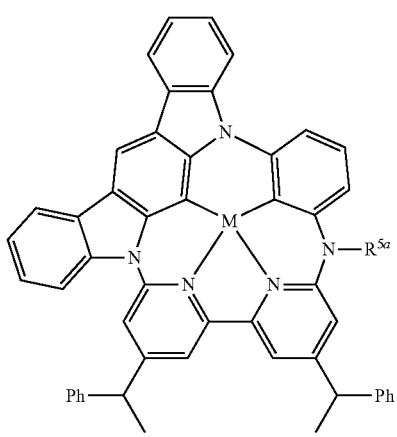
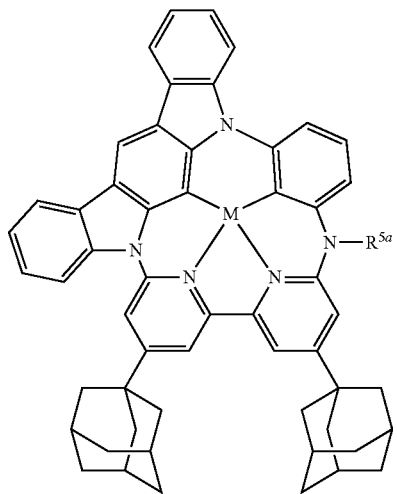

65
-continued
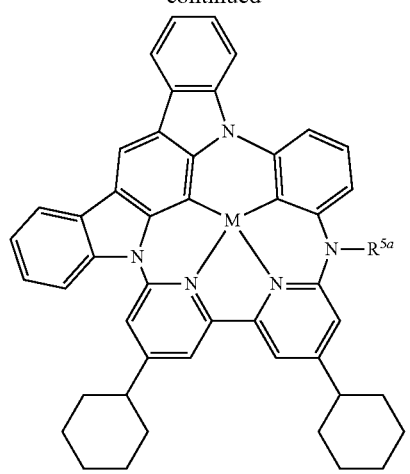
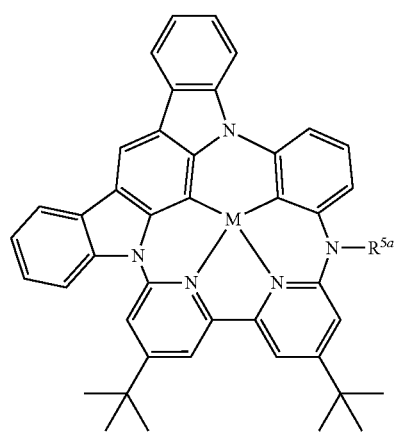
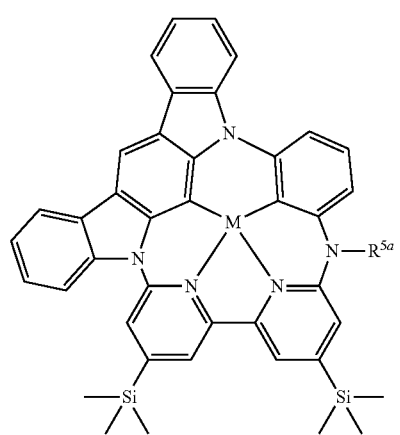
66
-continued
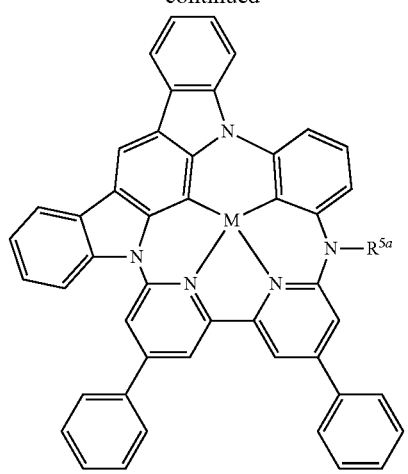
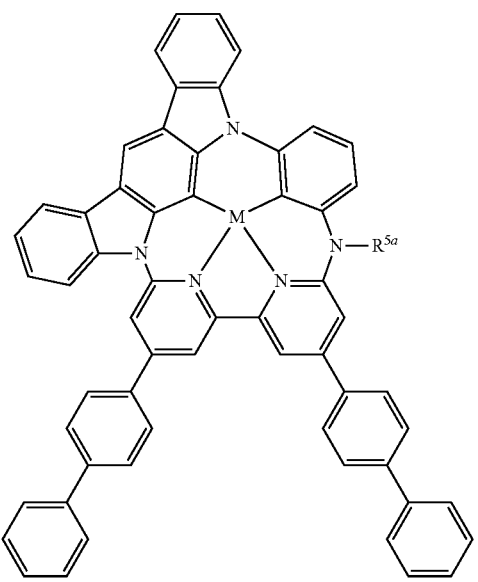
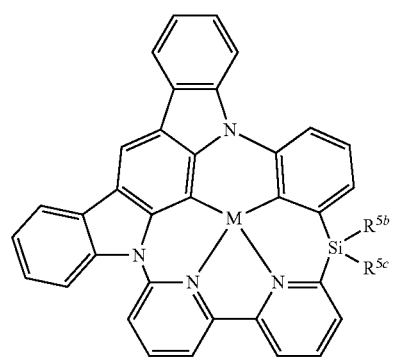

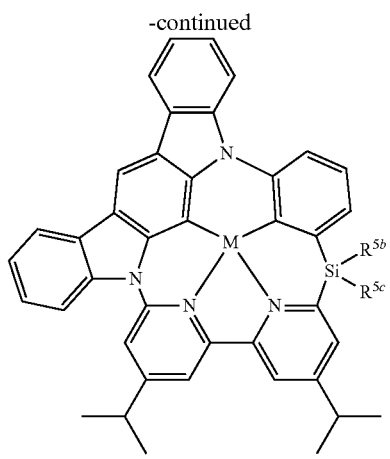
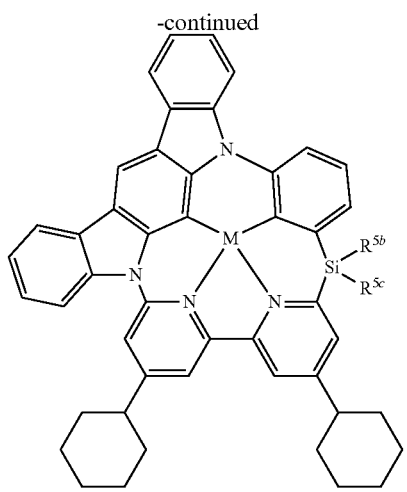
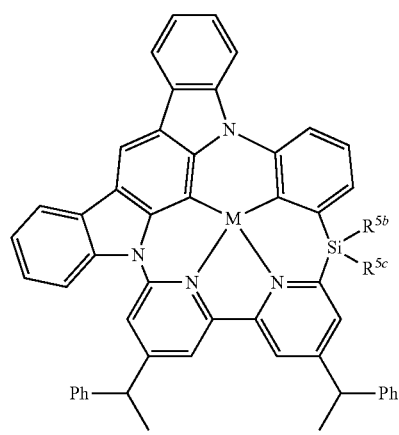
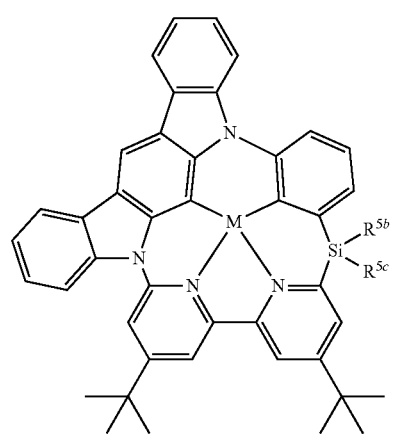
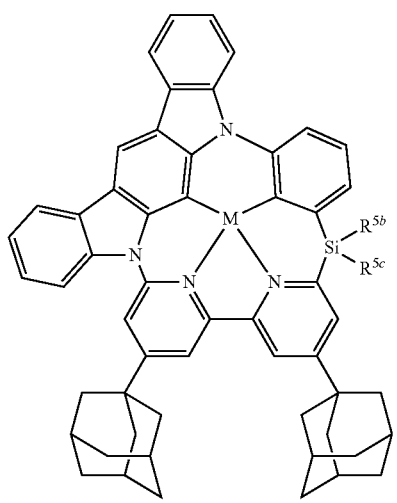
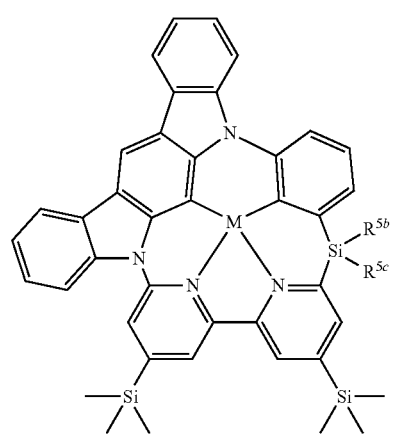

69
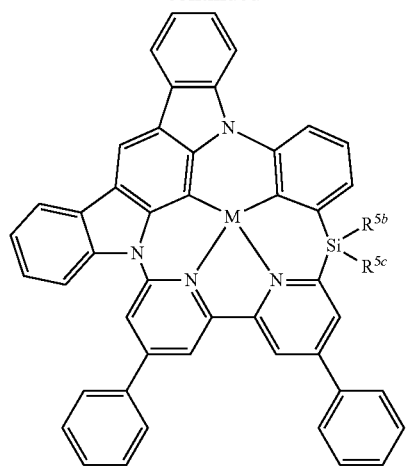
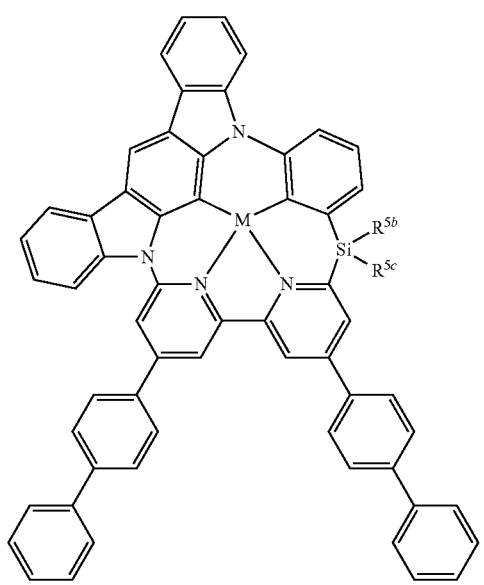
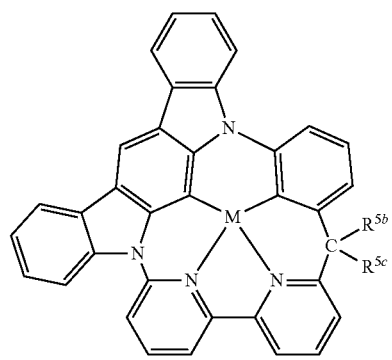
70
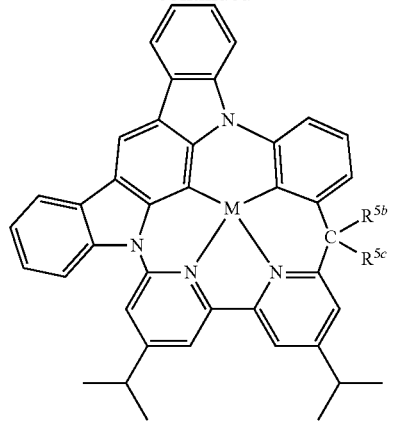
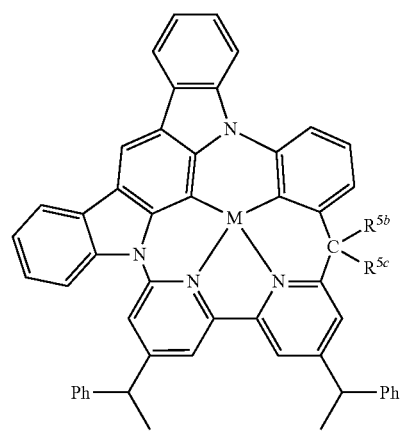
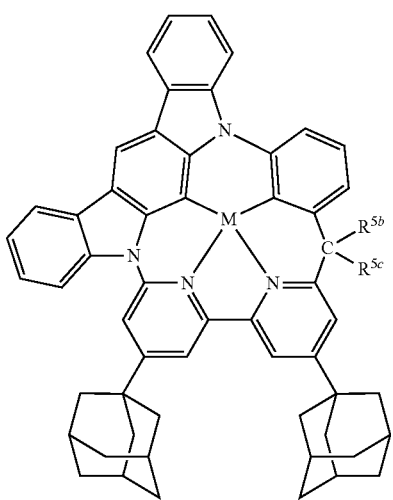

71
-continued
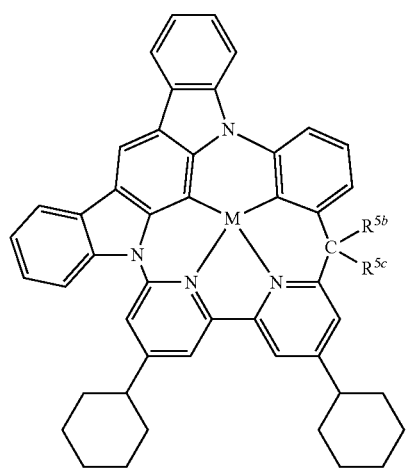
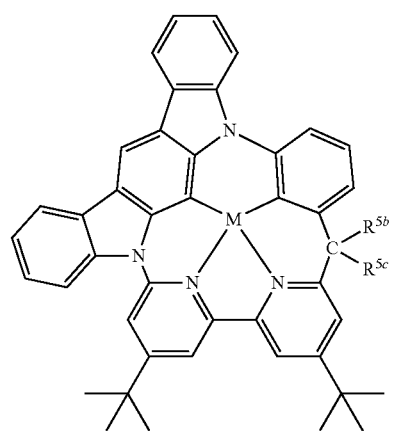
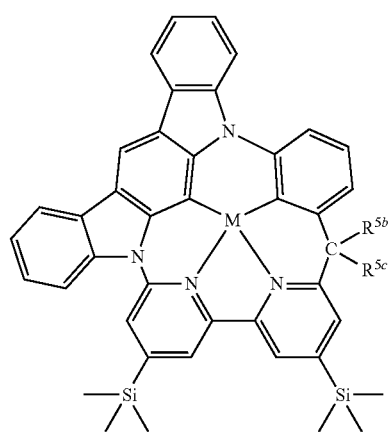
72
-continued
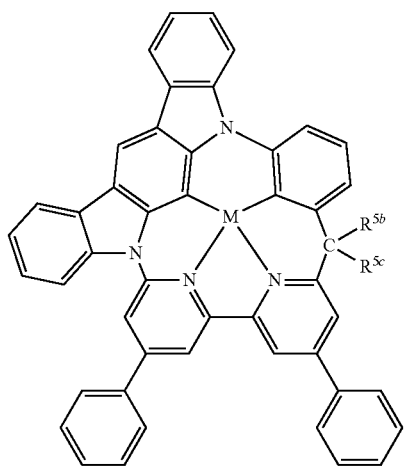
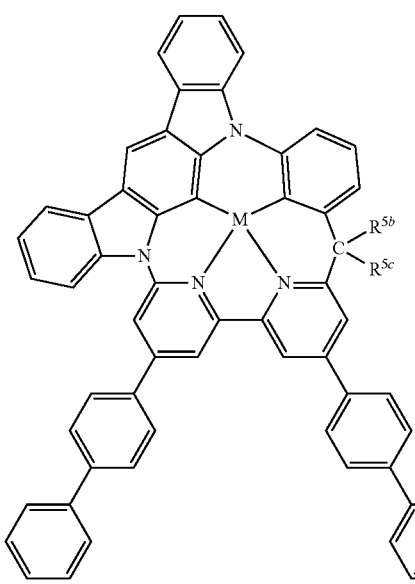
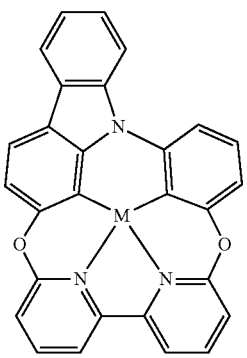

73
-continued
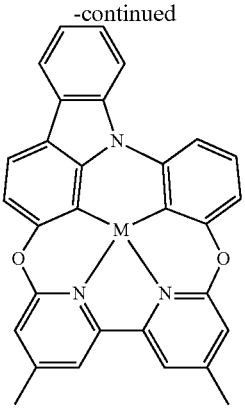
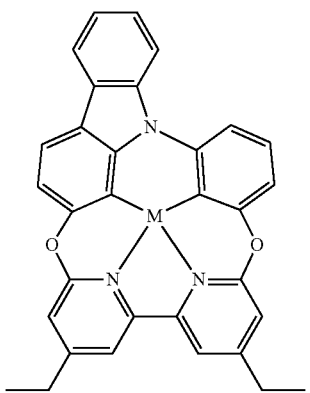
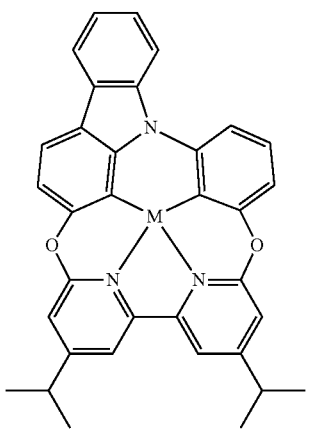
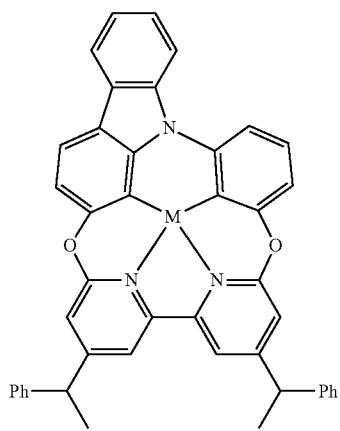
74
-continued
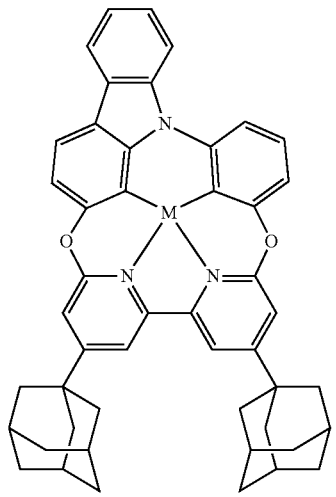
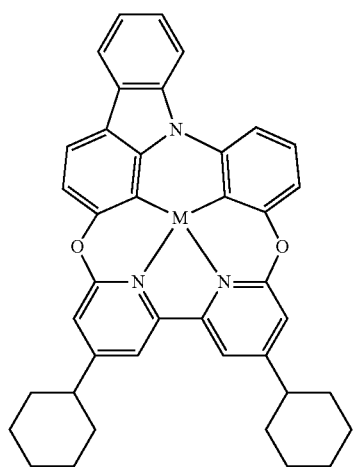
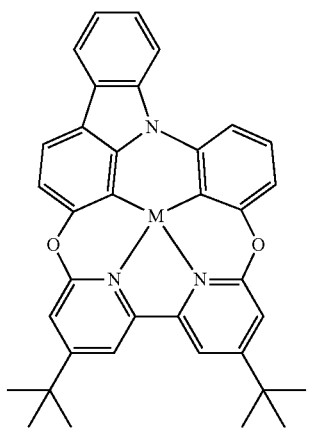

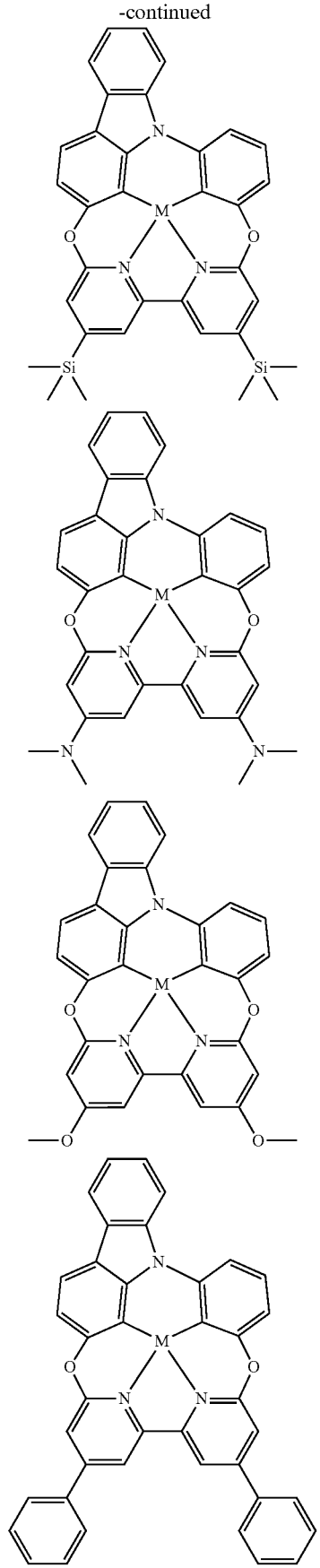
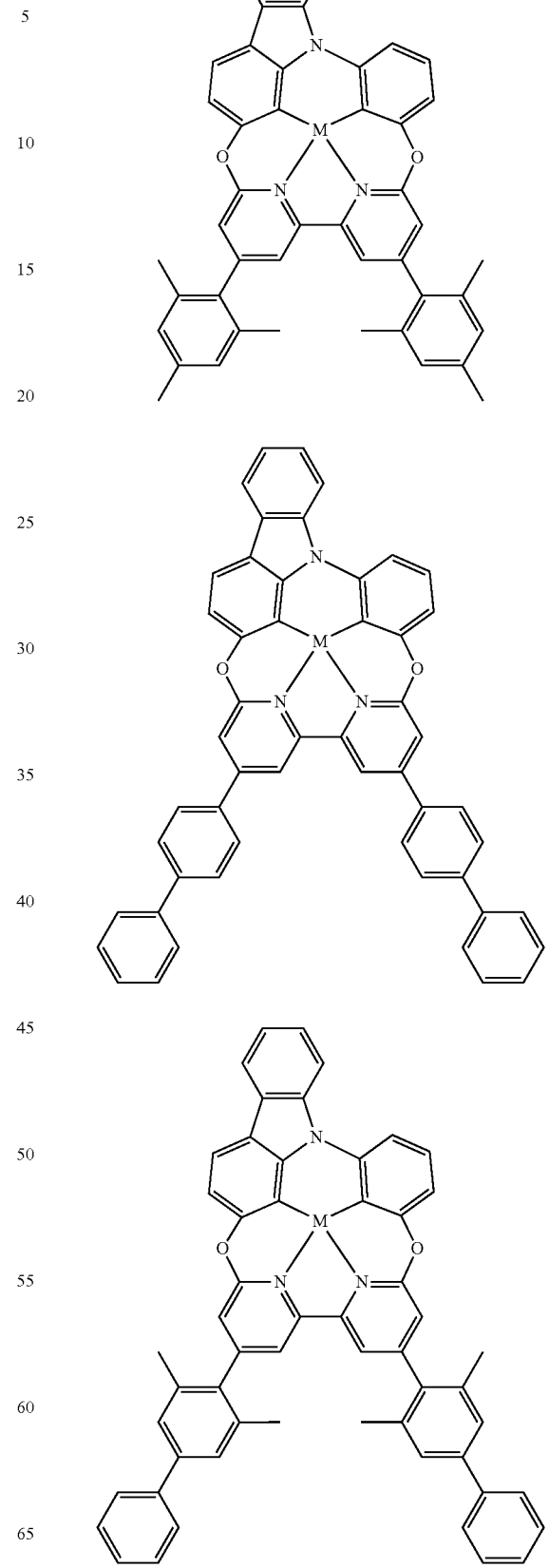

77
-continued
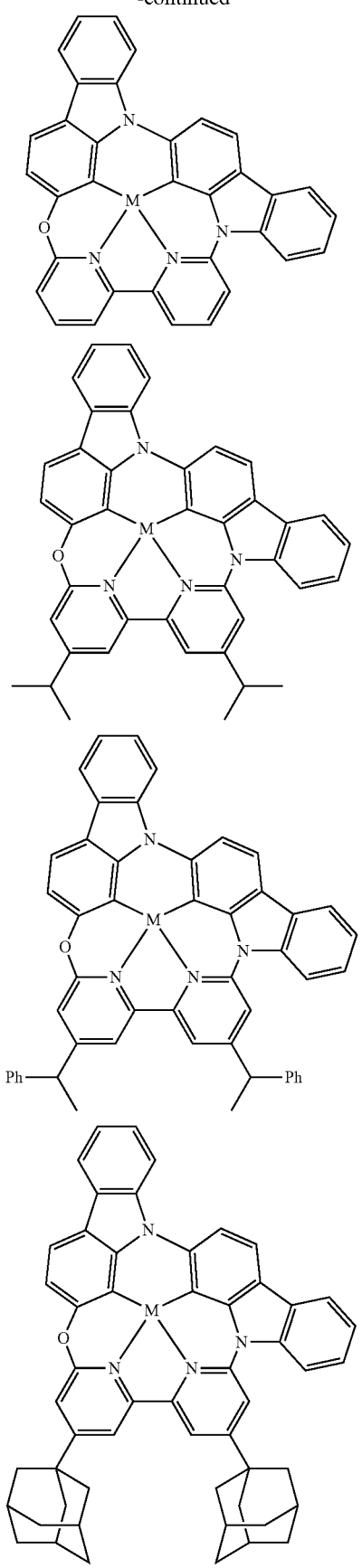
78
-continued
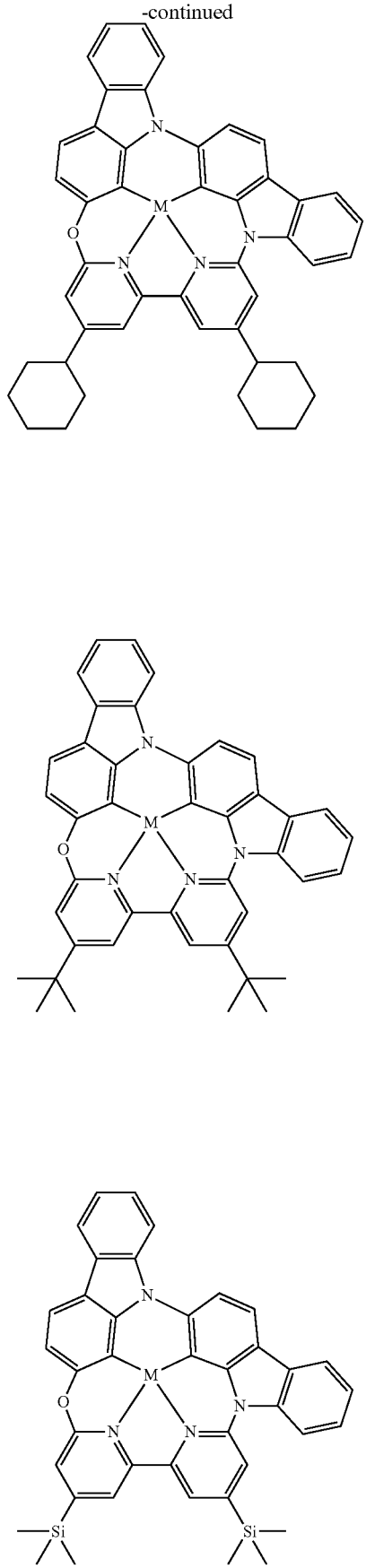

79
-continued
80
-continued
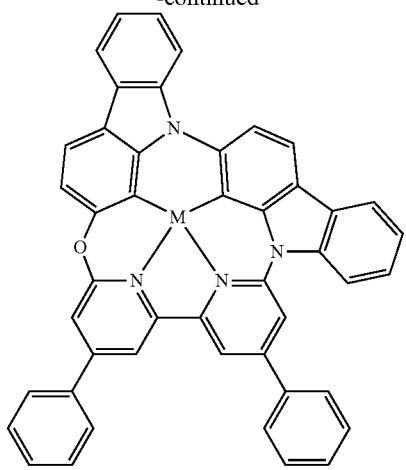
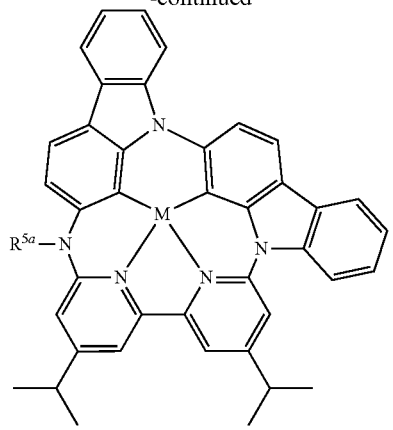
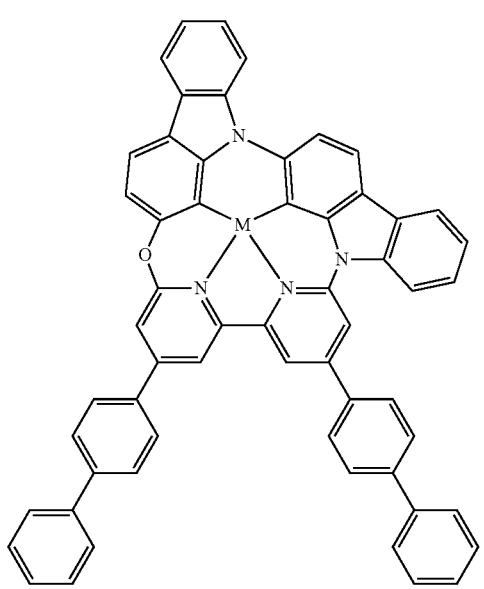
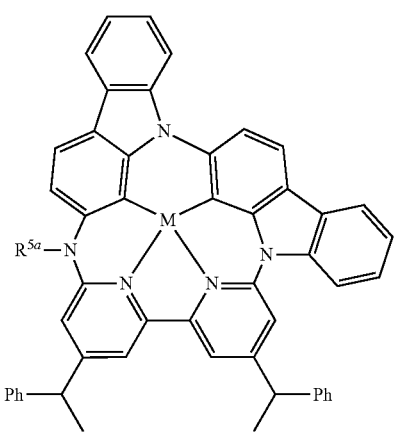
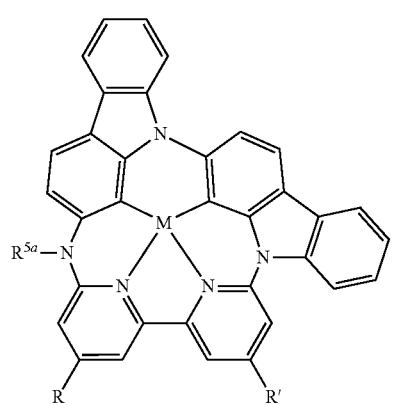
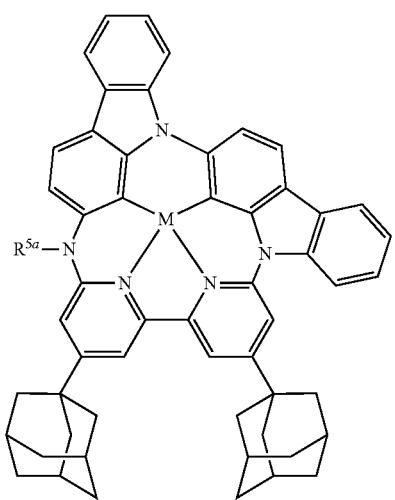

81
-continued
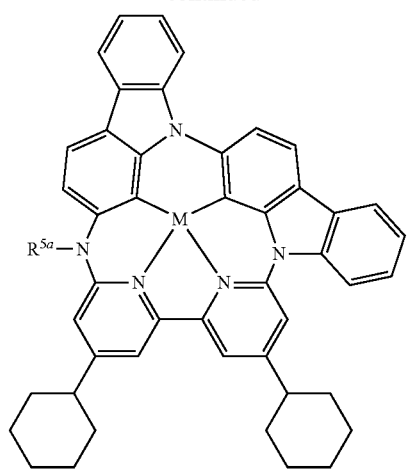
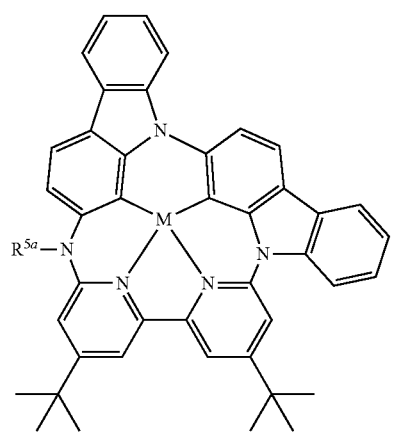
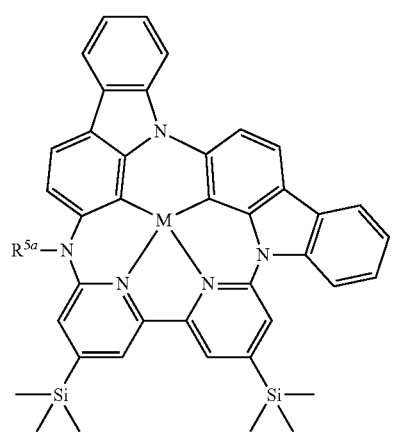
82
-continued
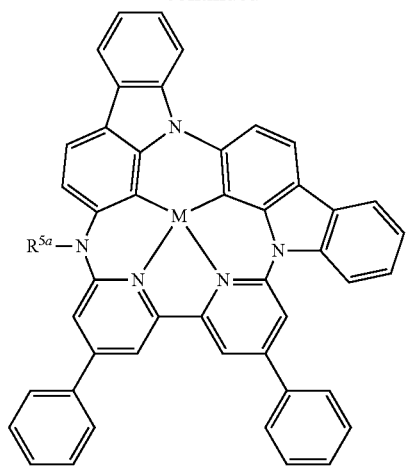
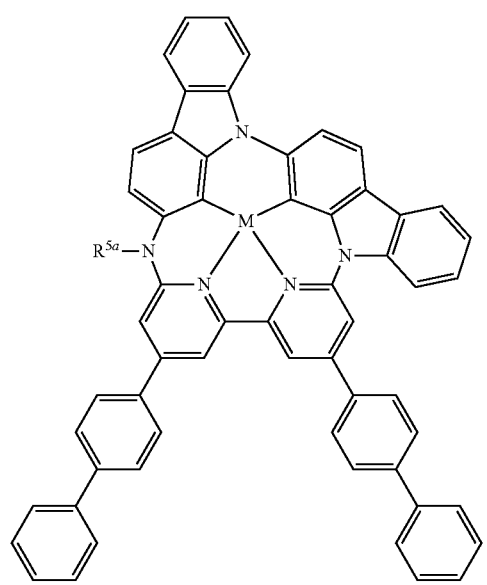
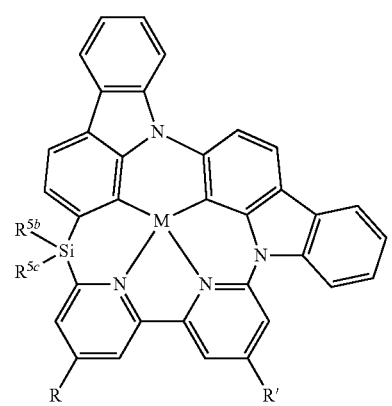

83
-continued
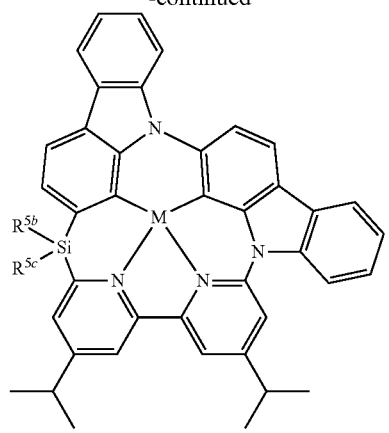
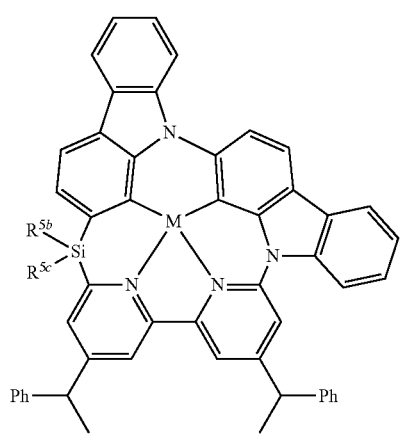
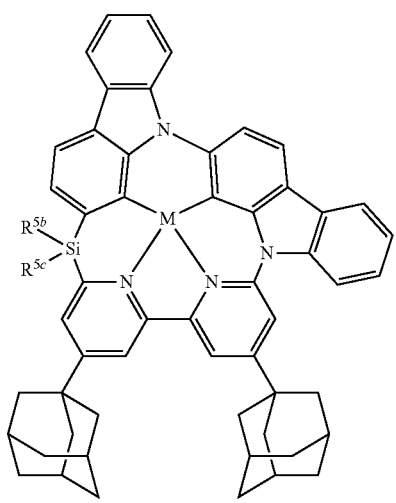
84
-continued
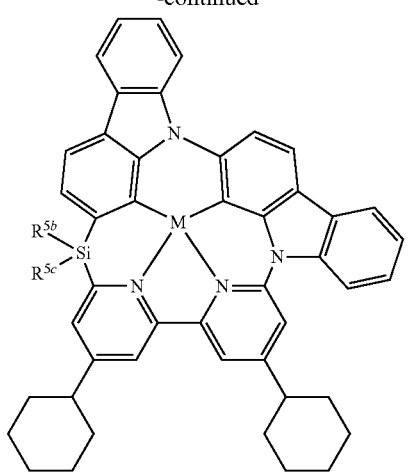
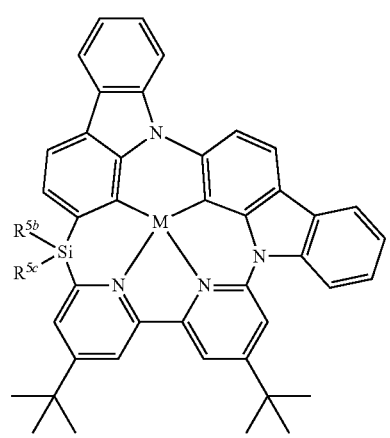
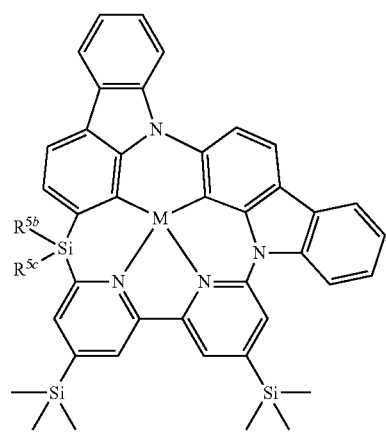

85
-continued
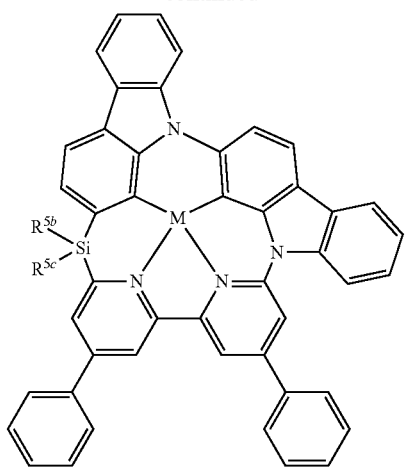
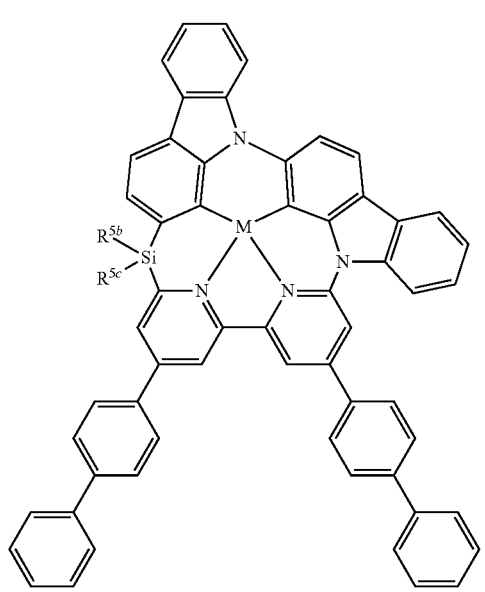
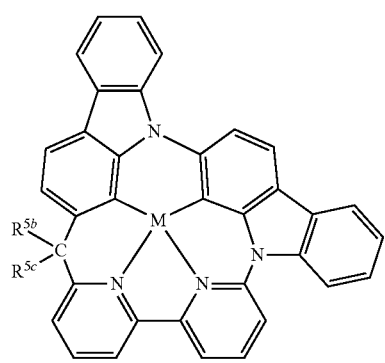
86
-continued
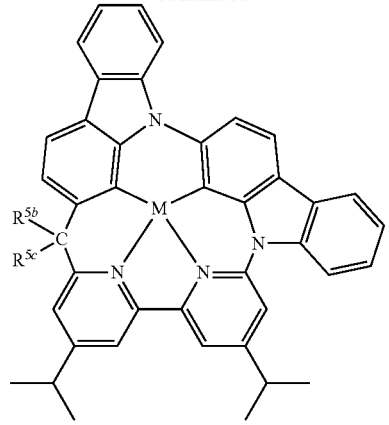
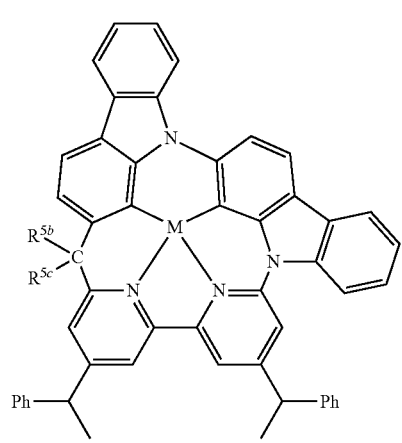
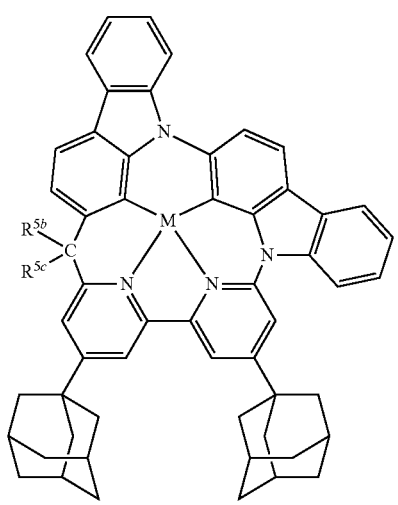

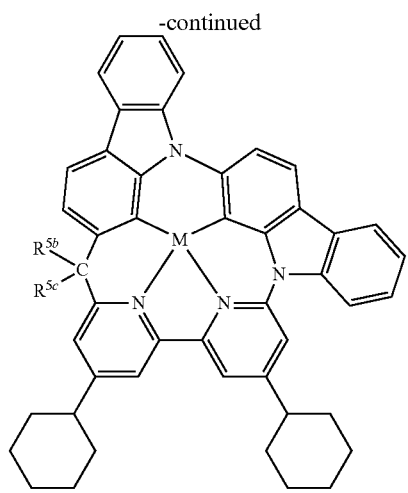
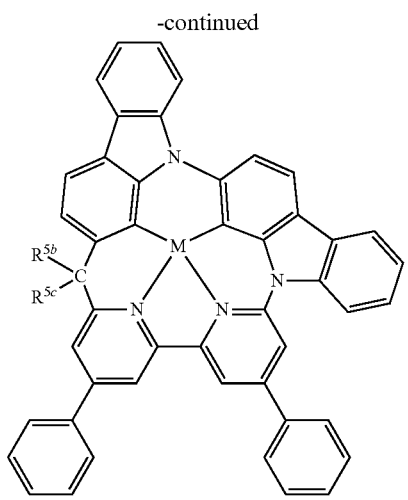
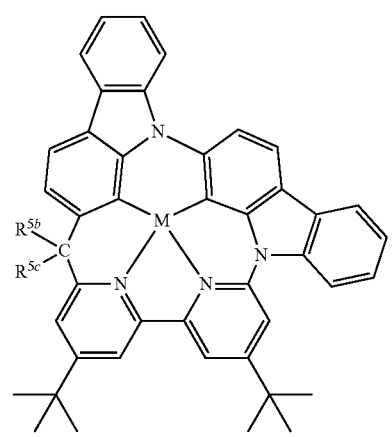
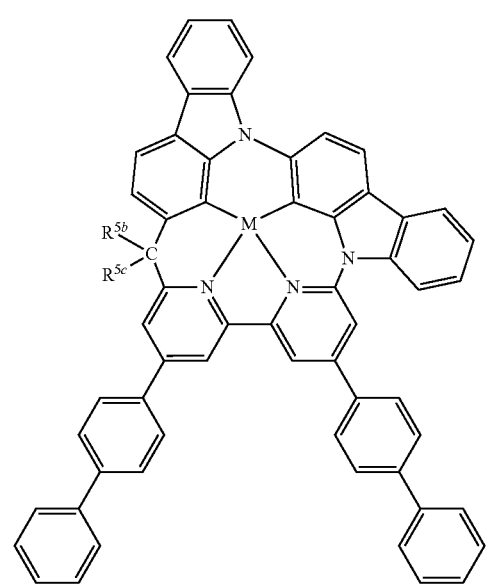
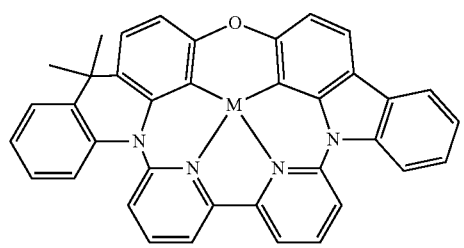
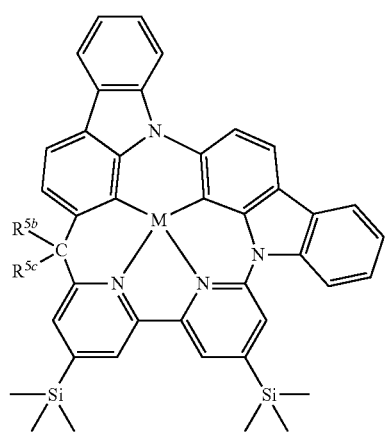
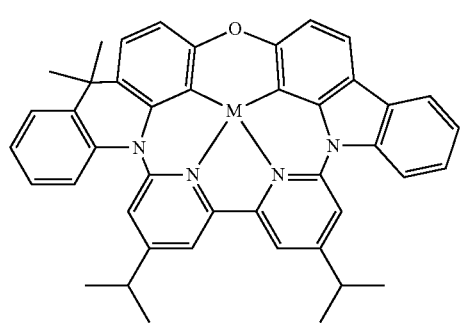

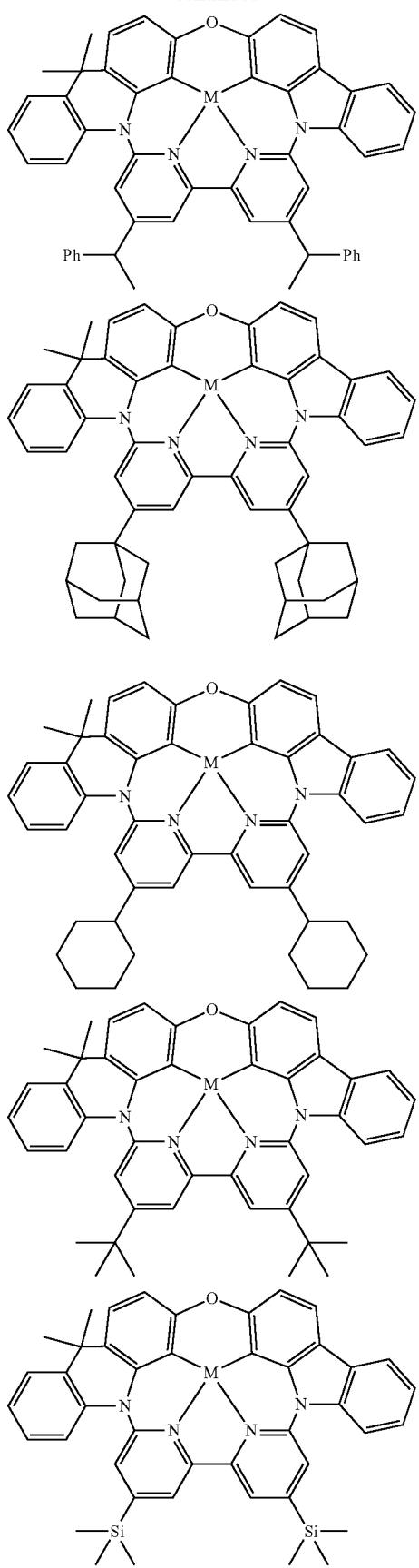
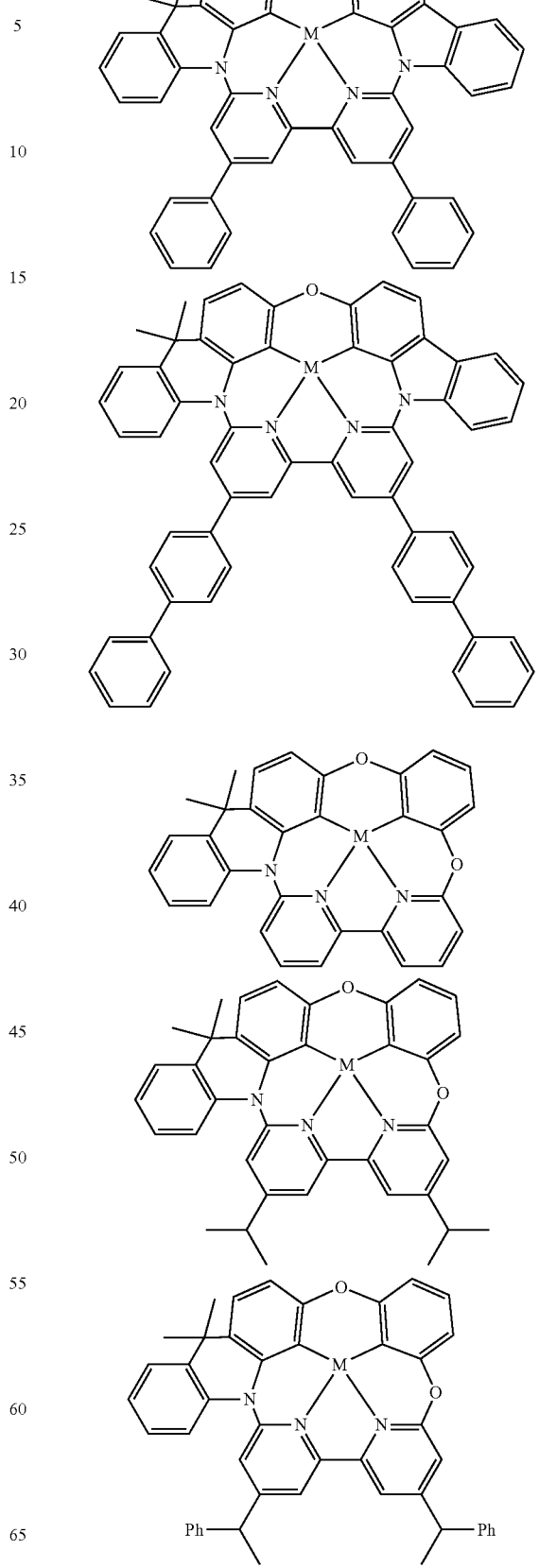

| 91 -continued | 92 -continued |
|---|---|
| 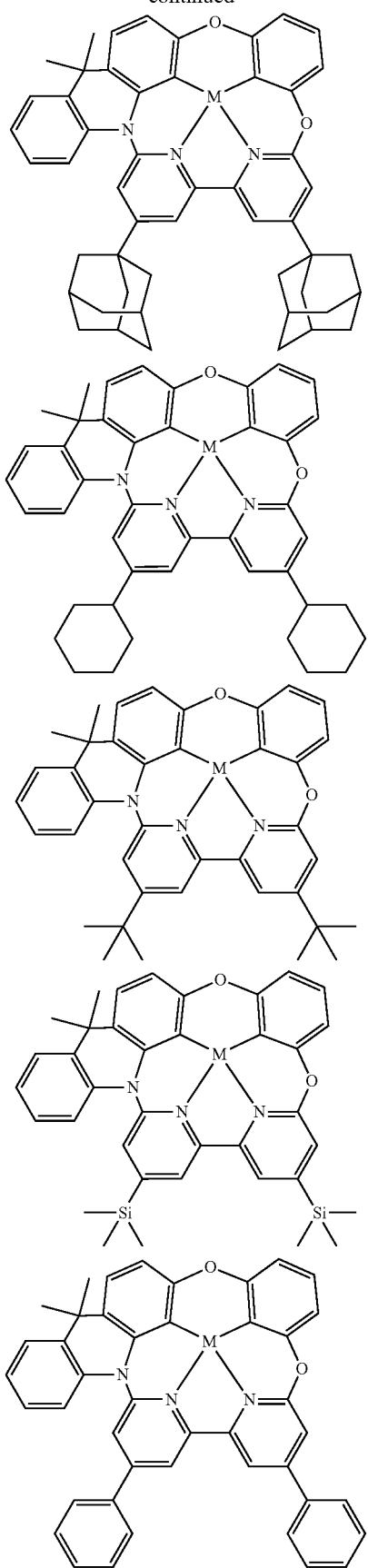 | 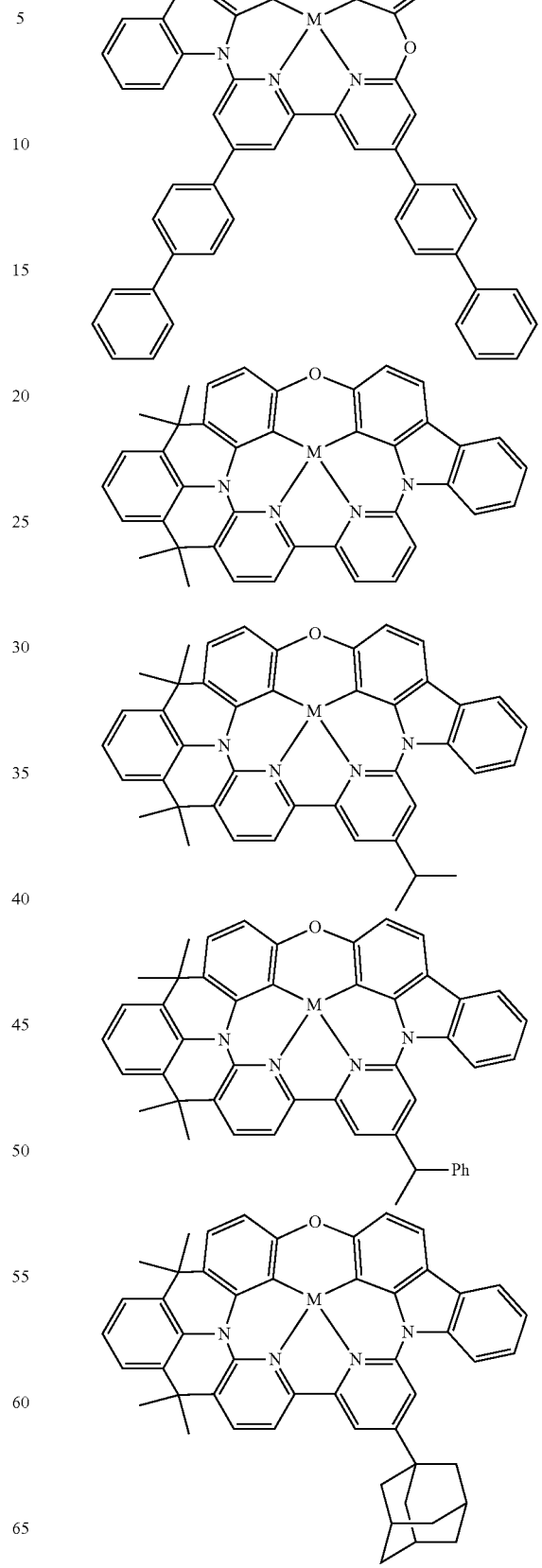 |

93
-continued
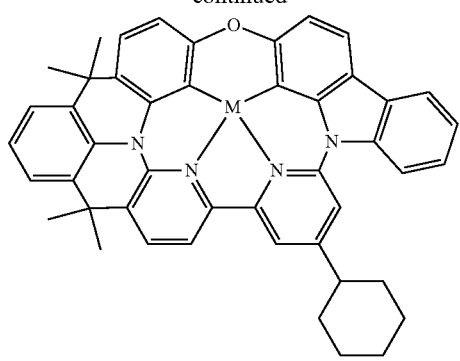
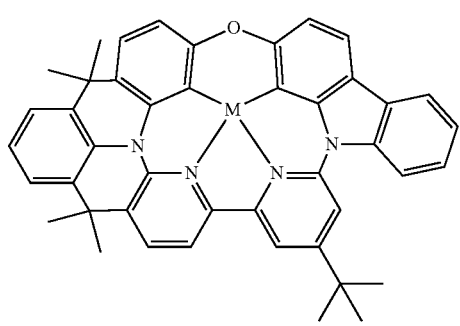
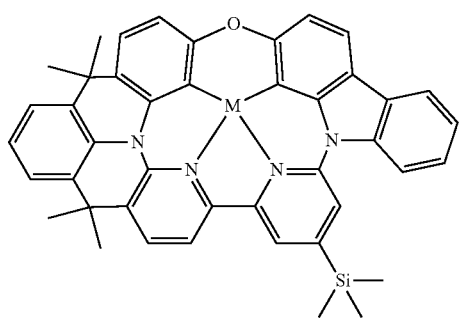
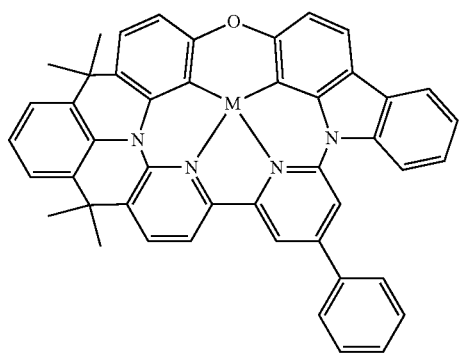
94
-continued
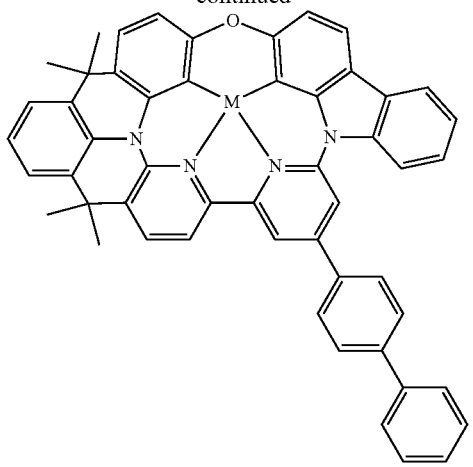
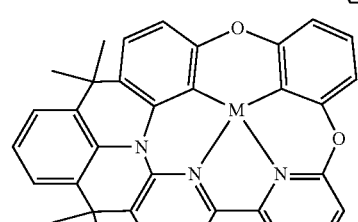
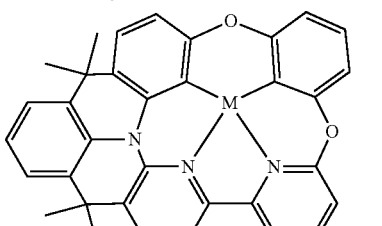
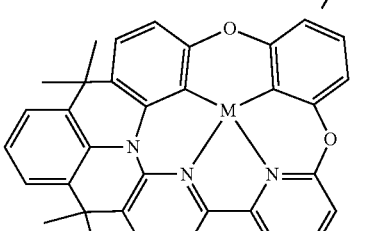
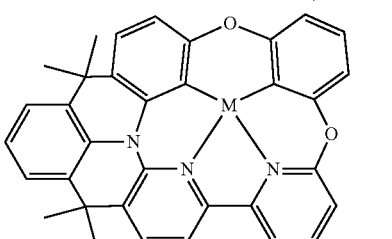

95
-continued
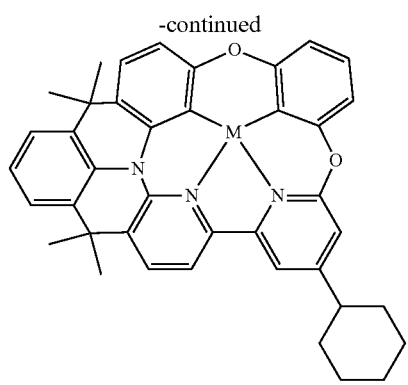
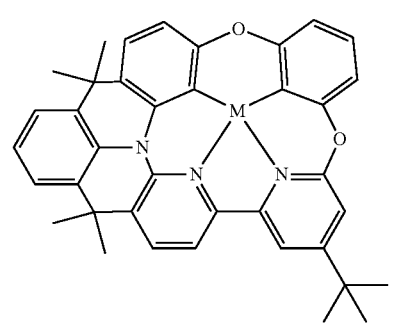
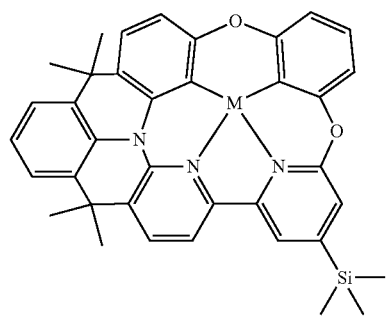
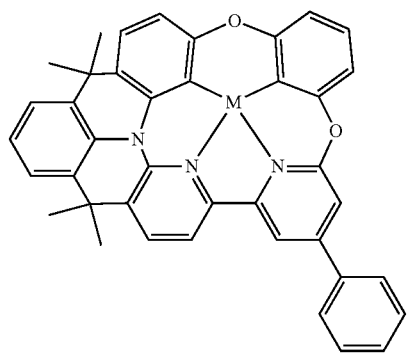
96
-continued
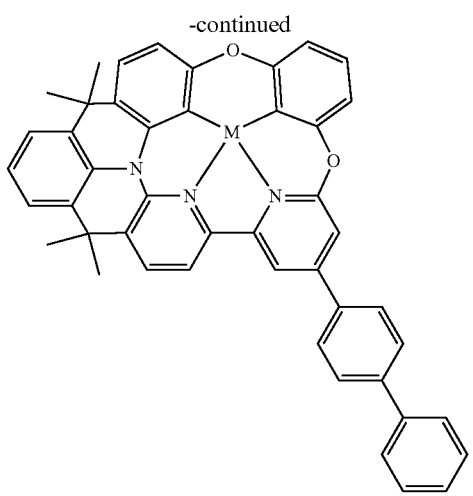
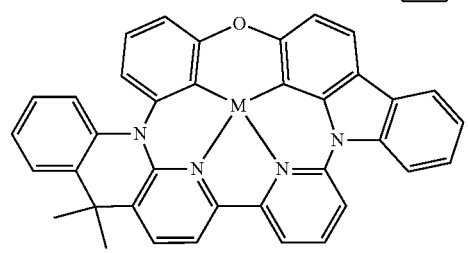
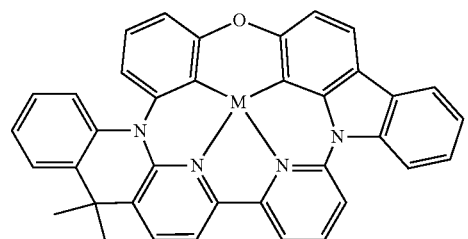
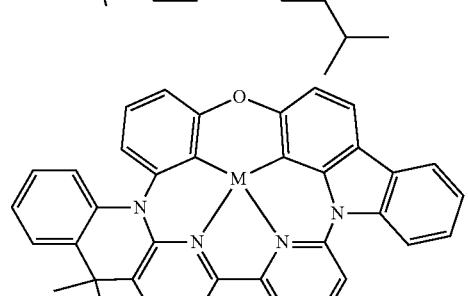
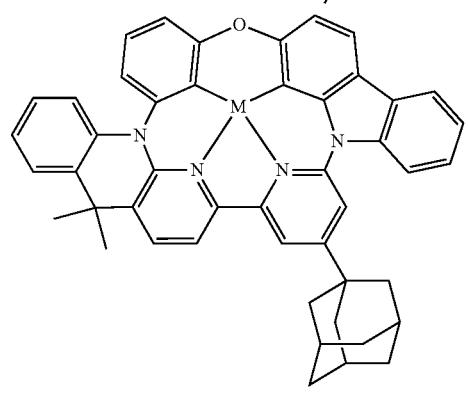

97
-continued
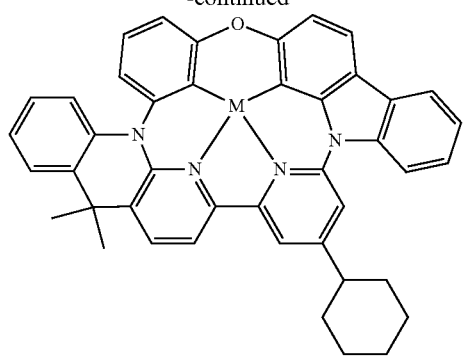
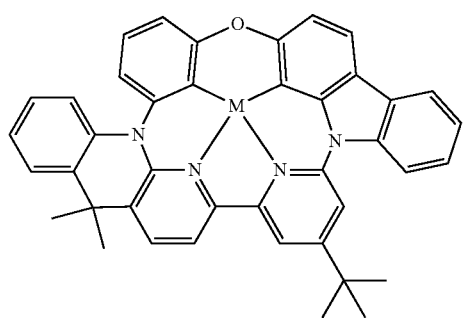
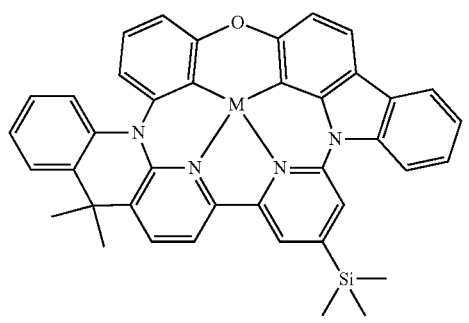
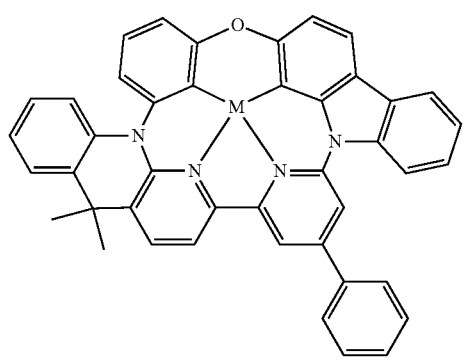
98
-continued
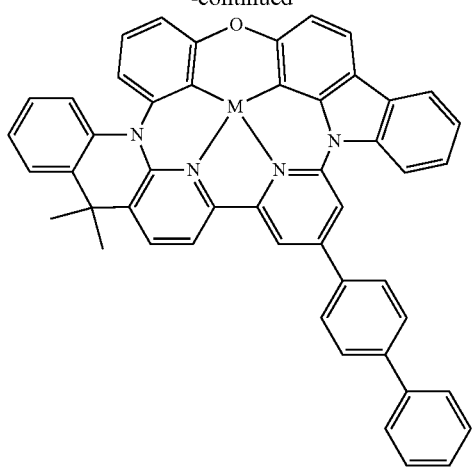
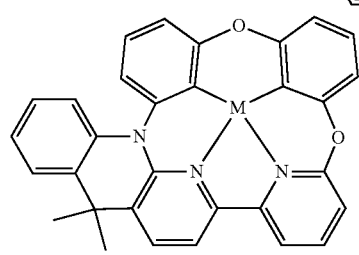
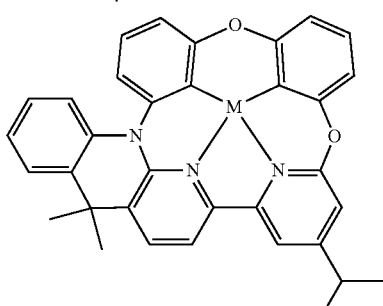
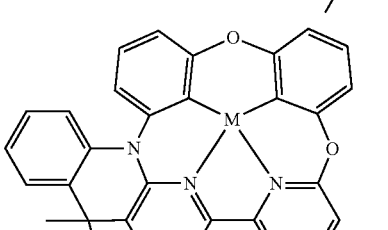
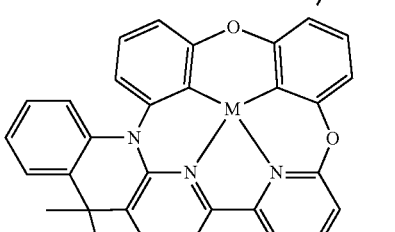
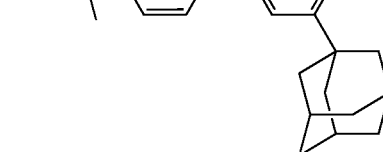

99
-continued
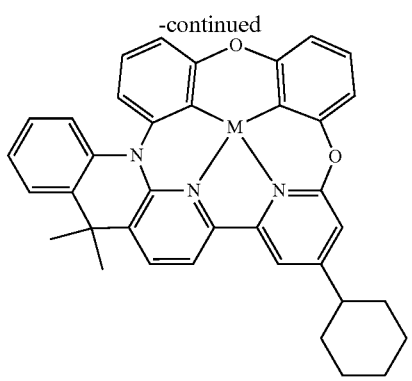
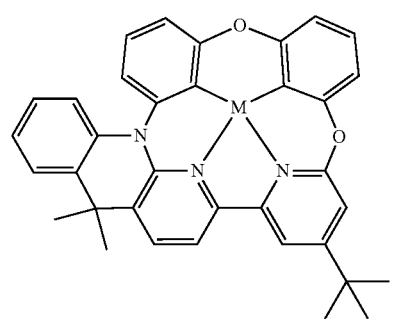
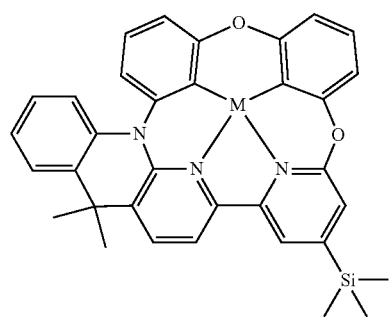
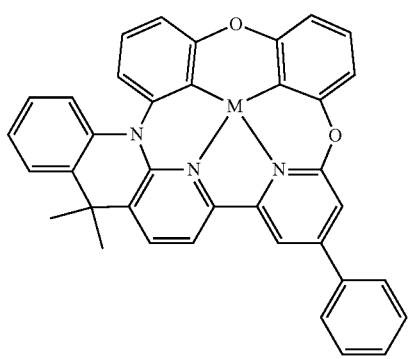
100
-continued
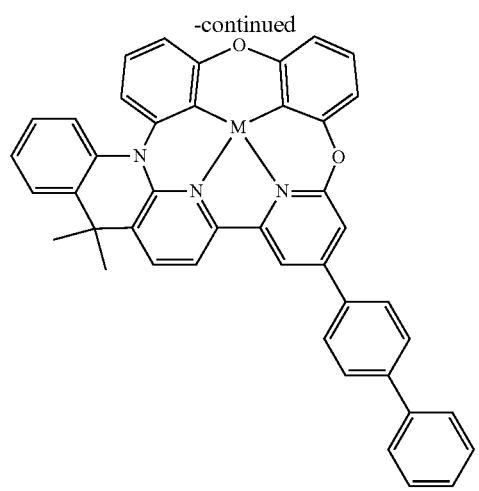
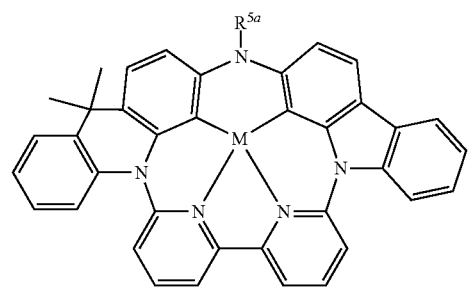
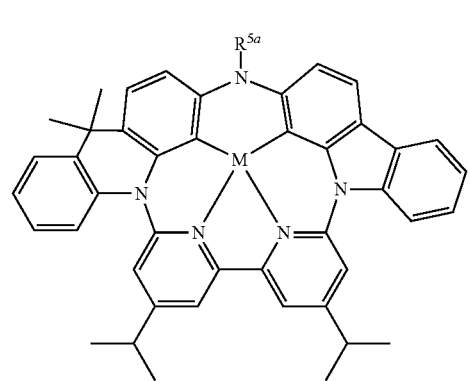
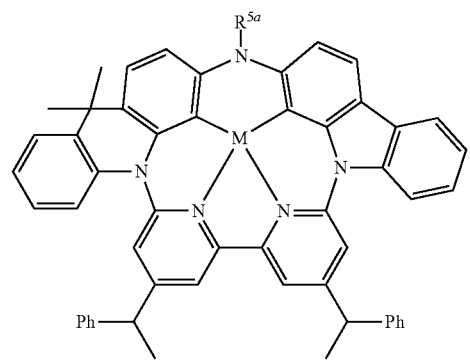

-continued
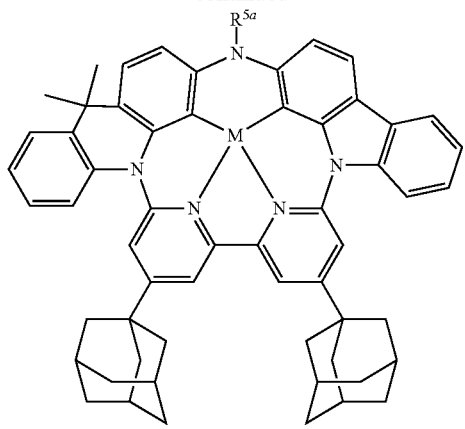
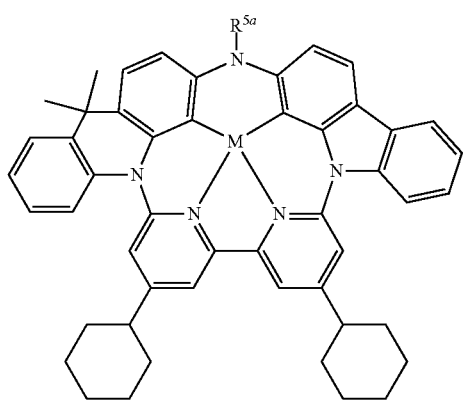
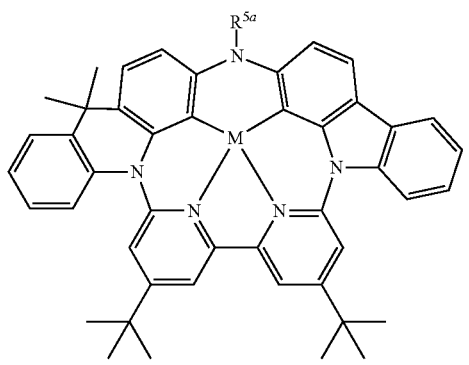
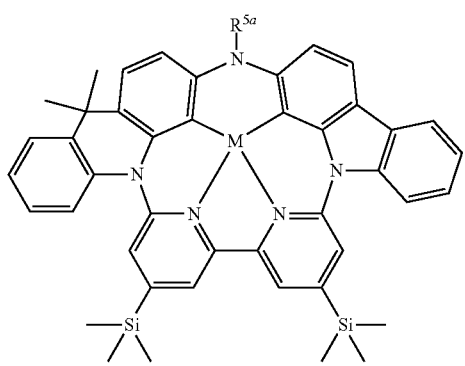
-continued
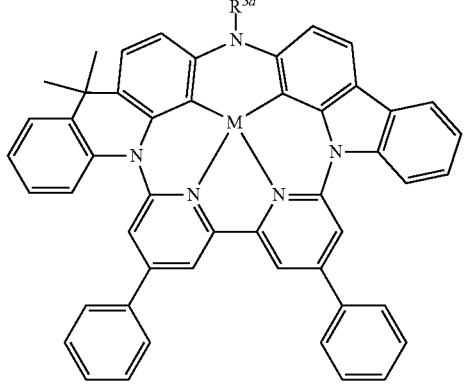
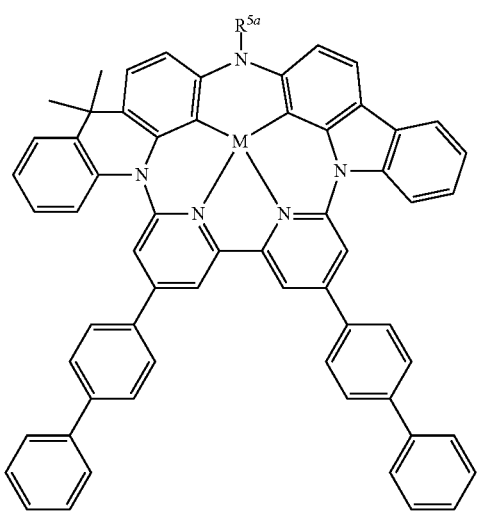
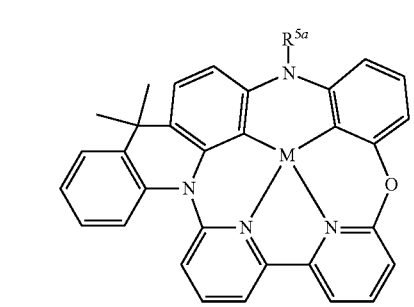
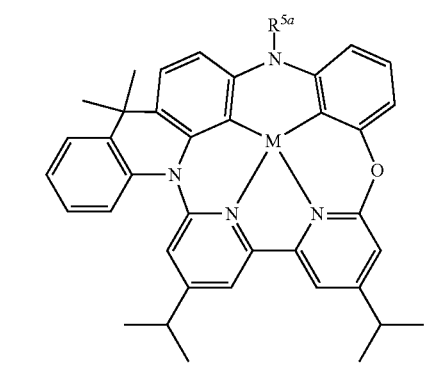

103
-continued
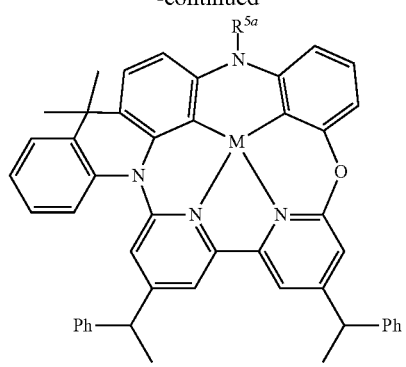
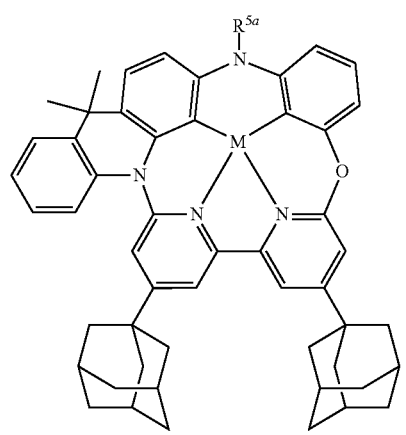
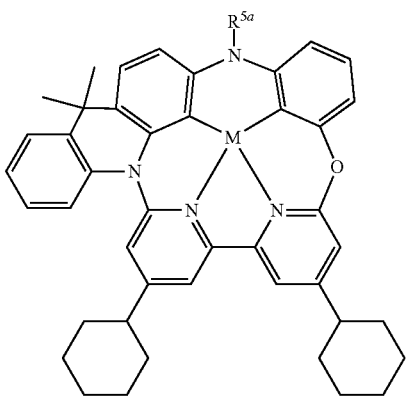
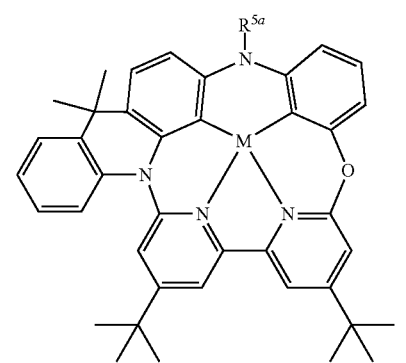
104
-continued
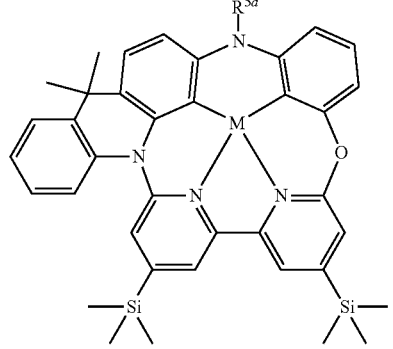
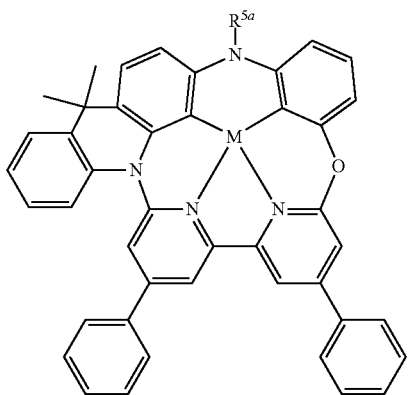
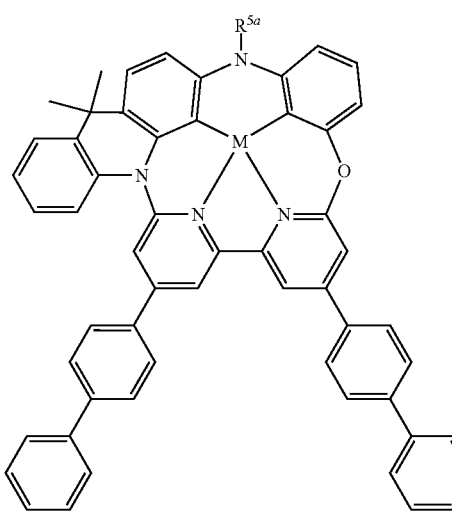
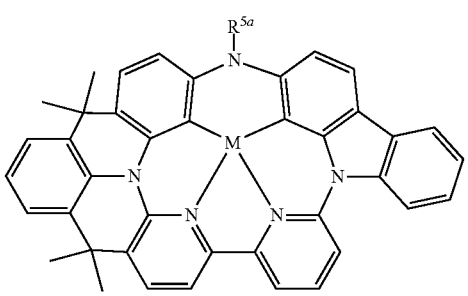

105
-continued
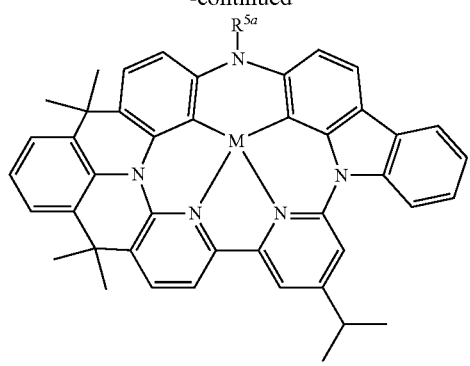
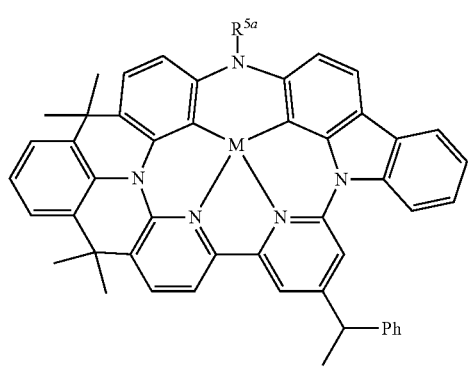
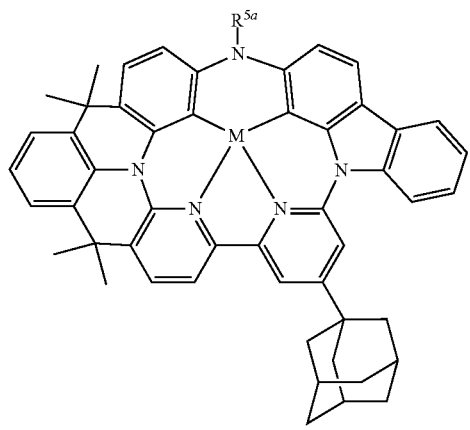
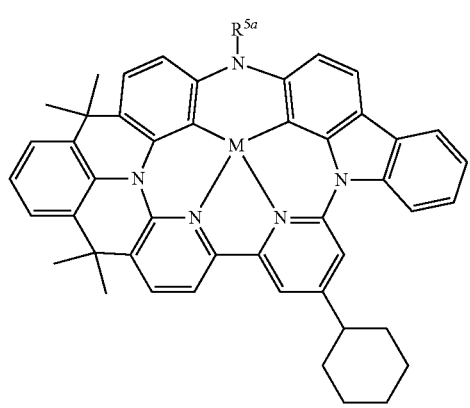
106
-continued
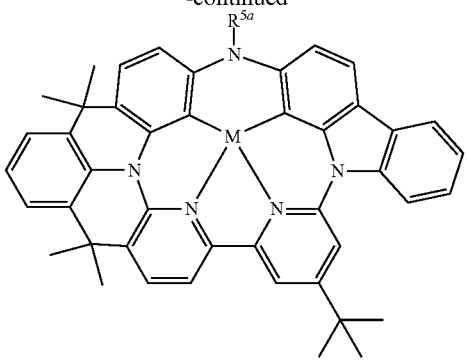
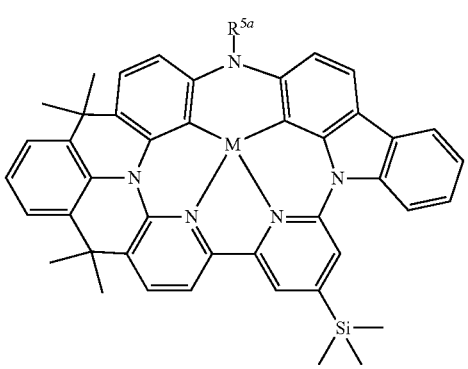
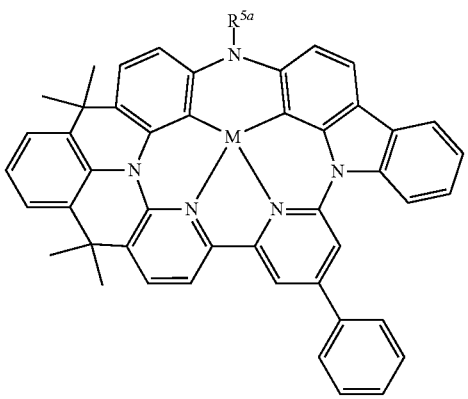
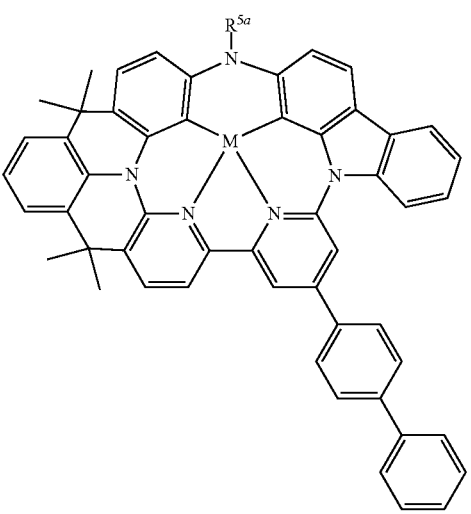

107
-continued
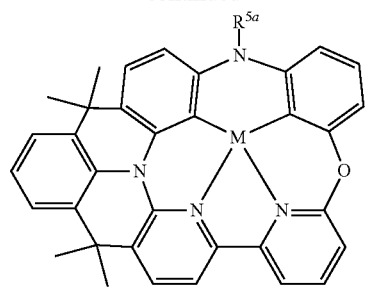
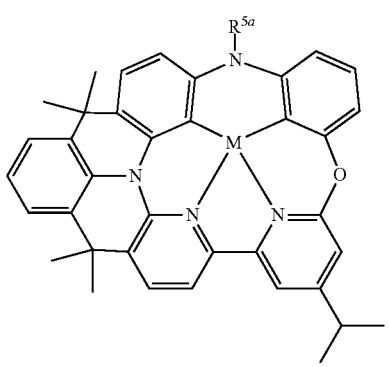
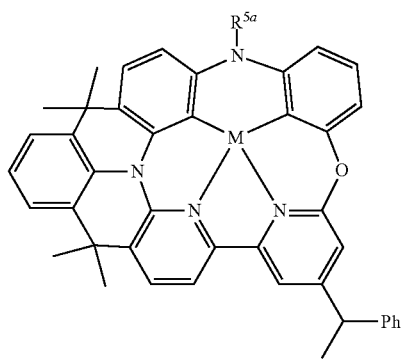
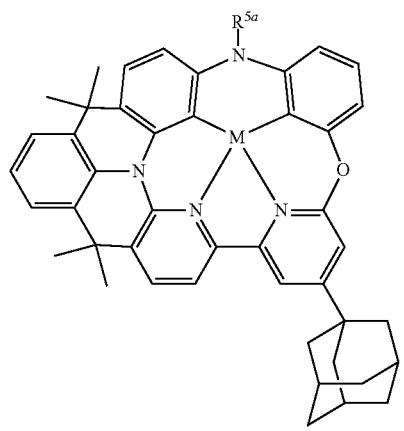
108
-continued
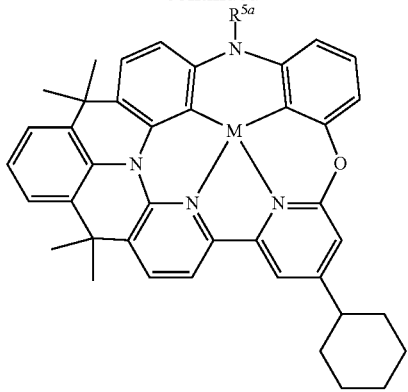
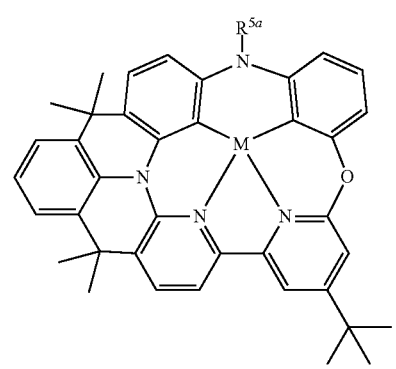
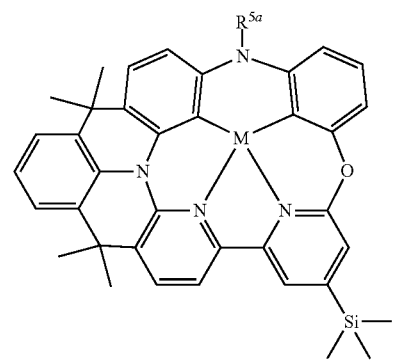
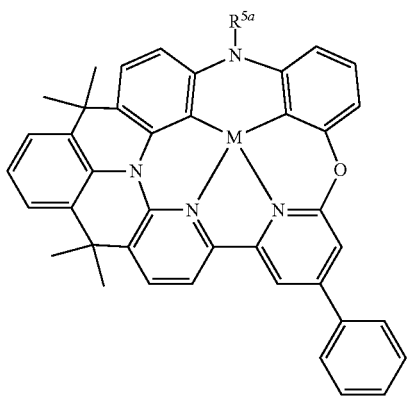

109
-continued
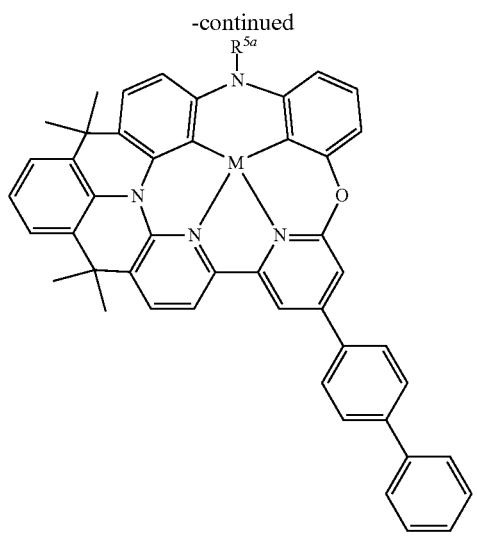
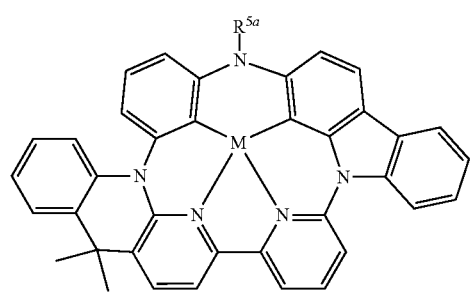
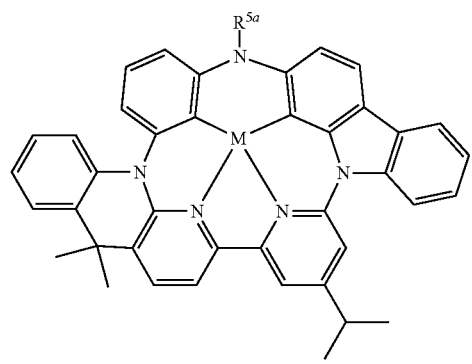
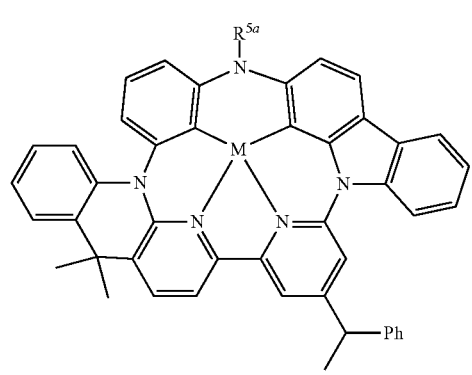
110
-continued
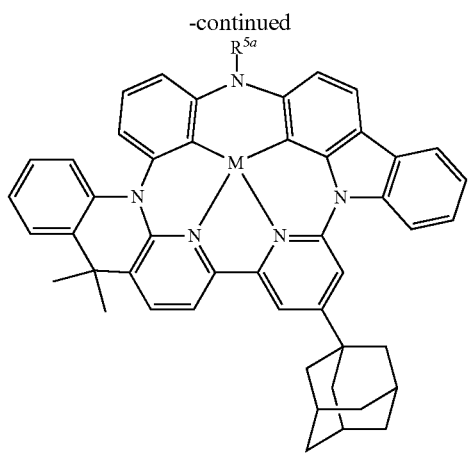
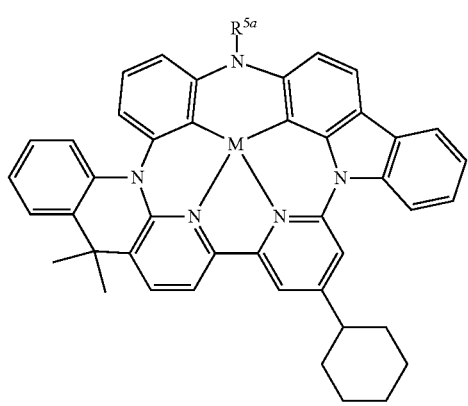
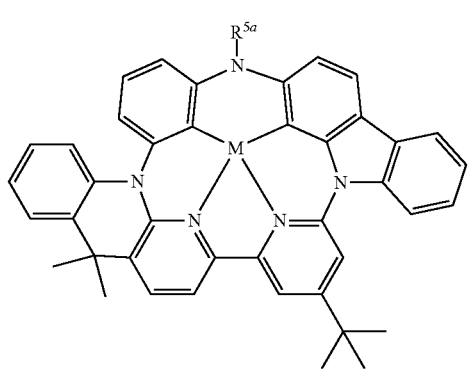
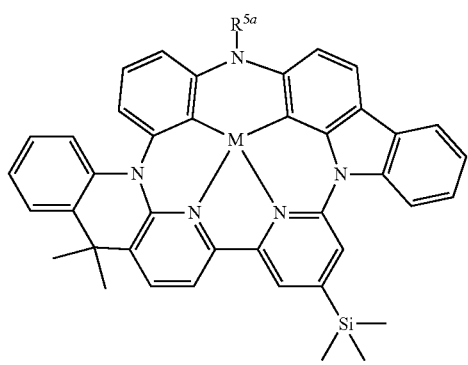

111
-continued
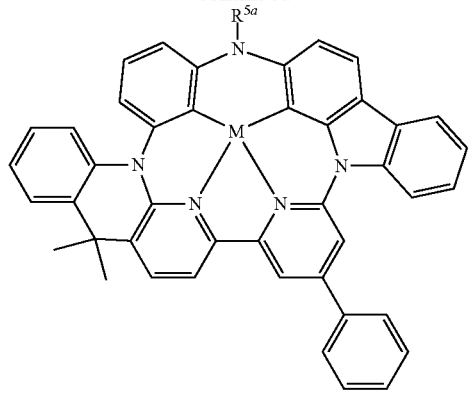
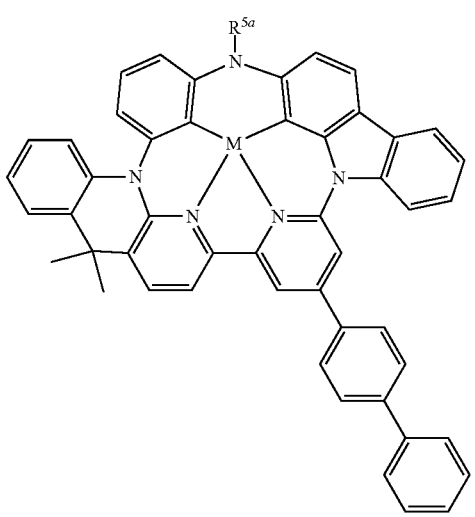
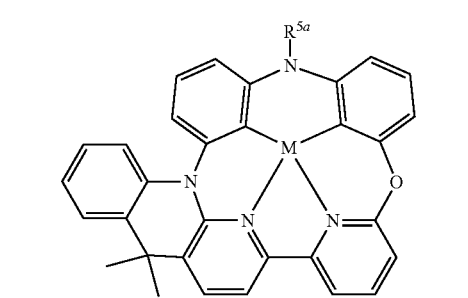
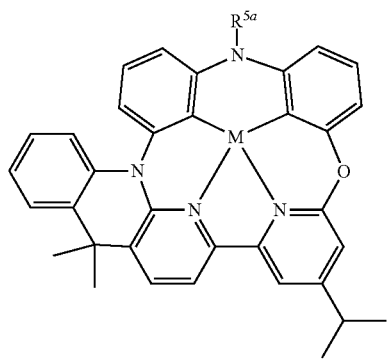
112
-continued
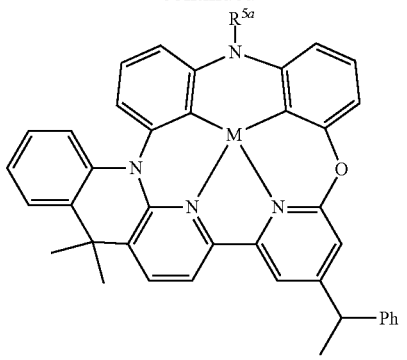
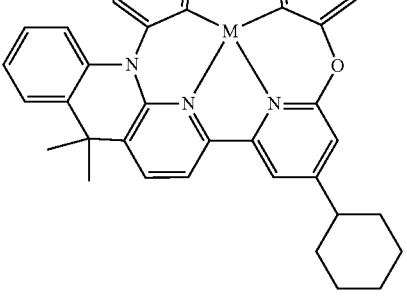
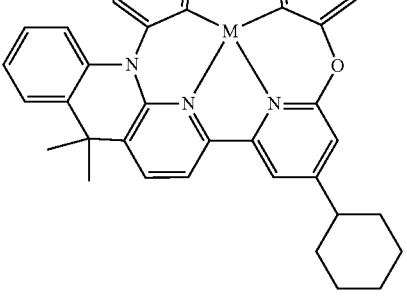
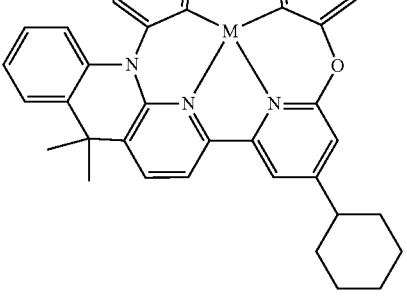

-continued
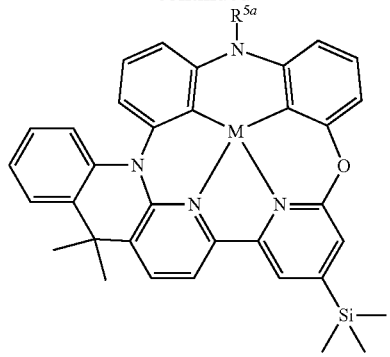
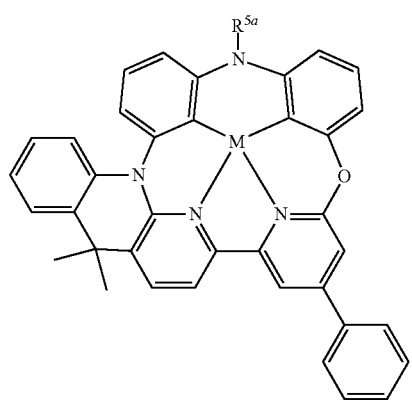
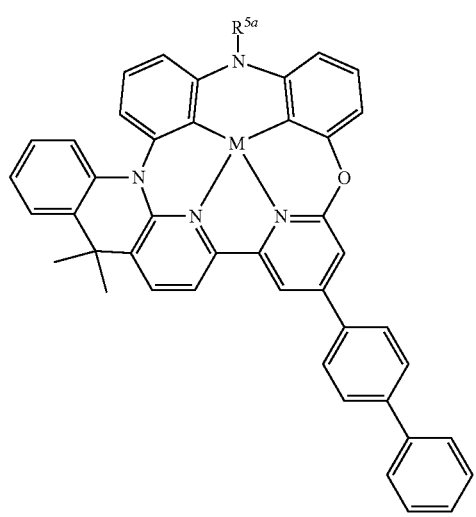
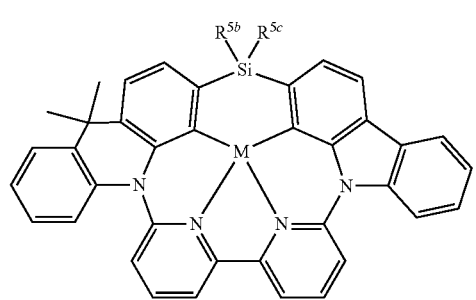
-continued
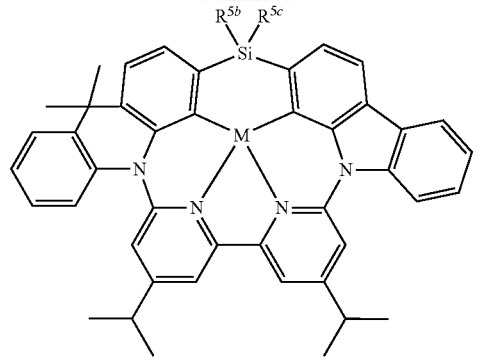
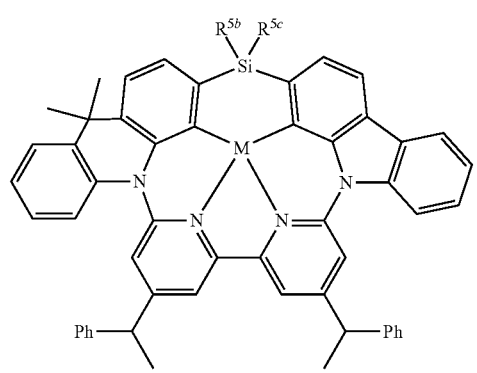
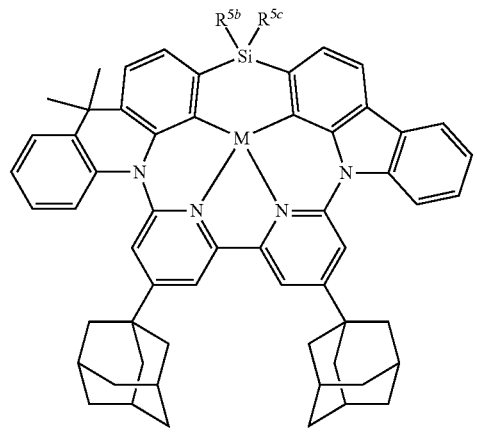
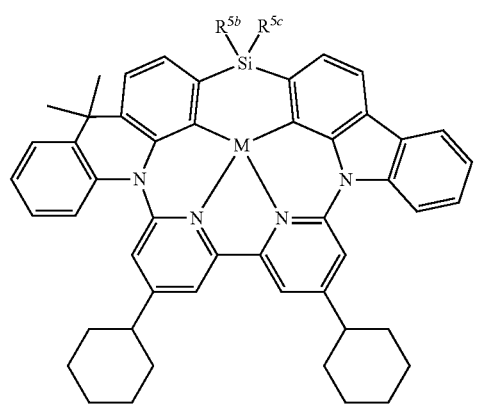

115
-continued
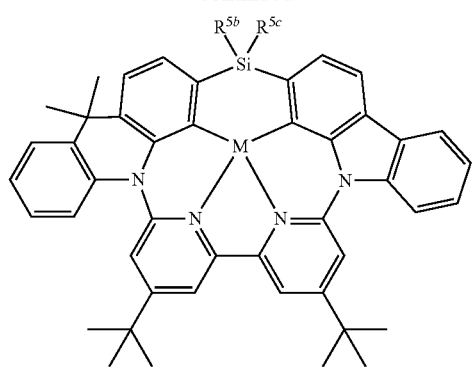
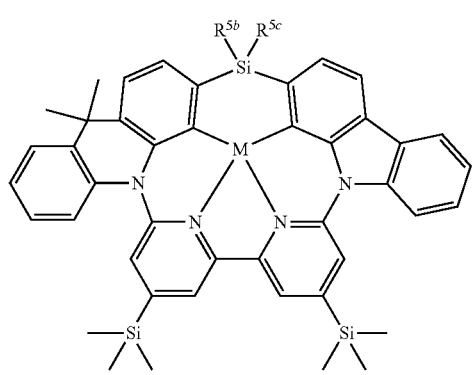
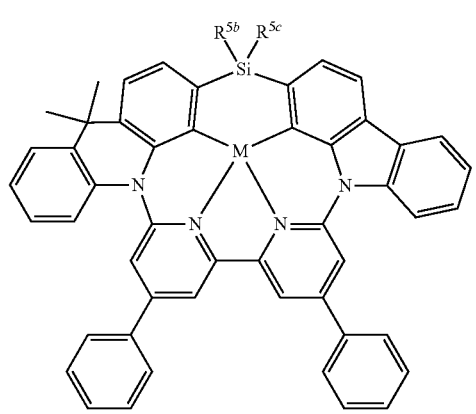
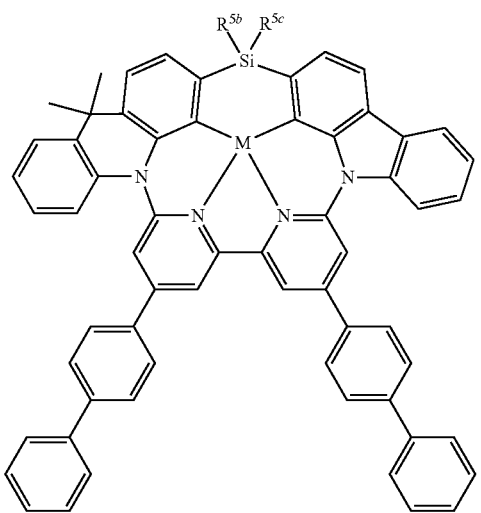
116
-continued
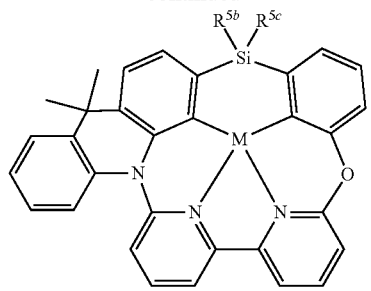
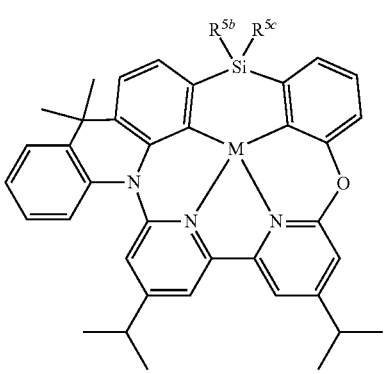
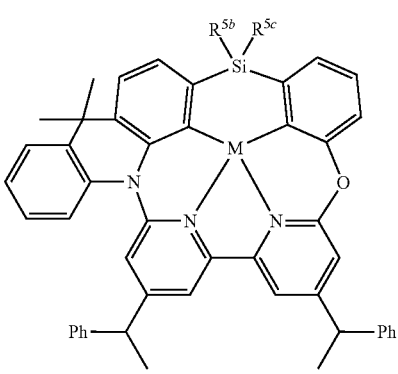
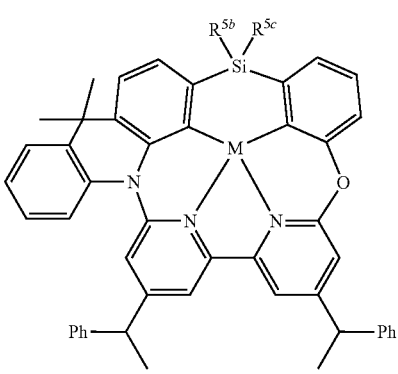

117
-continued
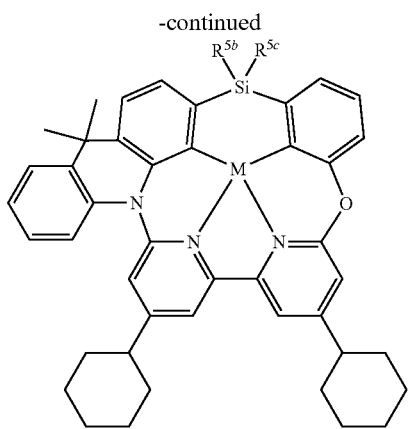
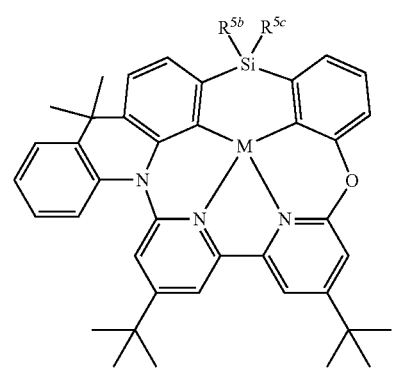
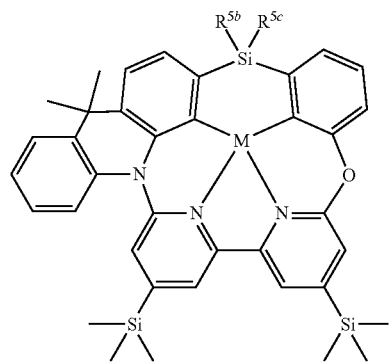
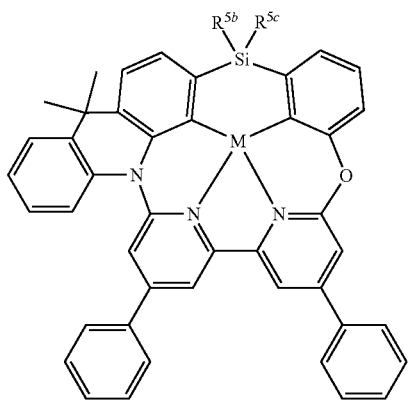
118
-continued
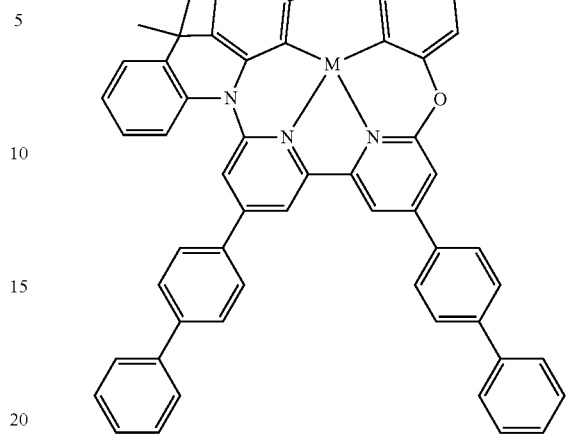
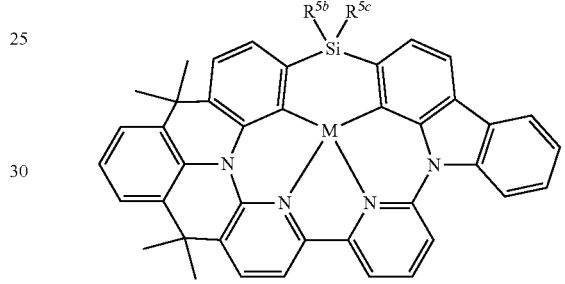
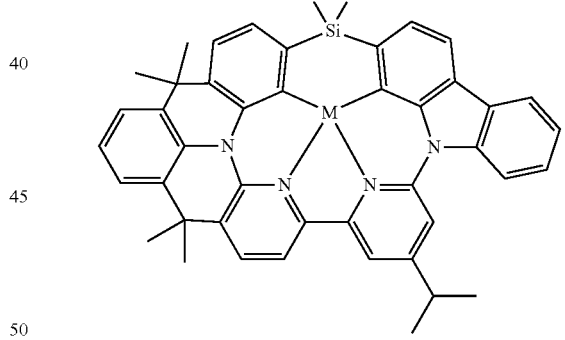
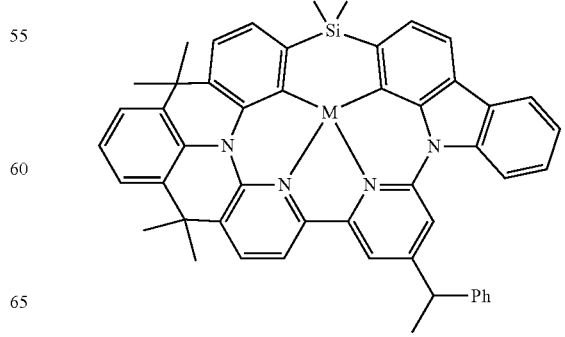

-continued
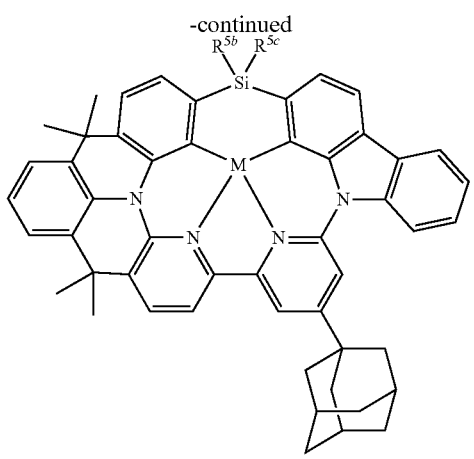
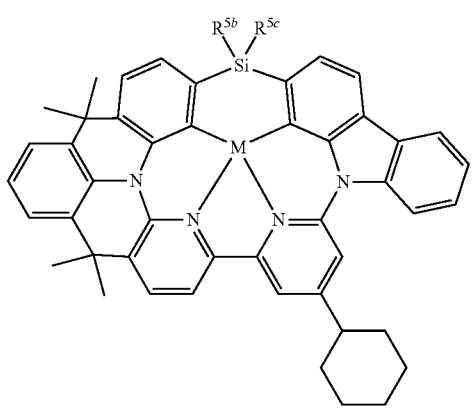
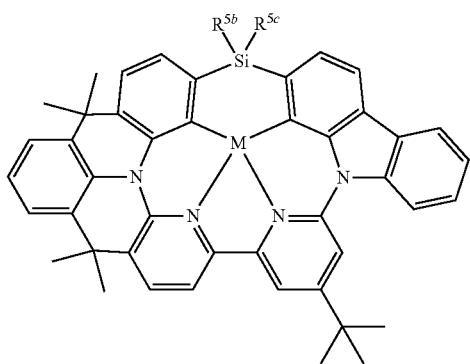
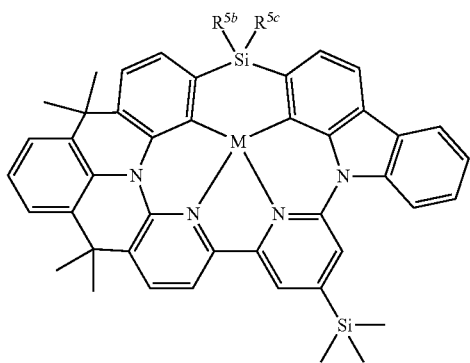
-continued
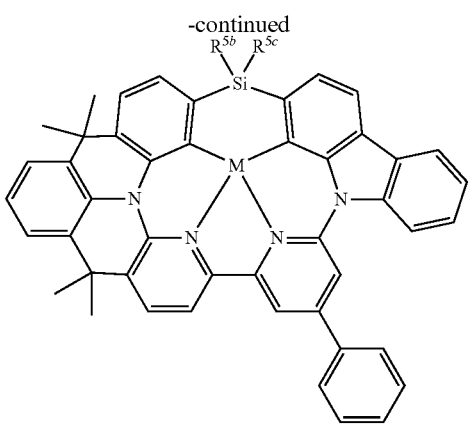
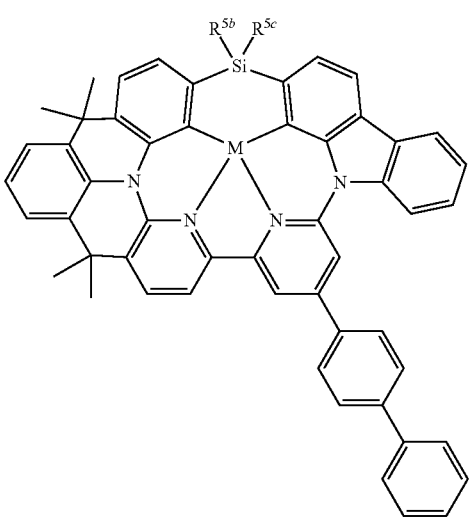
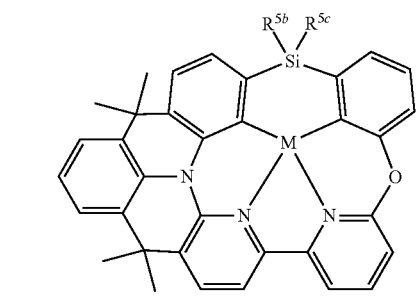
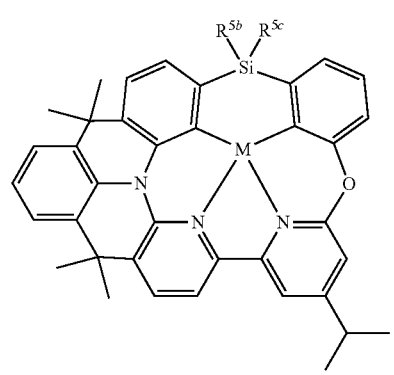

121
-continued
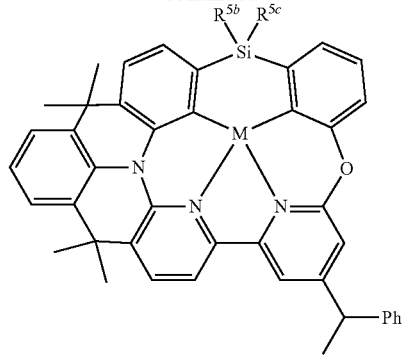
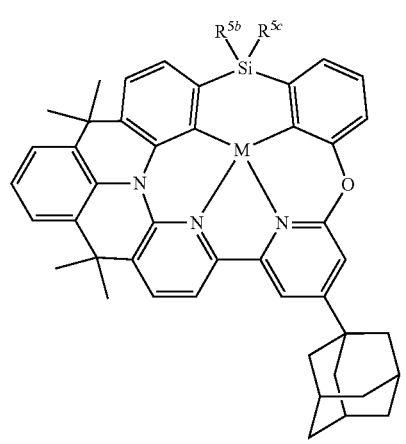
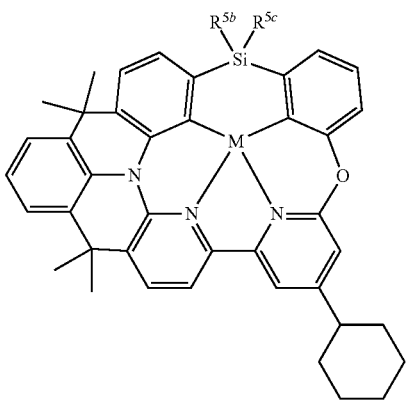
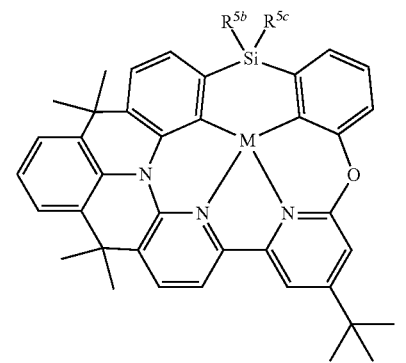
122
-continued
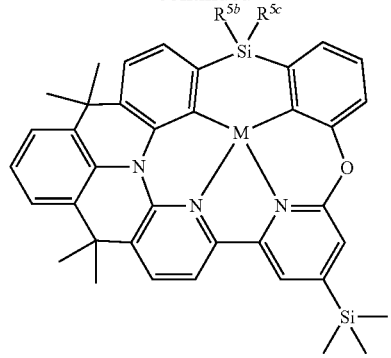
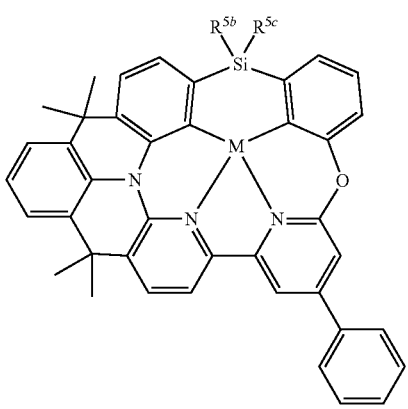
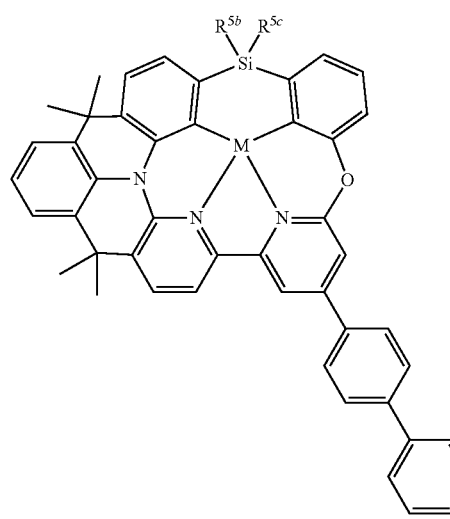
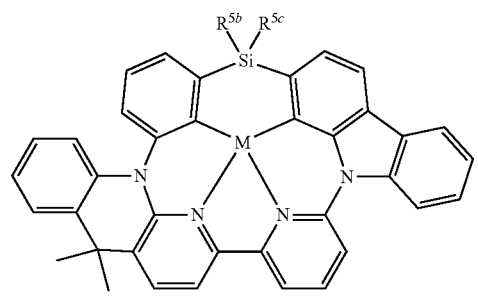

123
-continued
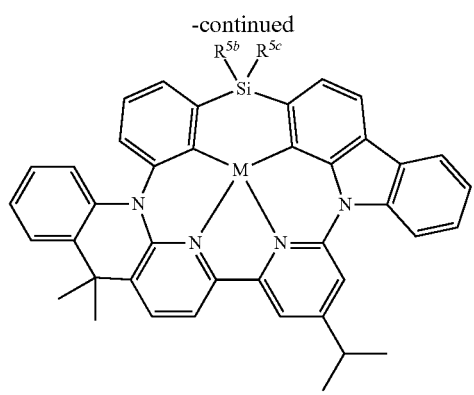
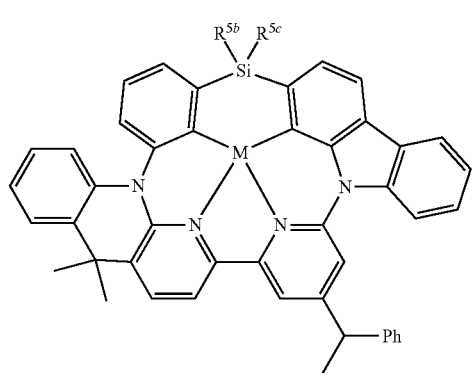
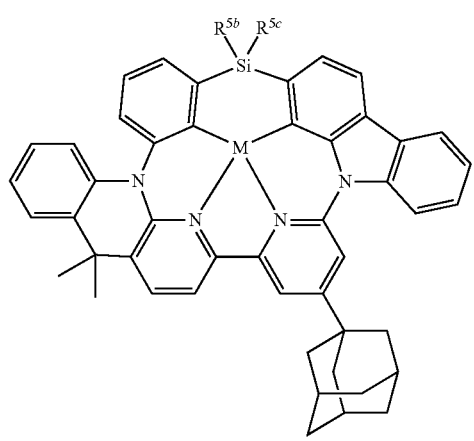
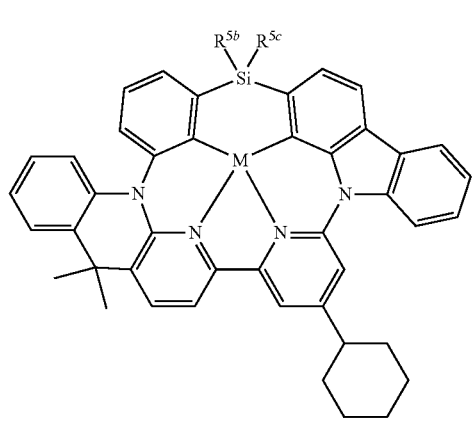
124
-continued
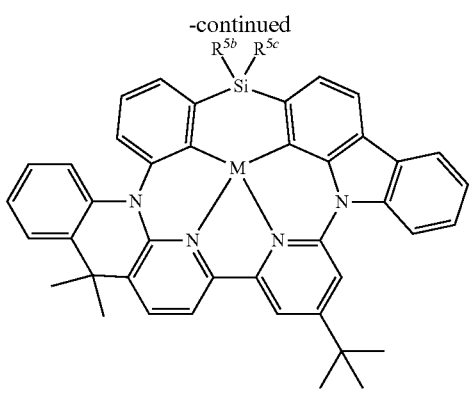
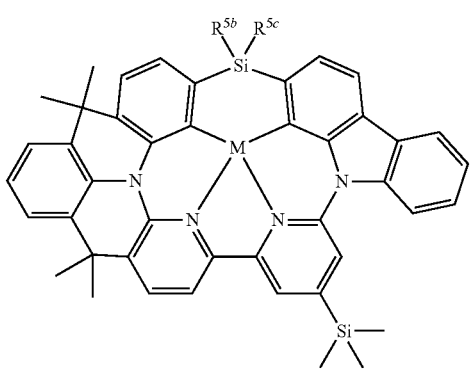
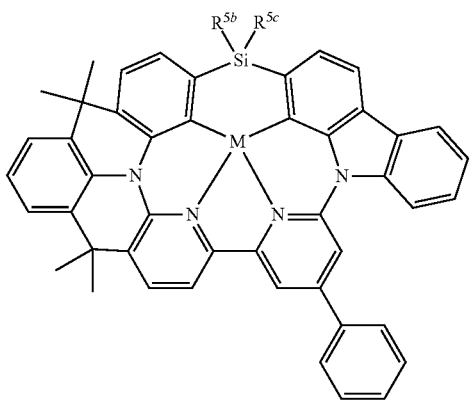
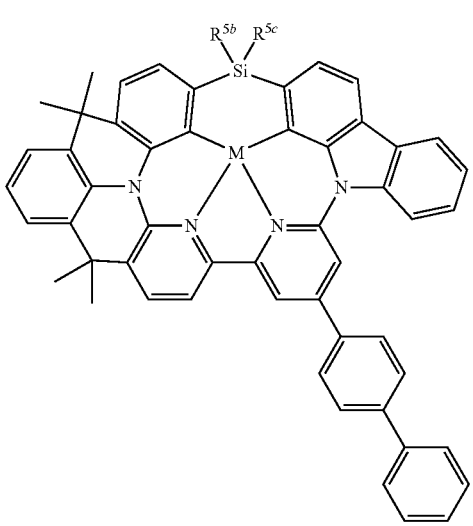

-continued
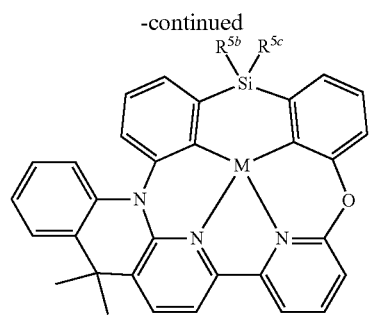
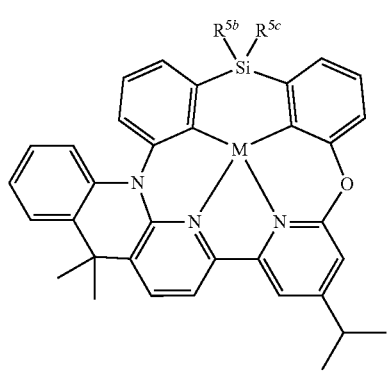
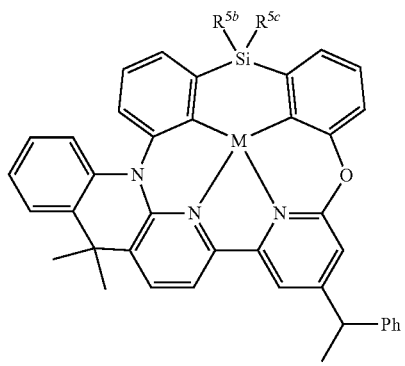
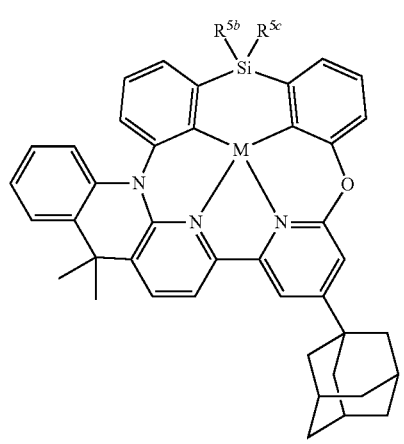
-continued
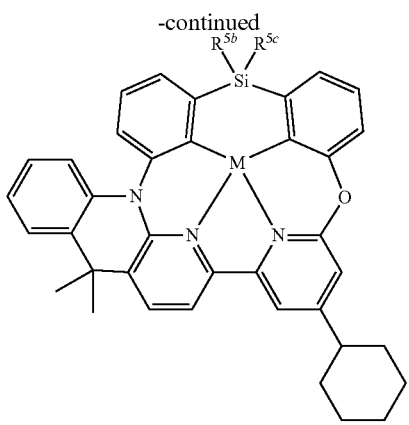
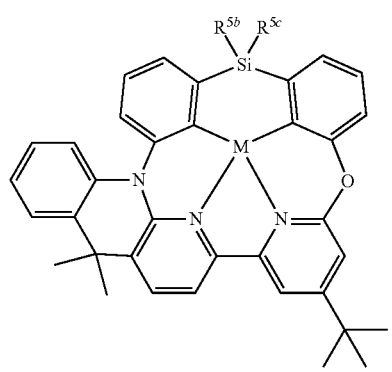
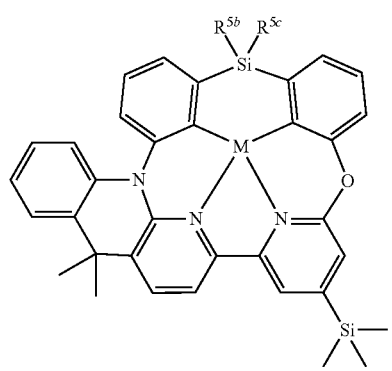
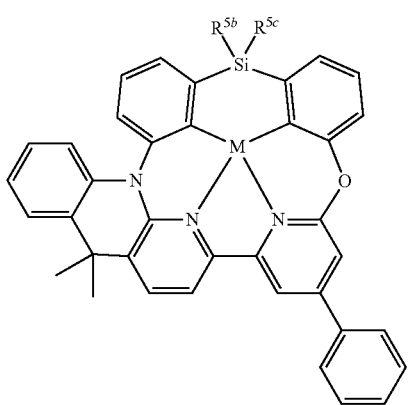

127
-continued
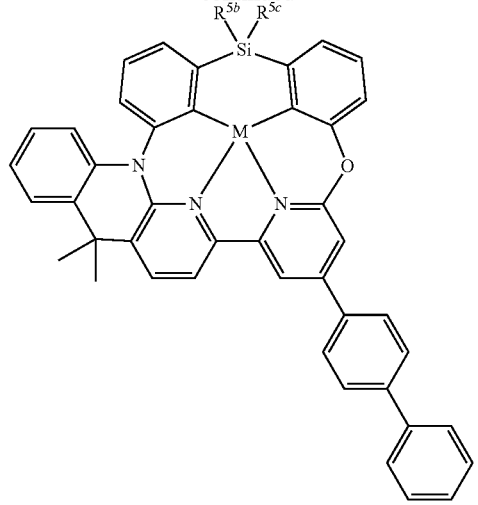
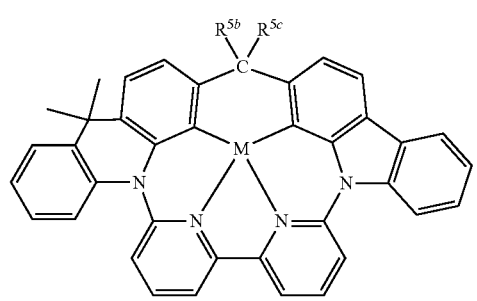
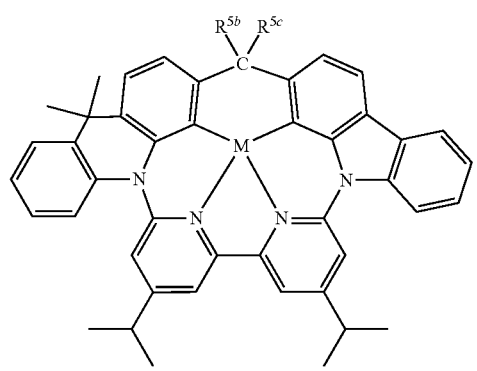
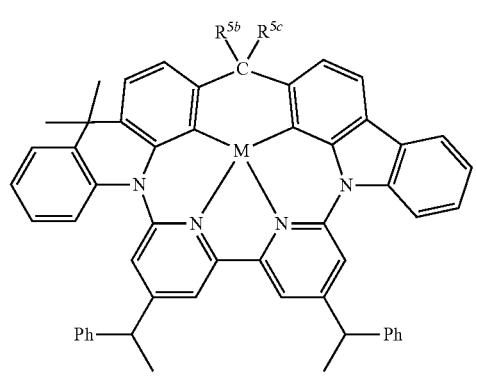
128
-continued
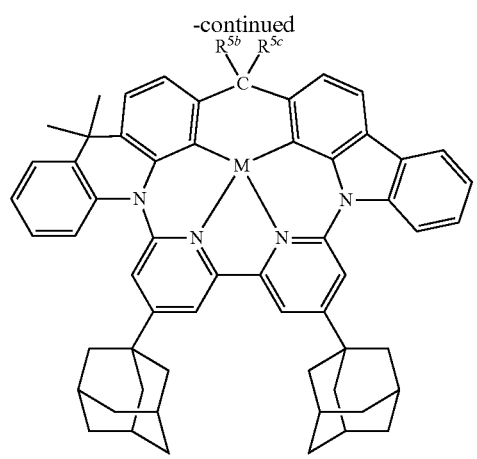
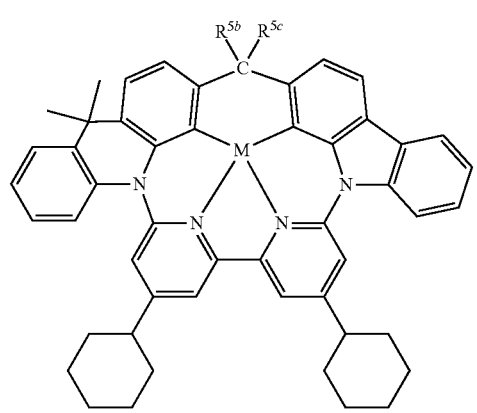
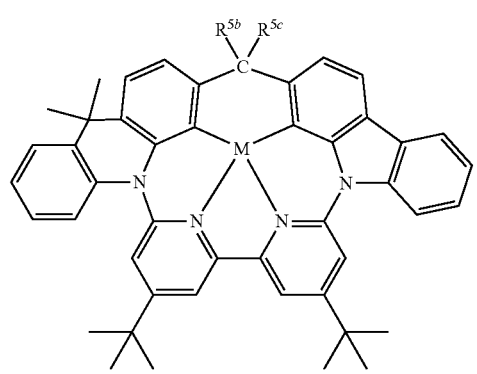
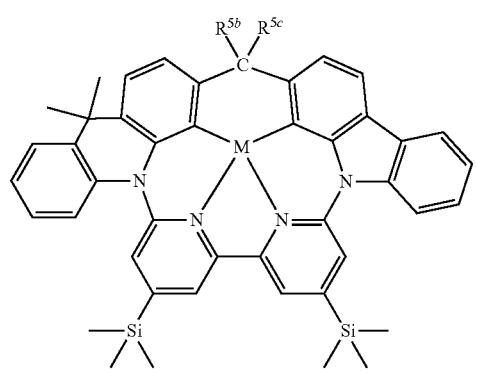

-continued
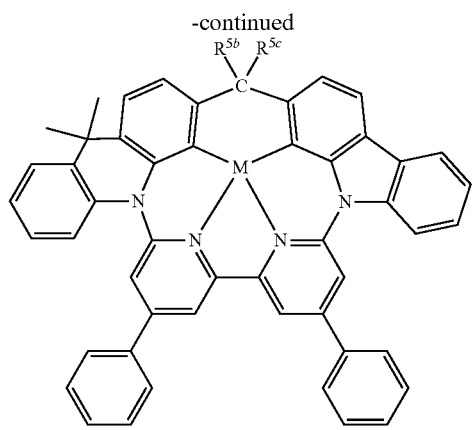
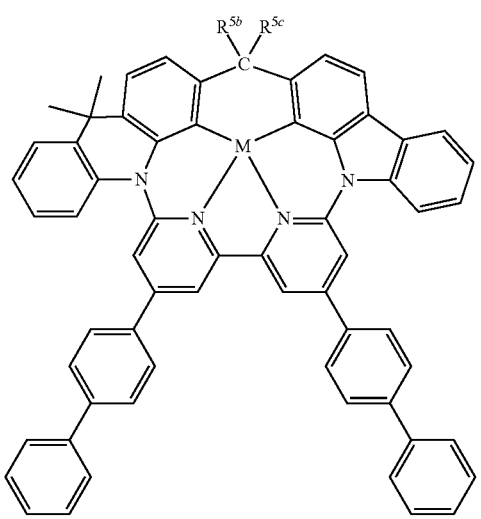
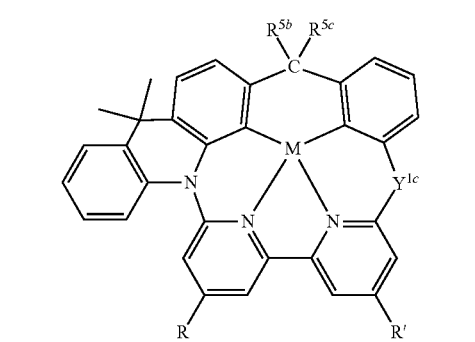
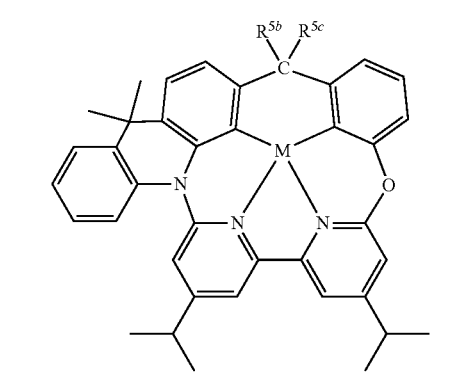
-continued
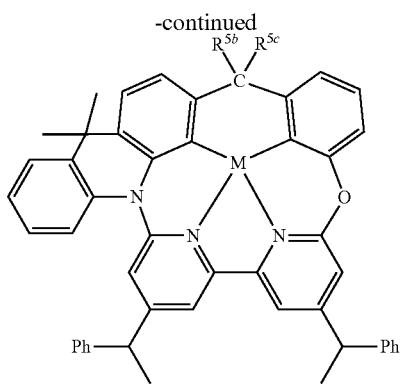
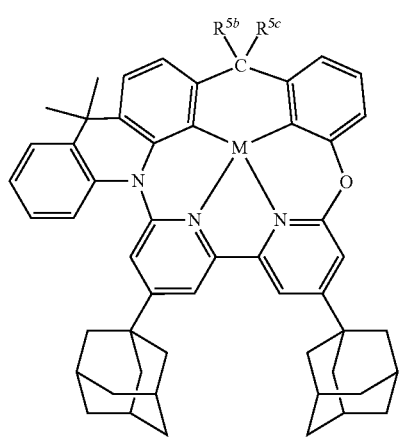
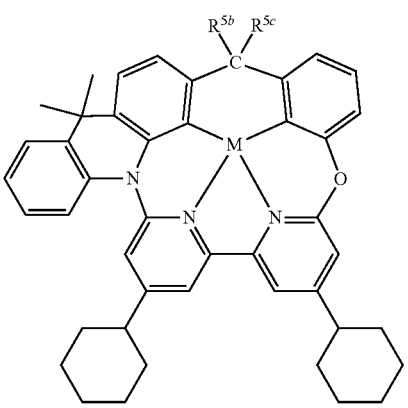
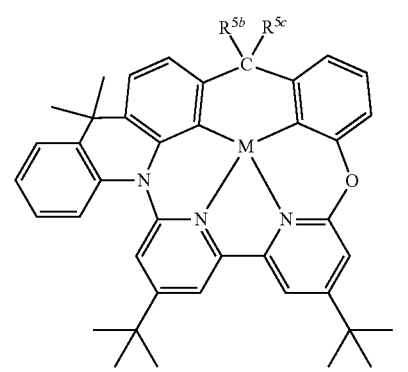

131
-continued
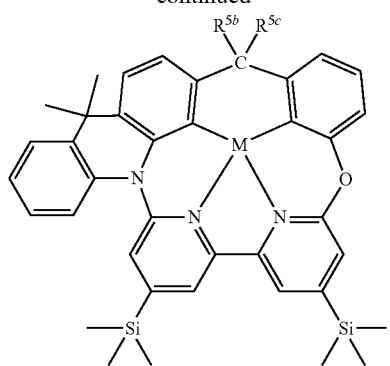
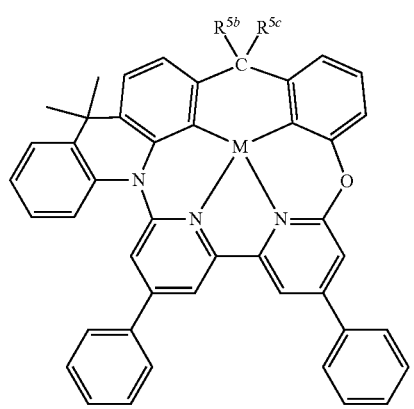
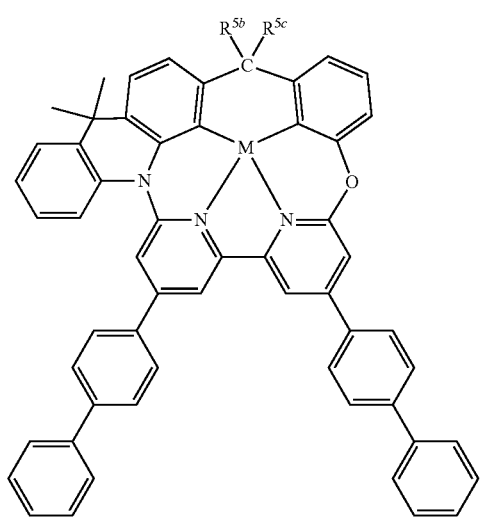
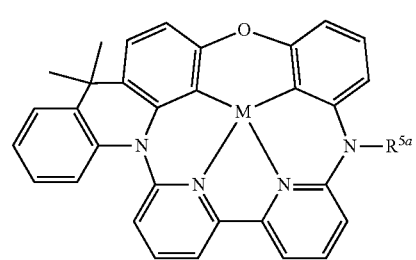
132
-continued
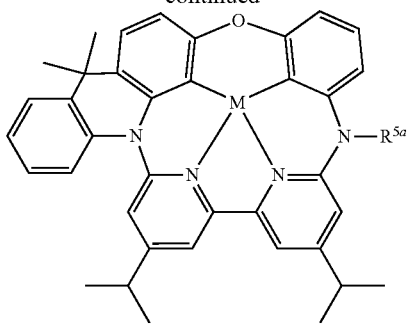
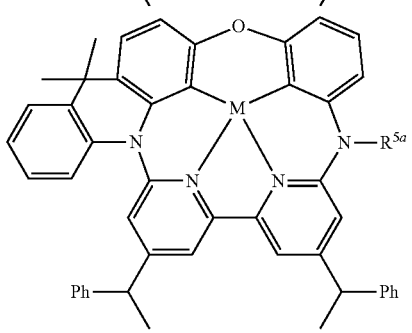
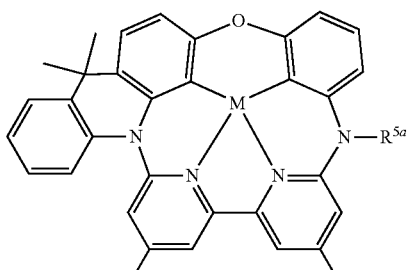
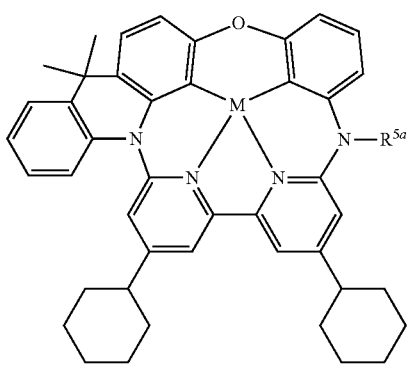
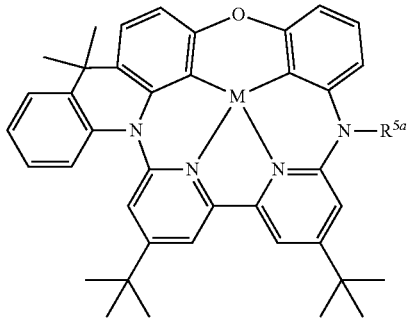

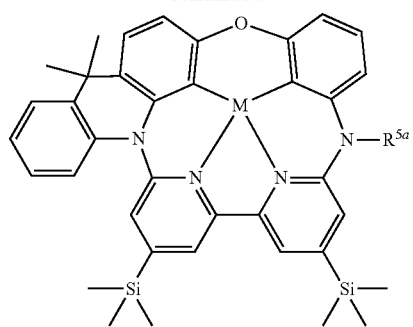
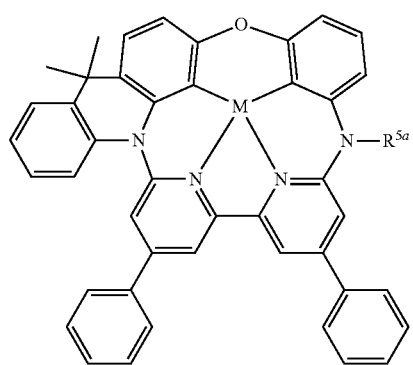
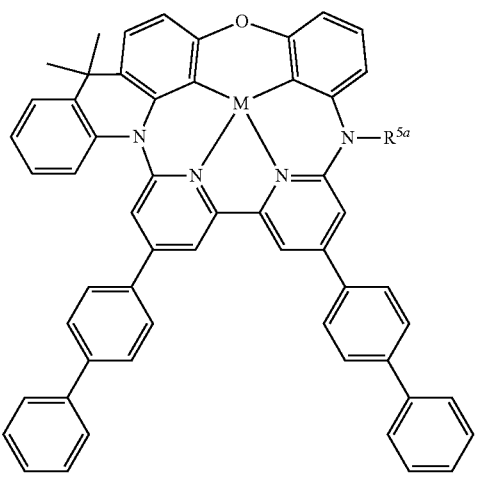
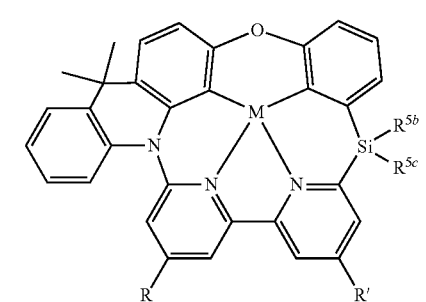
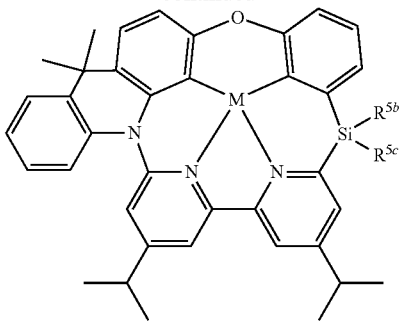
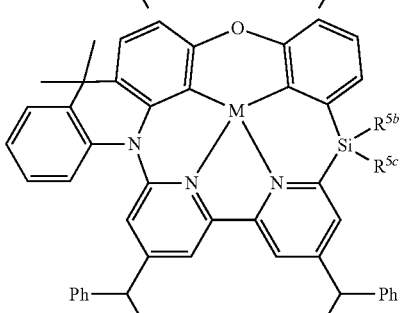
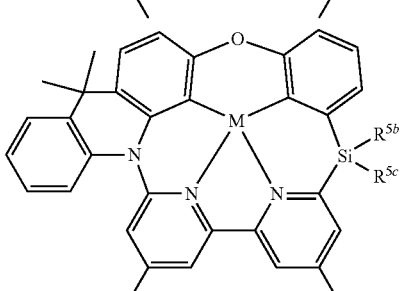
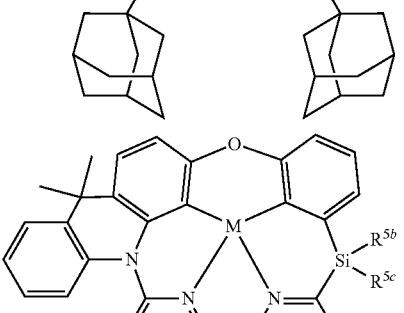
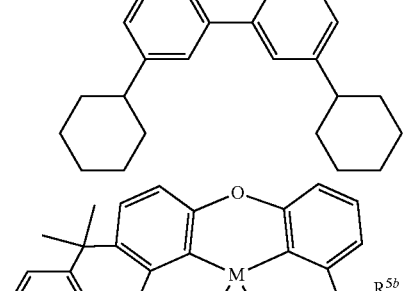
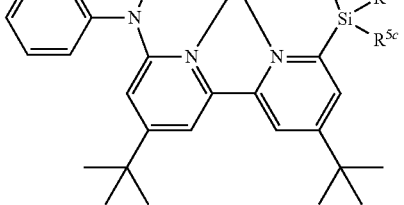

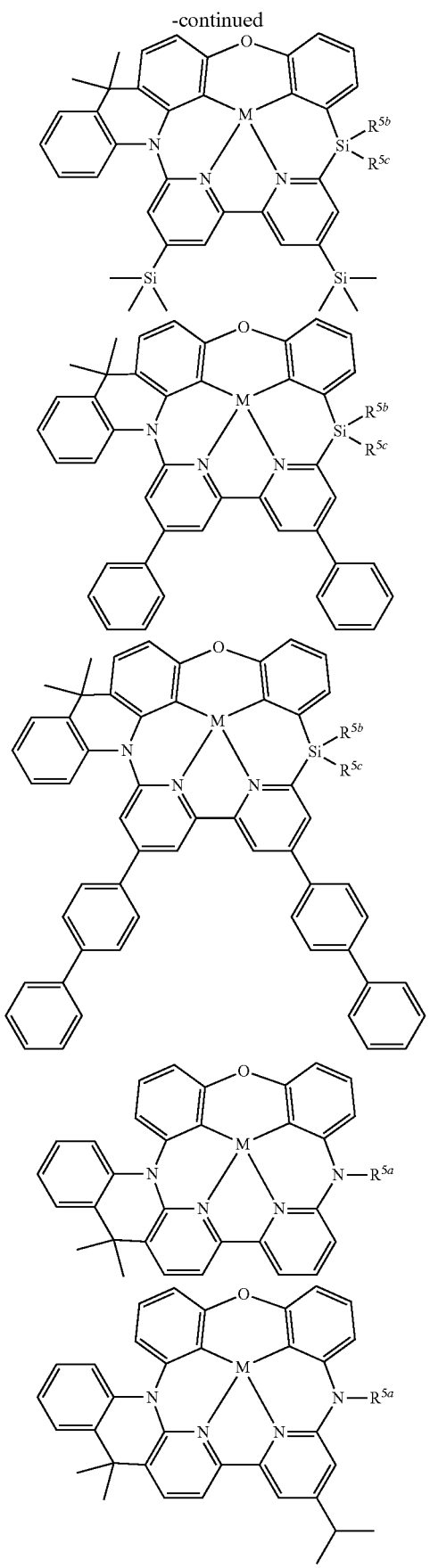
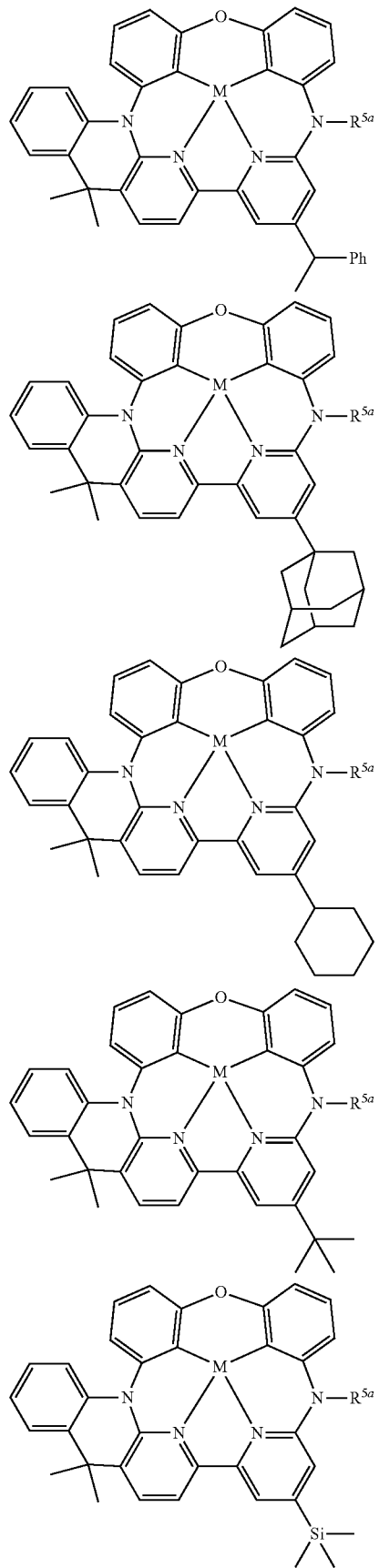

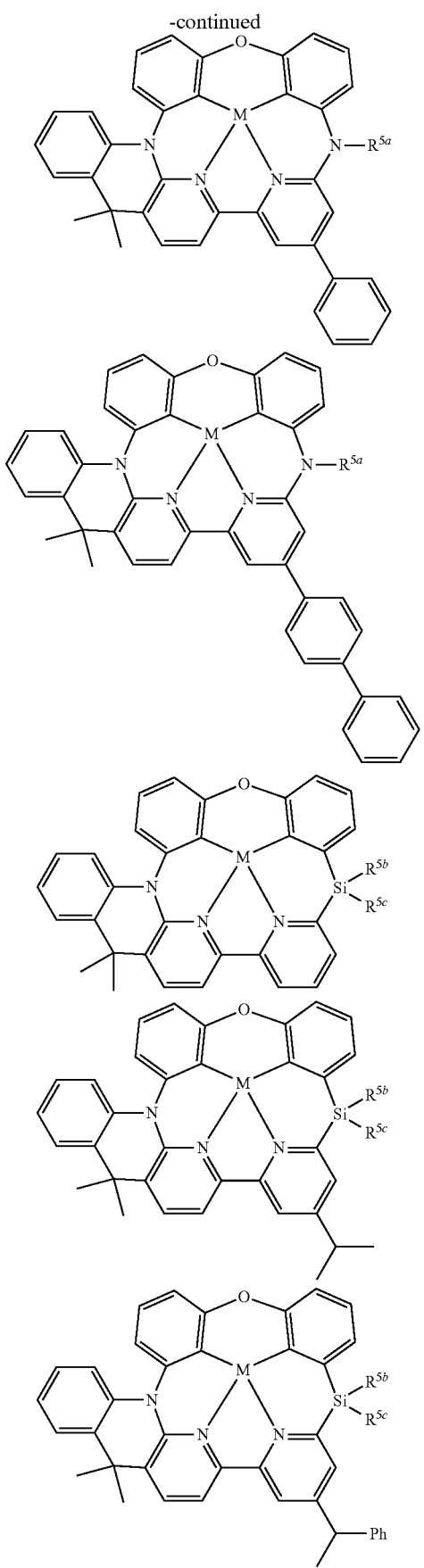
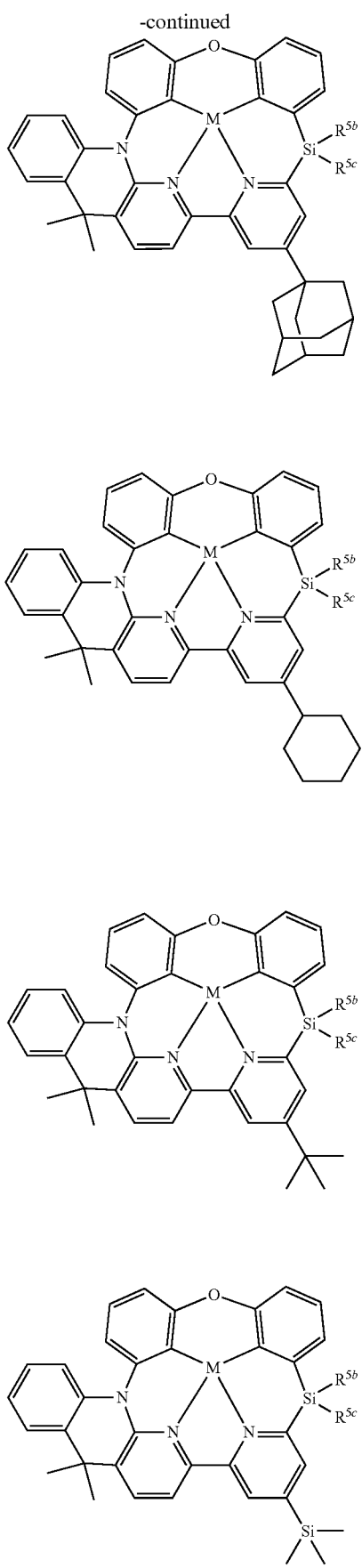

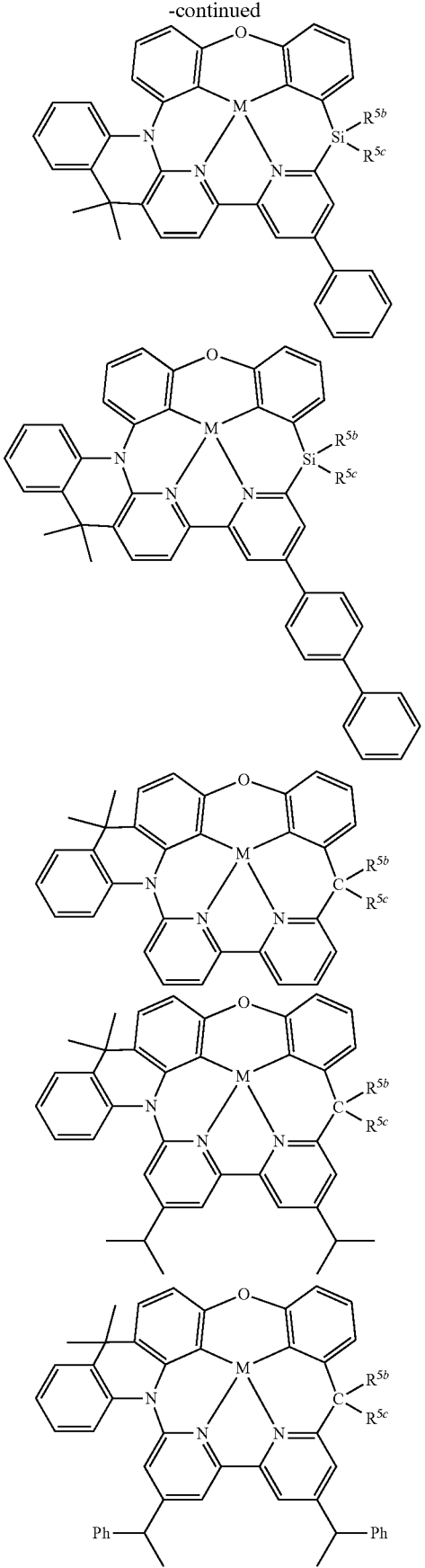
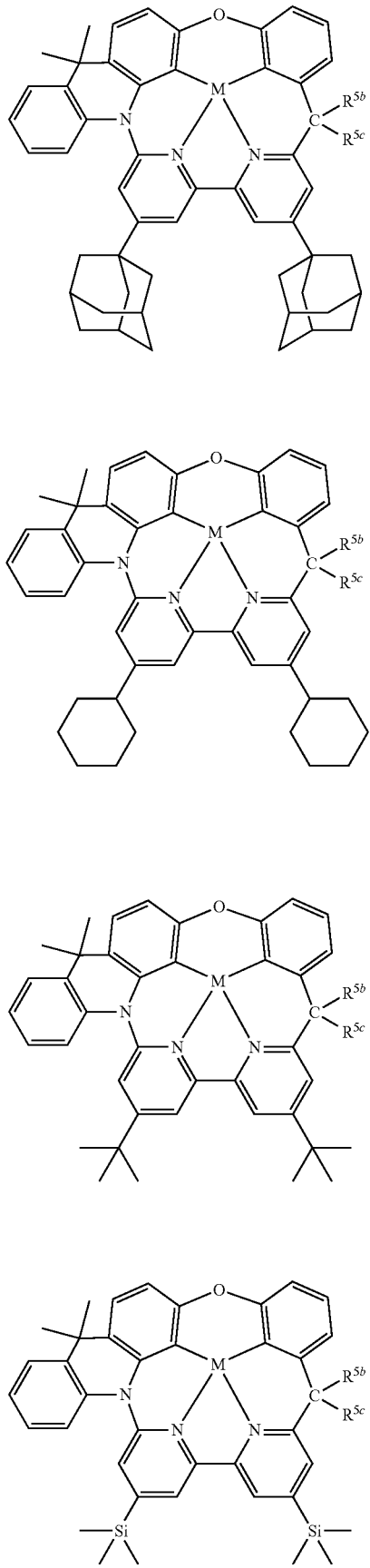

141
-continued
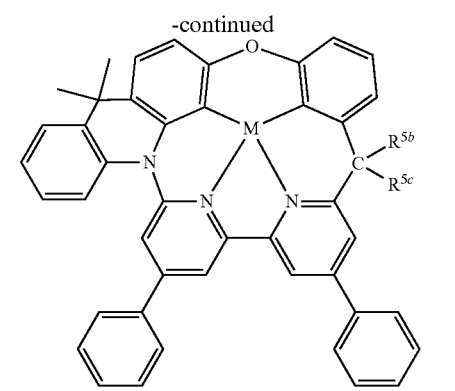
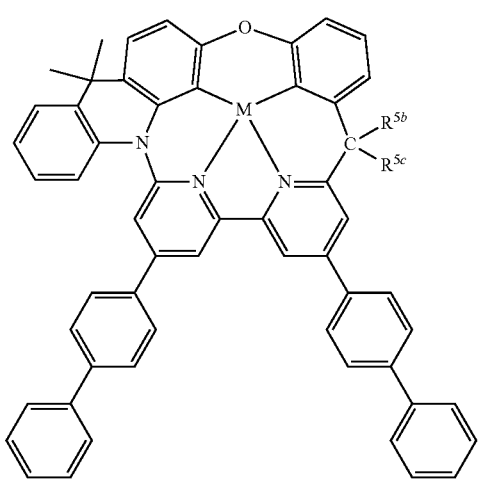
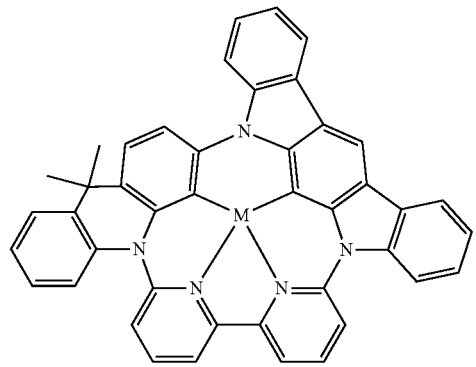
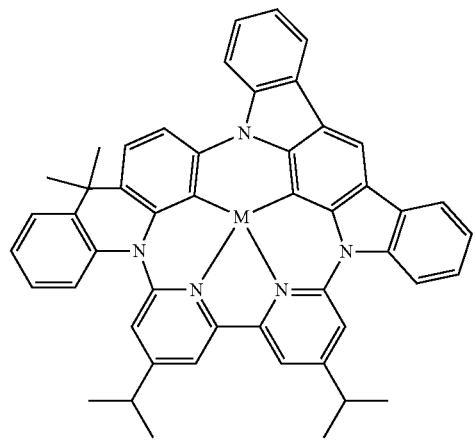
142
-continued
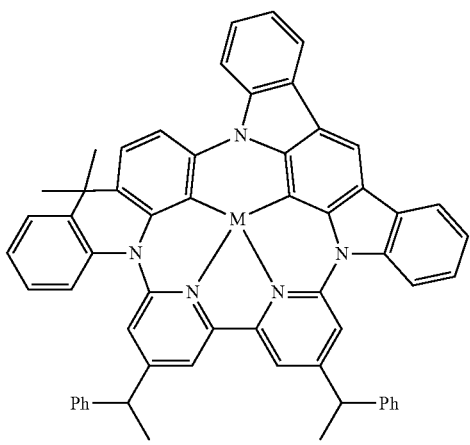
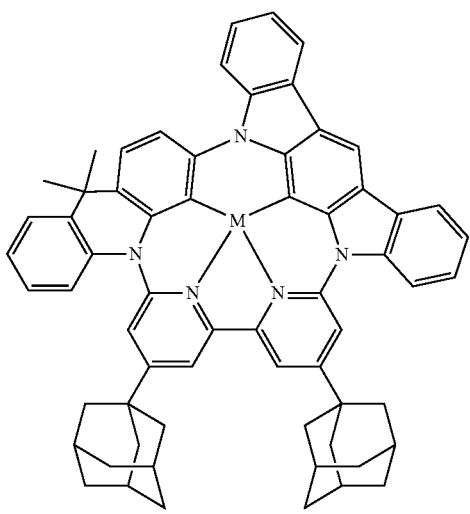
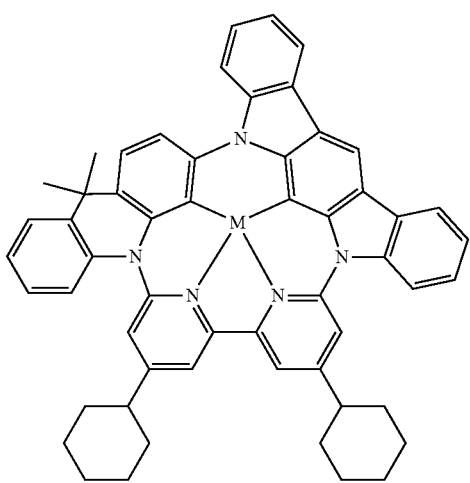

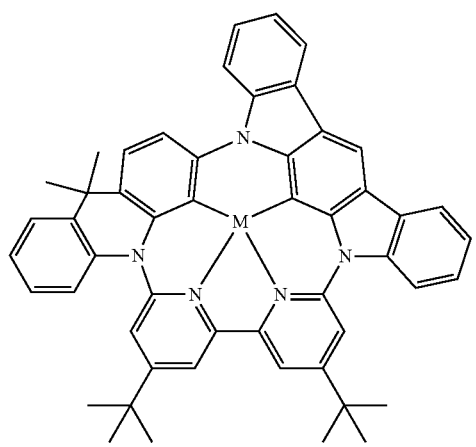
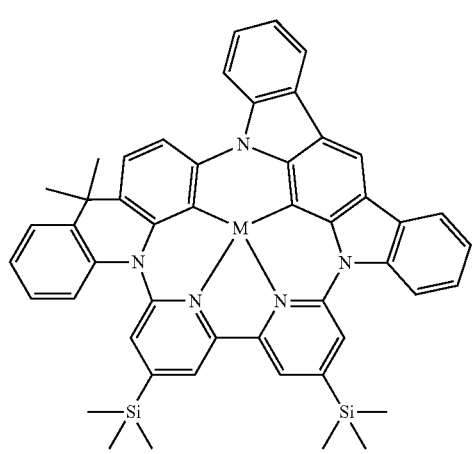
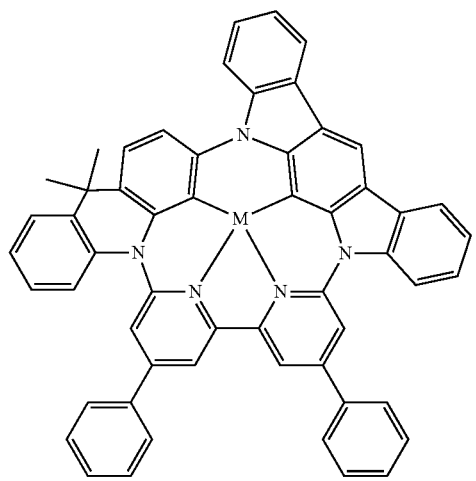
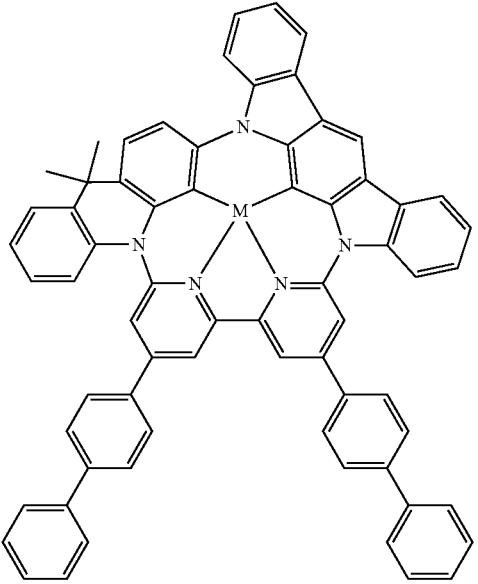
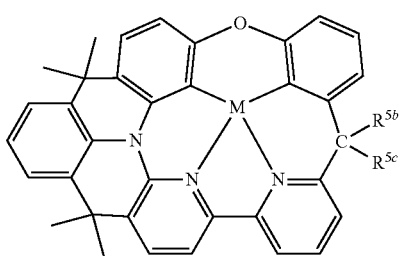
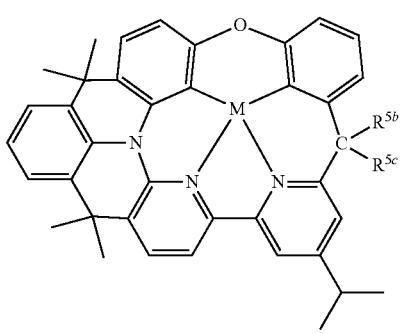
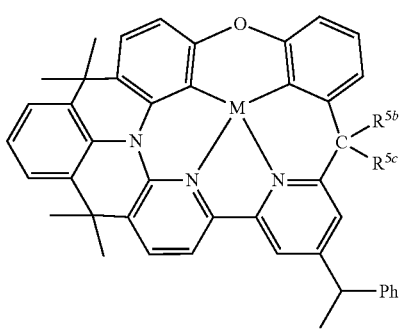

145
-continued
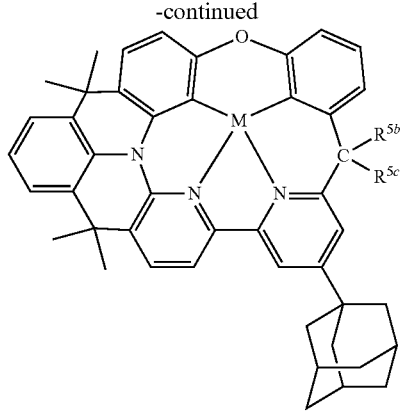
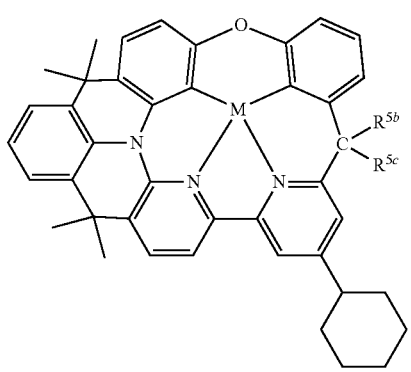
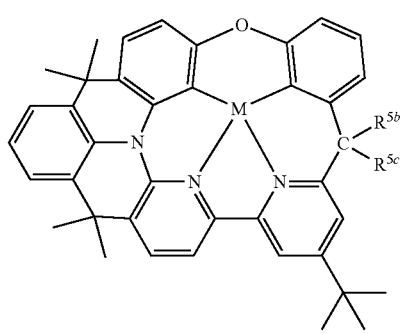
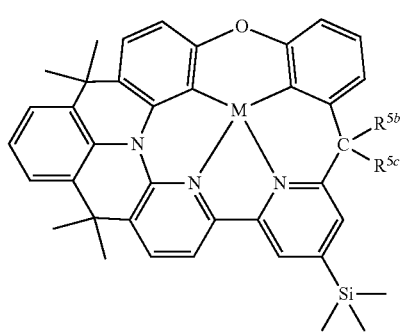
146
-continued
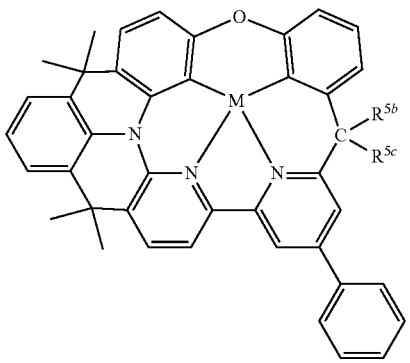
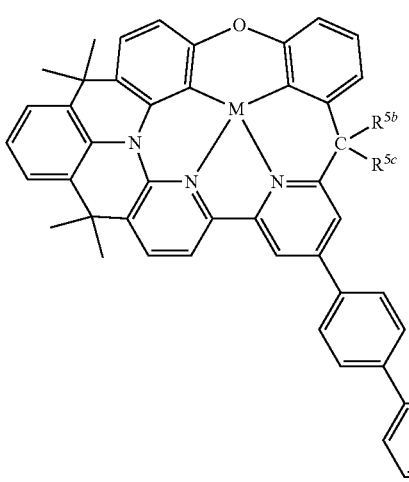
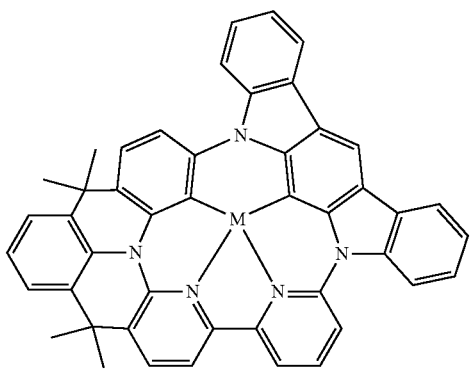
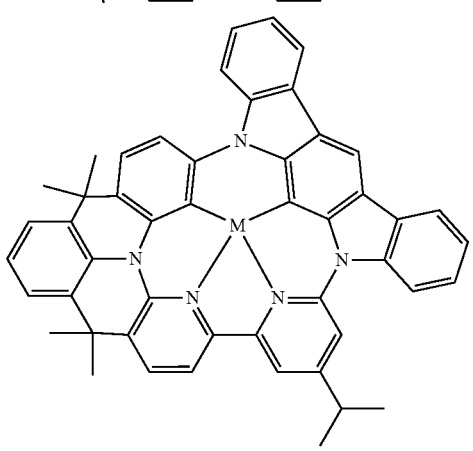

147
-continued
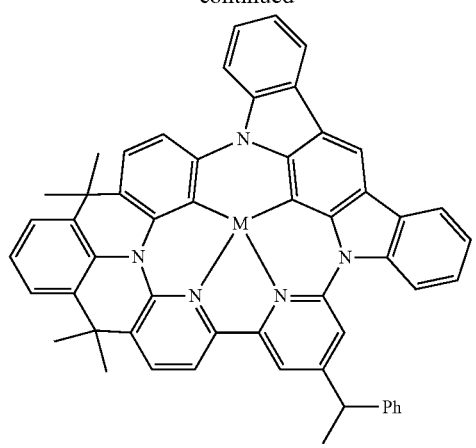
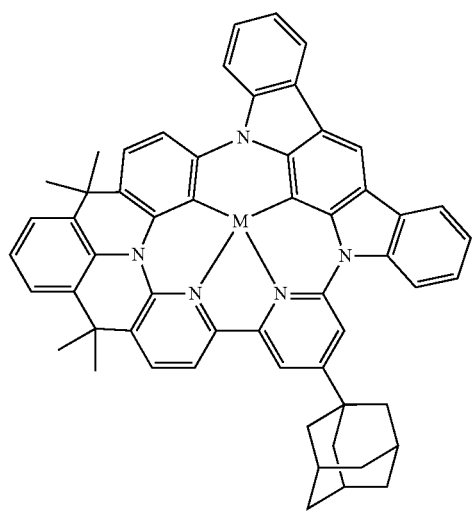
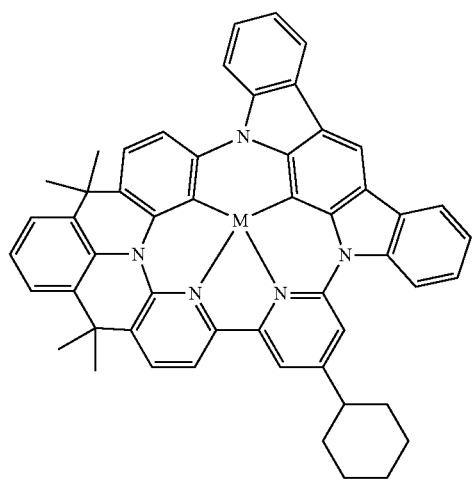
148
-continued
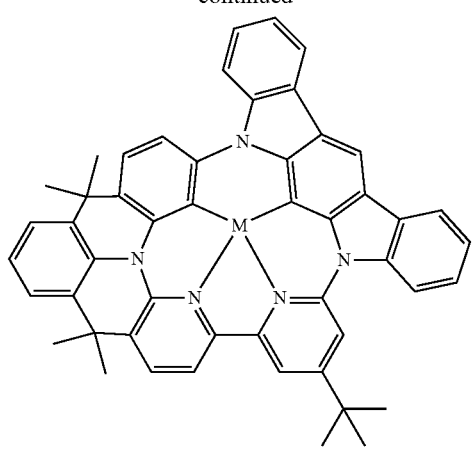
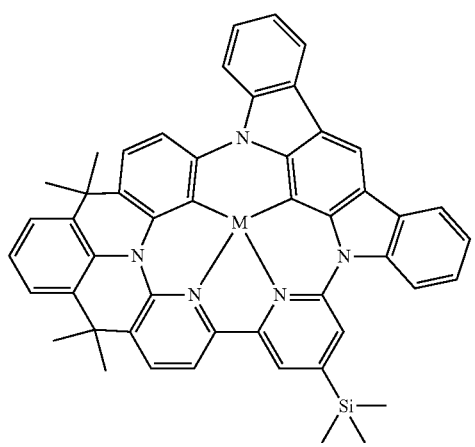
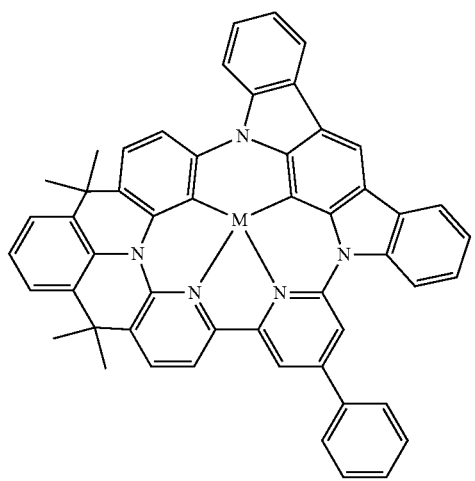

149
-continued
150
-continued
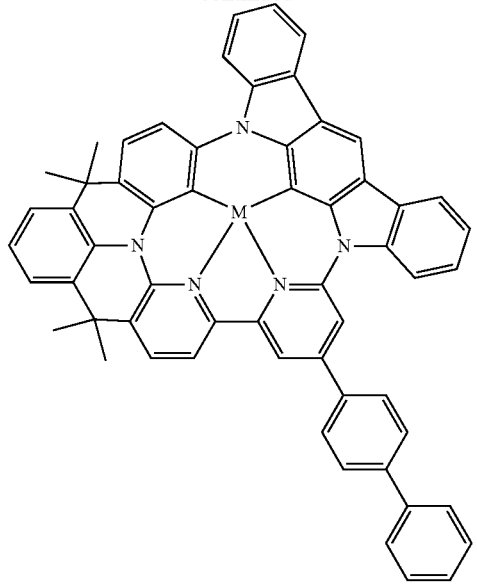
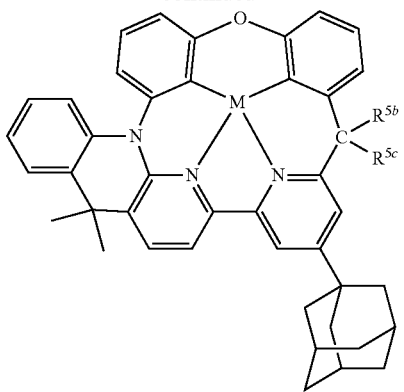
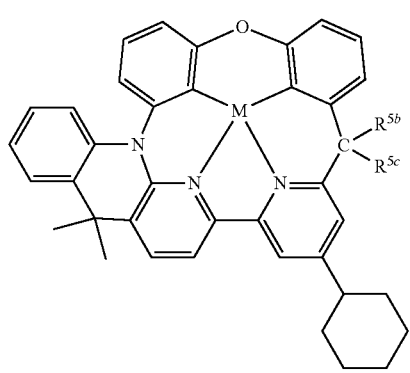
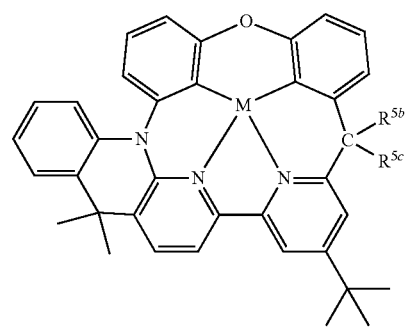
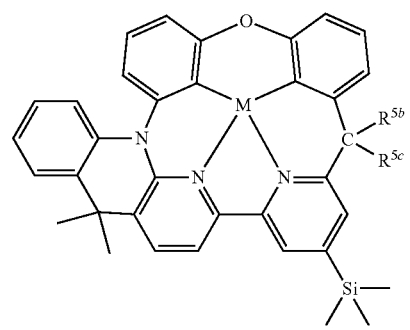

151
-continued
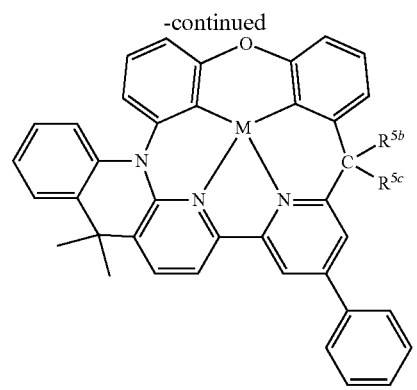
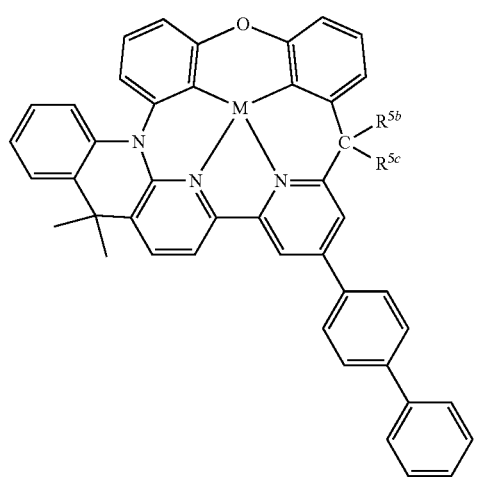
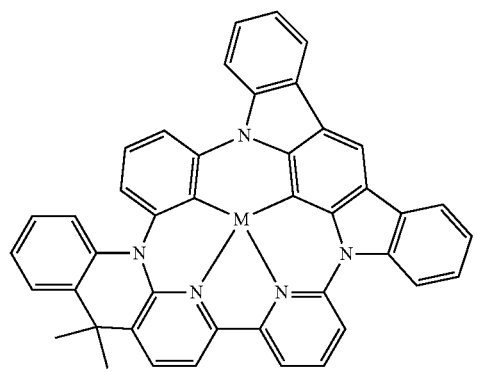
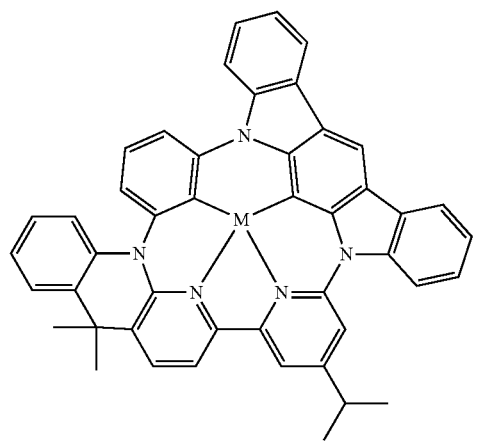
152
-continued
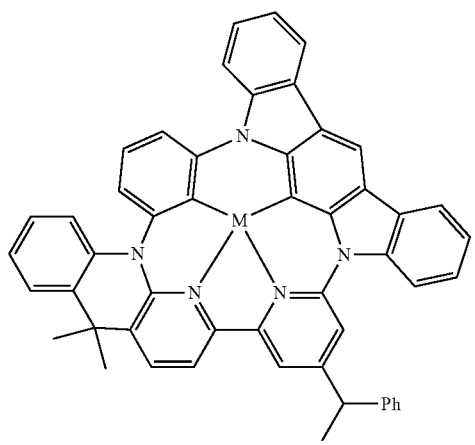
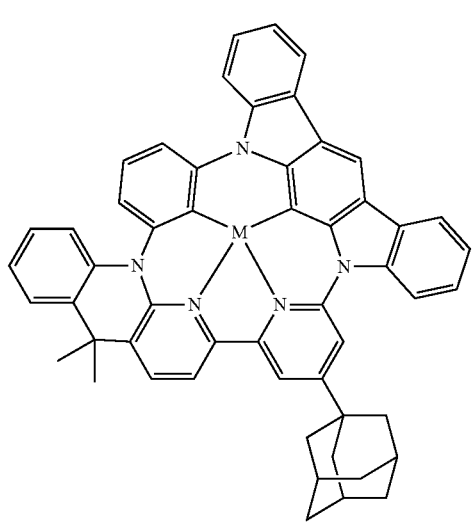
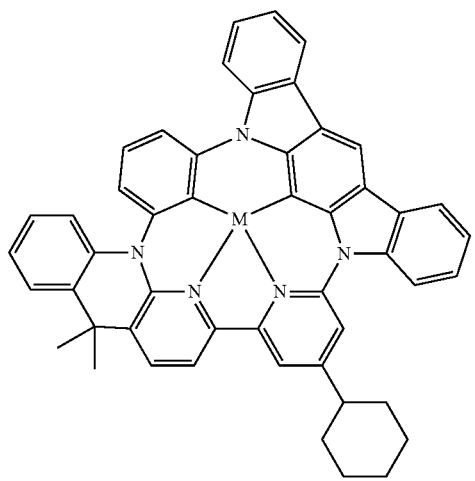

153
-continued
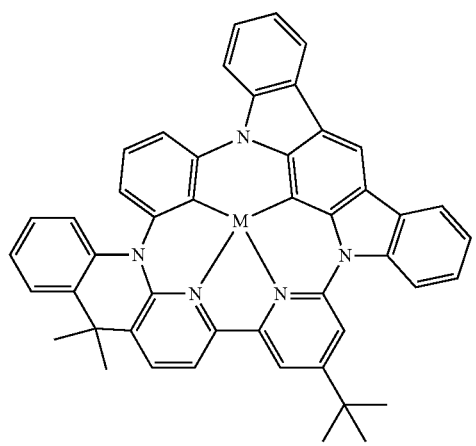
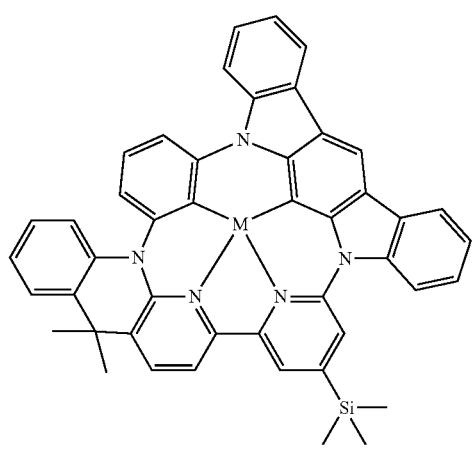
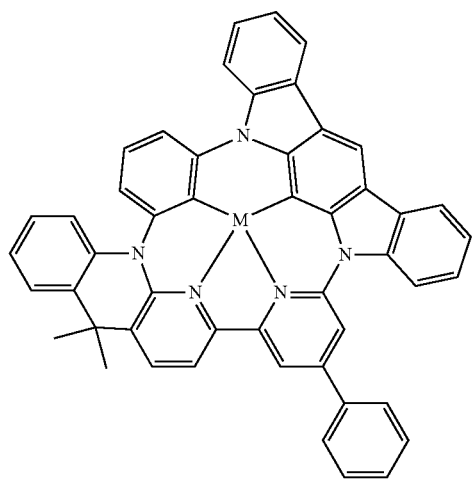
154
-continued
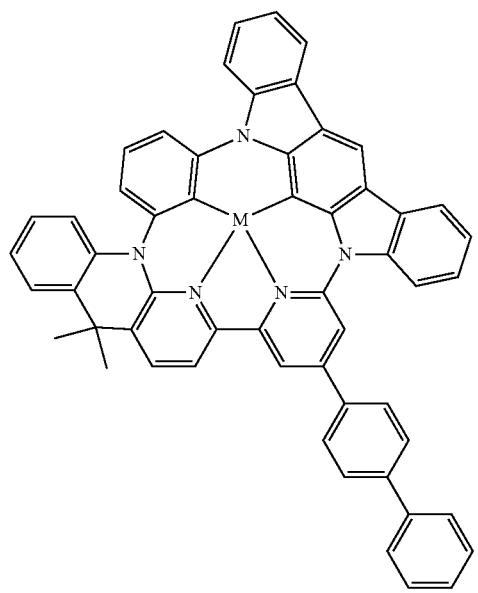
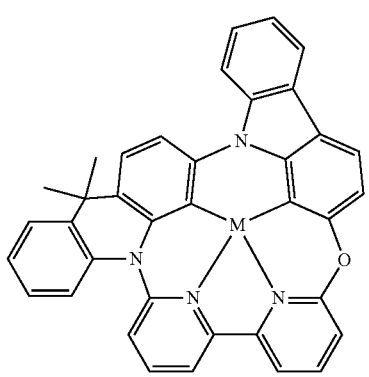
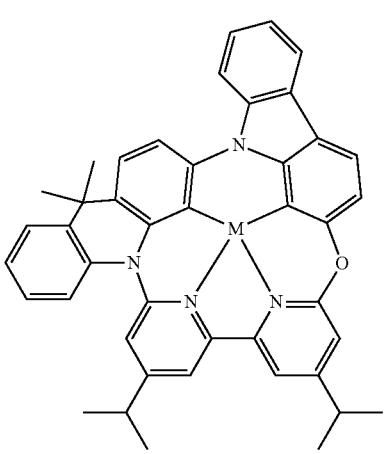

155
-continued
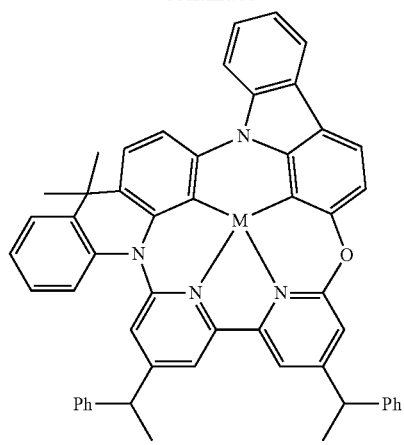
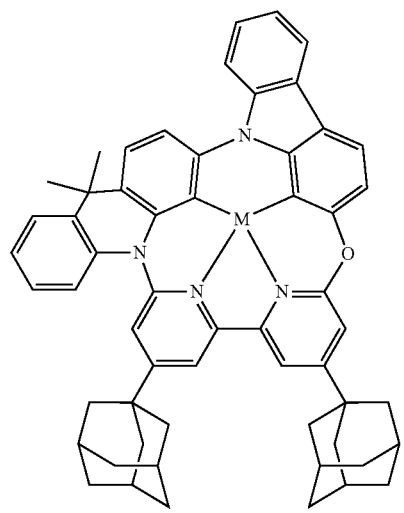
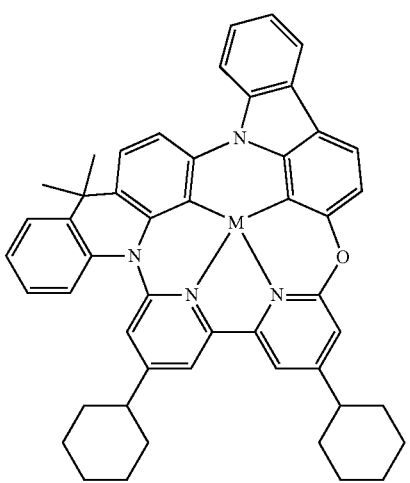
156
-continued
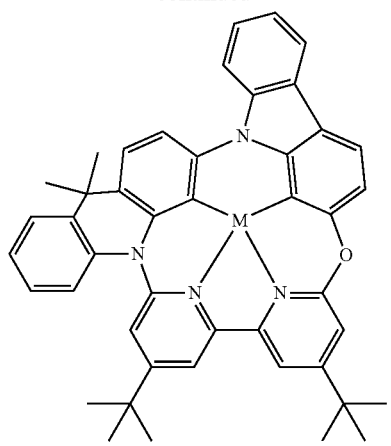
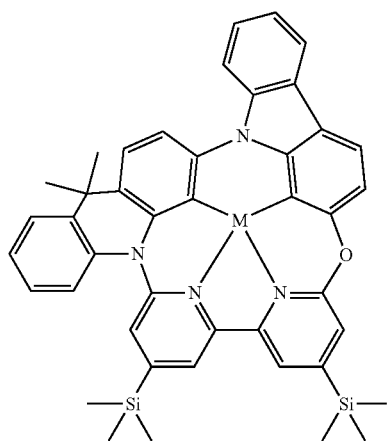
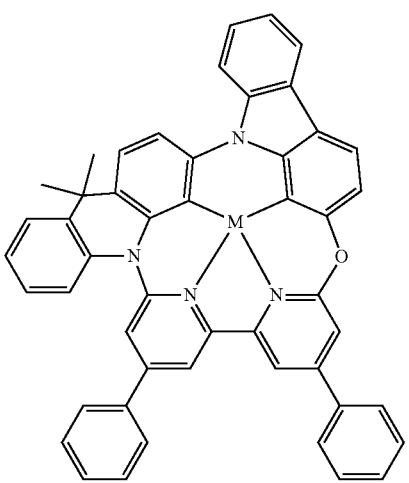

-continued
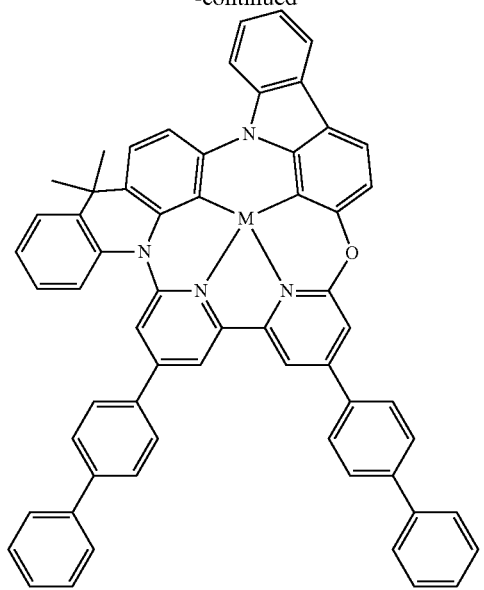
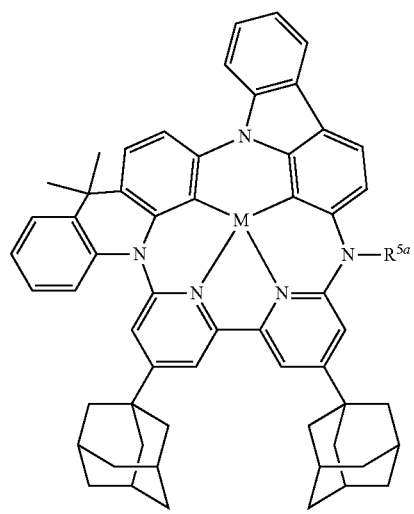
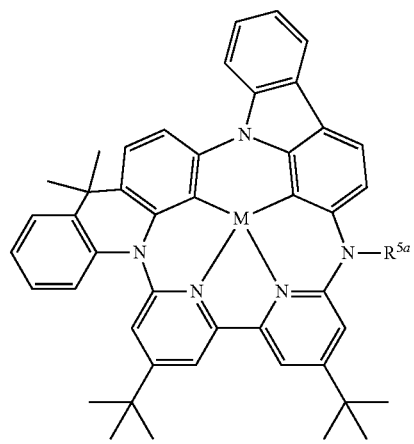
-continued
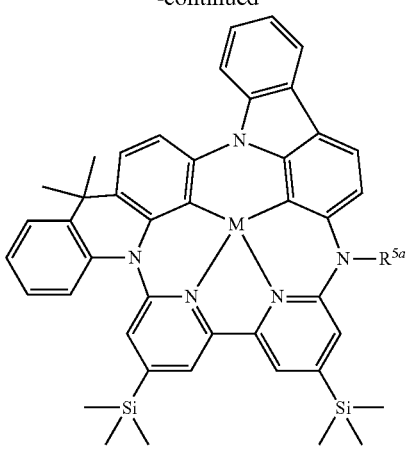
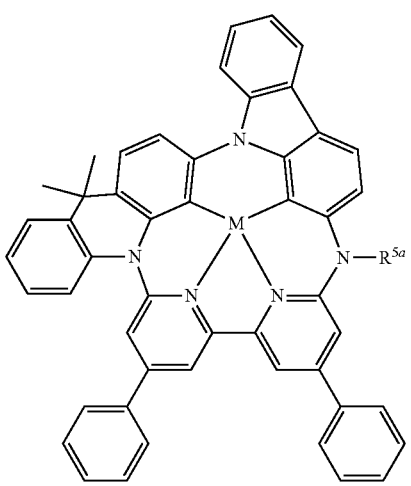
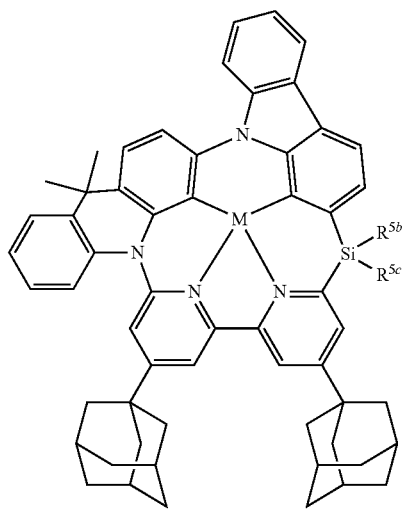

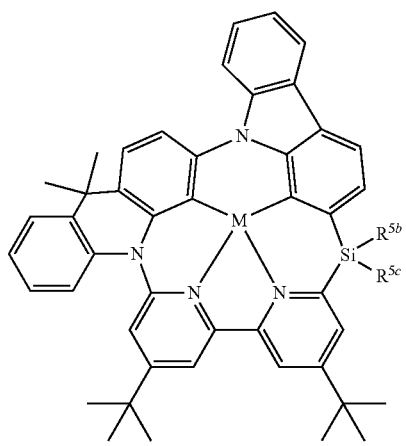
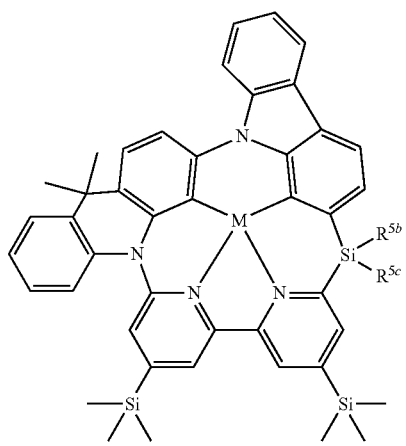
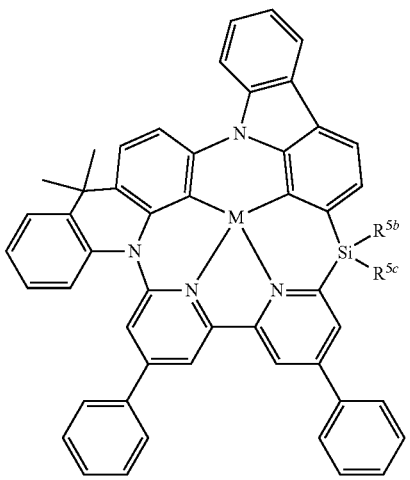
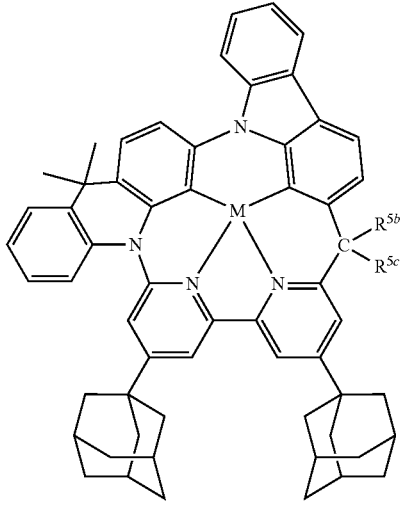
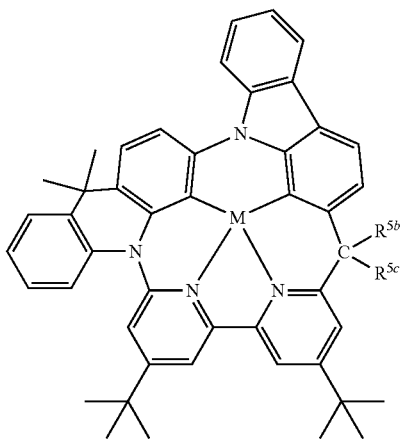
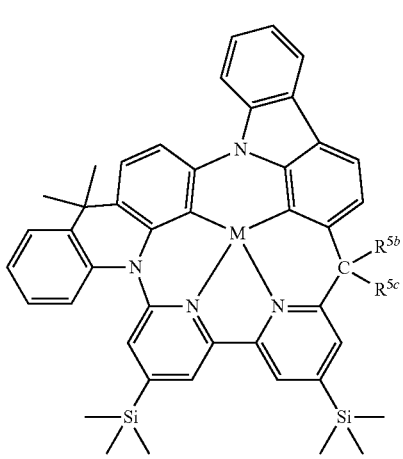

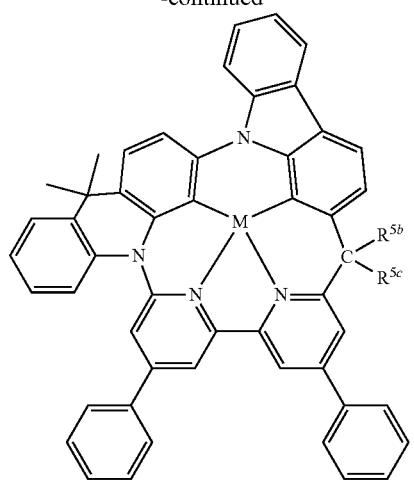
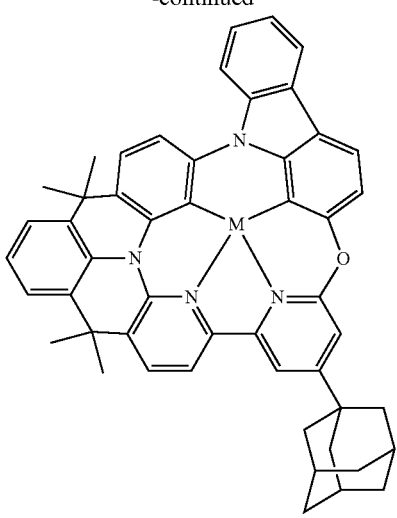

163
-continued
164
-continued
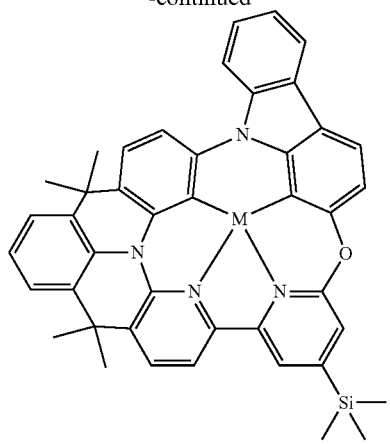
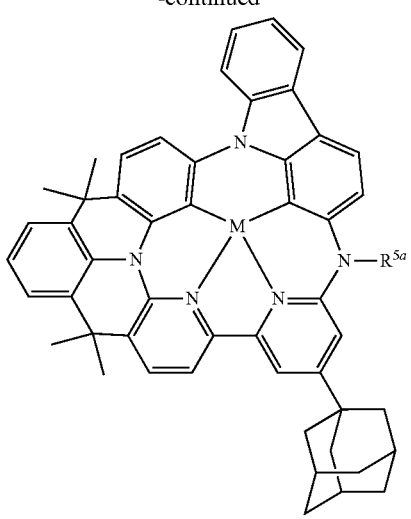
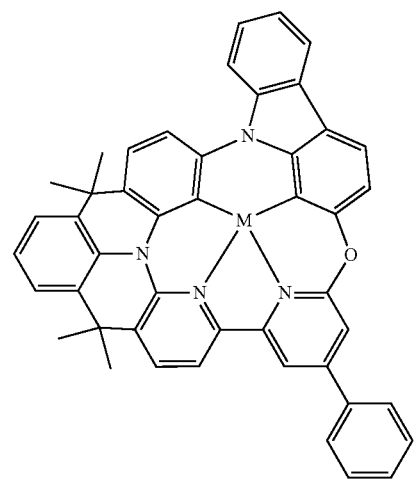
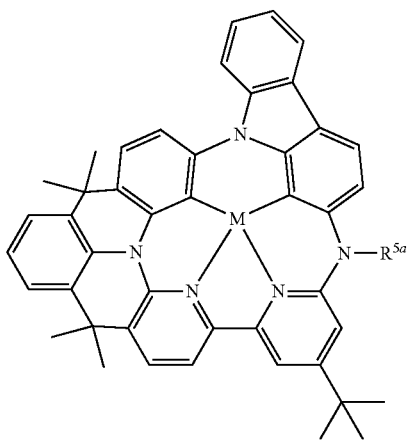
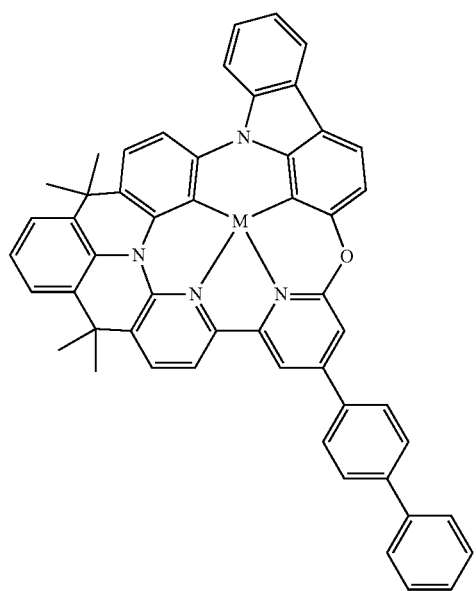
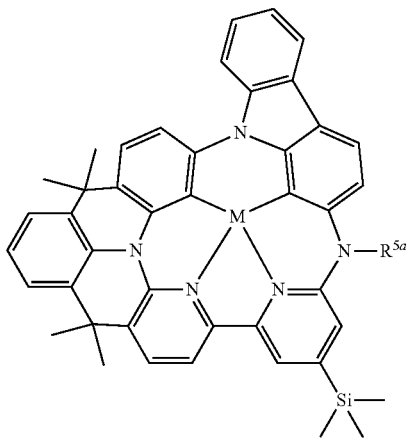

-continued
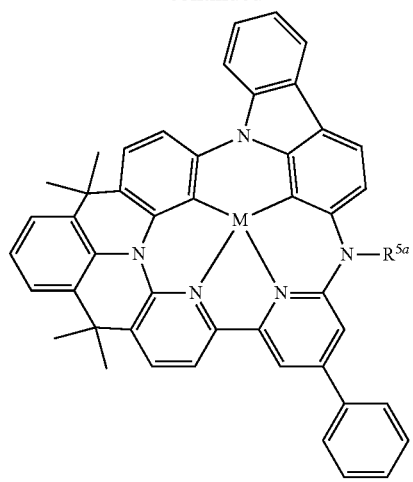
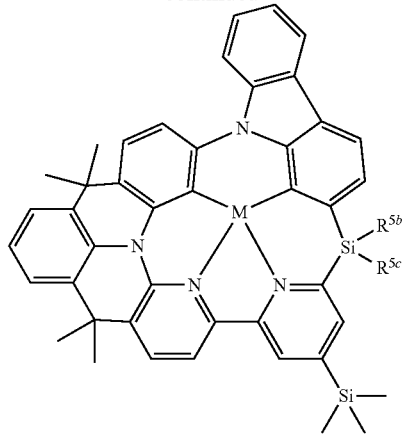
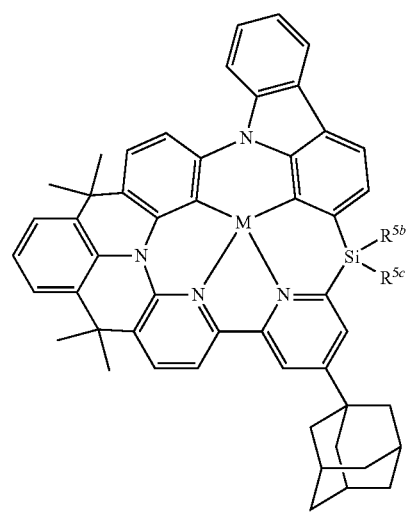
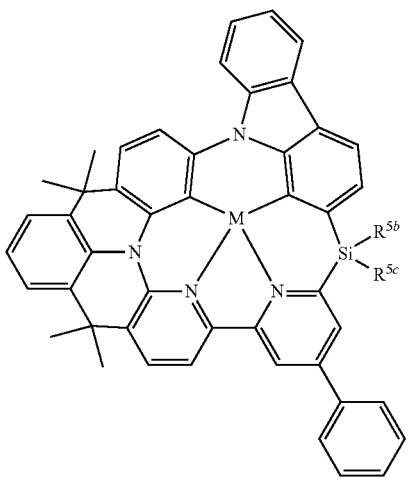
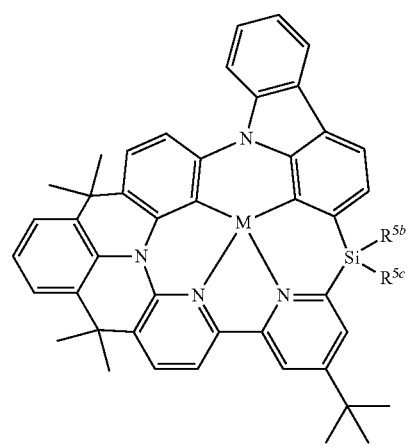
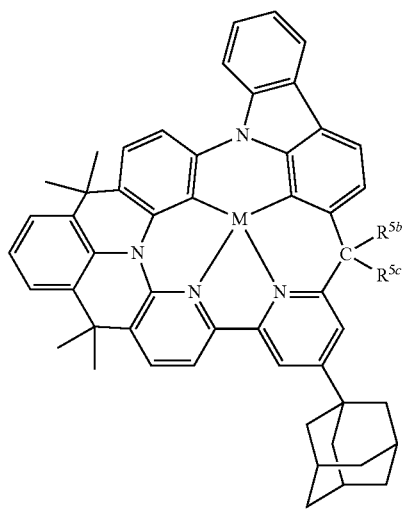

167
-continued
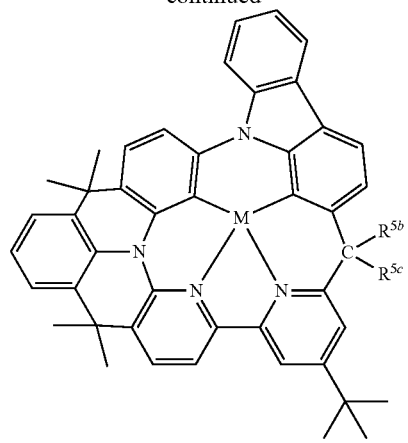
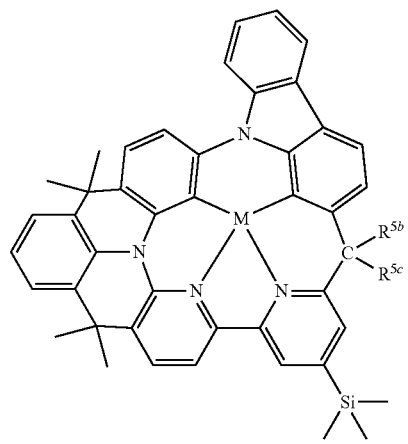
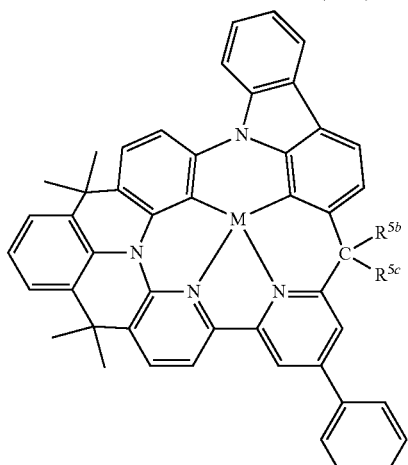
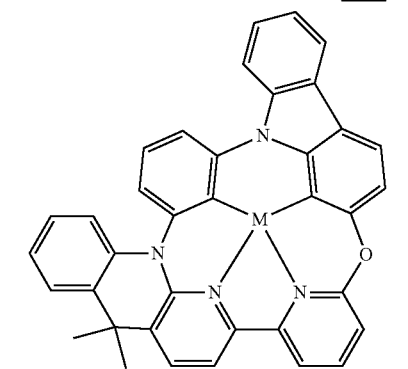
168
-continued
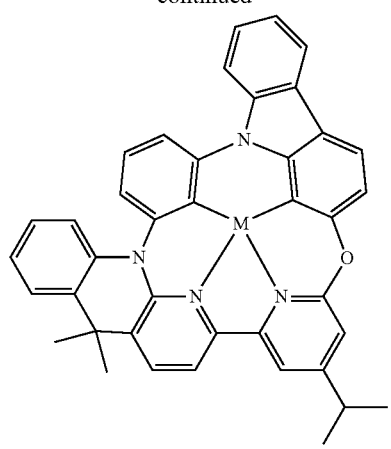
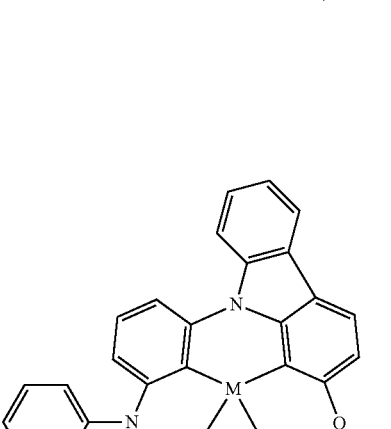
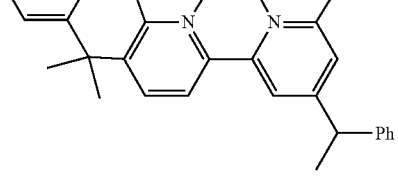
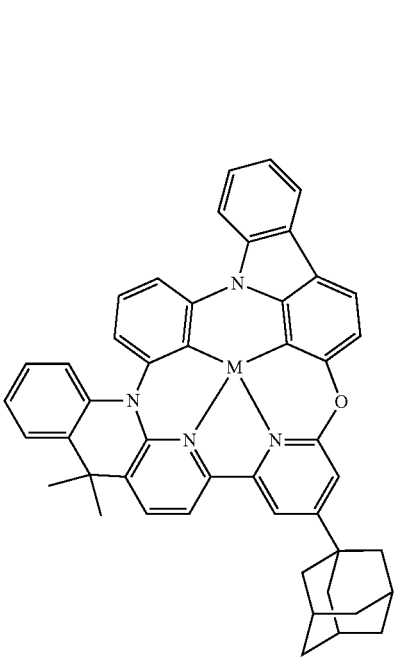

169
-continued
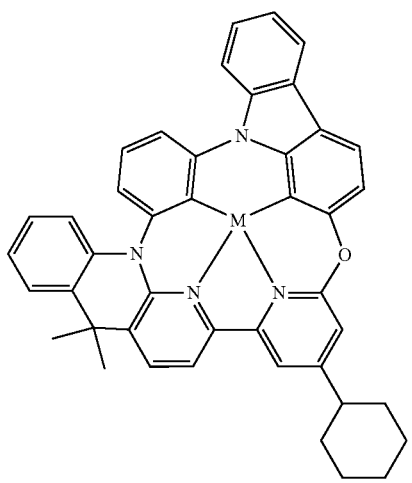
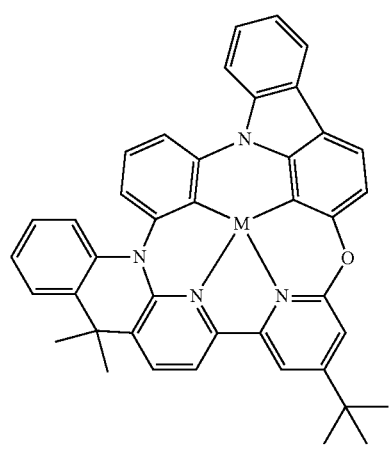
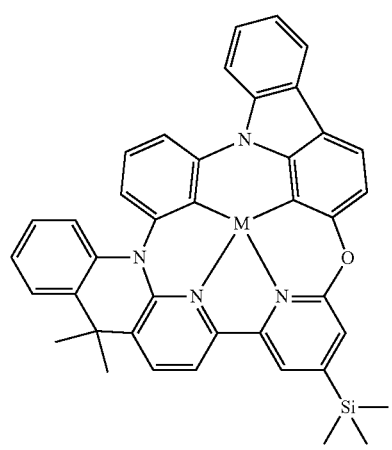
170
-continued
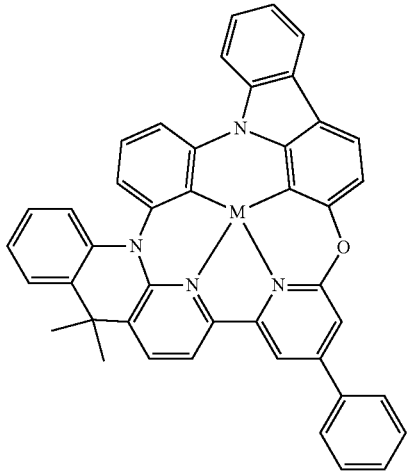
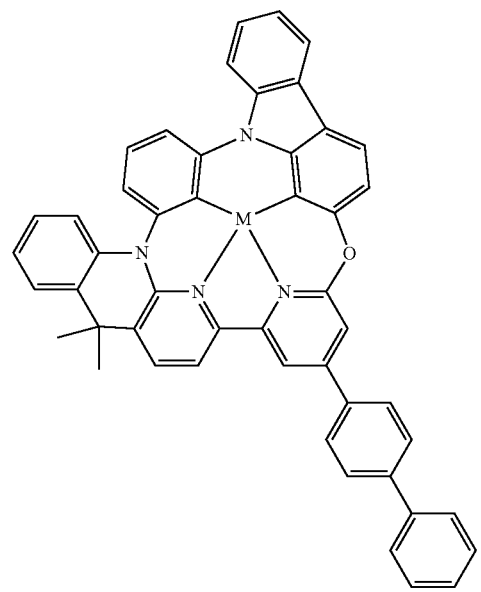
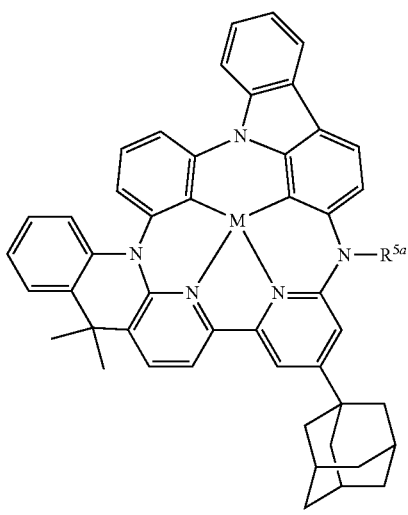

171
-continued
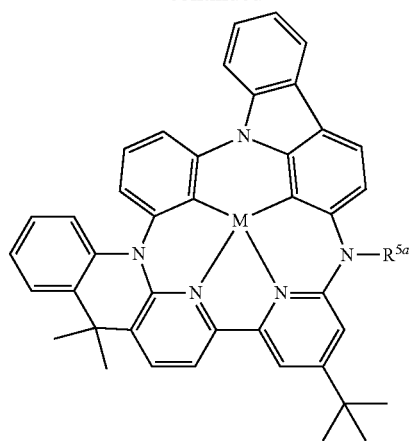
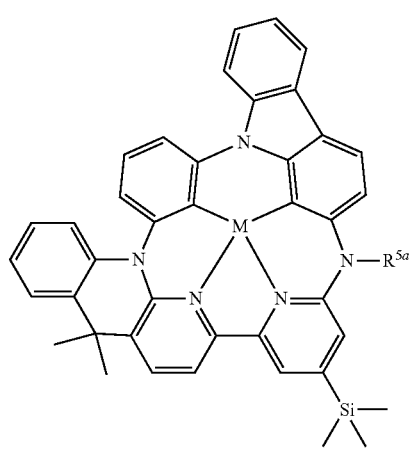
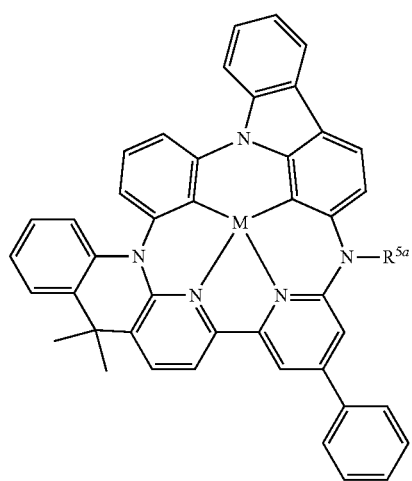
172
-continued
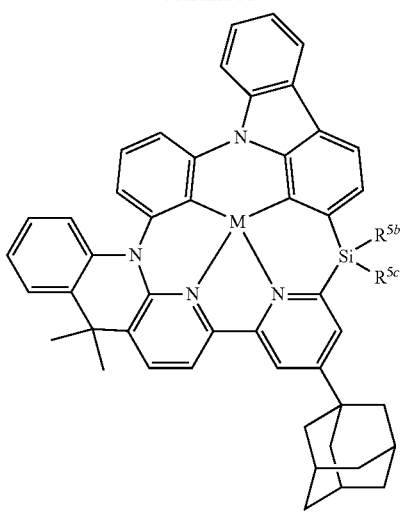
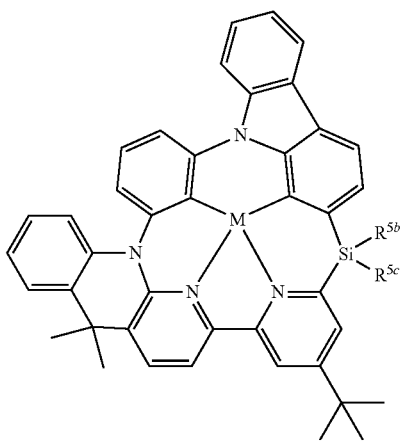
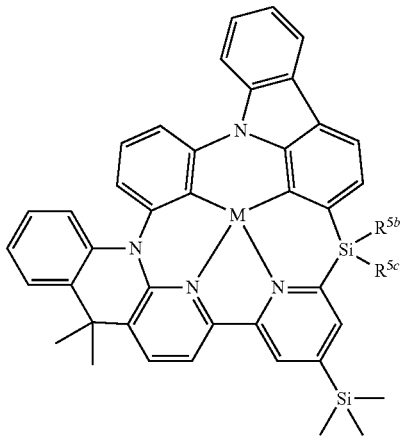

173
-continued
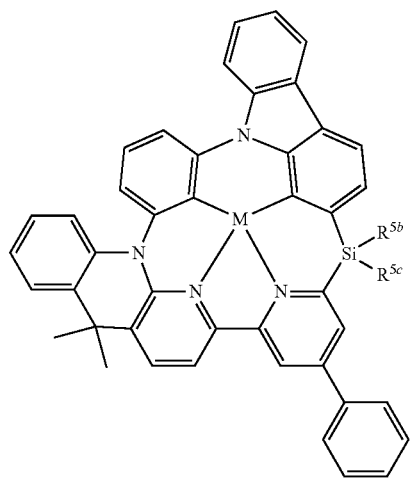
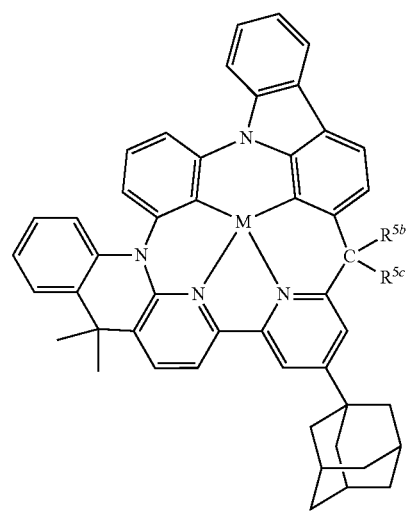
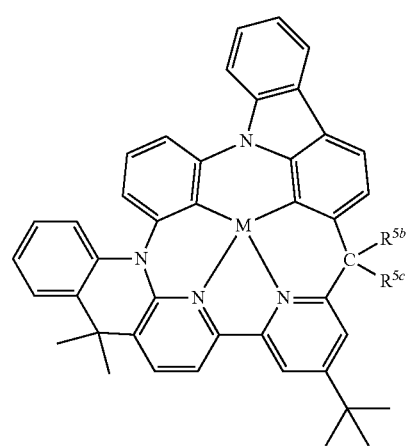
174
-continued
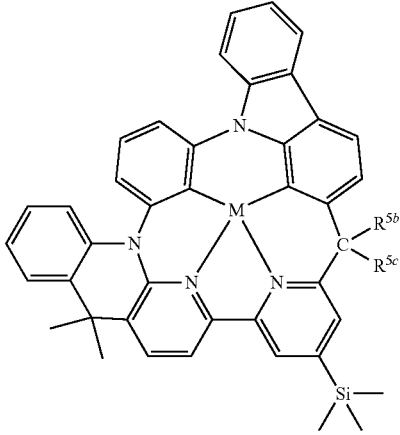
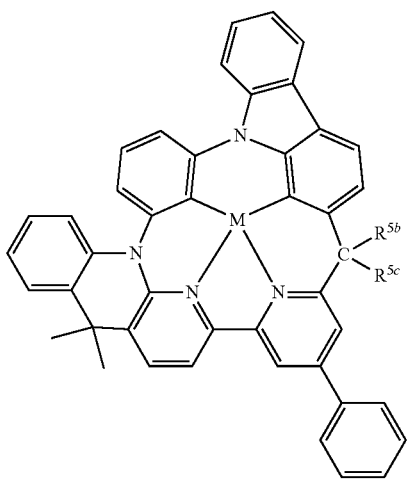
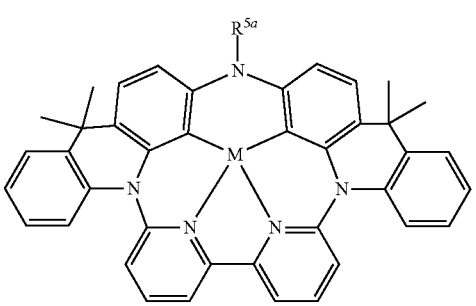
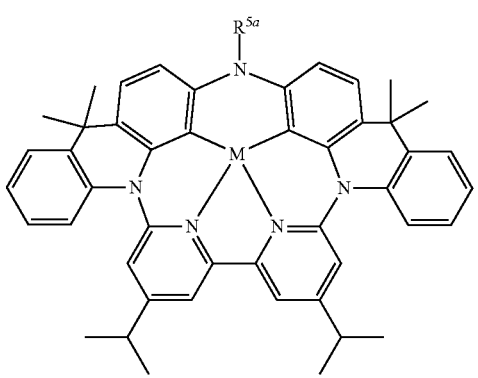

175
-continued
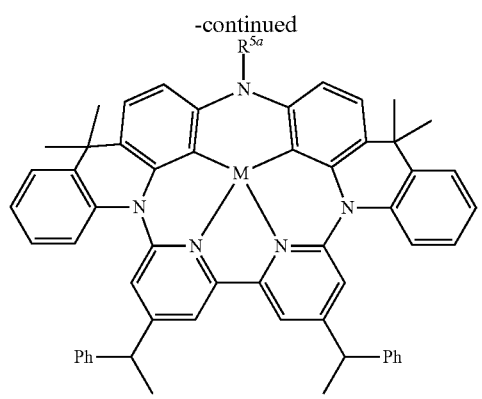
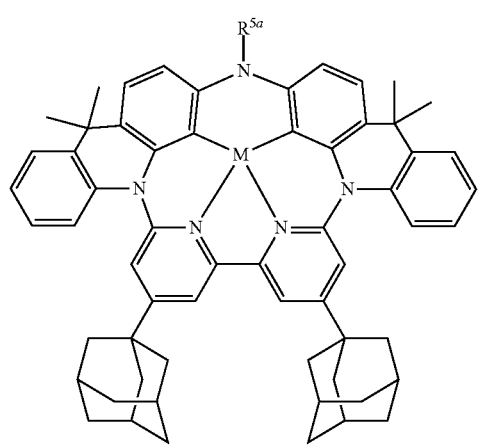
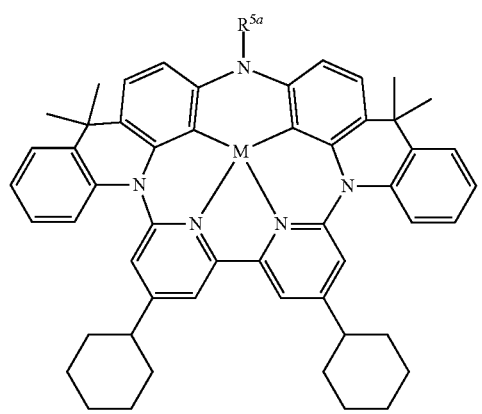
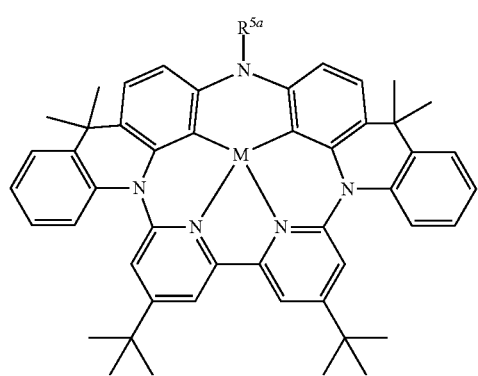
176
-continued
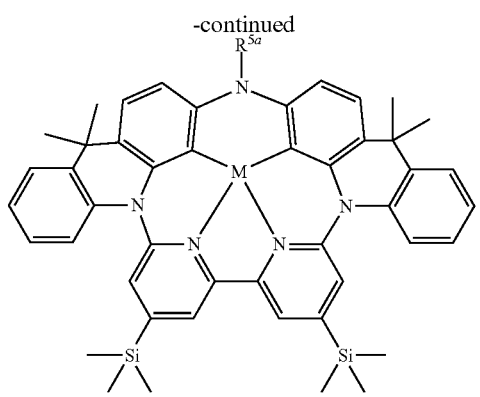
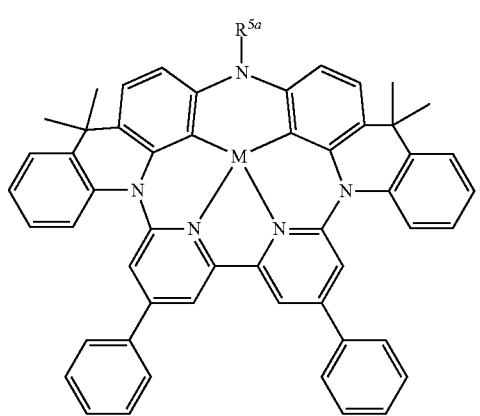
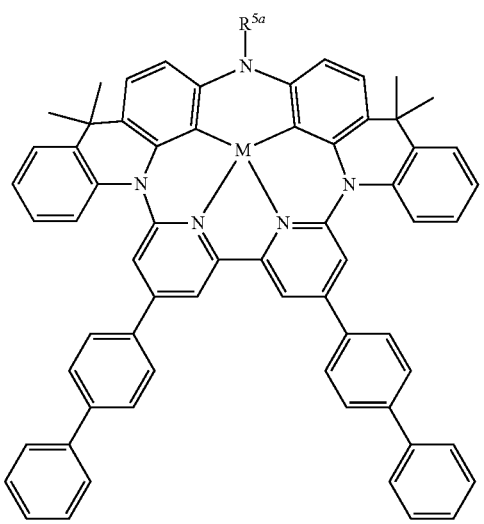
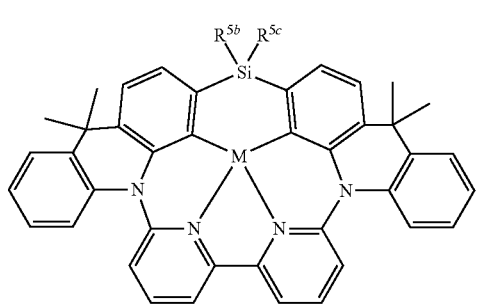

-continued
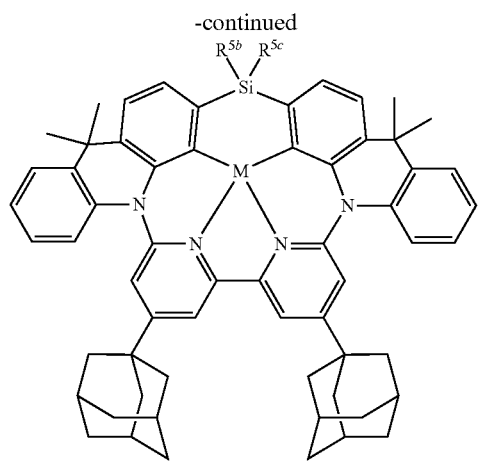
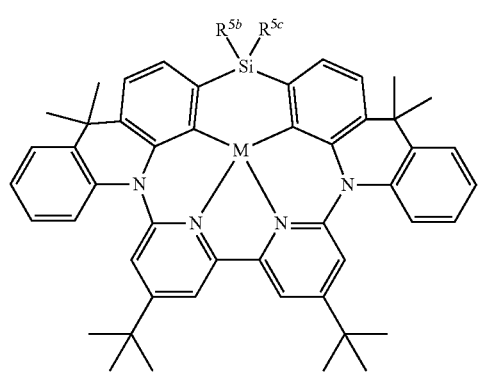
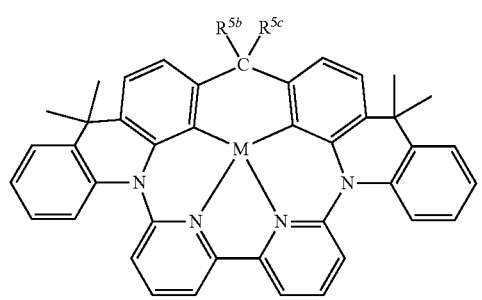
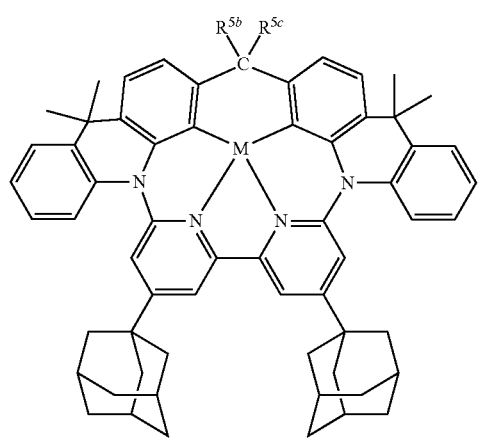
-continued
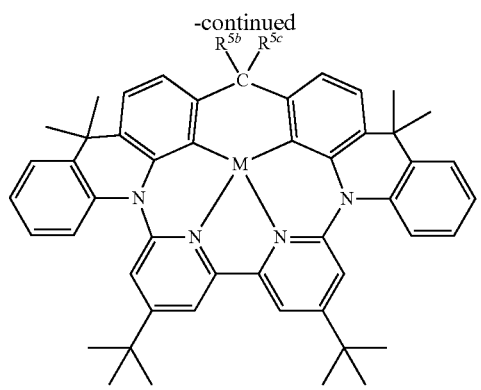
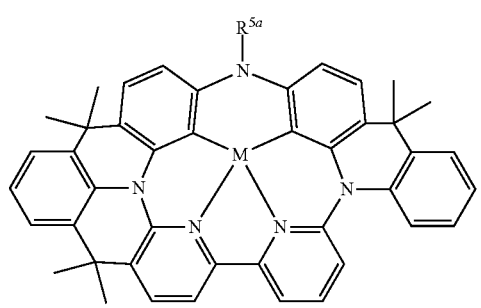
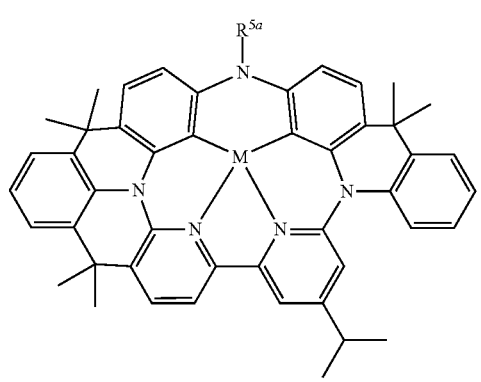
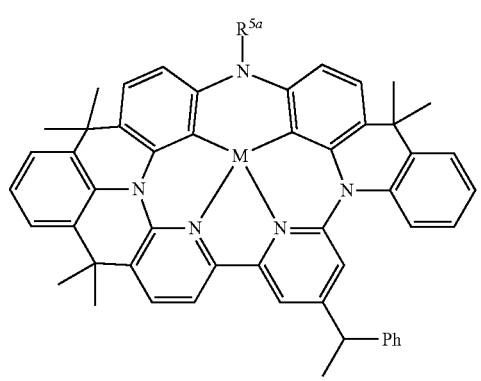

-continued
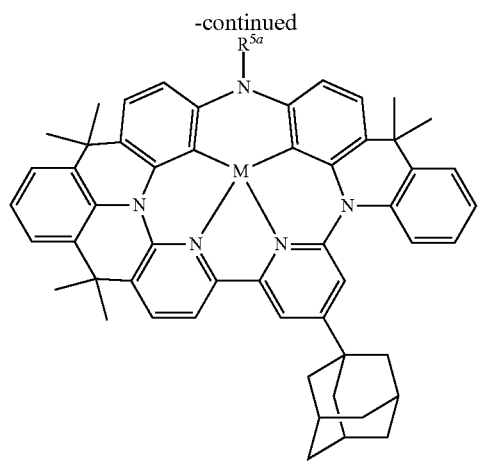
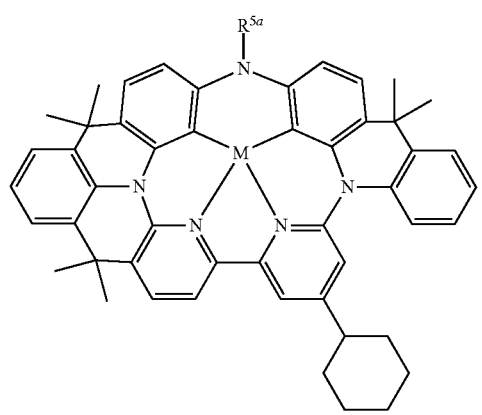
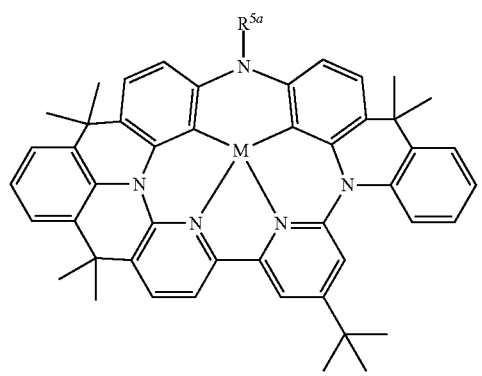
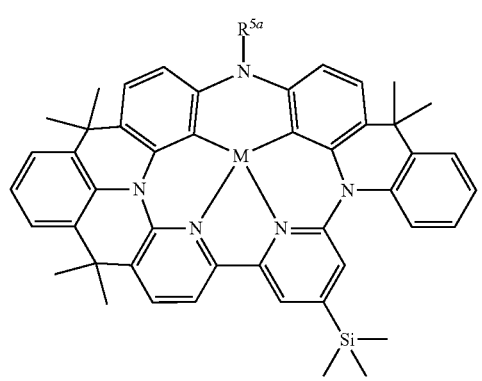
-continued
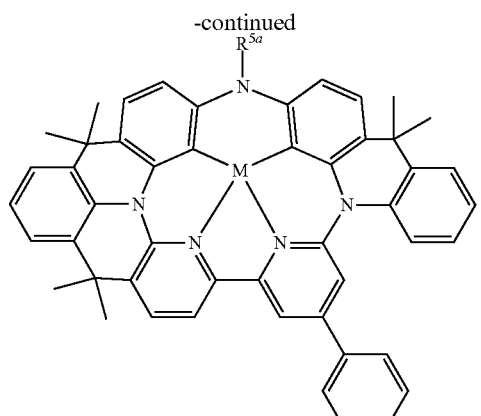
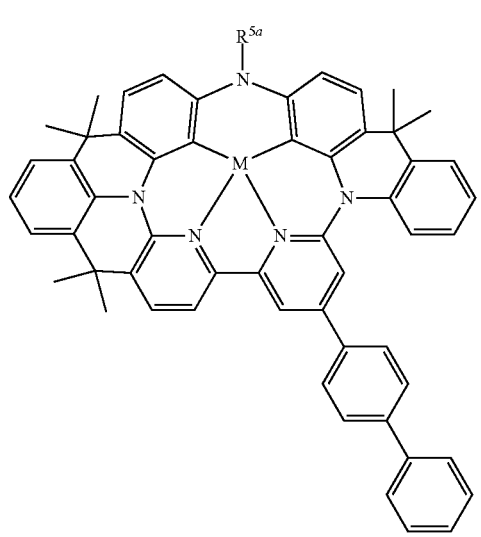
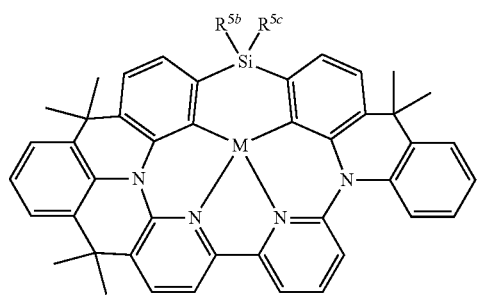
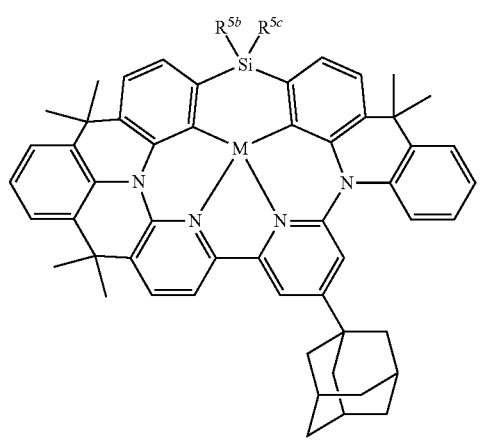

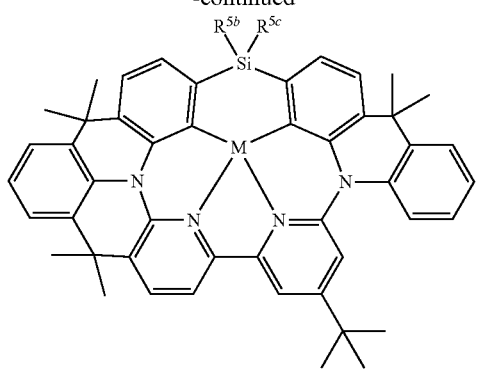
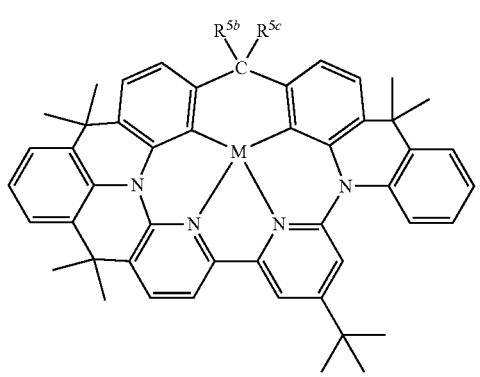
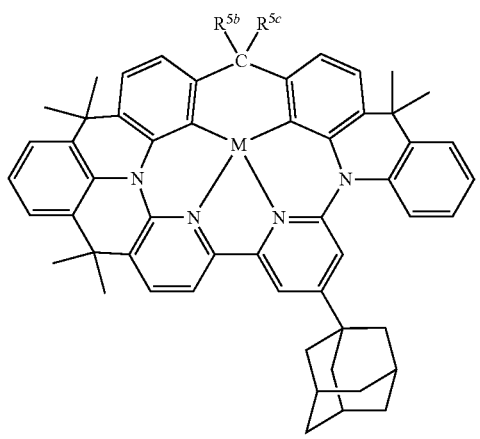
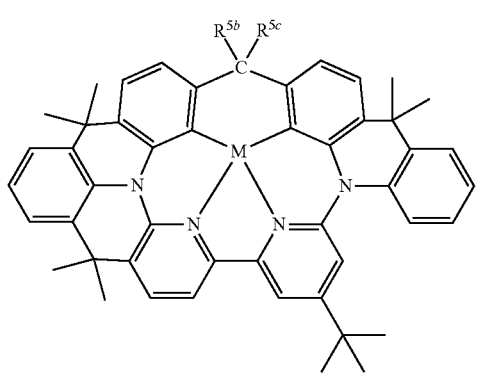
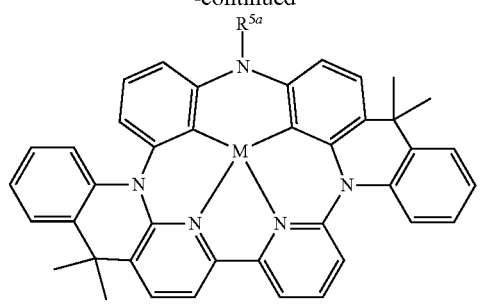
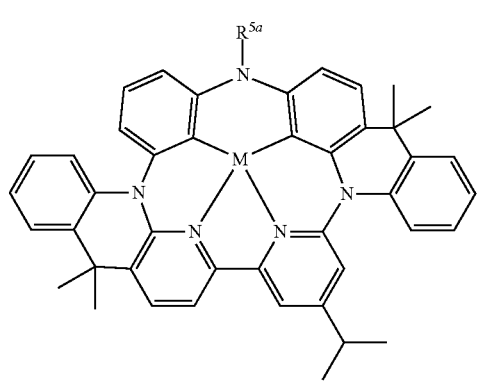
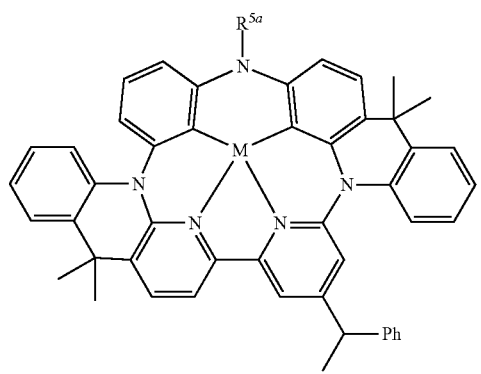
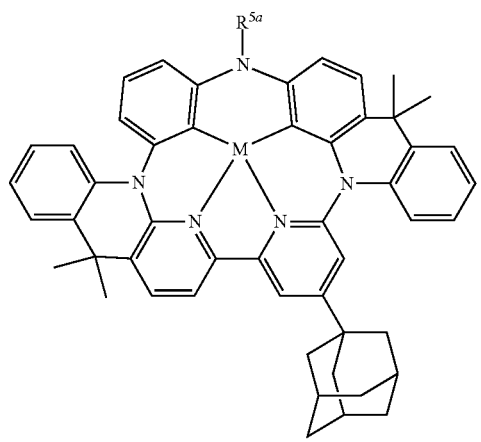

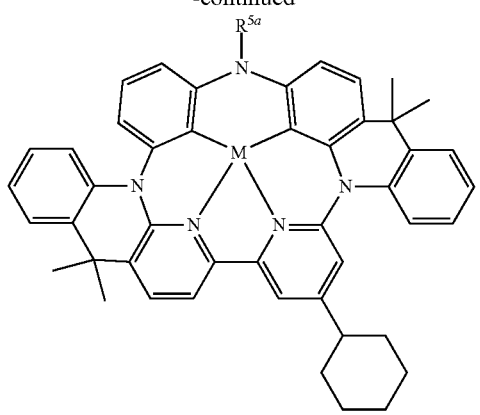
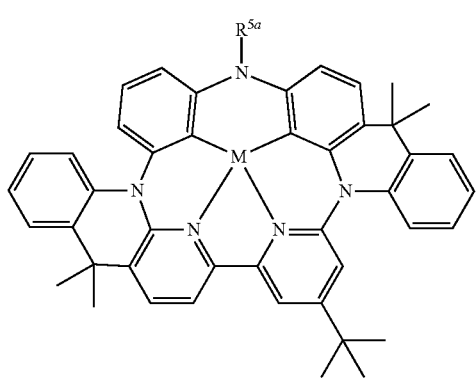
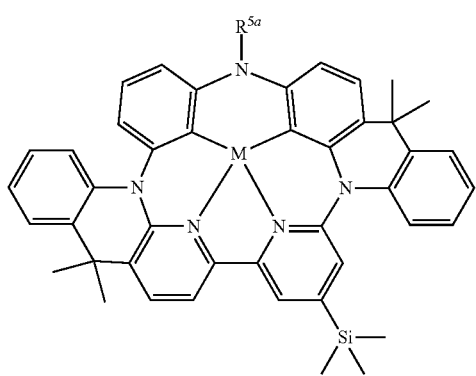
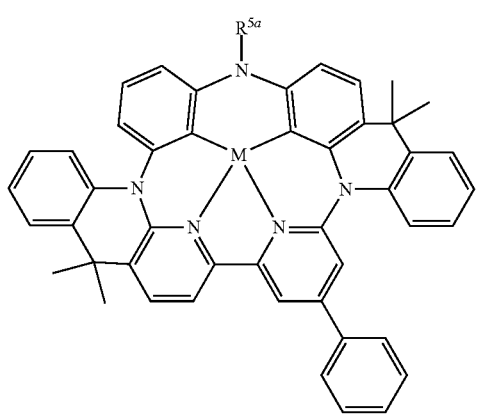
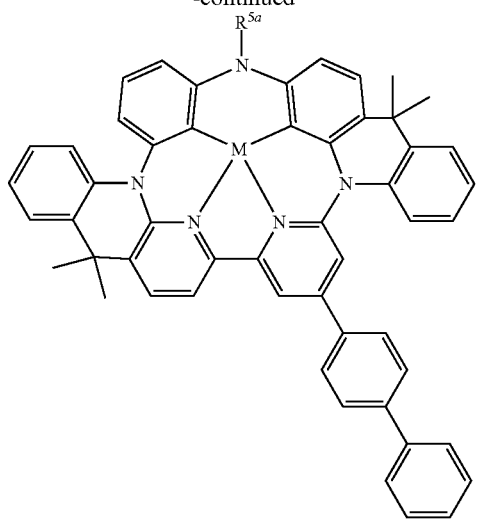
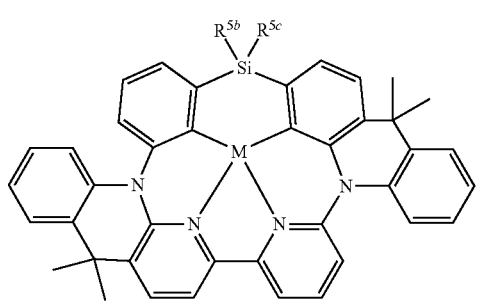
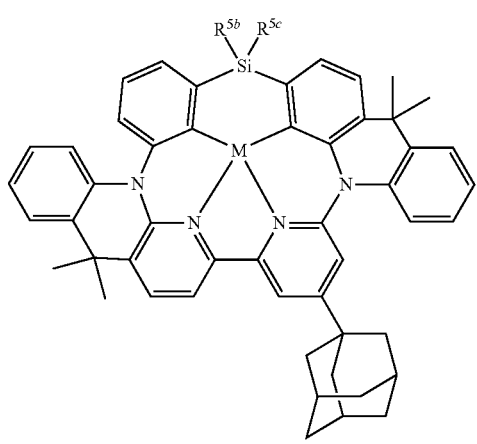
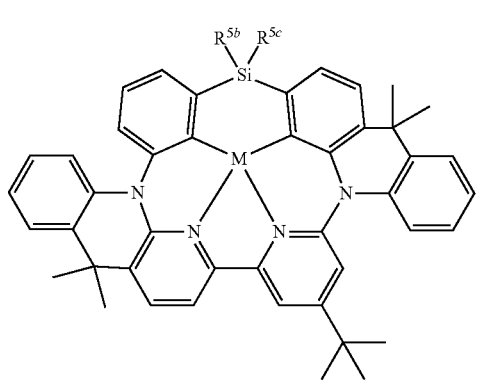

-continued
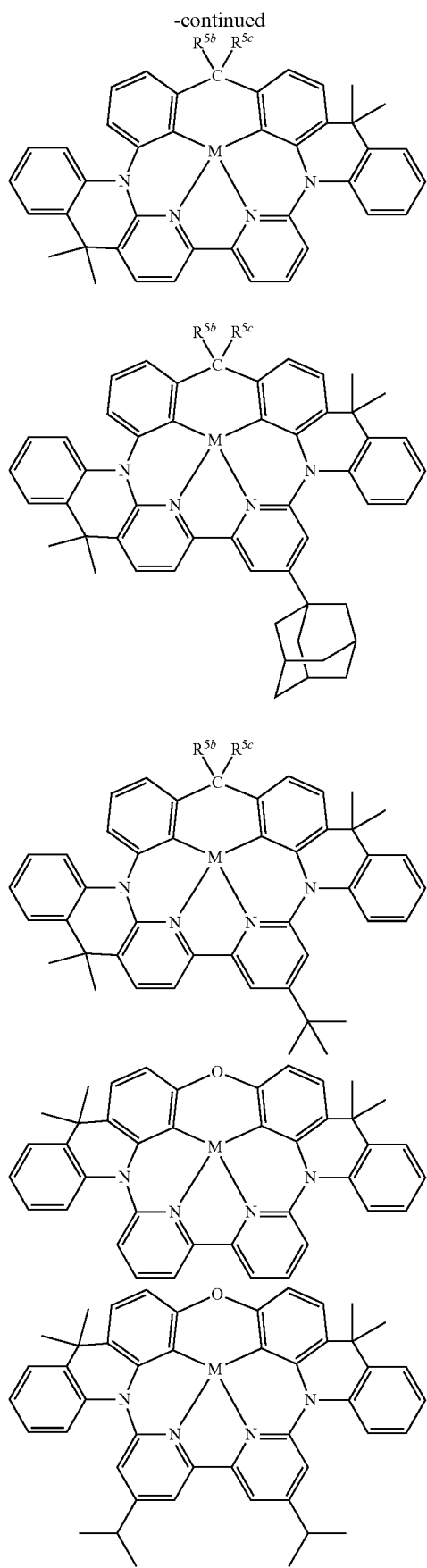
-continued
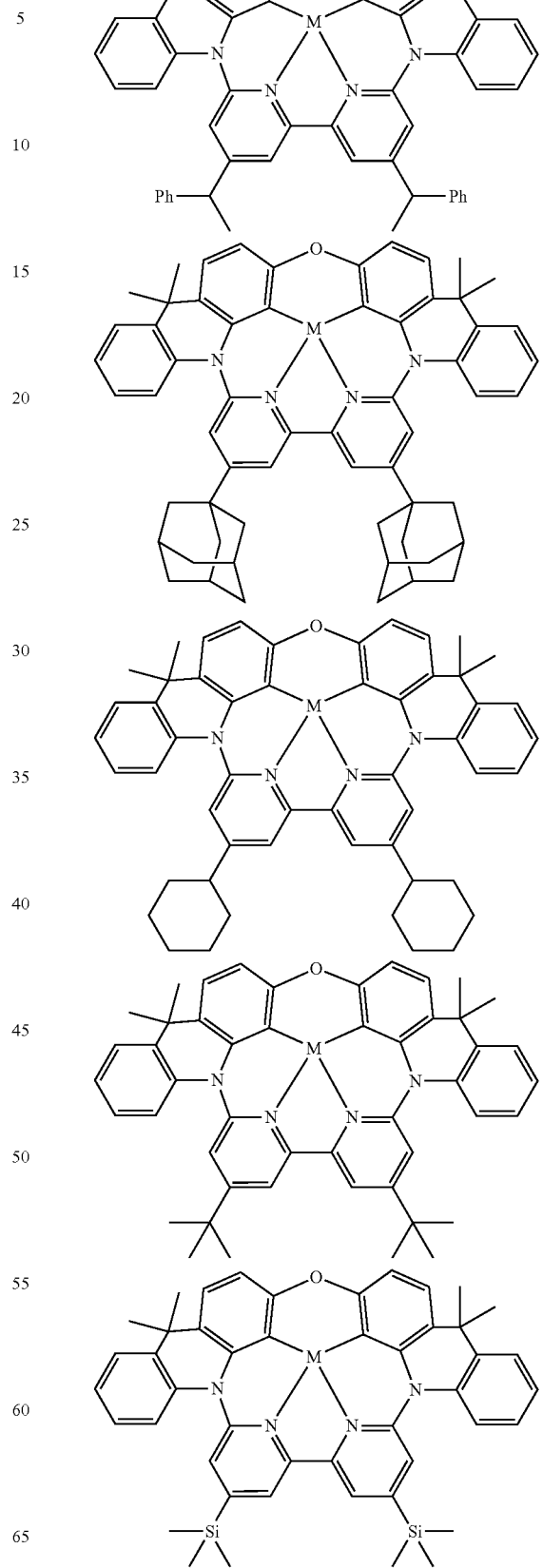

187
-continued
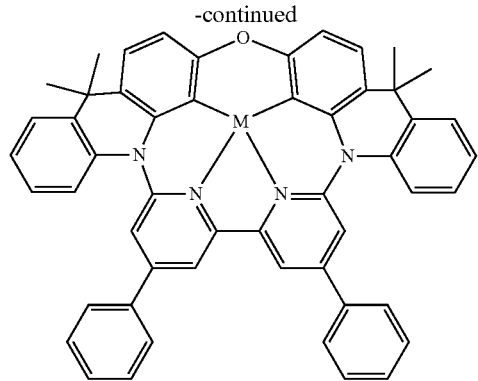
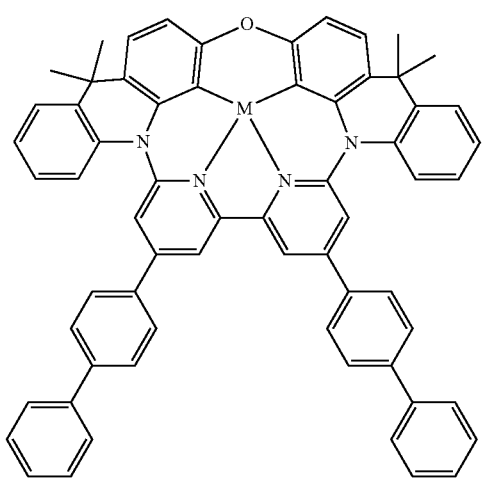
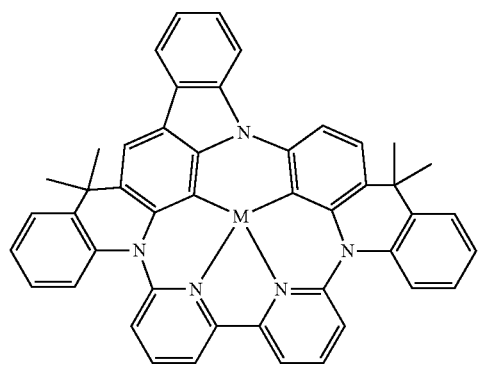
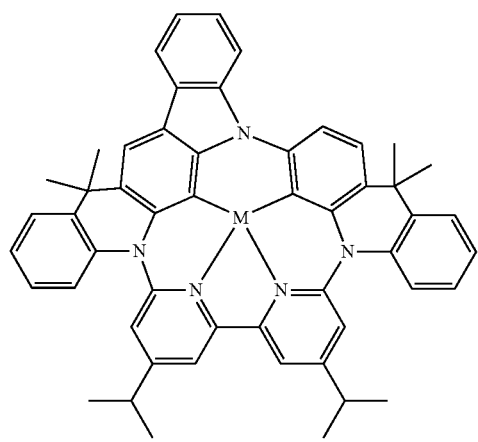
188
-continued
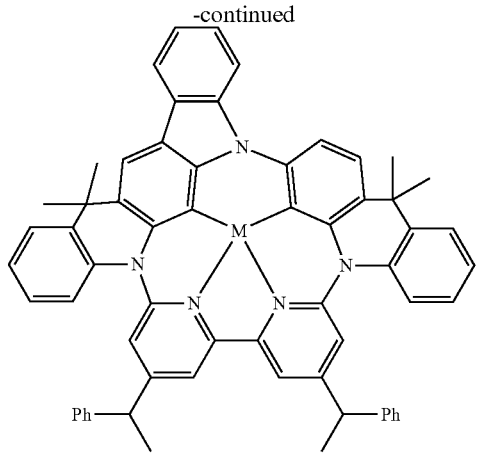
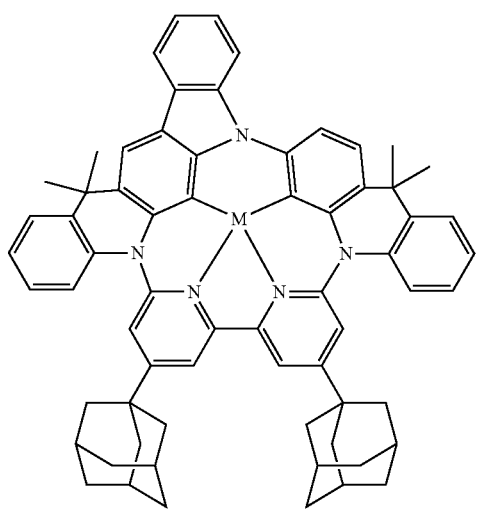
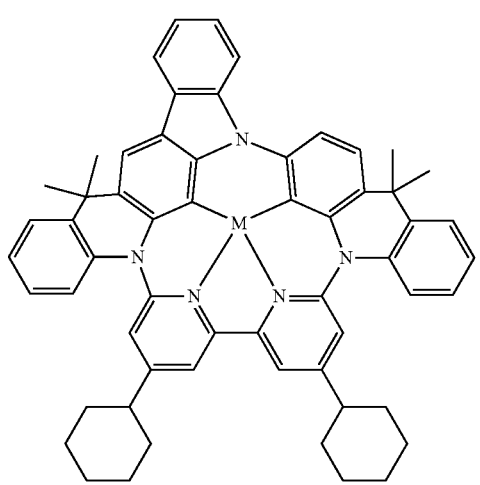

189
-continued
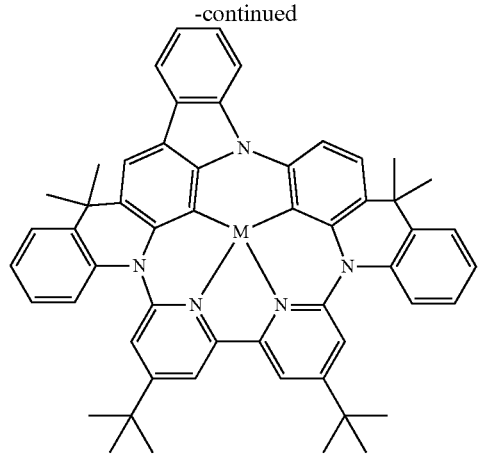
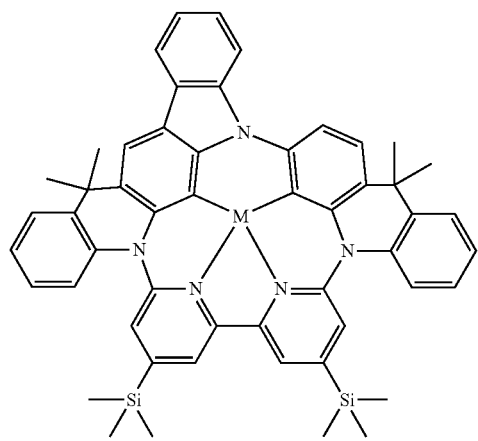
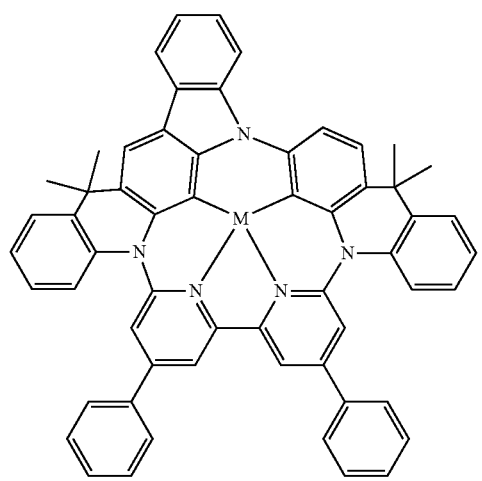
190
-continued
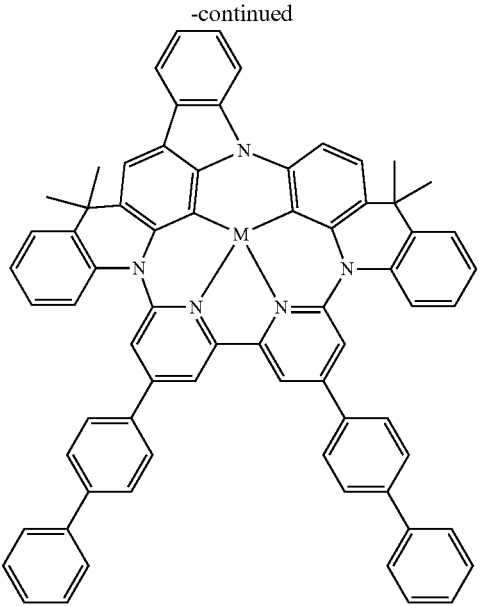
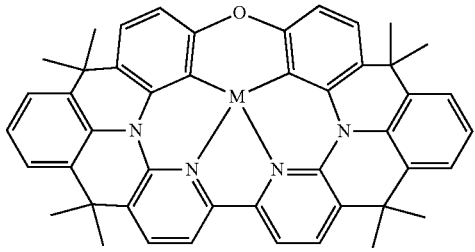
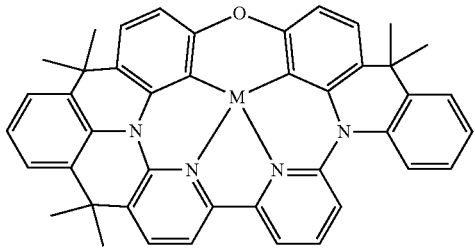
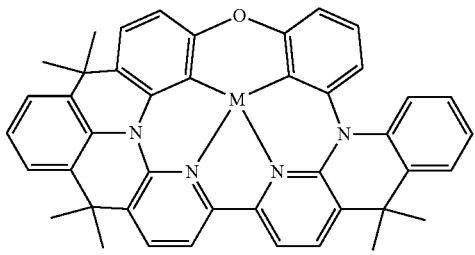
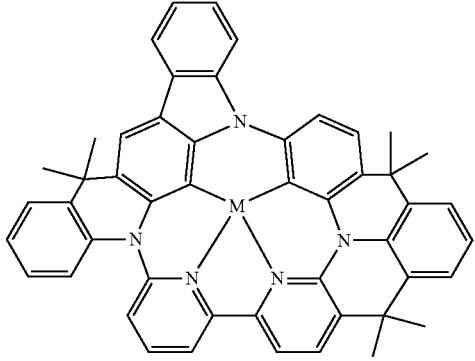

191
-continued
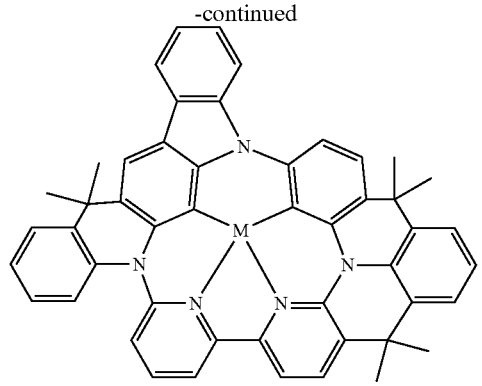
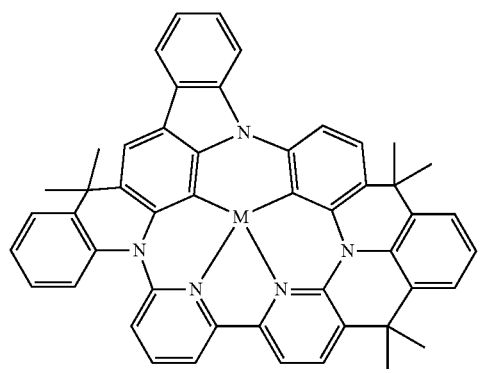
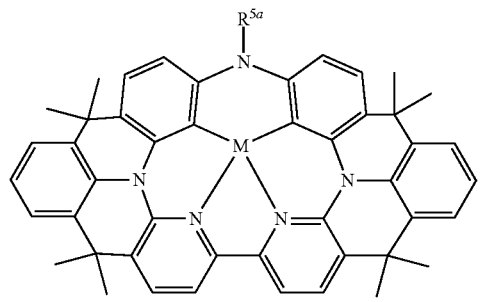
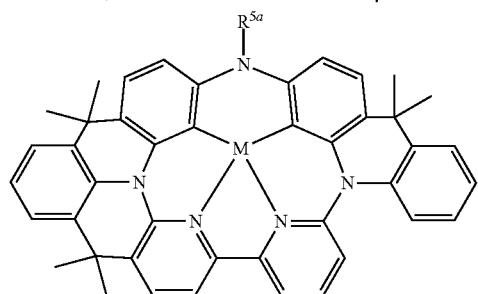
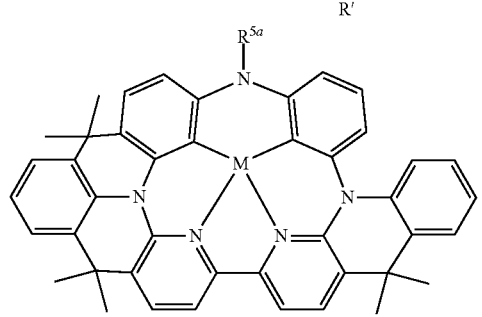
192
-continued
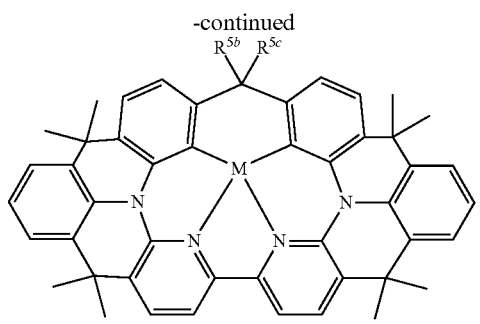
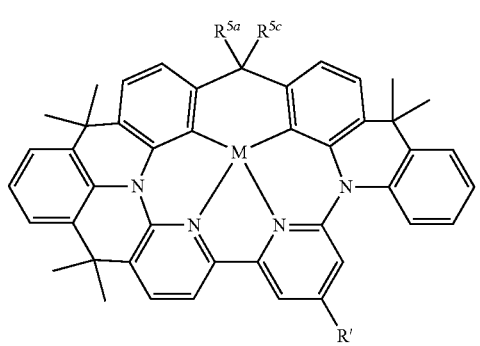
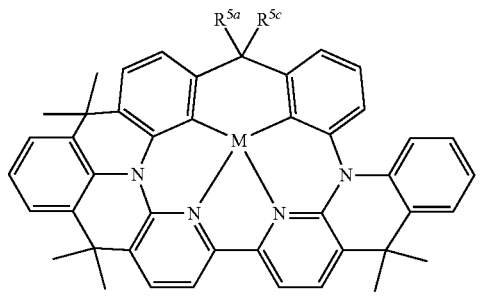
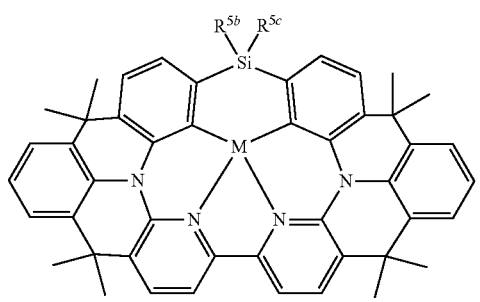
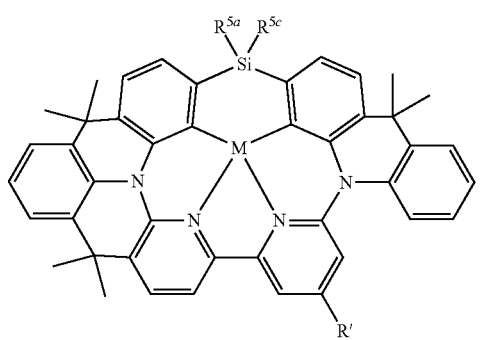

193
-continued
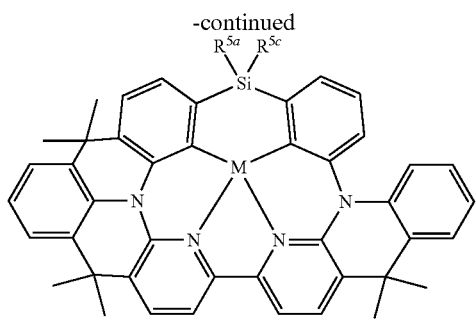
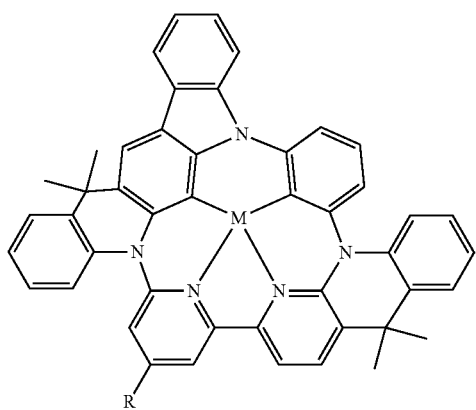
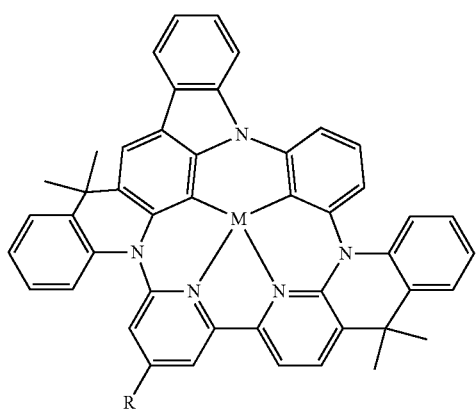
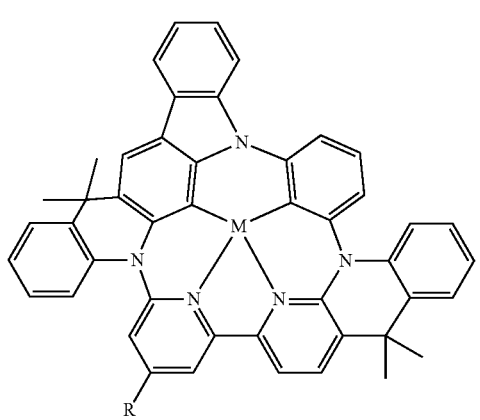
194
-continued
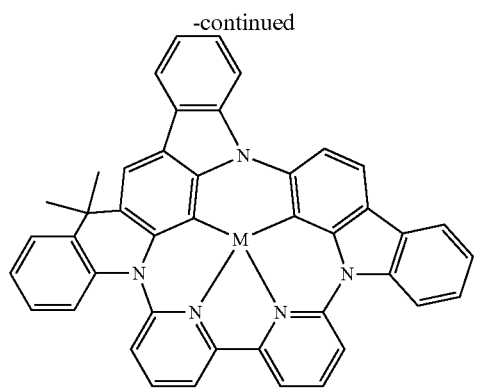
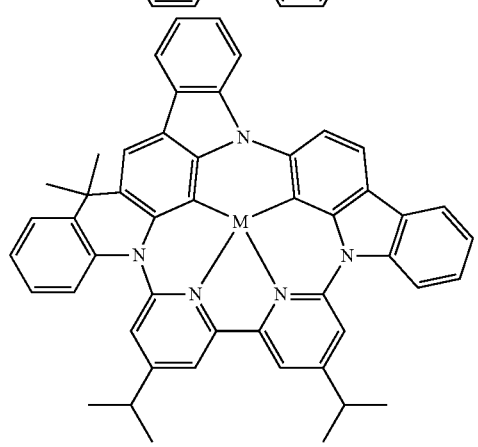
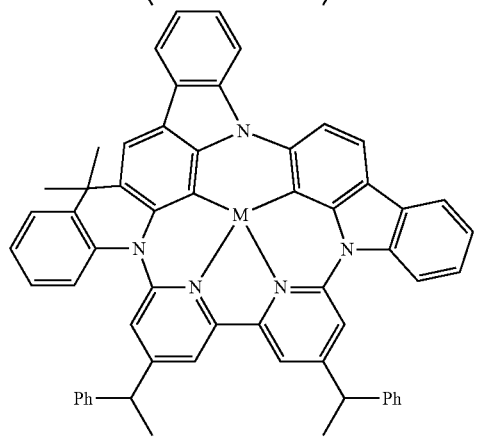
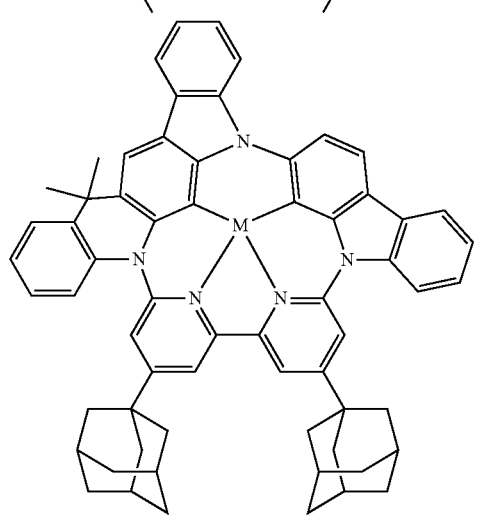

195
-continued
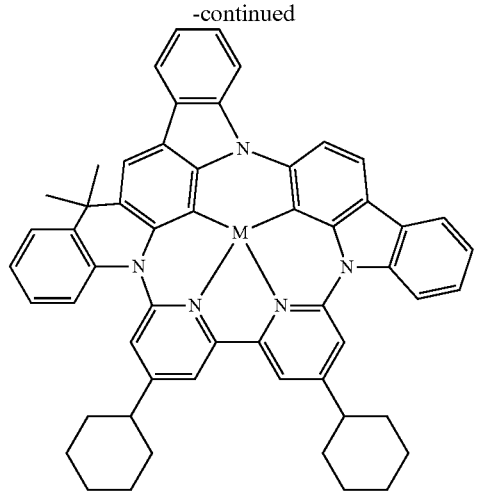
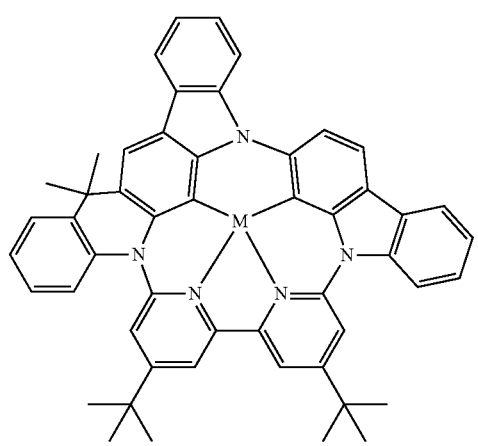
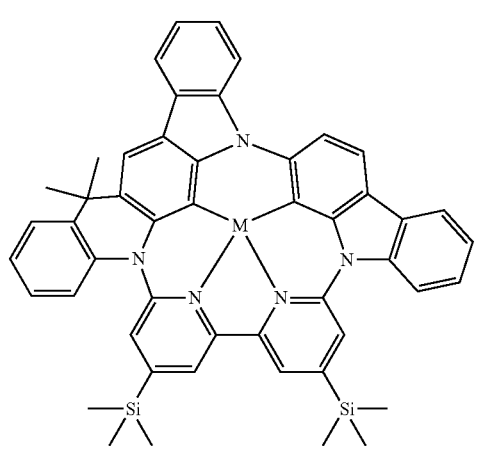
196
-continued
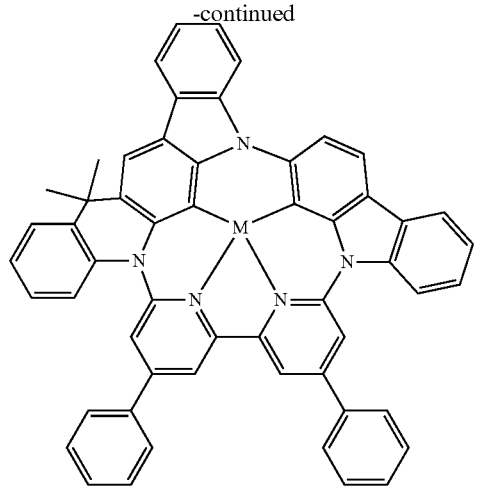
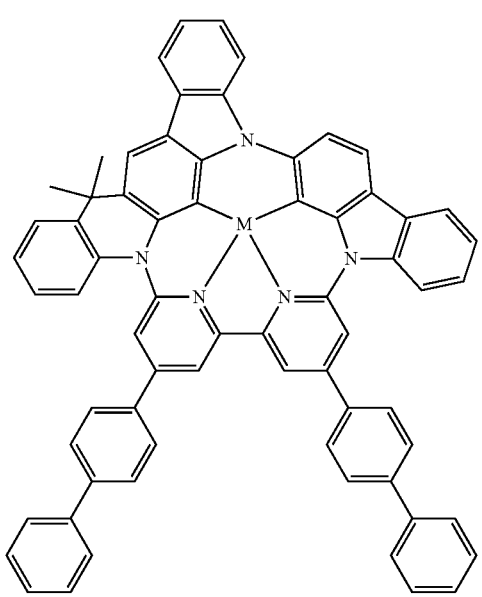
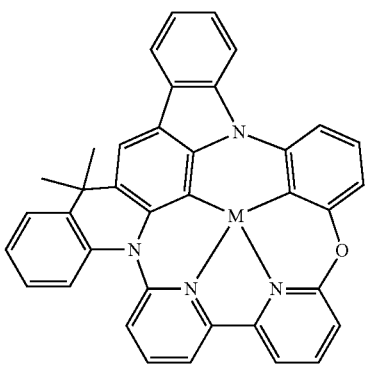

197
-continued
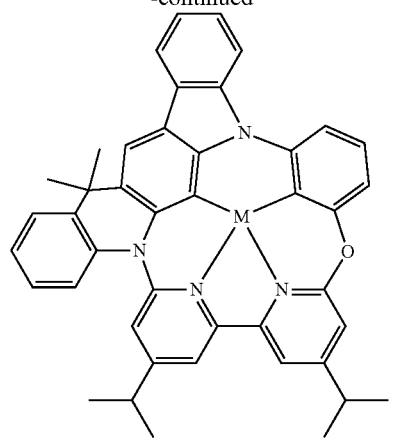
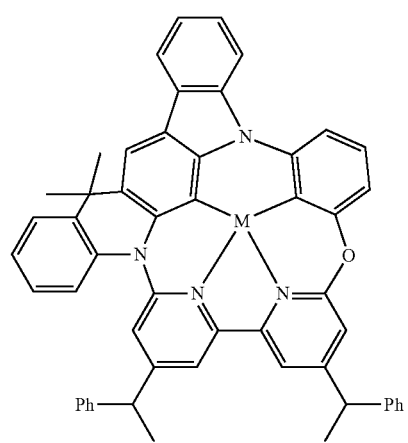
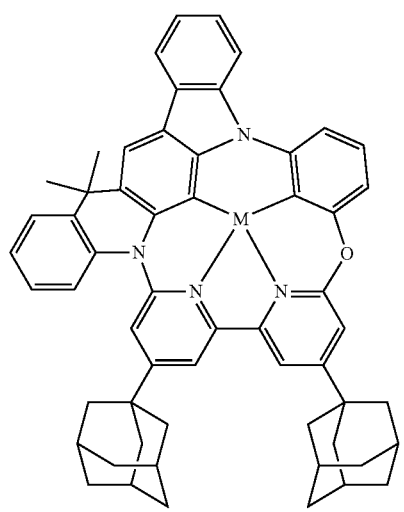
198
-continued
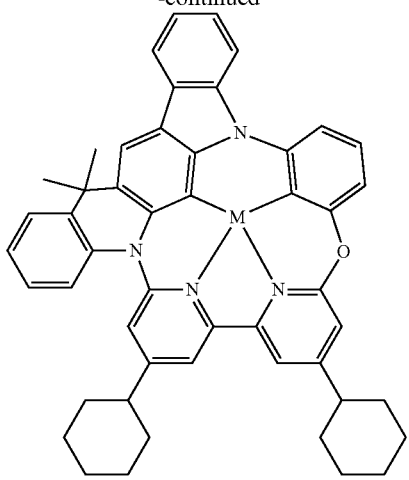
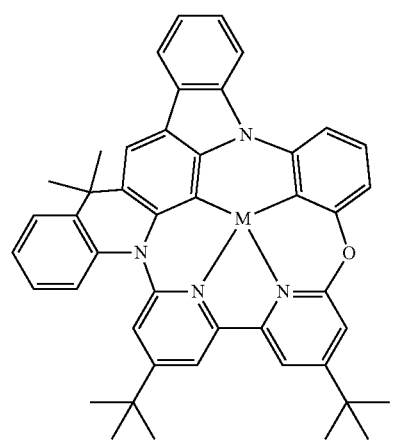
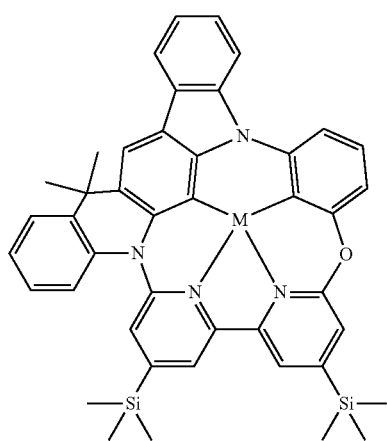

| 199 -continued | 200 -continued |
|---|---|
| 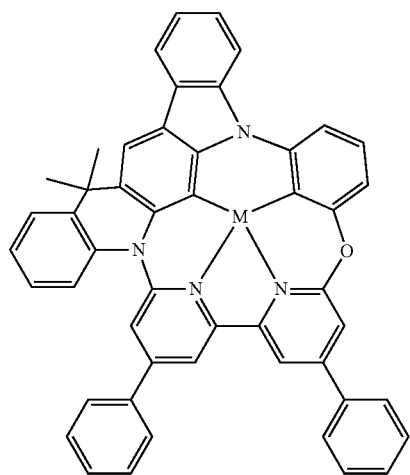 | 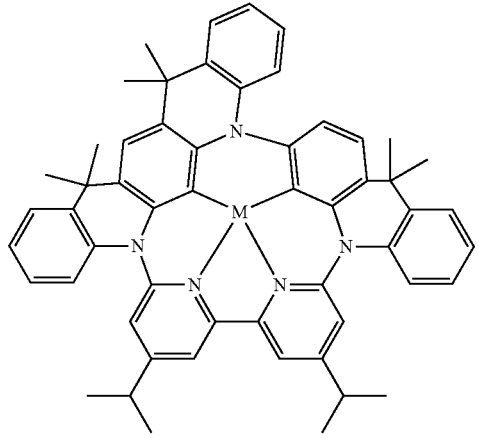 |
| 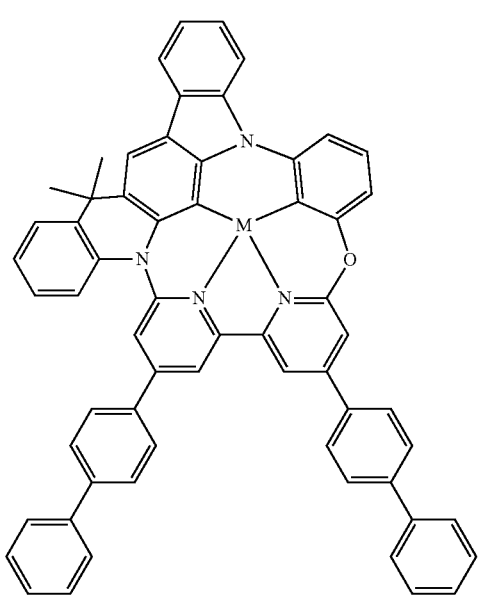 | 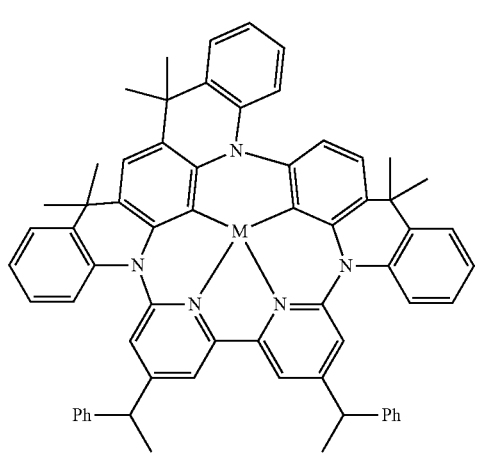 |
| 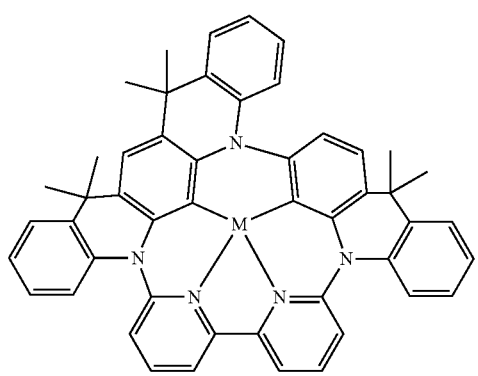 | 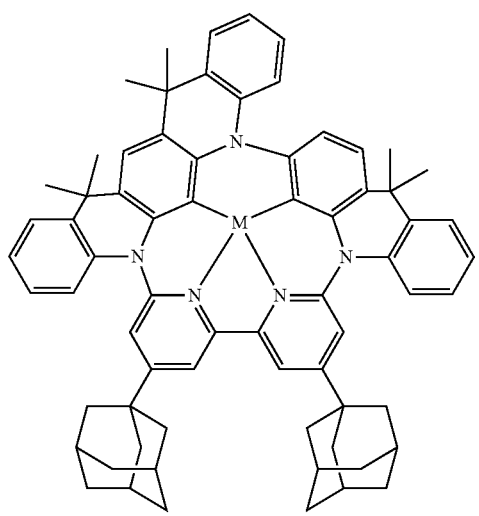 |

201
-continued
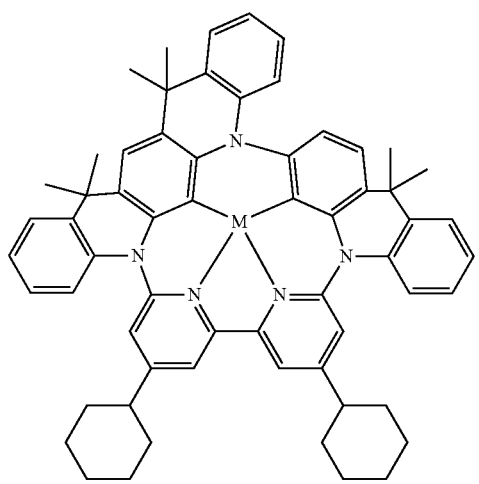
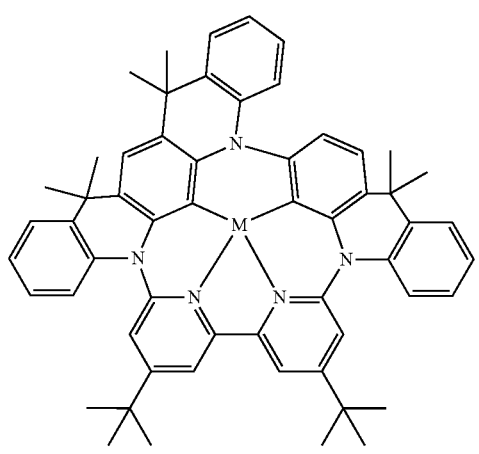
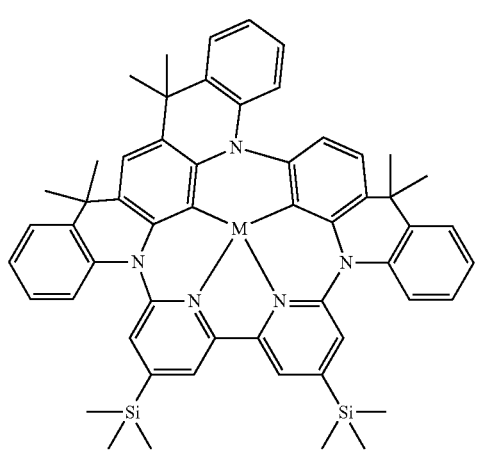
202
-continued
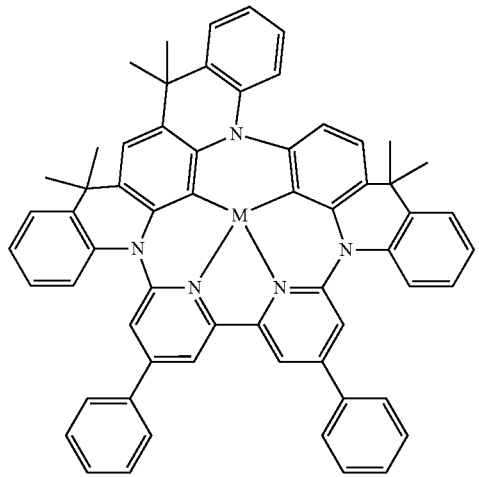
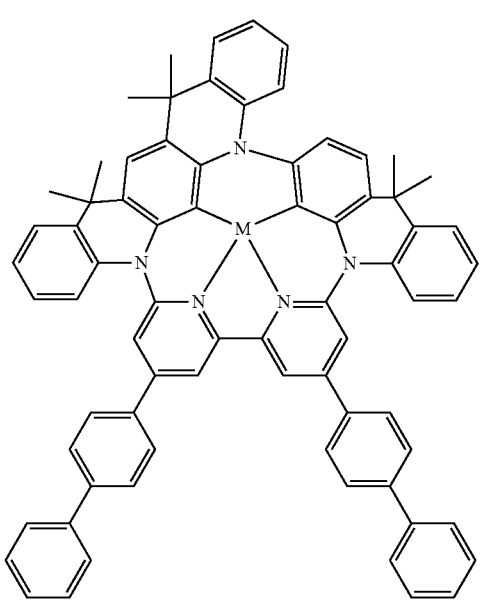
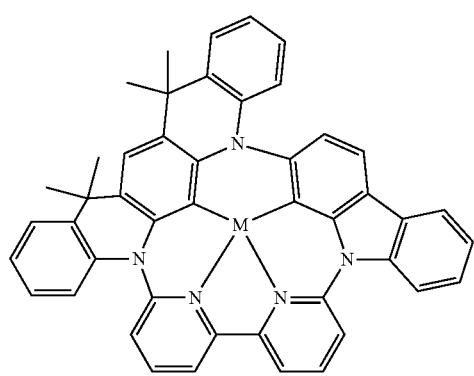

203
-continued
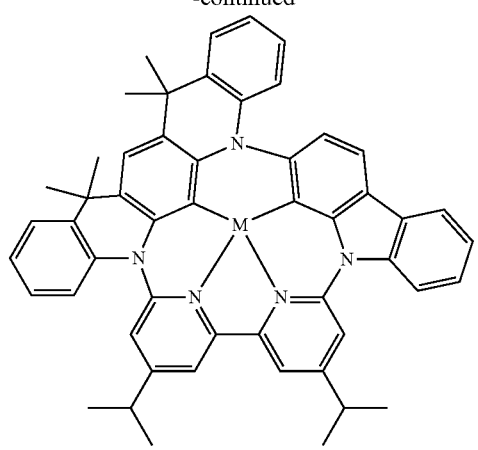
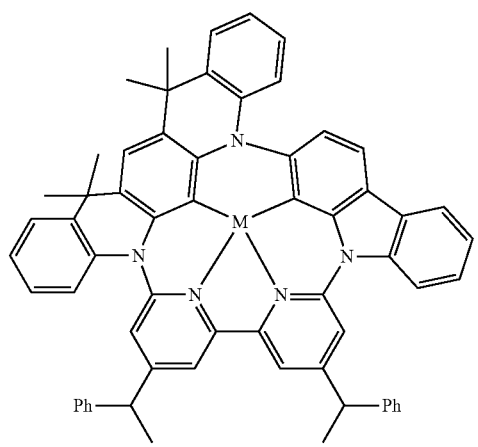
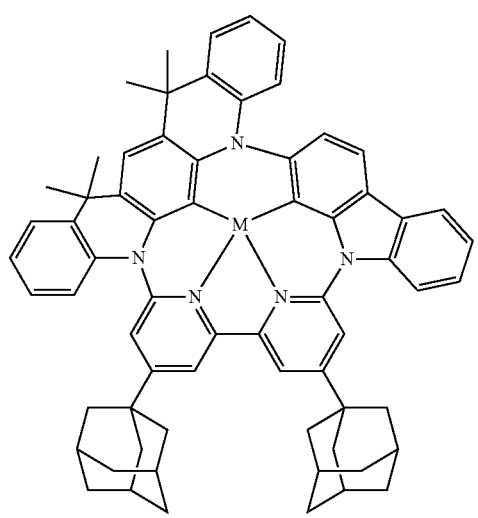
204
-continued
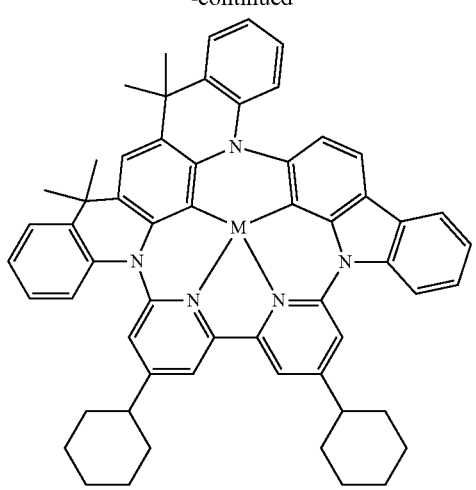
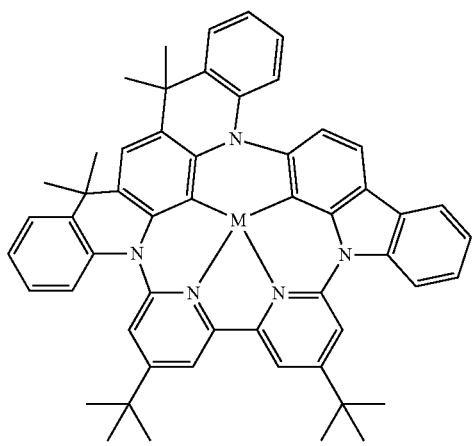
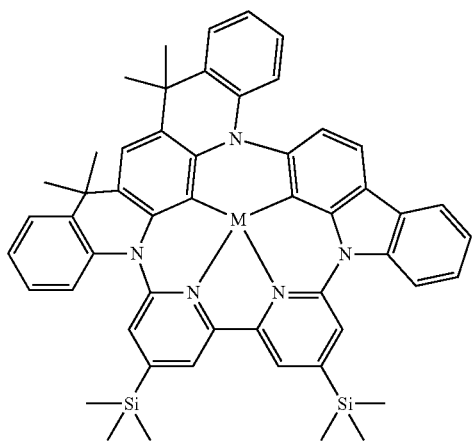

205
-continued
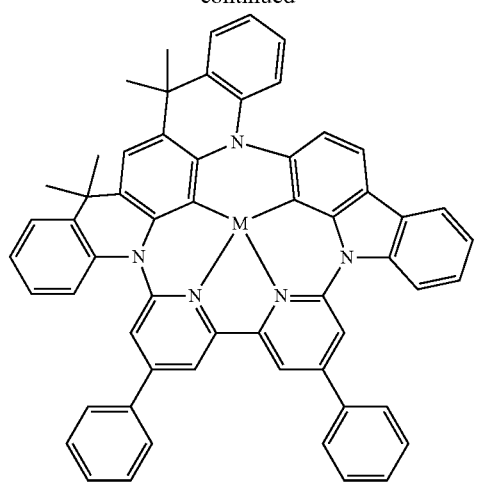
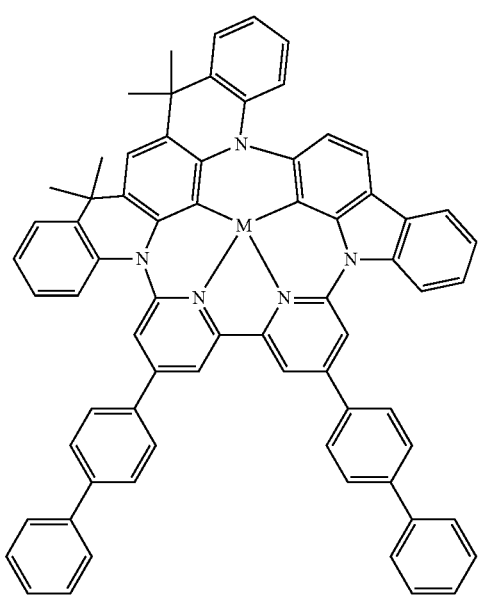
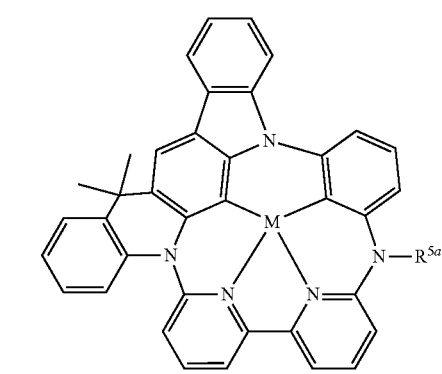
206
-continued
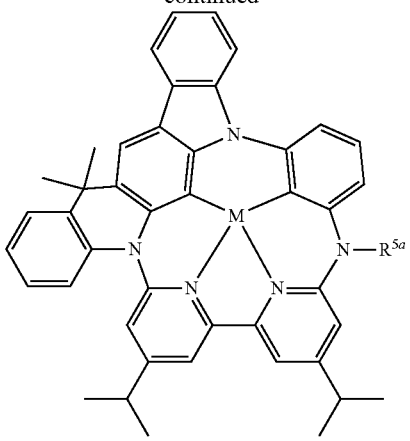
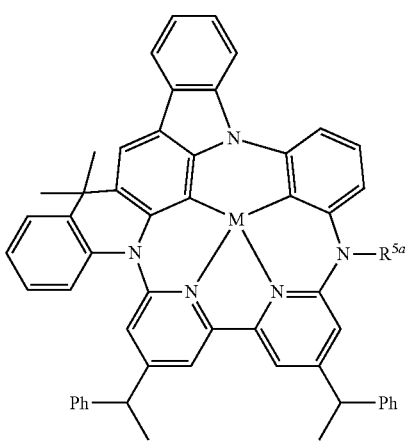
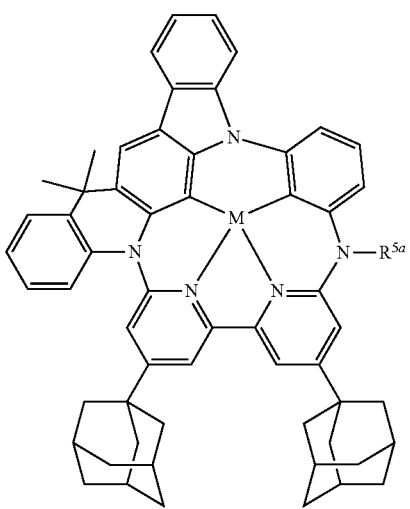

207
-continued
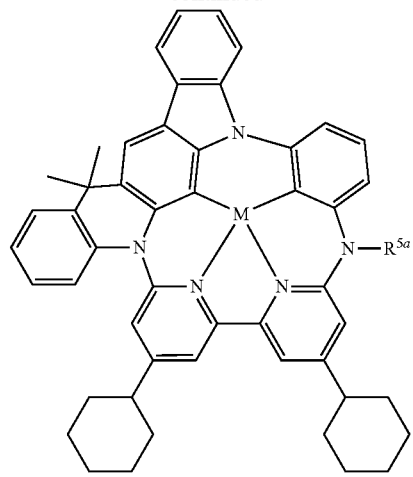
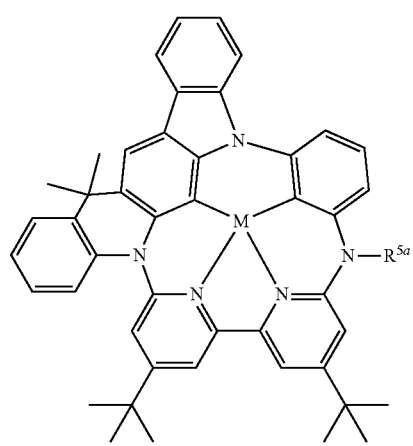
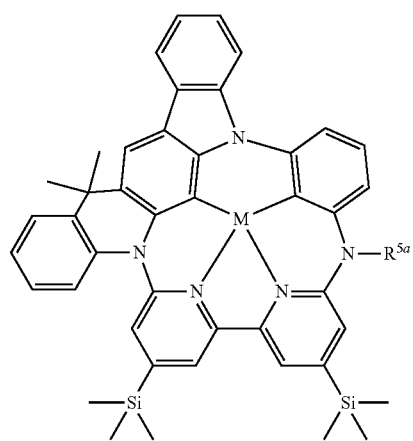
208
-continued
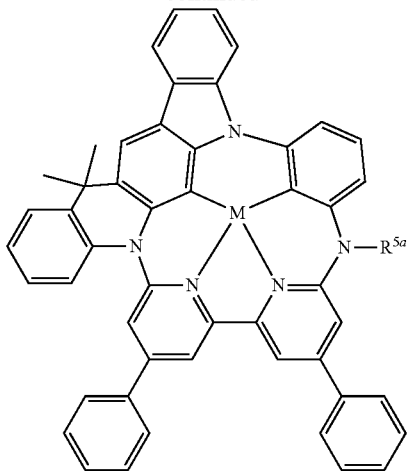
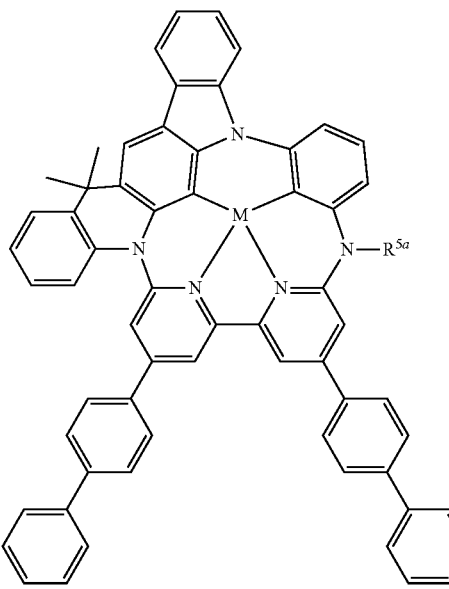
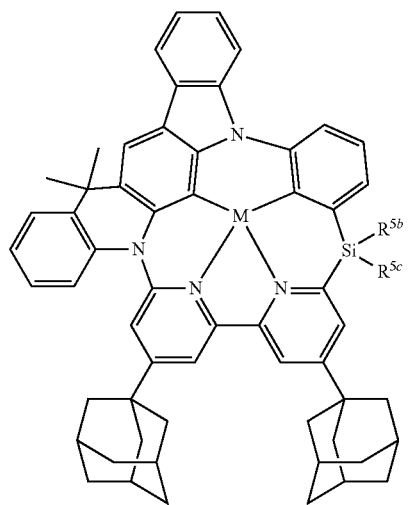

209
-continued
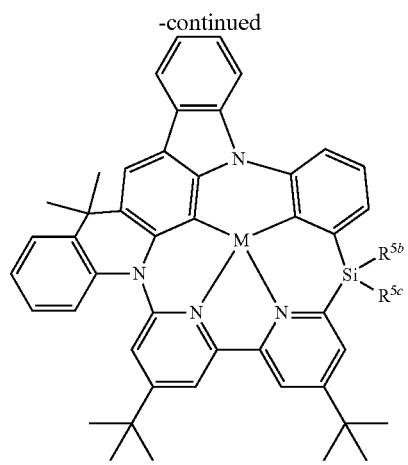
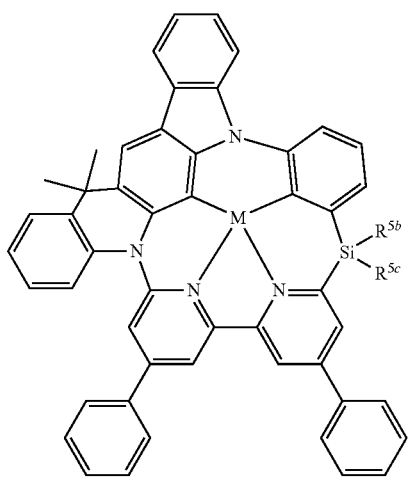
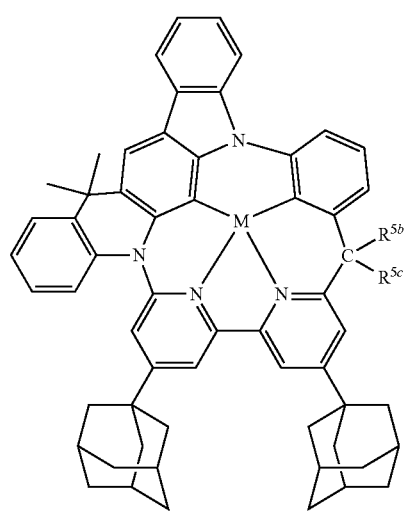
210
-continued
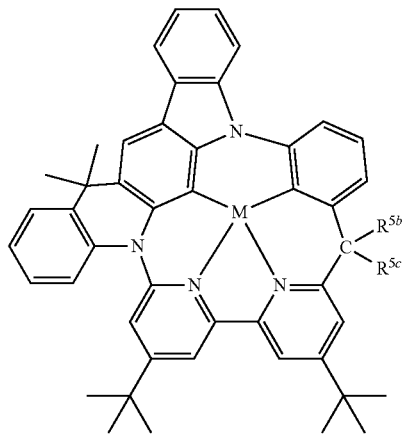
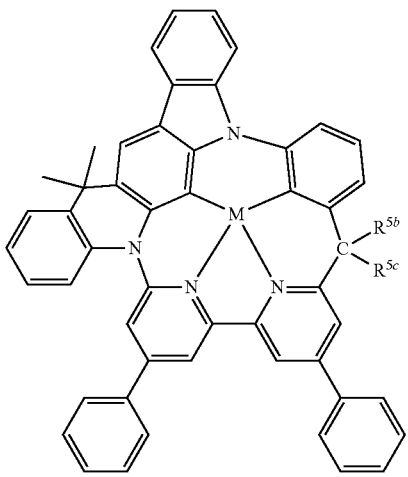
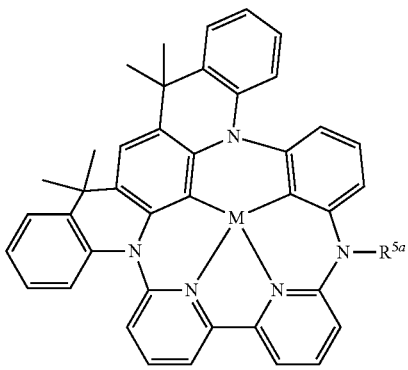
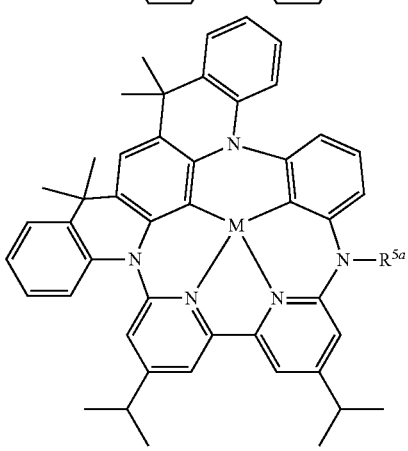

211
-continued
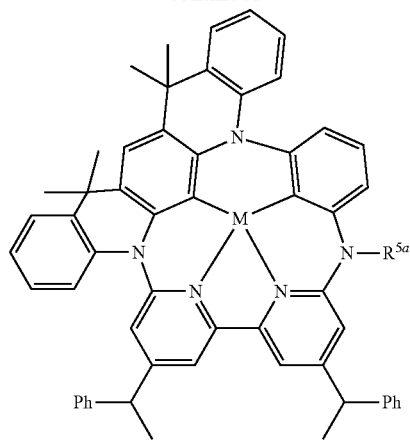
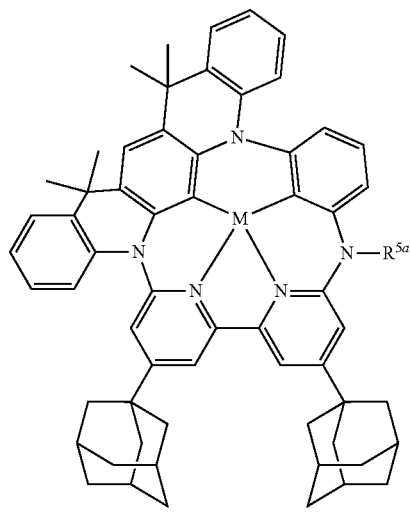
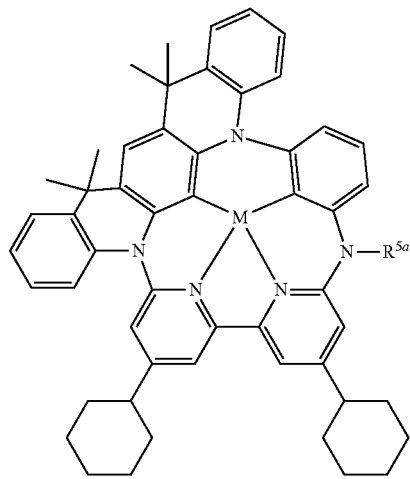
212
-continued
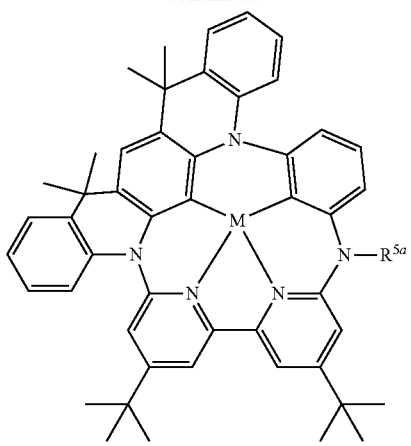
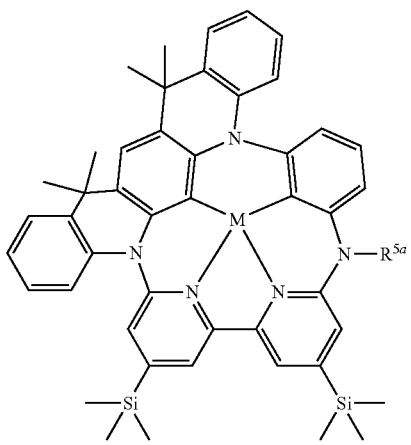
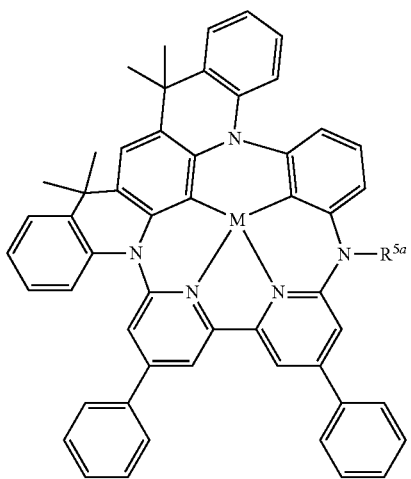

213
-continued
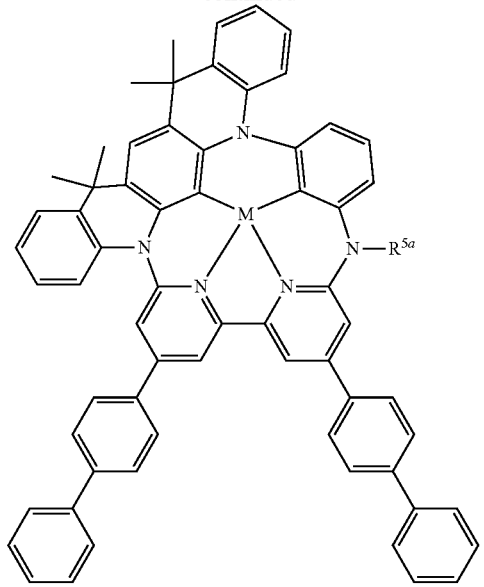
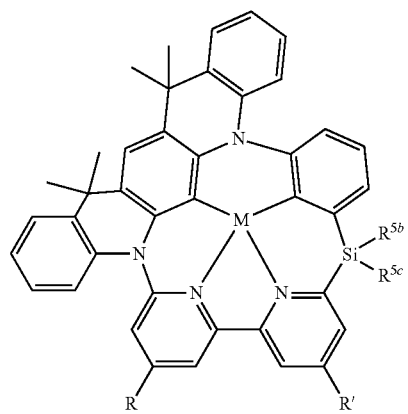
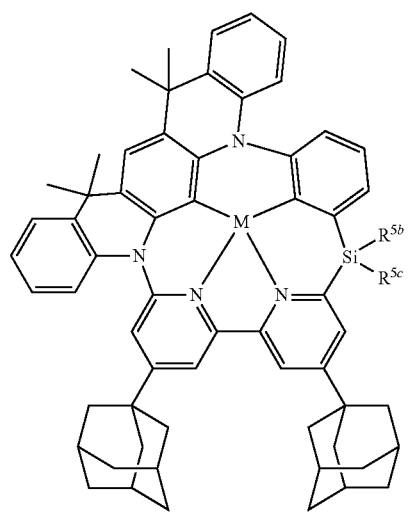
214
-continued
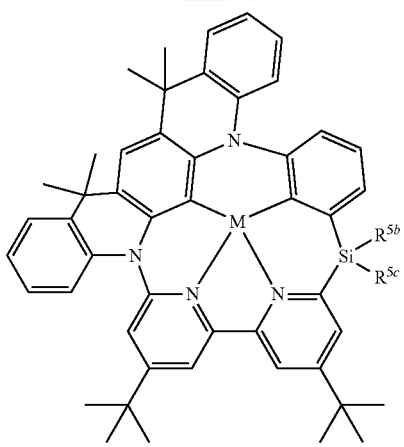
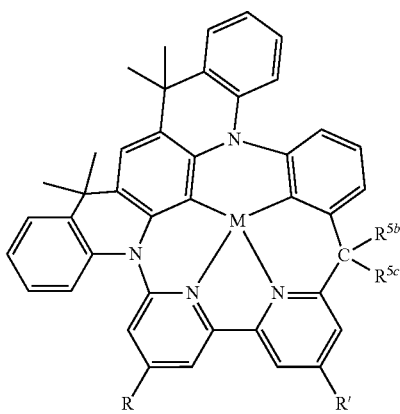
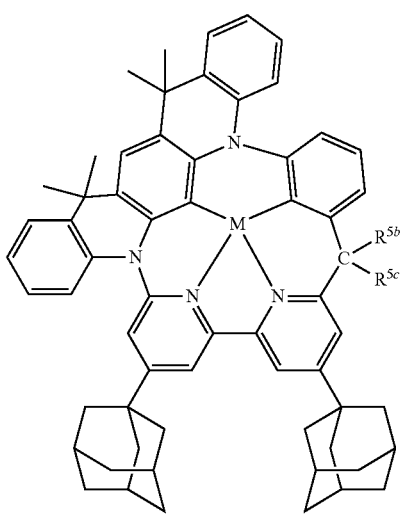

215
-continued
216
-continued
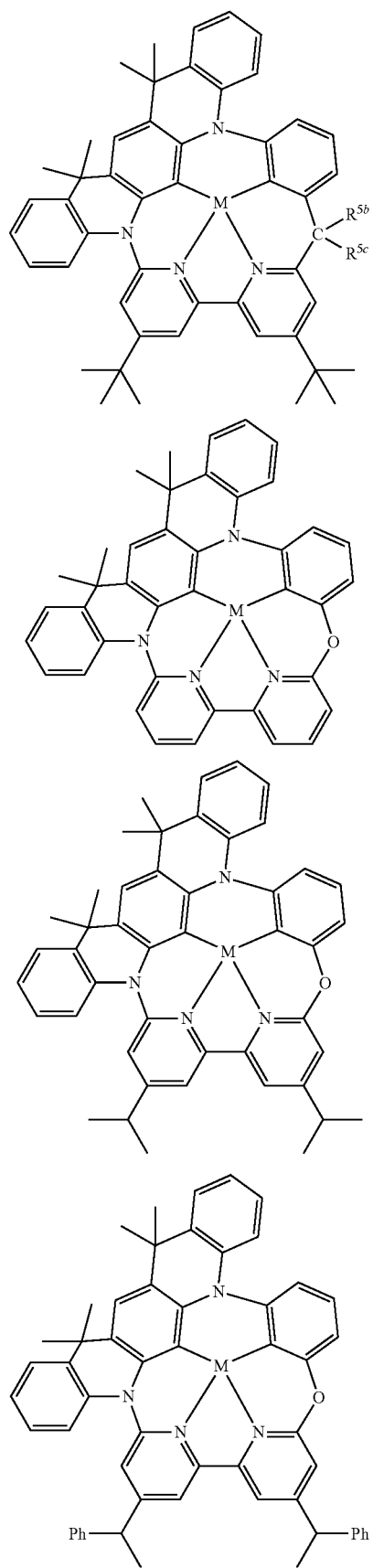
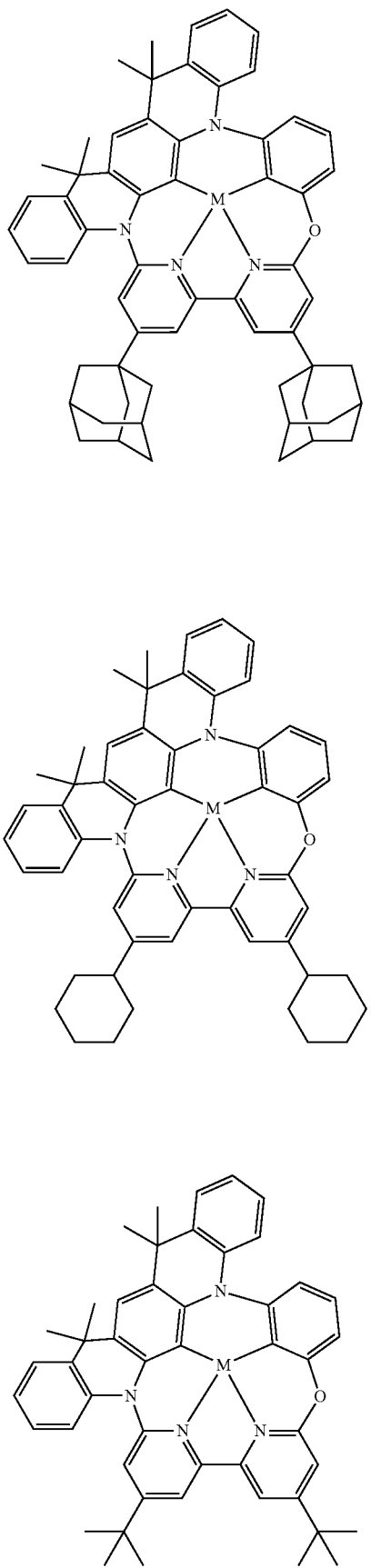

217
-continued
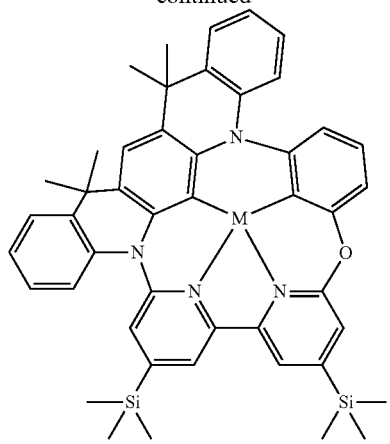
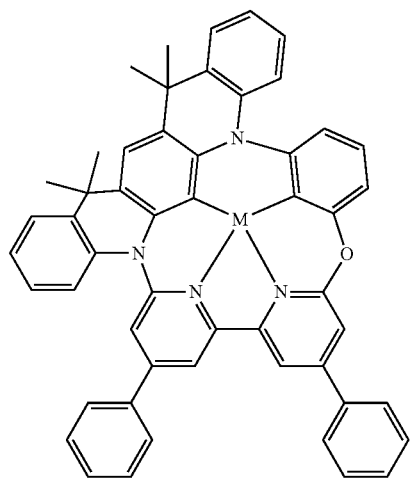
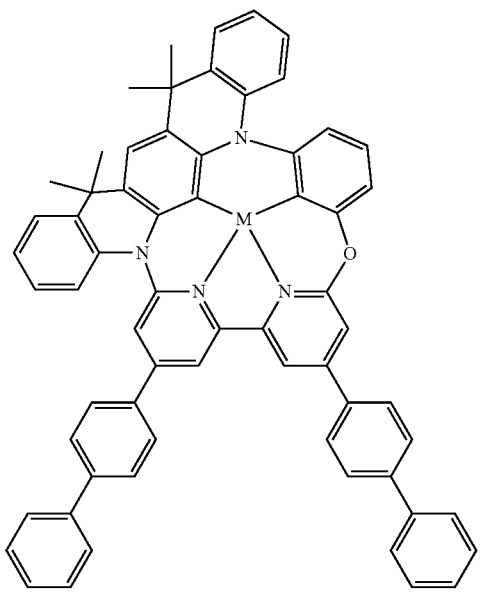
218
-continued
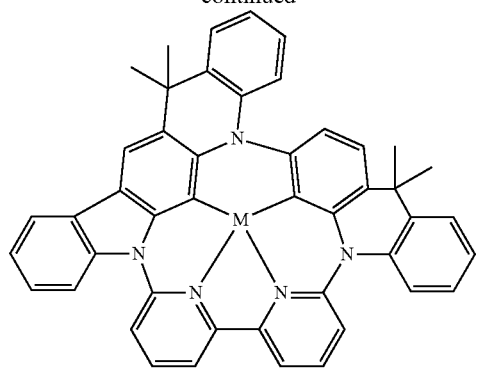
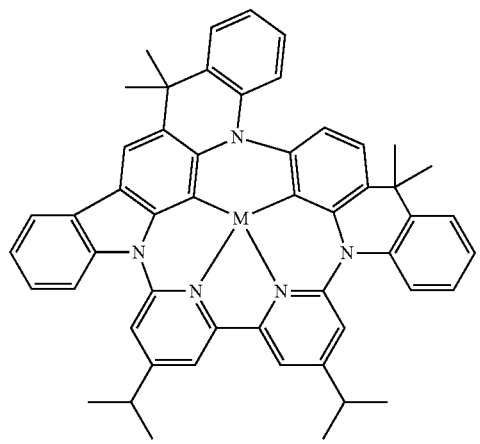
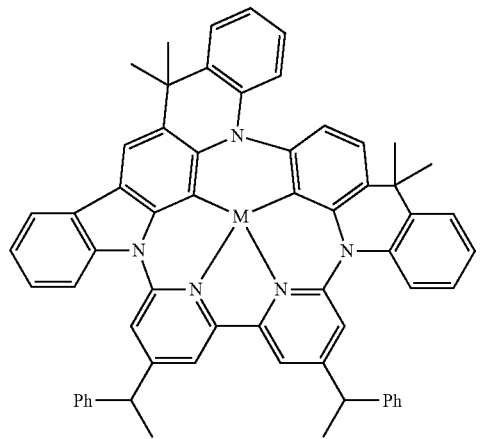

219
-continued
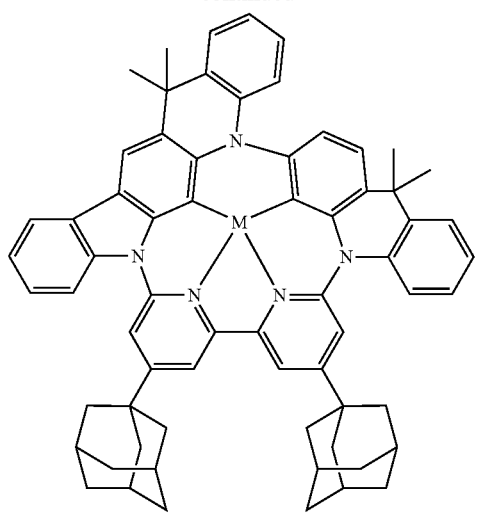
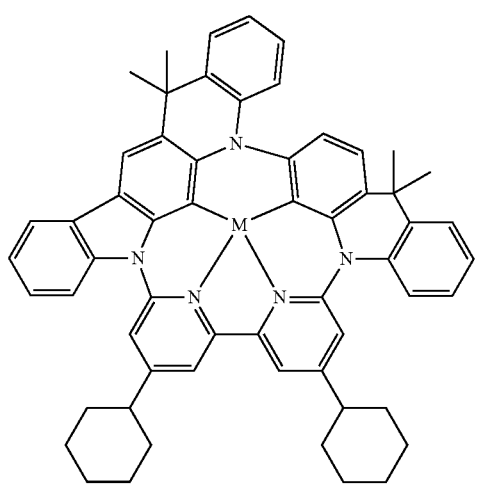
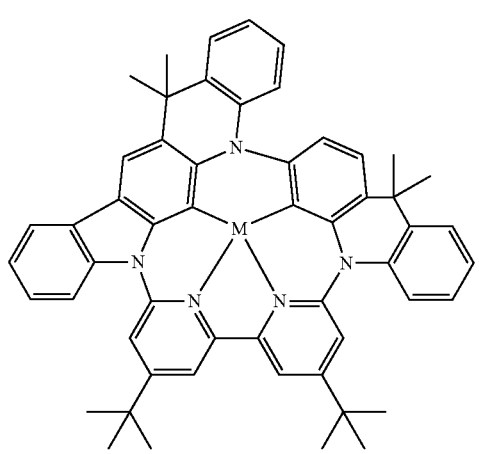
220
-continued
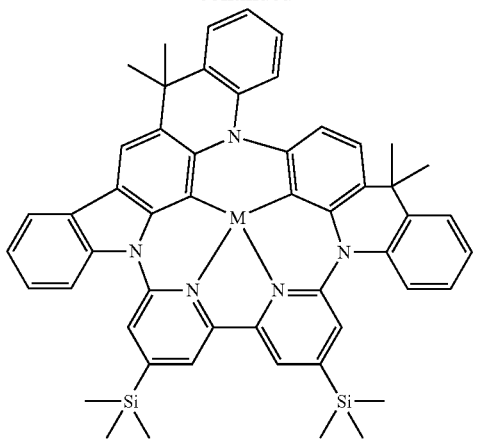
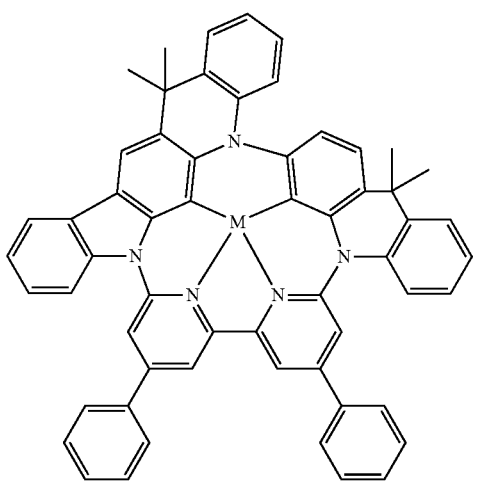
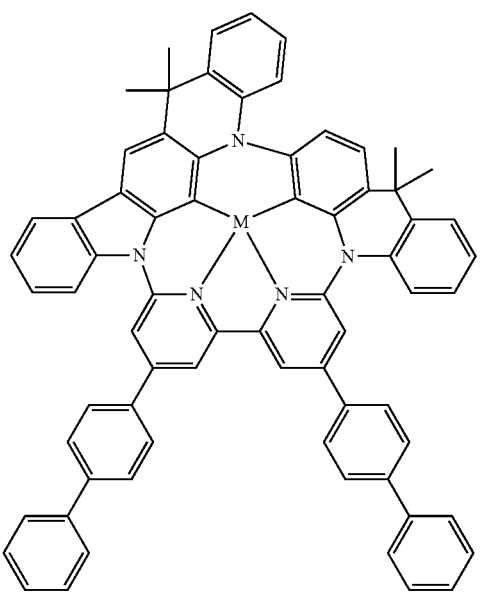

221
-continued
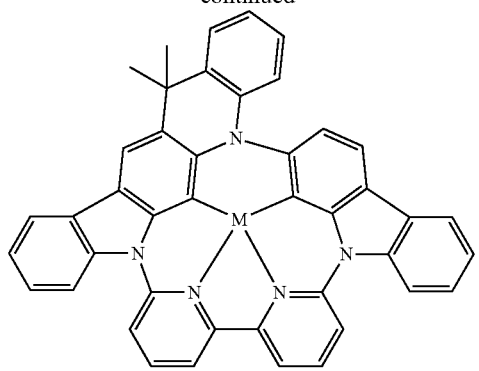
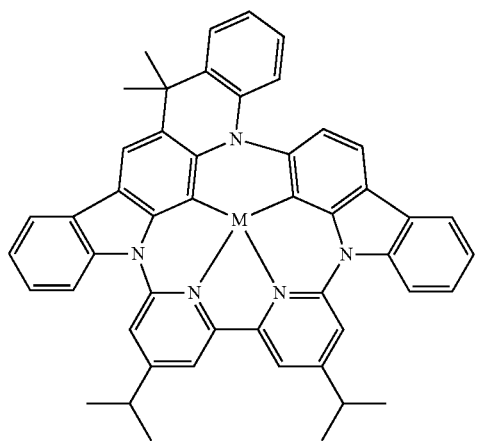
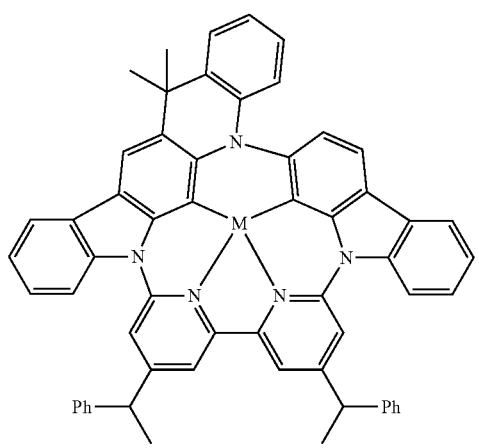
222
-continued
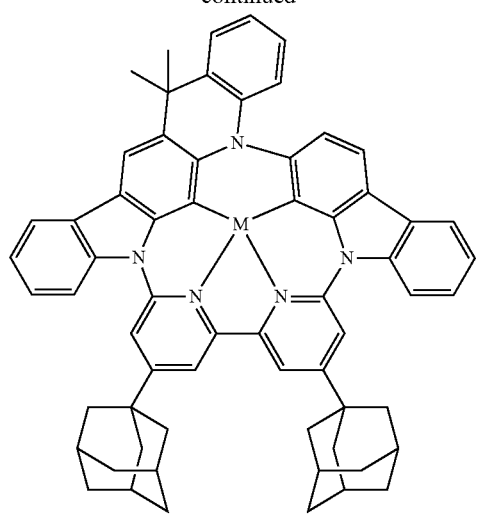
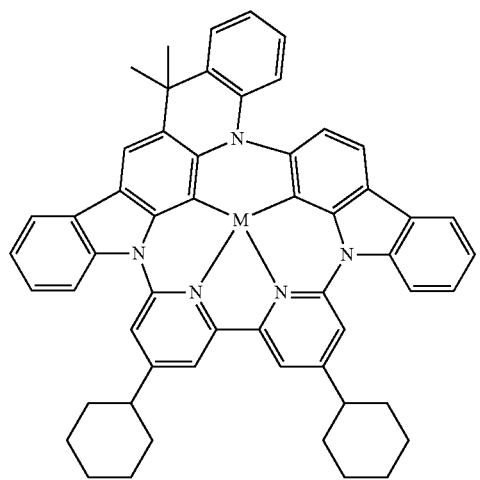
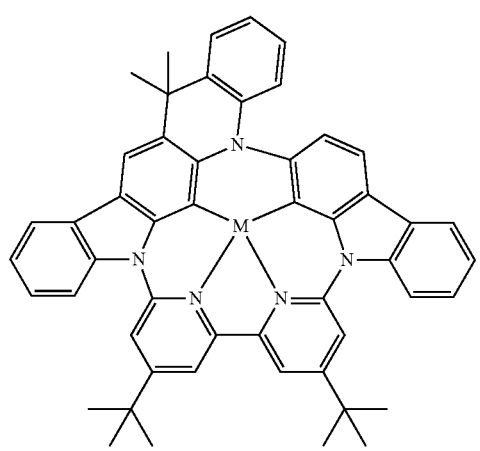

223
-continued
224
-continued
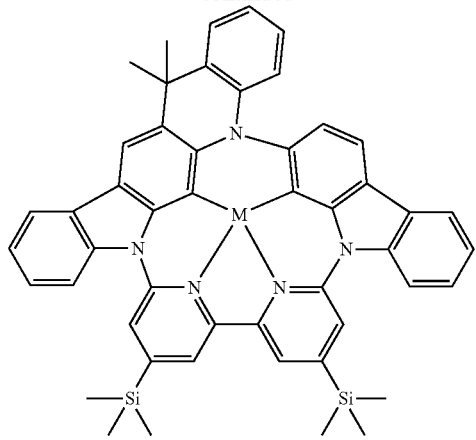
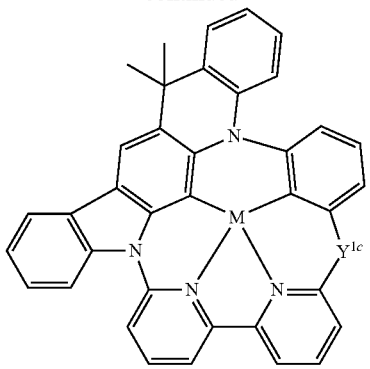
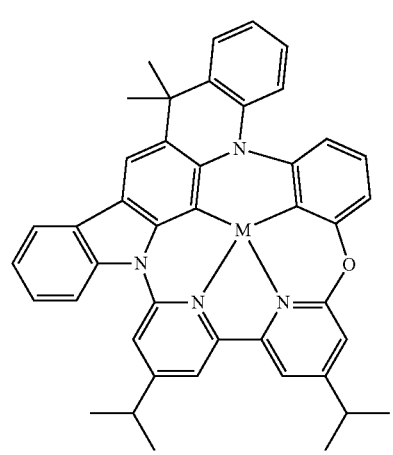
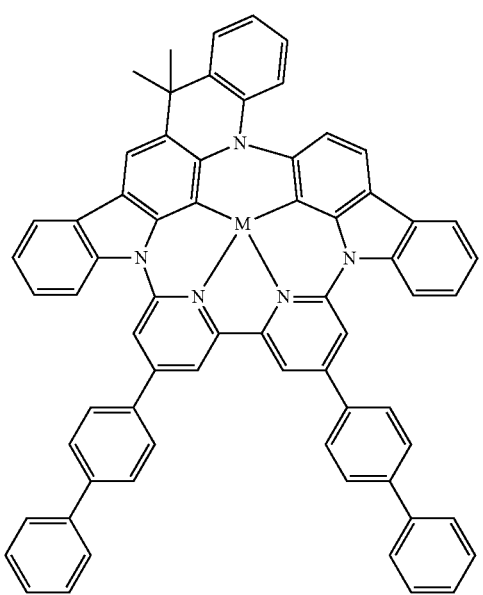
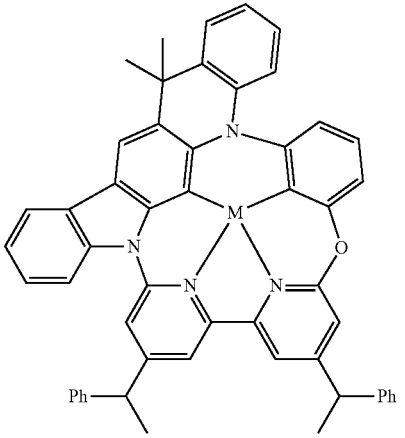

225
-continued
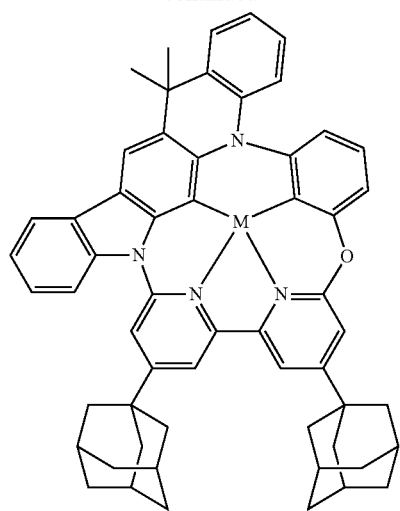
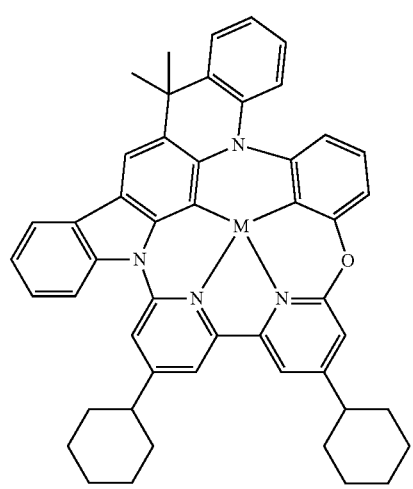
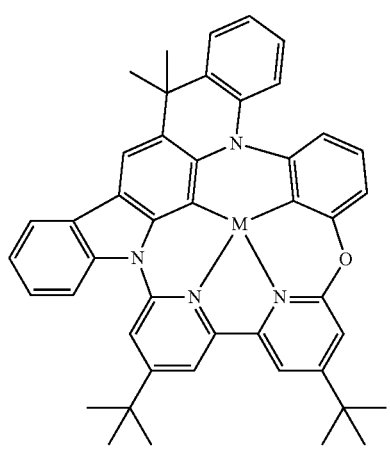
226
-continued
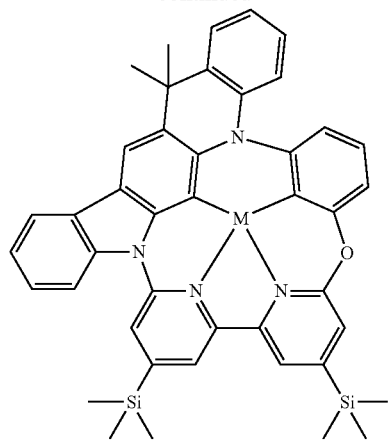
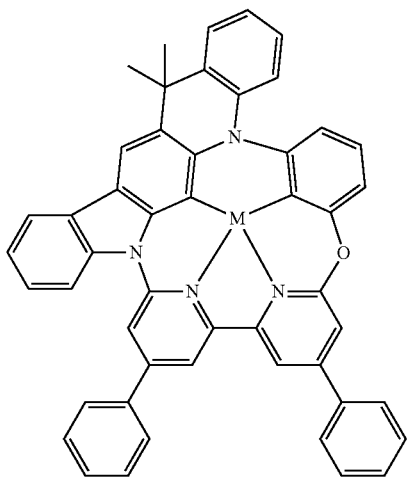
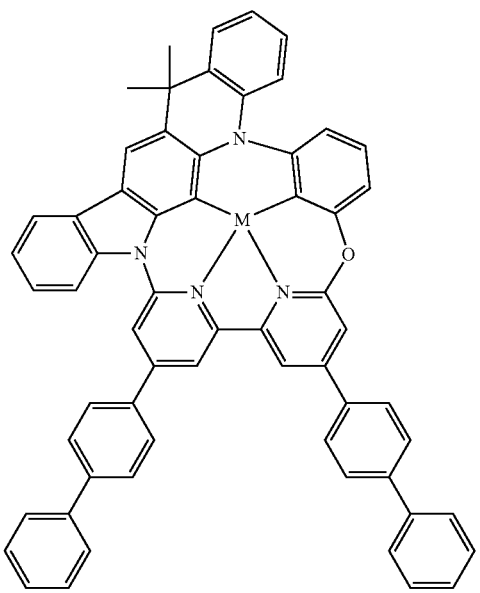

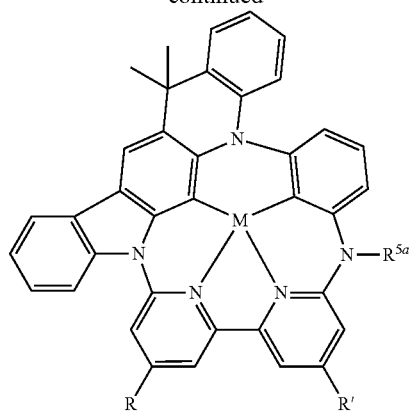
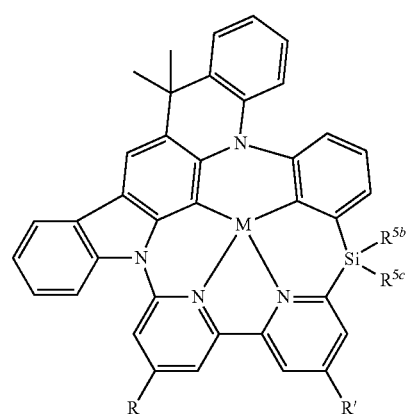
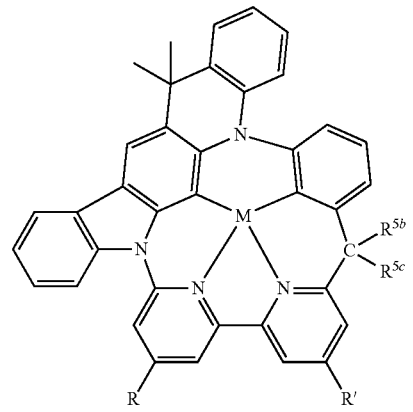
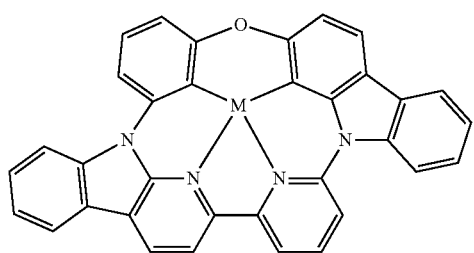
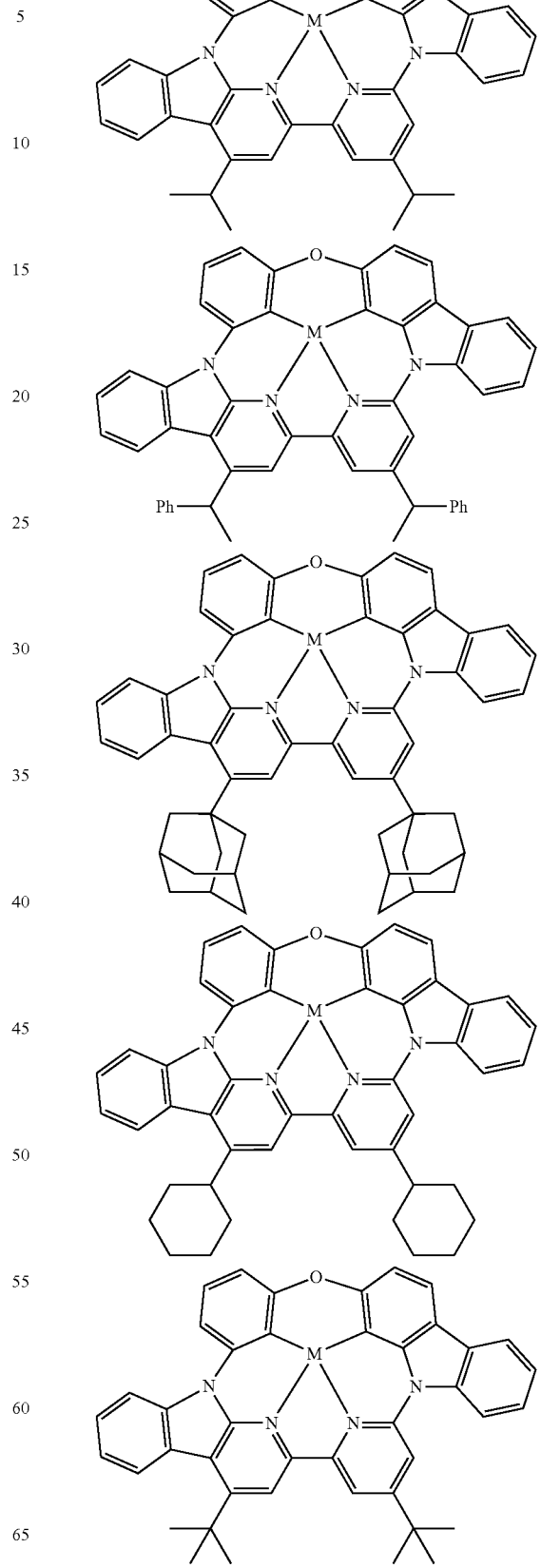

229
-continued
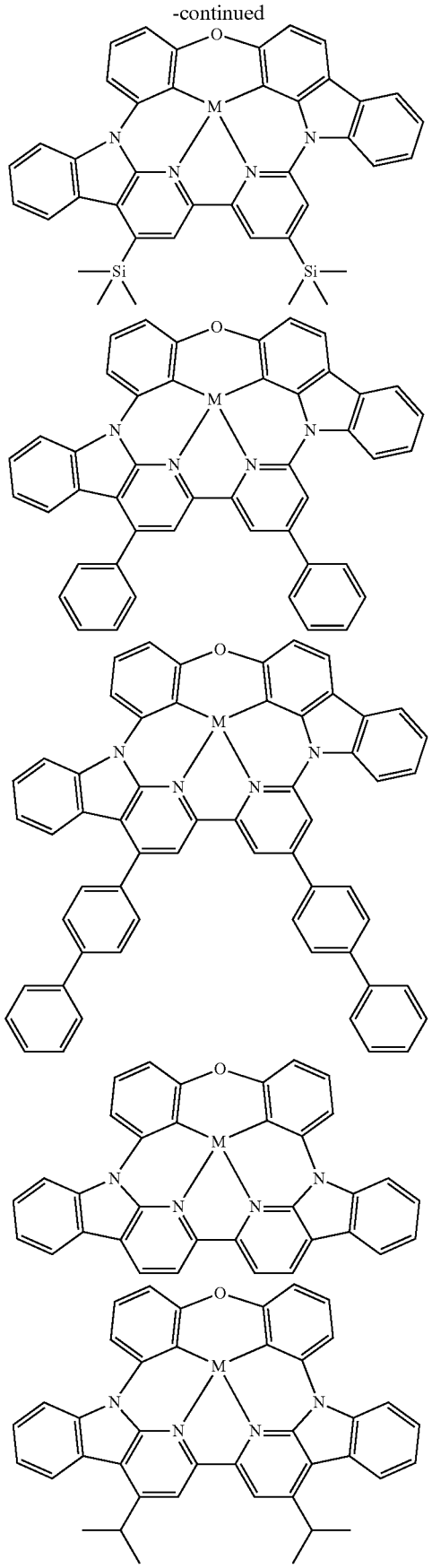
230
-continued
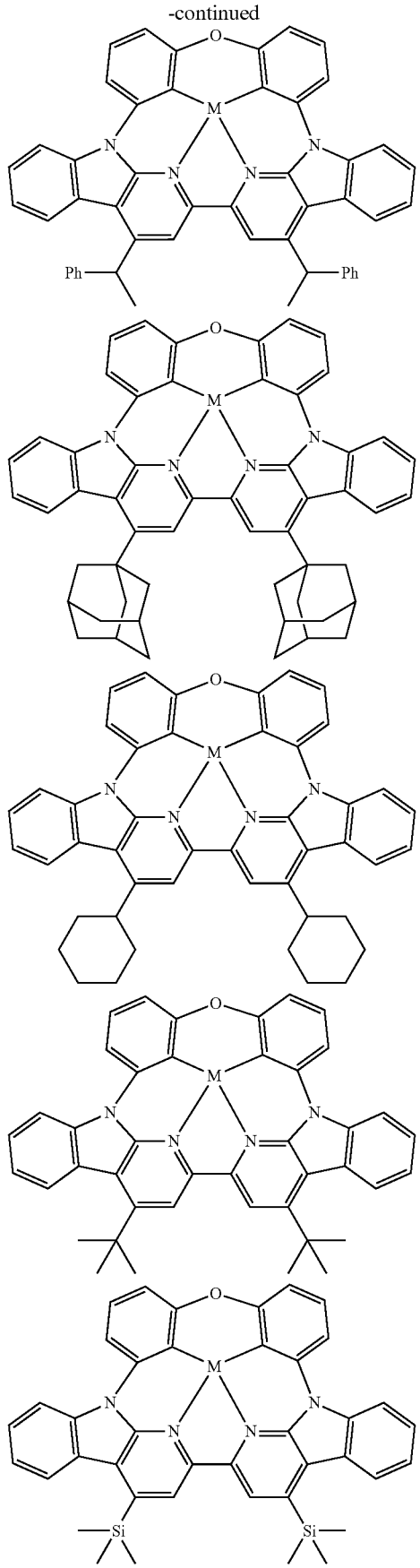

231
-continued
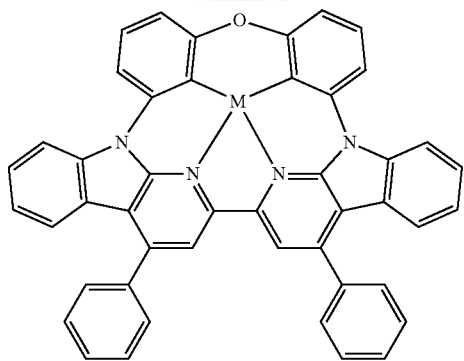
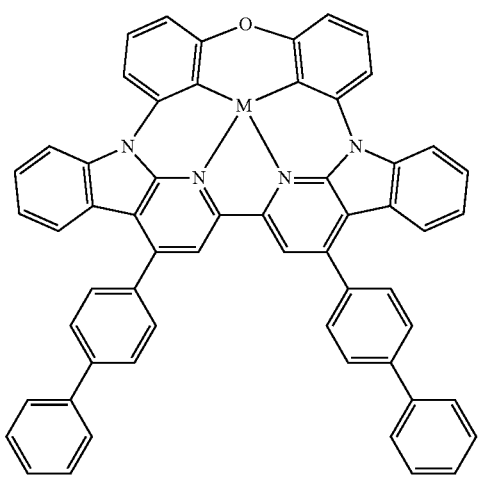
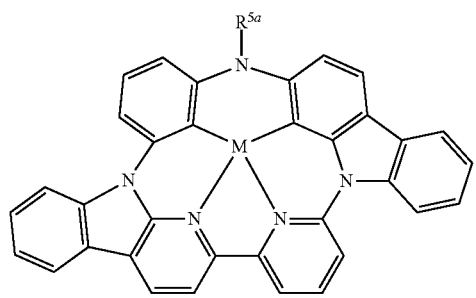
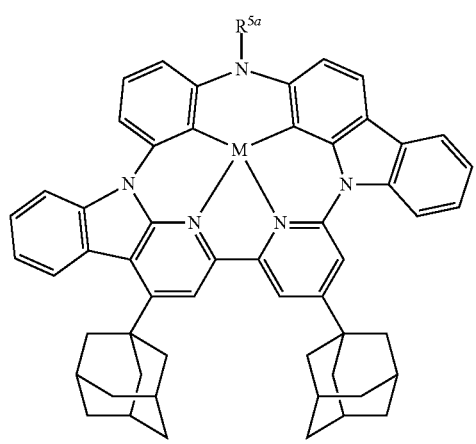
232
-continued
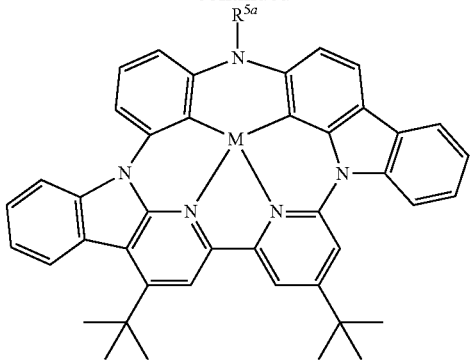
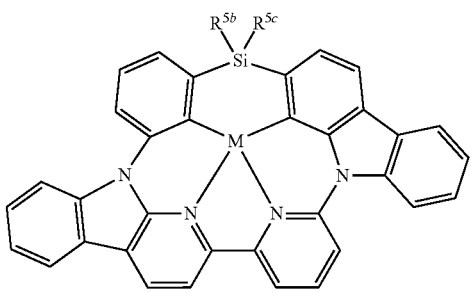
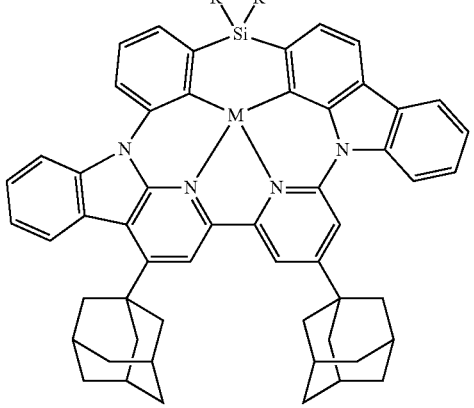
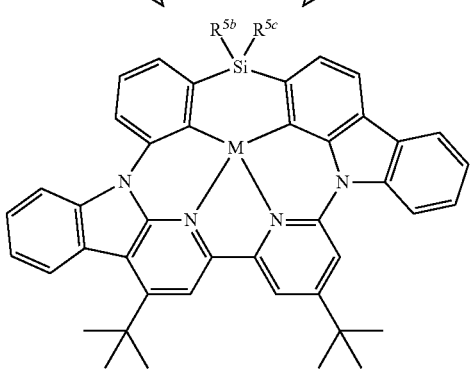
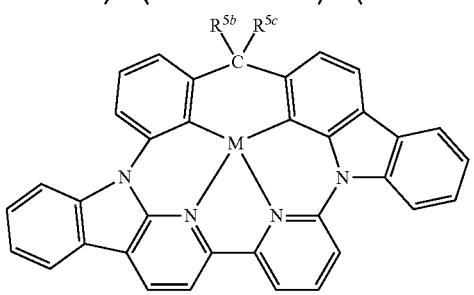

233
-continued
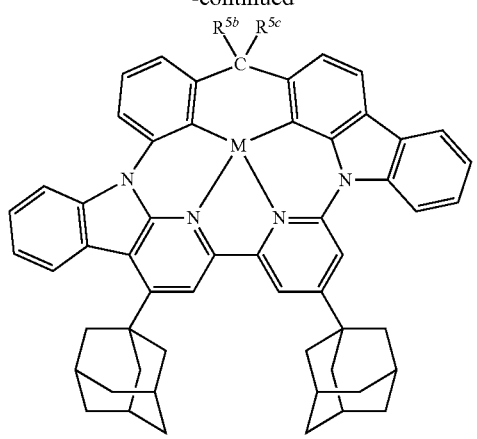
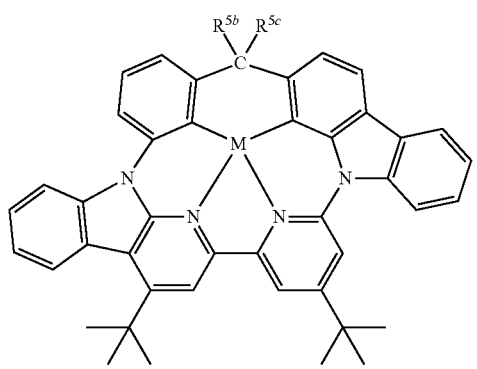
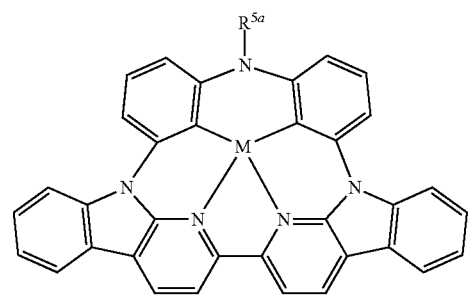
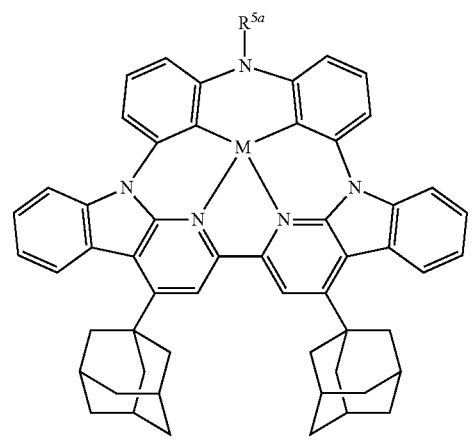
234
-continued
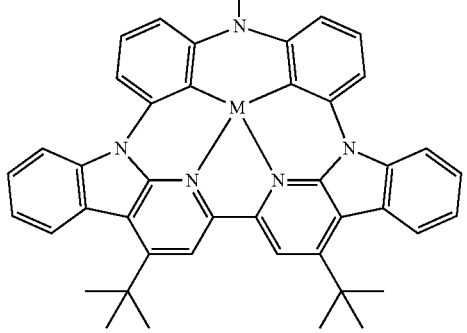
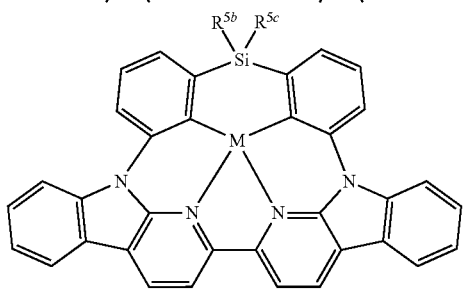
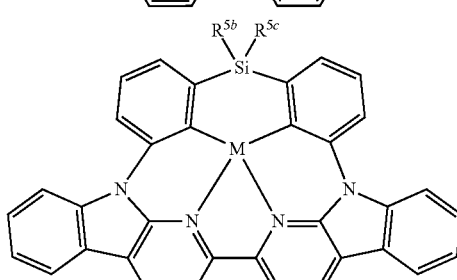
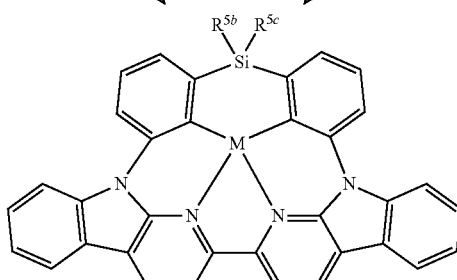
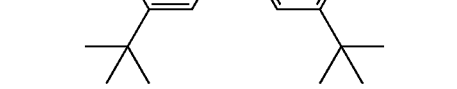
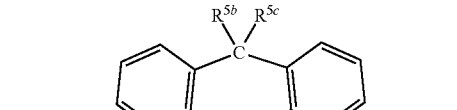
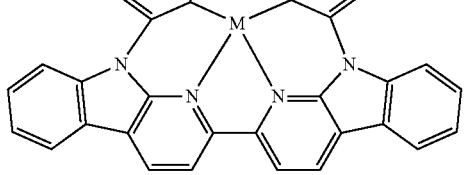

-continued
235
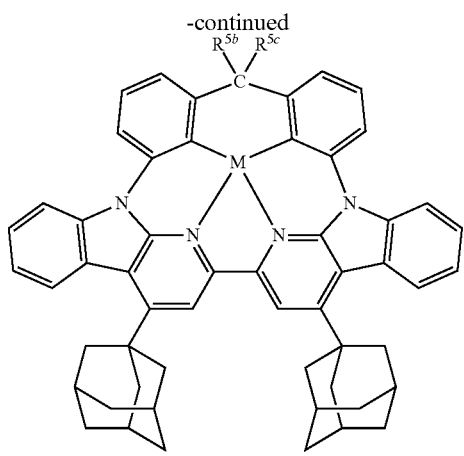
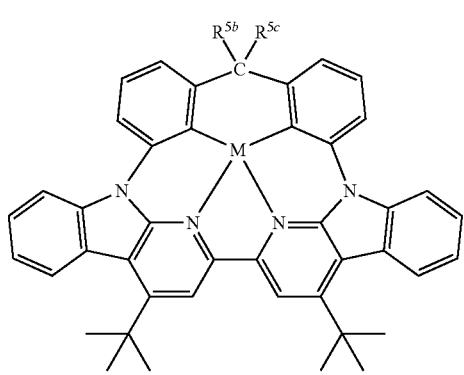
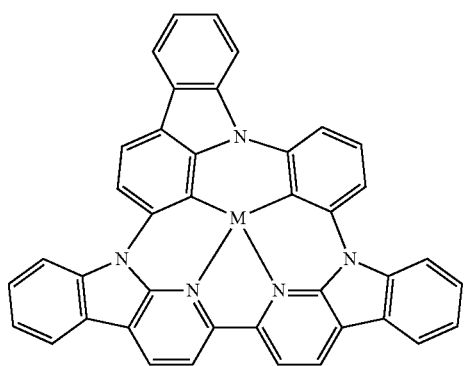
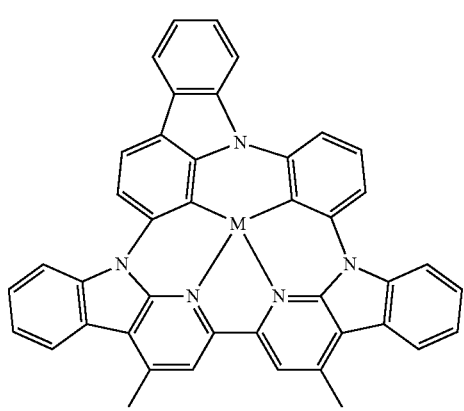
236
-continued
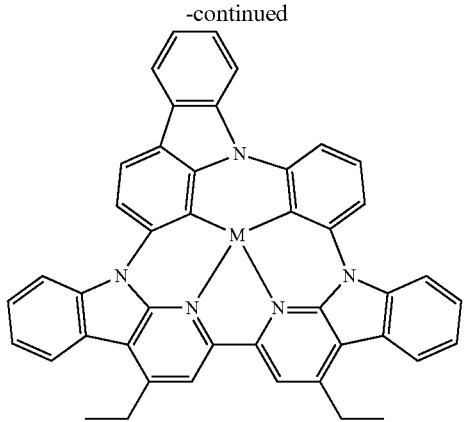
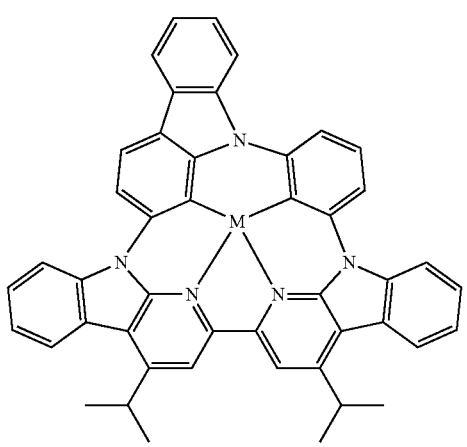
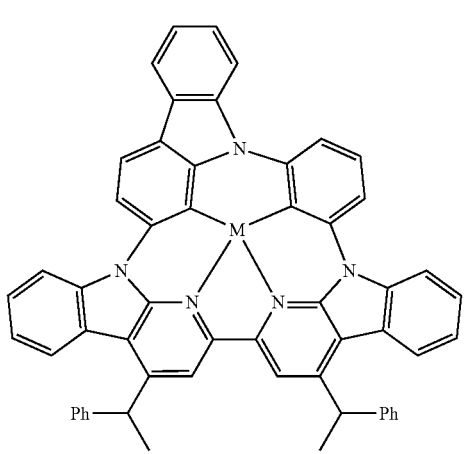

237
-continued
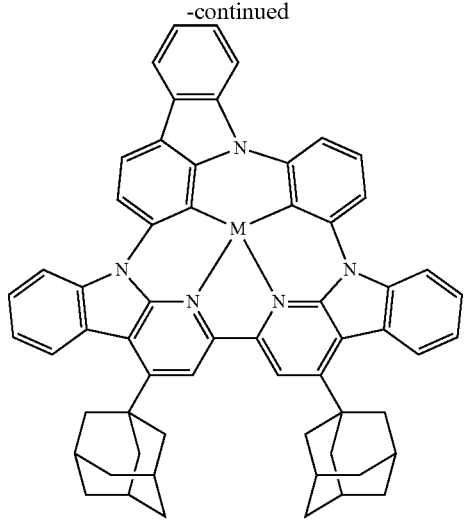
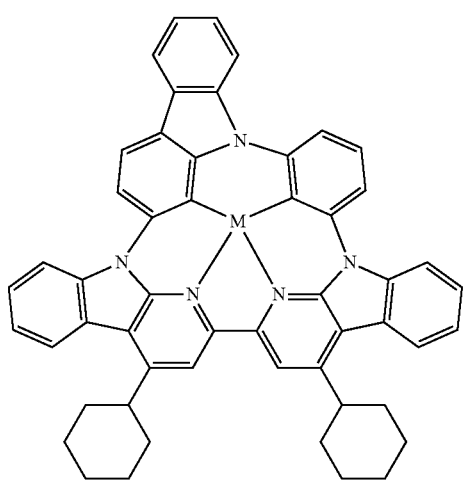
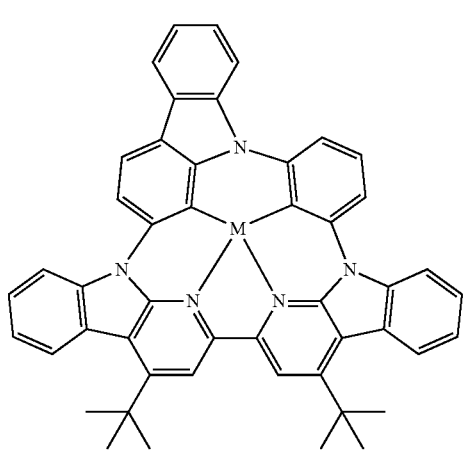
238
-continued
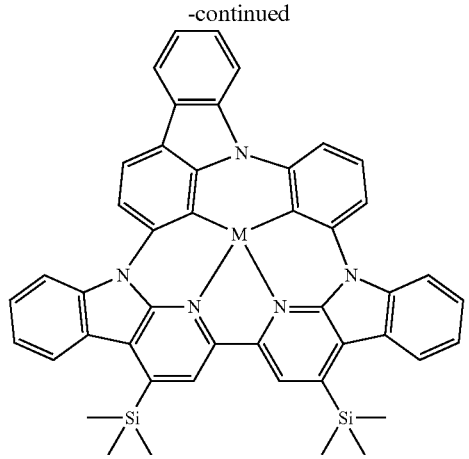
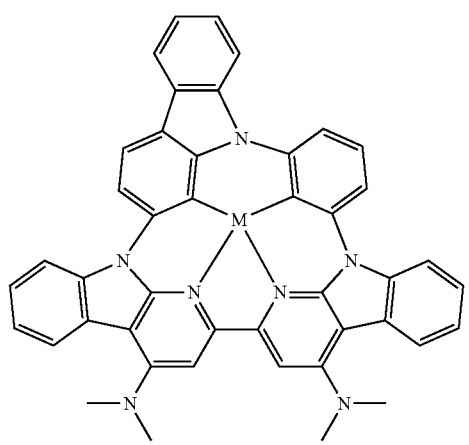
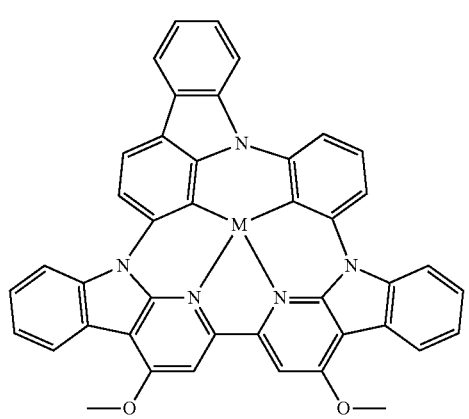

239
-continued
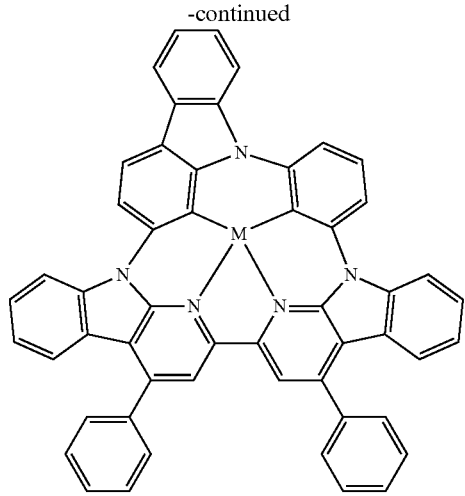
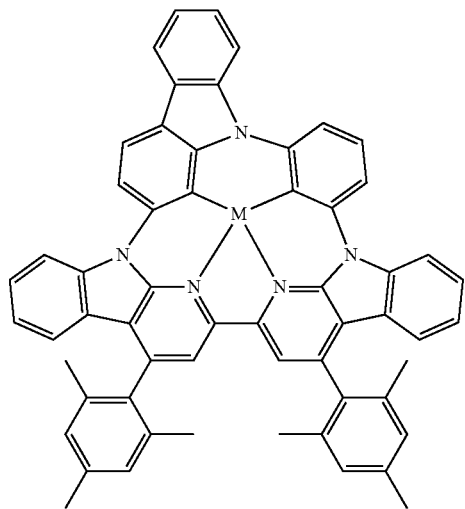
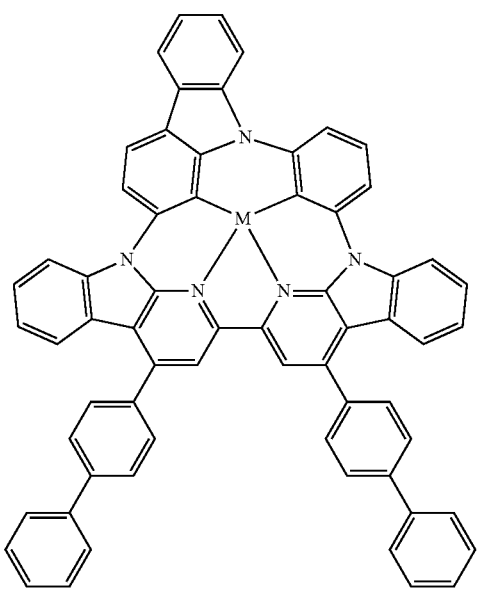
240
-continued
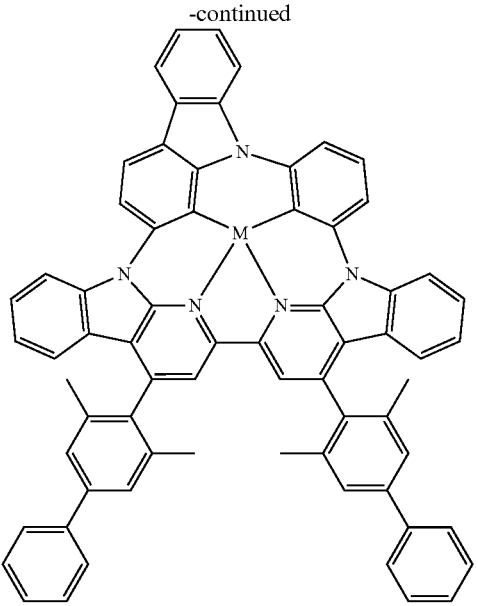
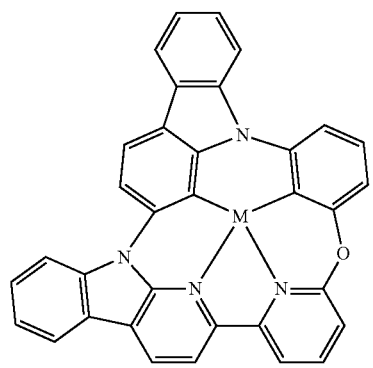
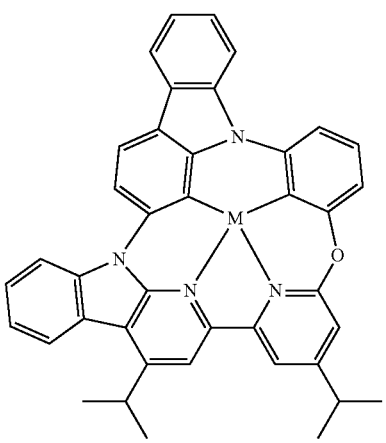

241
-continued
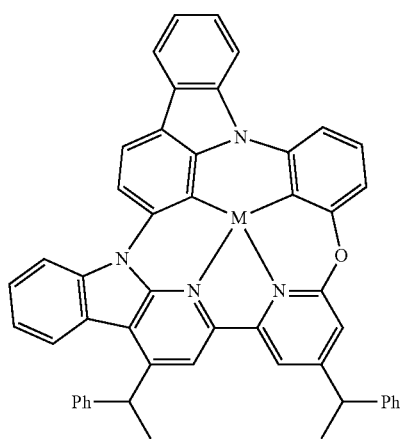
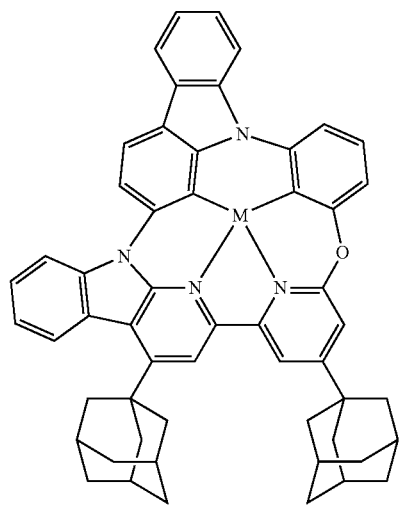
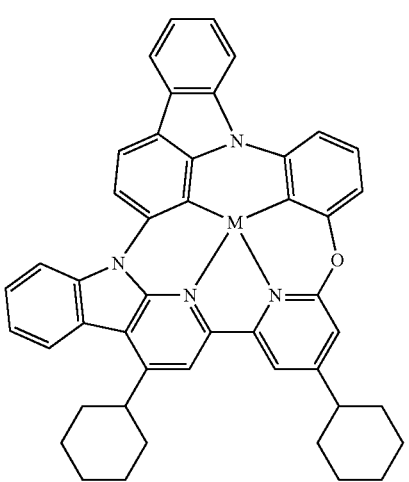
242
-continued
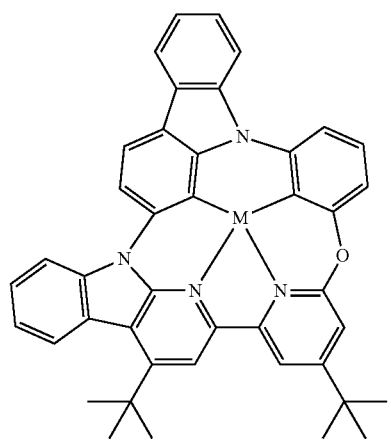
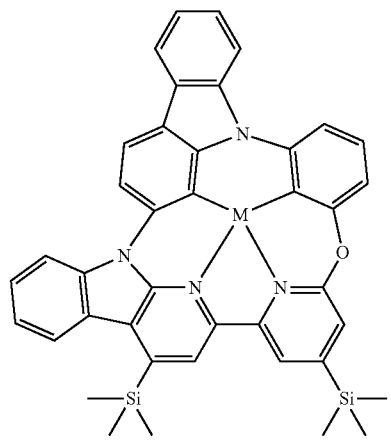
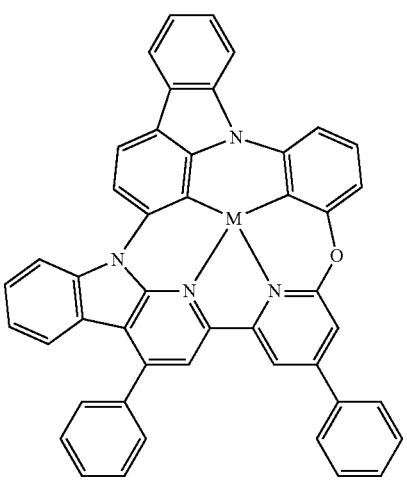

243
-continued
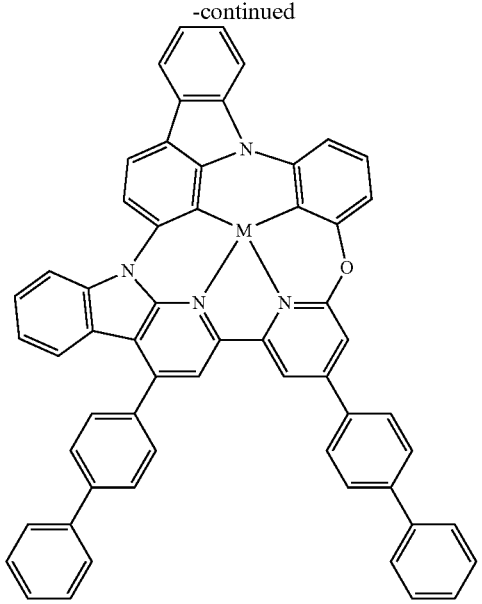
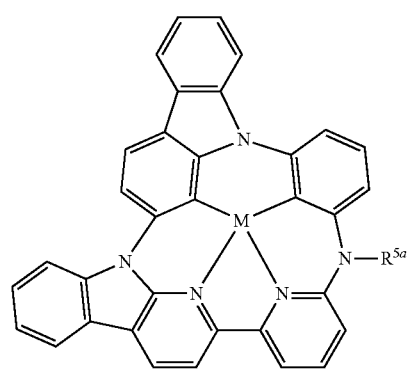
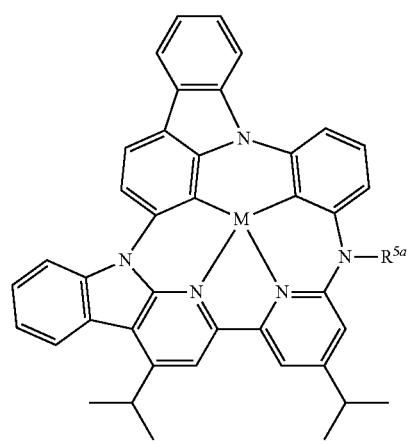
244
-continued
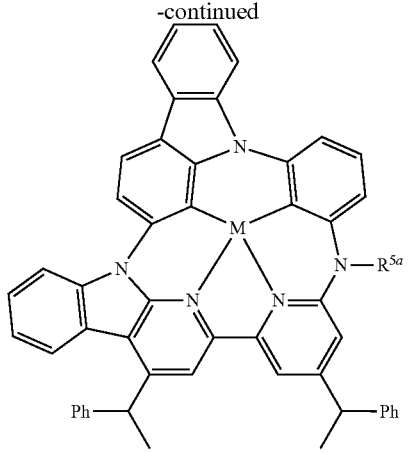
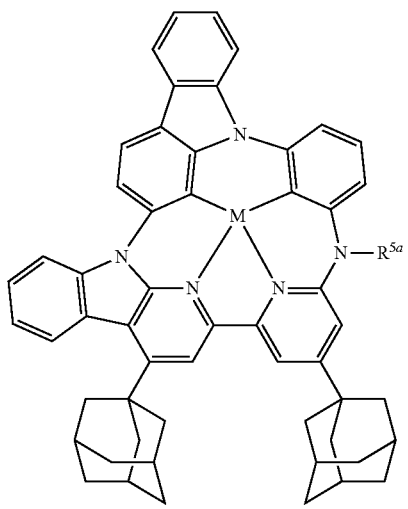
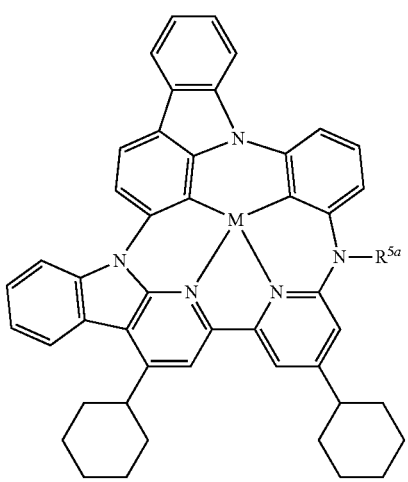

245
-continued
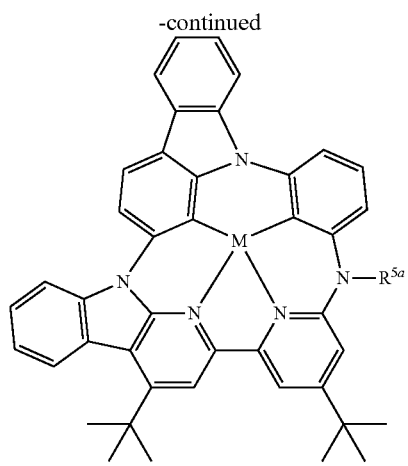
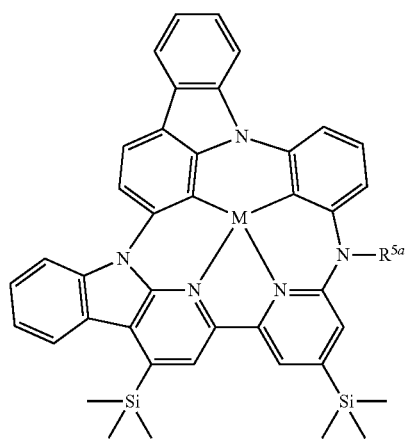
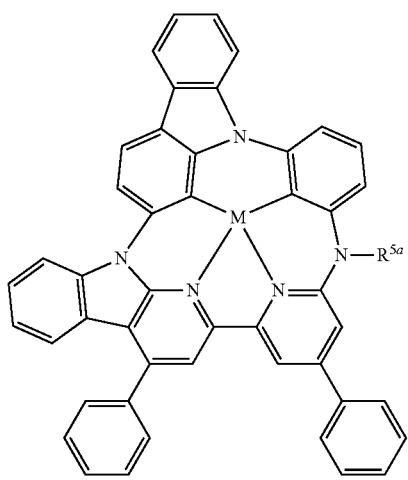
246
-continued
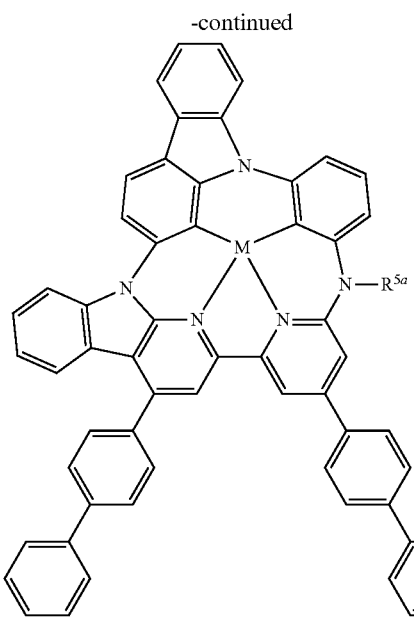
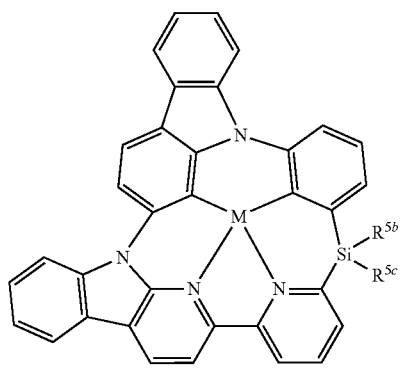
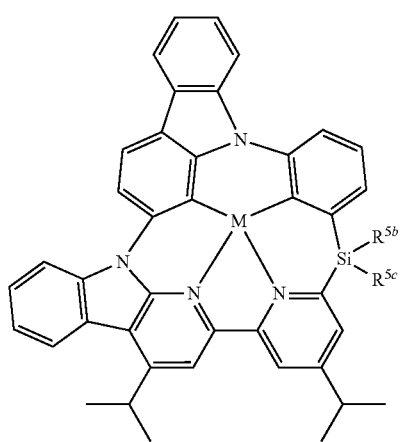

247
-continued
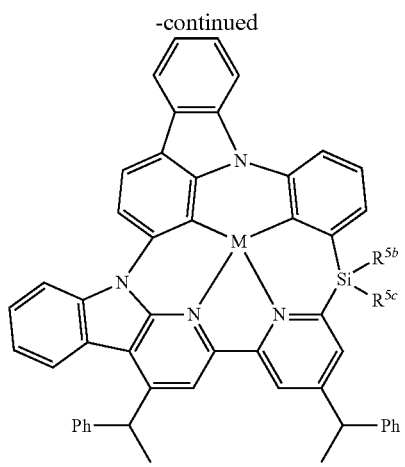
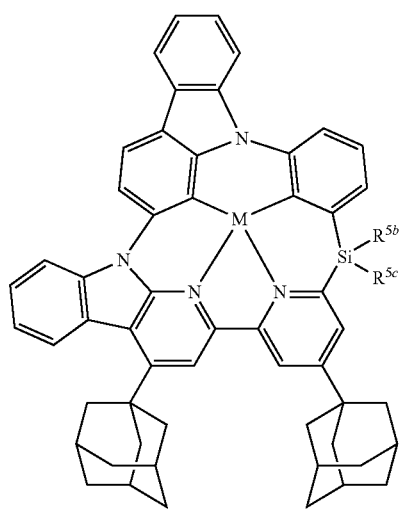
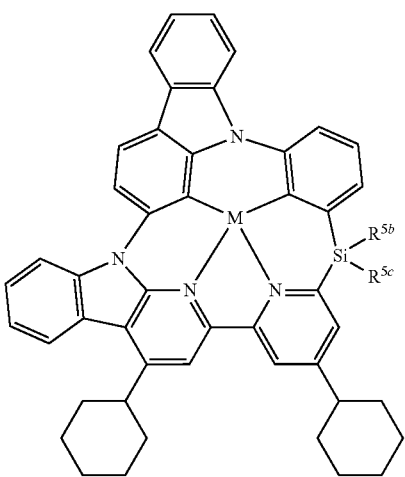
248
-continued
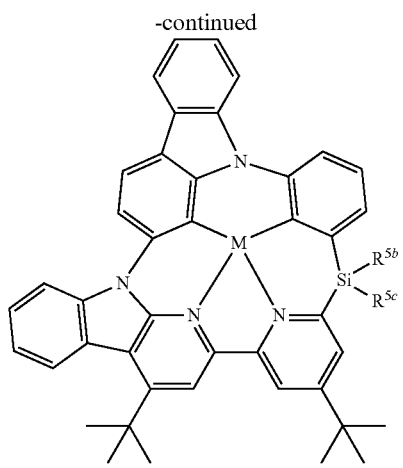
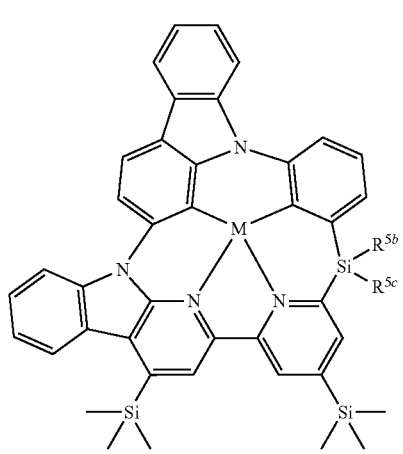
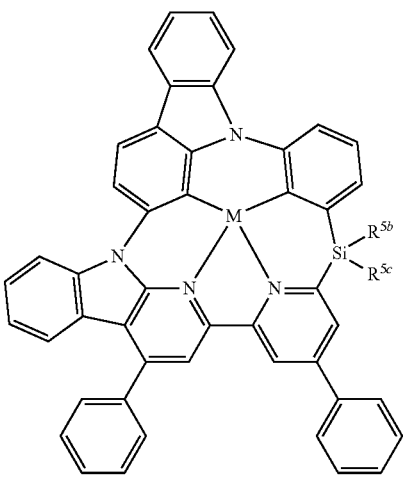

249
-continued
250
-continued
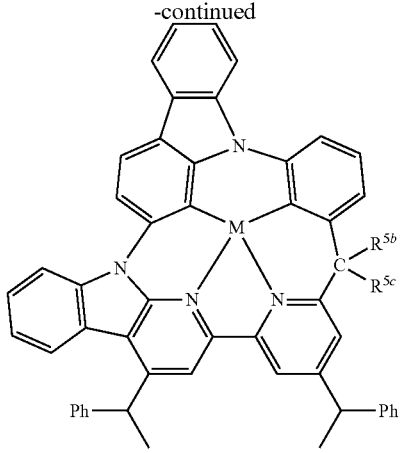
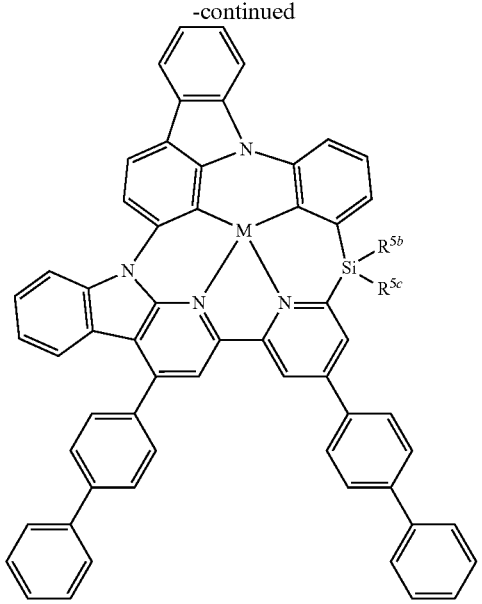
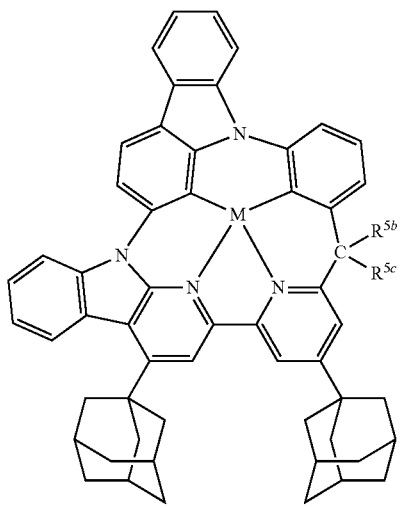
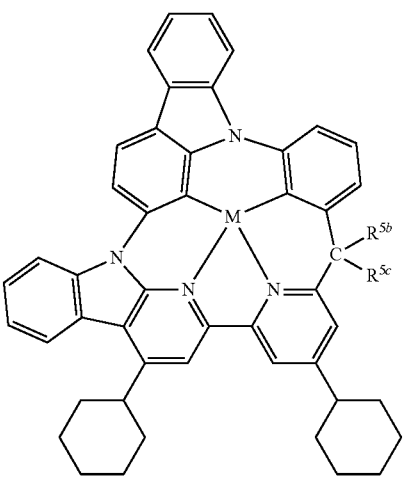

251
-continued
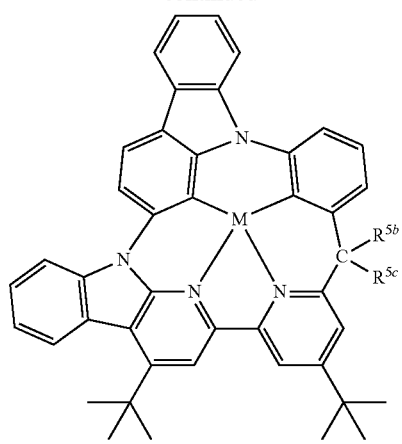
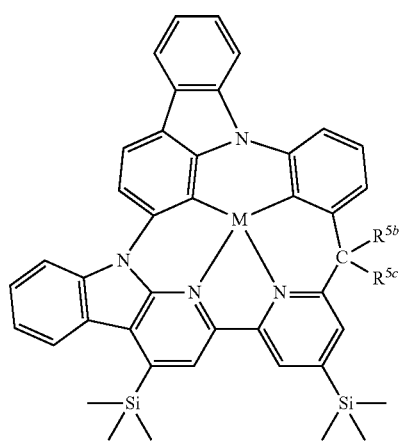
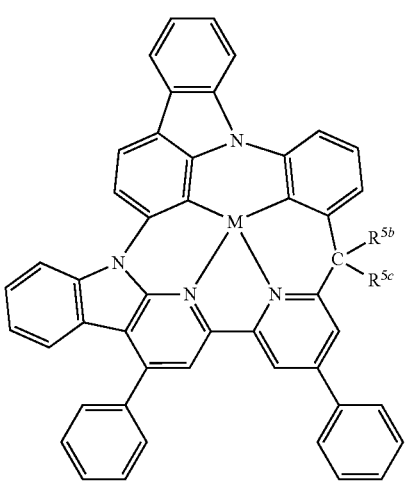
252
-continued
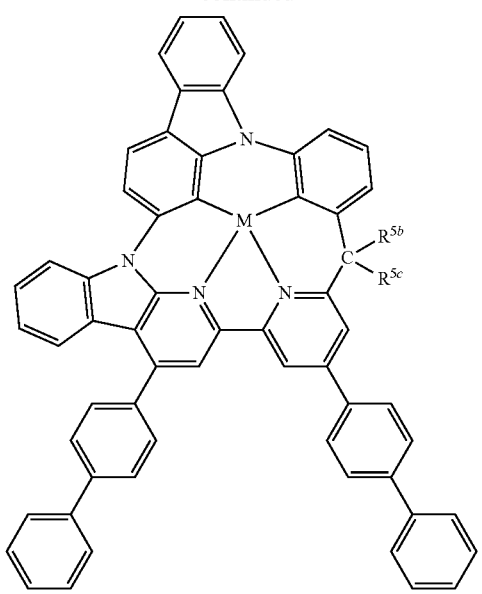
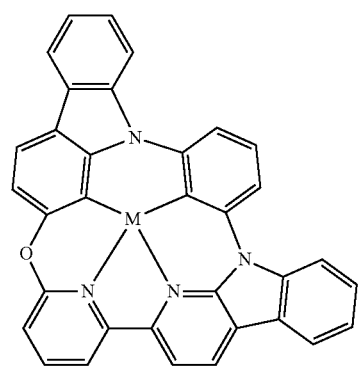
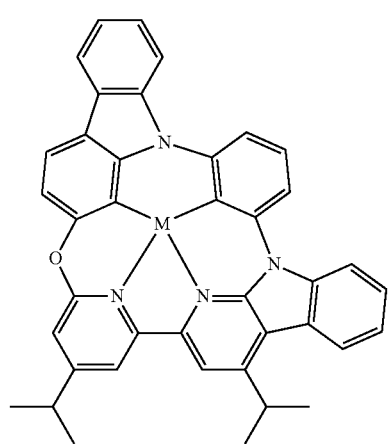

253
-continued
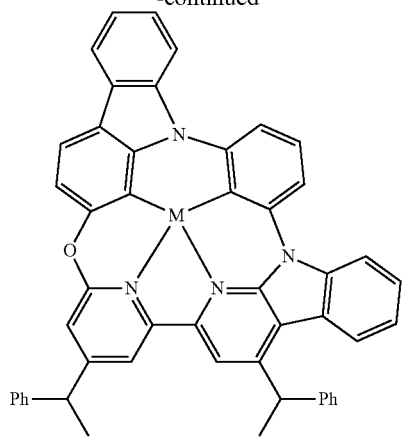
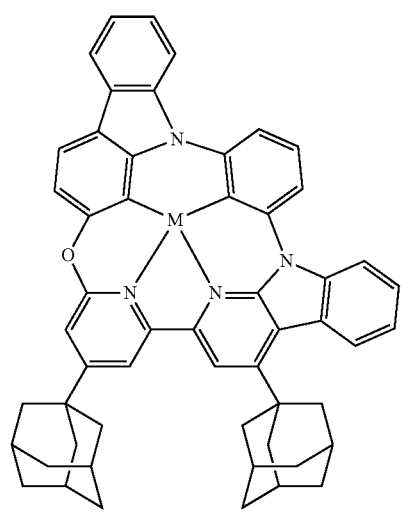
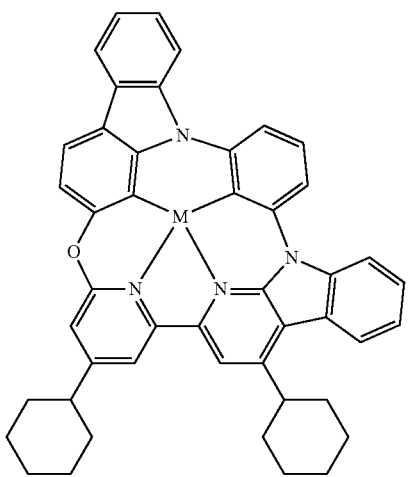
254
-continued
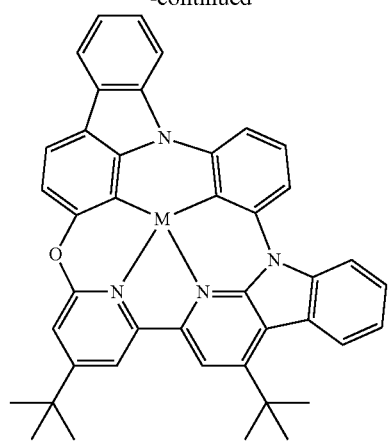
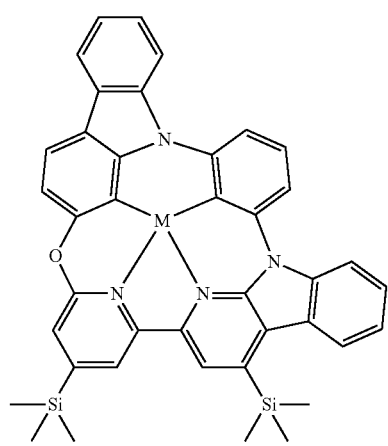
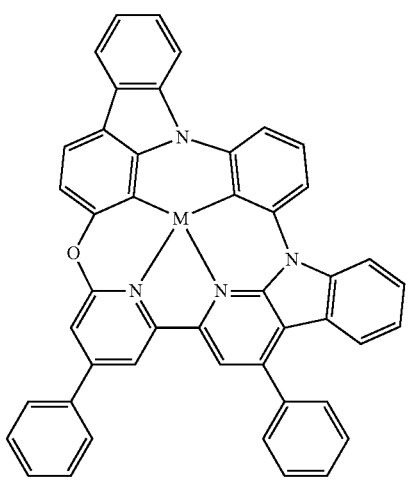

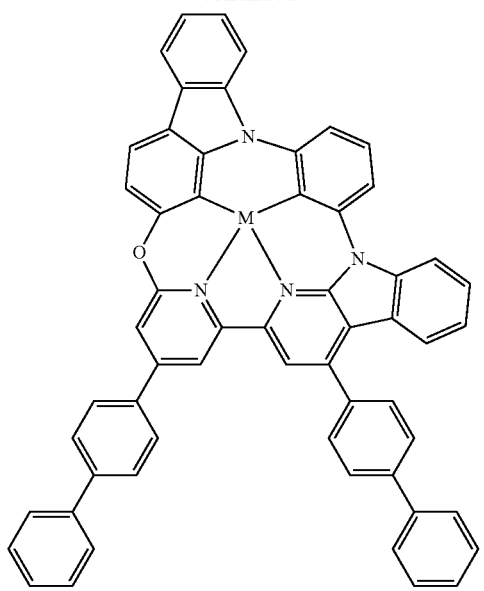
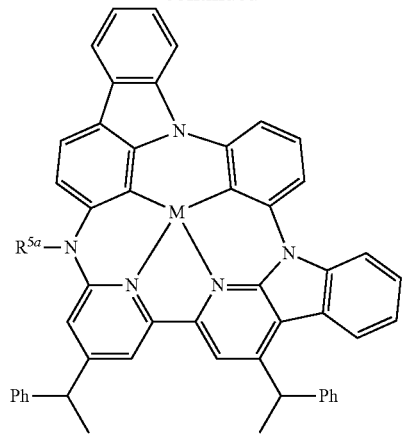
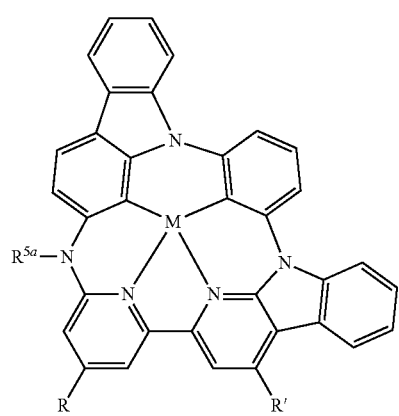
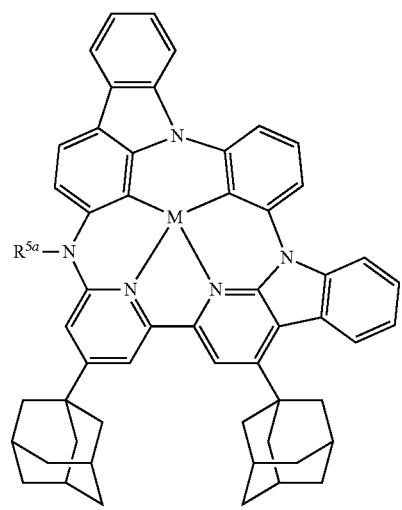
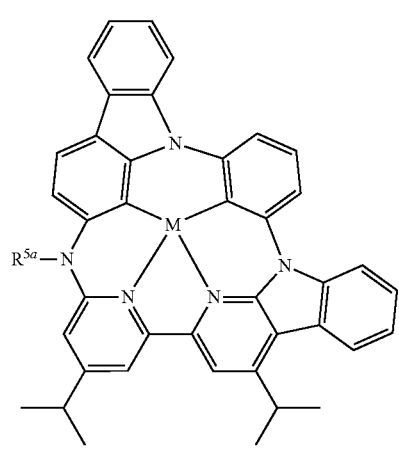
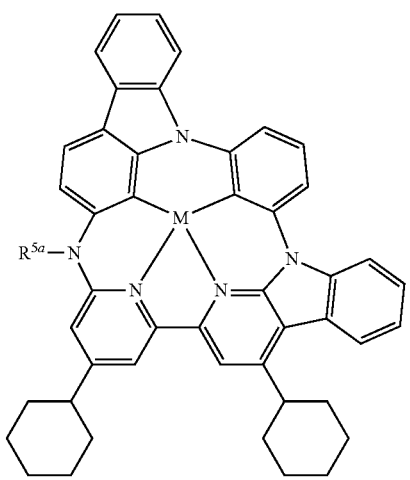

257
-continued
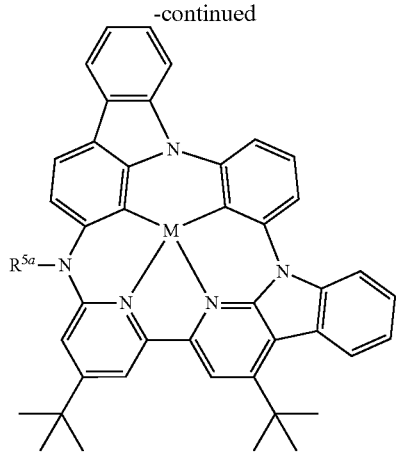
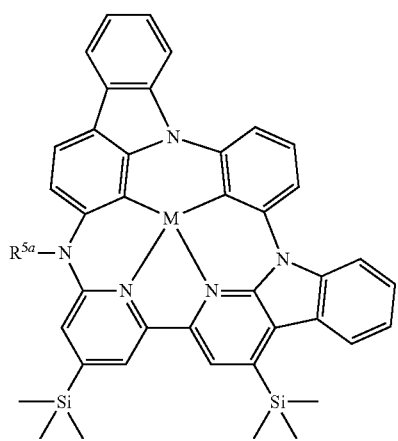
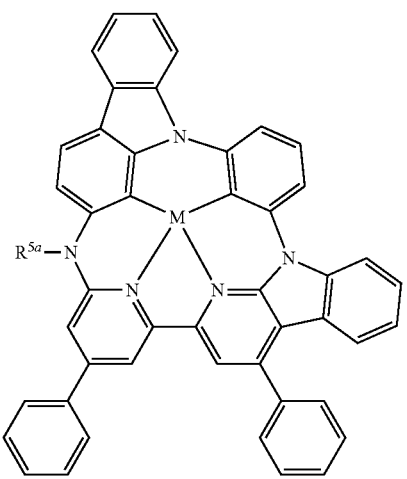
258
-continued
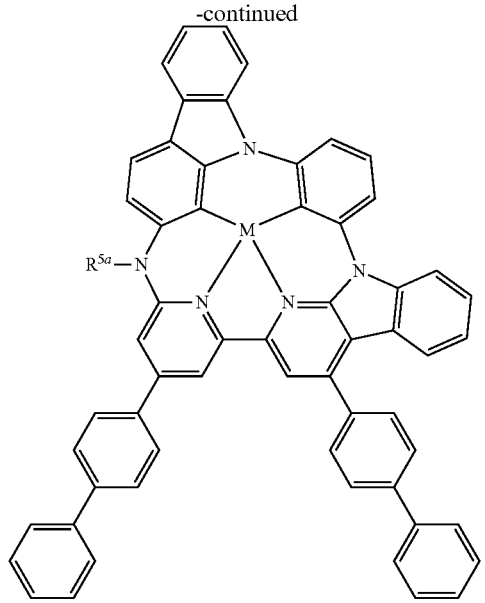
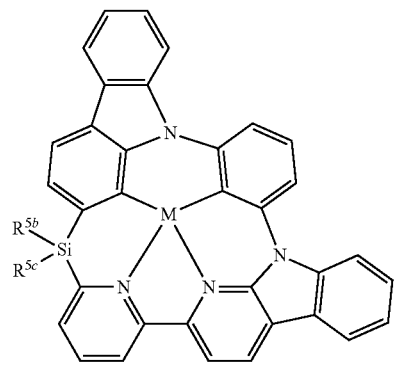
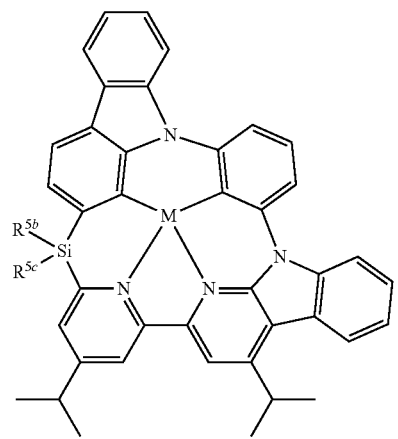

259
-continued
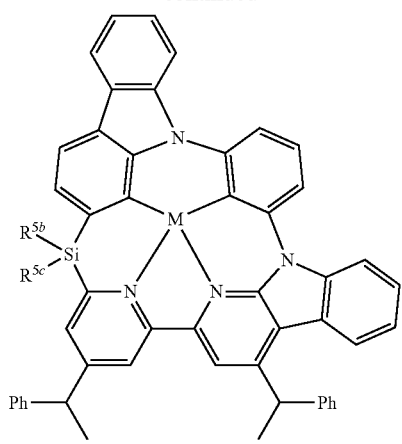
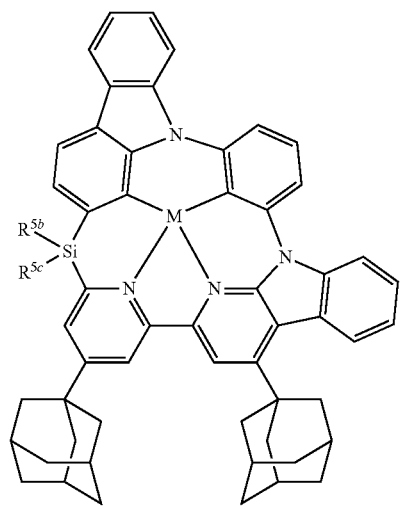
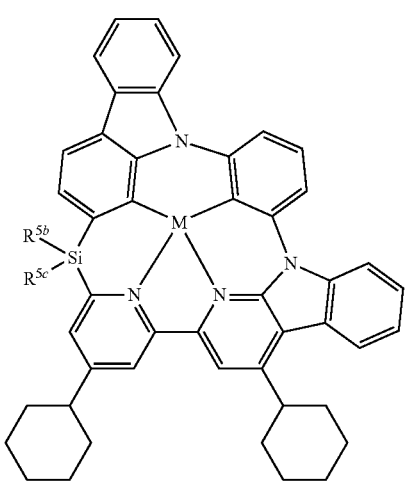
260
-continued
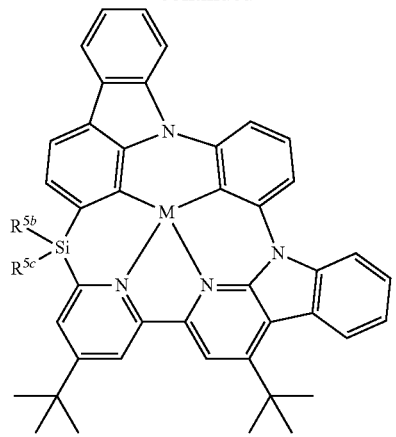
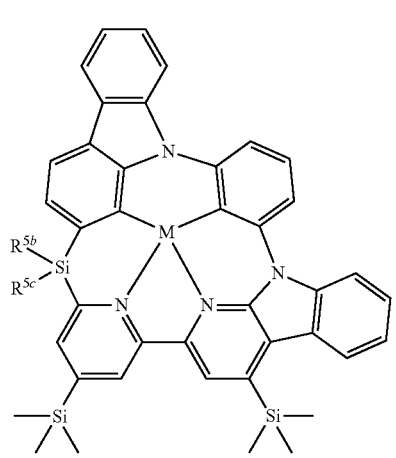
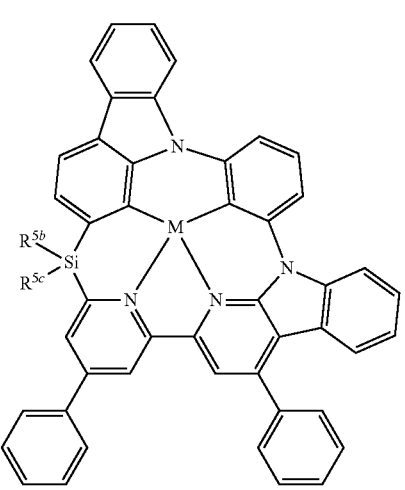

261
-continued
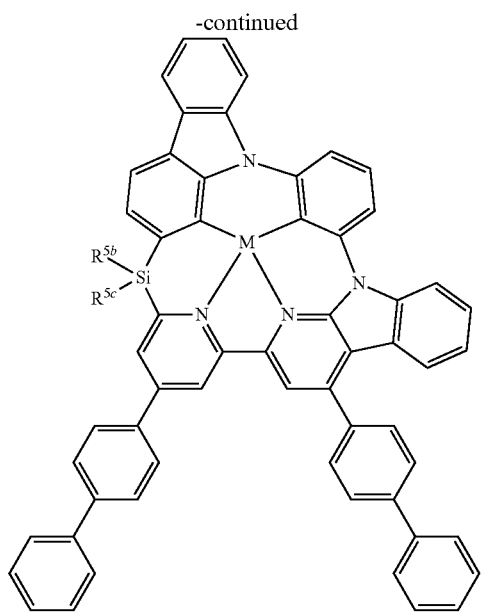
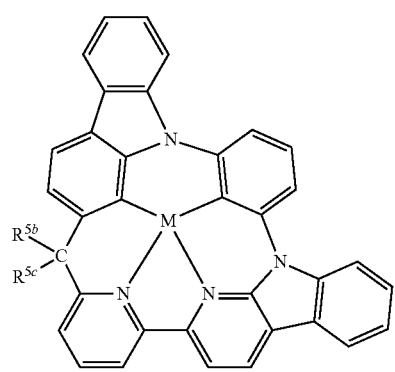
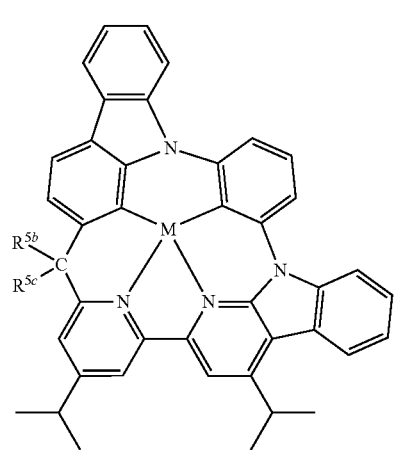
262
-continued
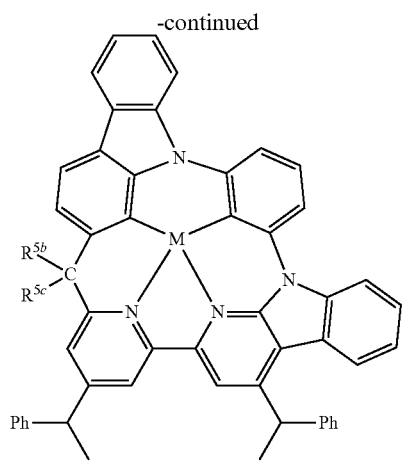
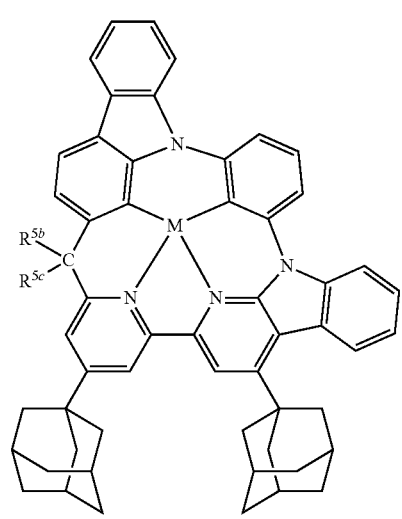
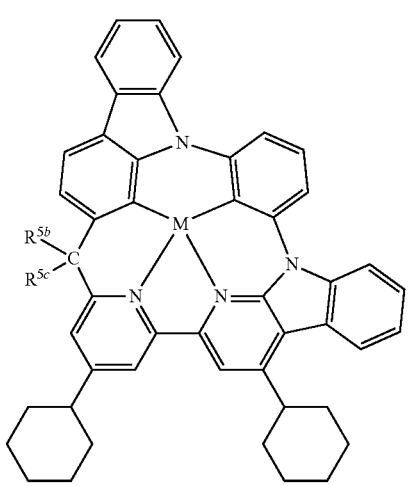

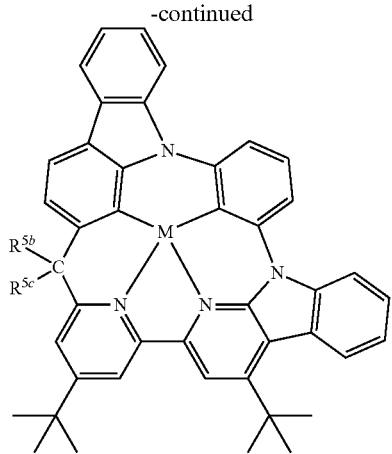
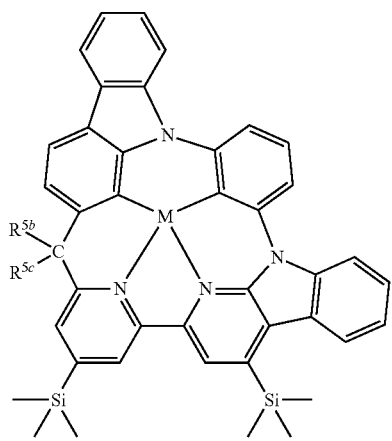
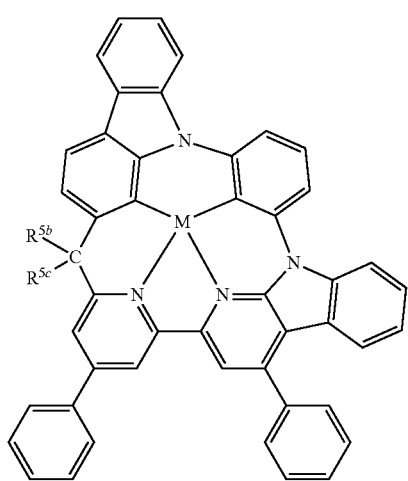
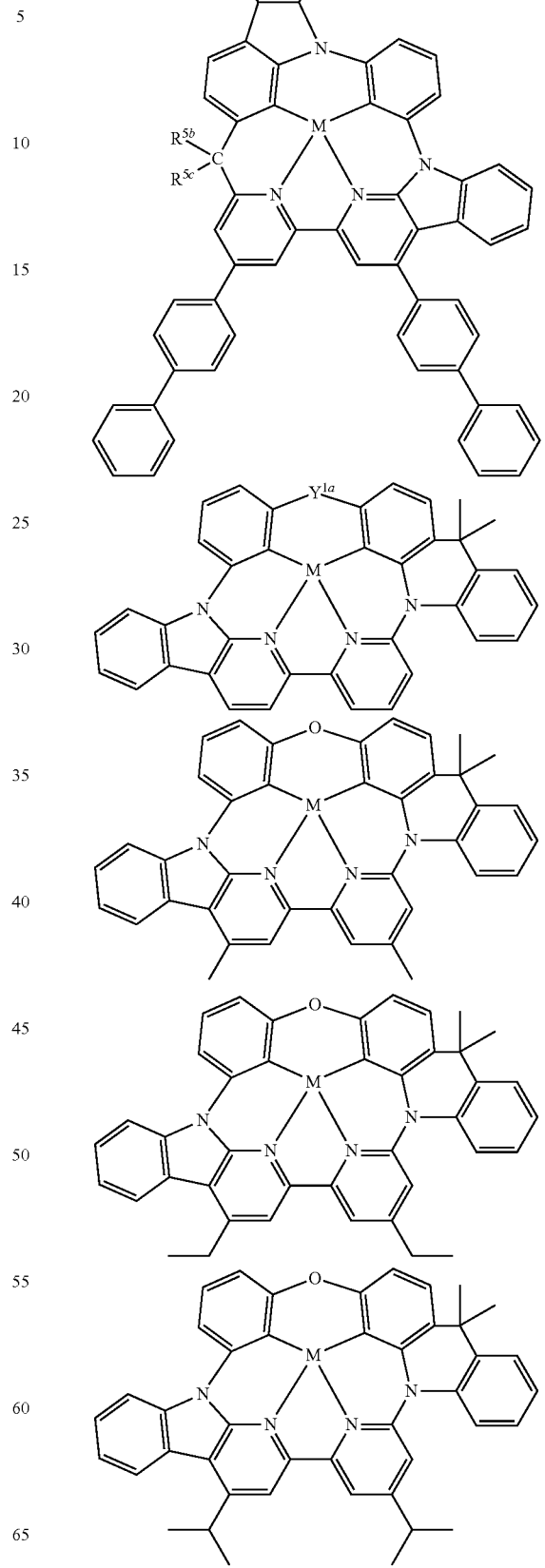

265
-continued
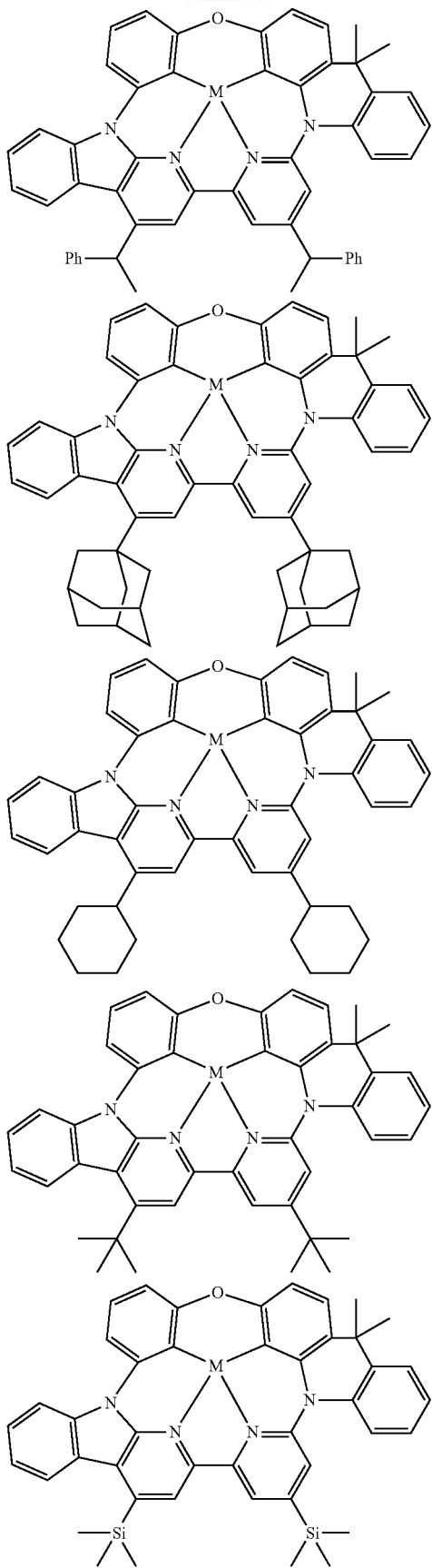
266
-continued
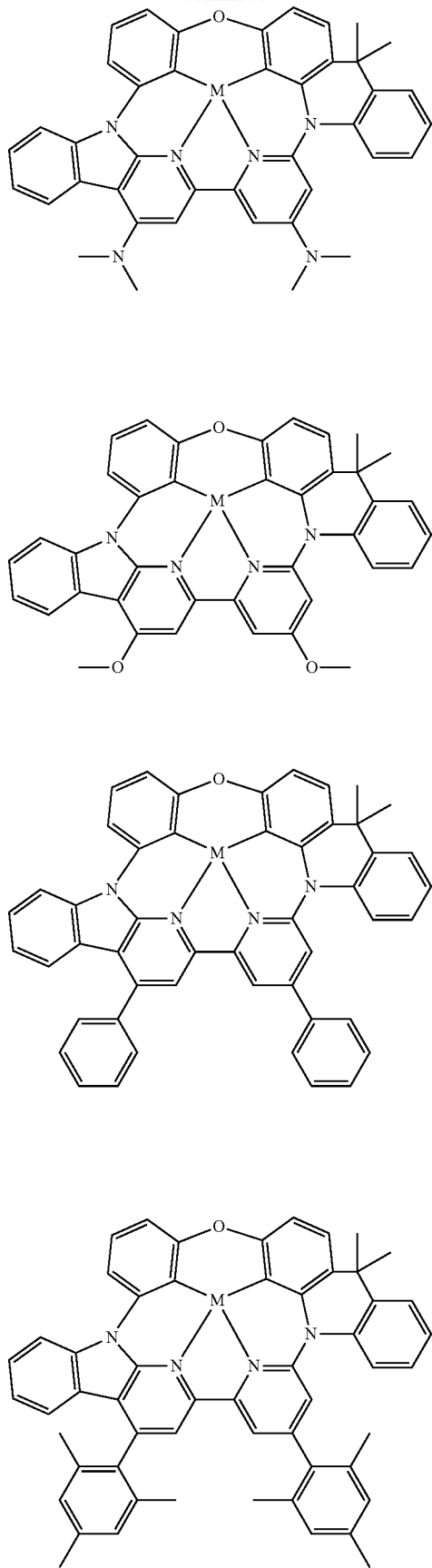

267
-continued
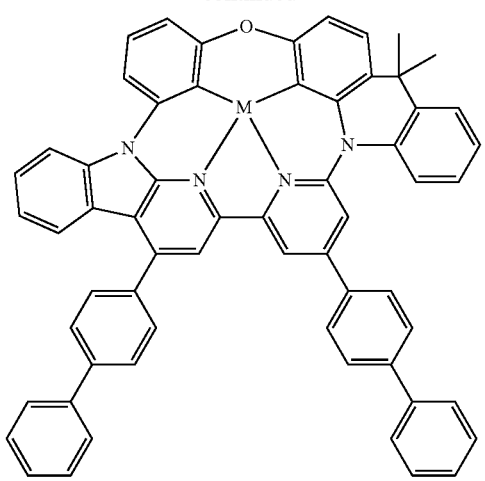
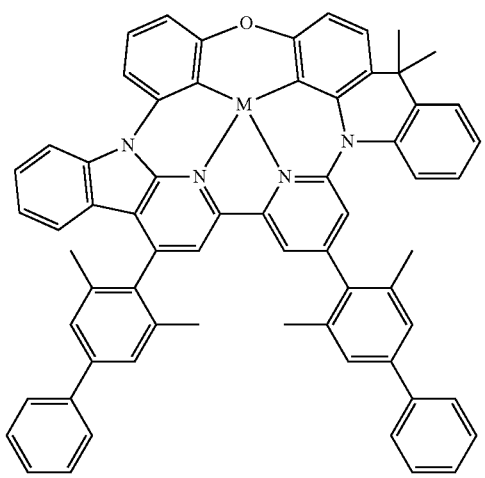
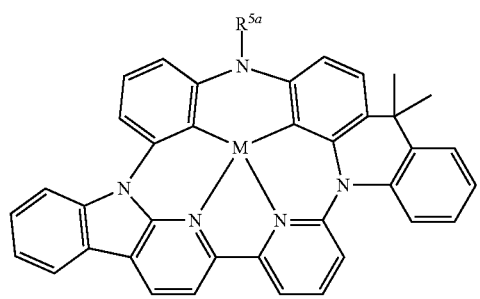
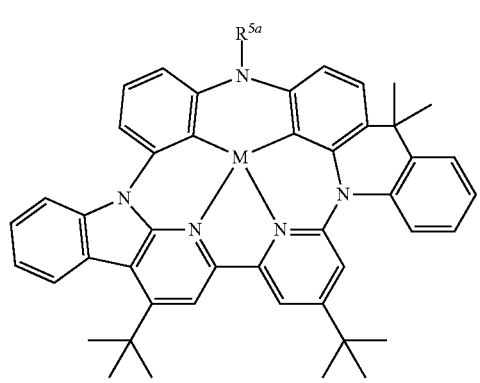
268
-continued
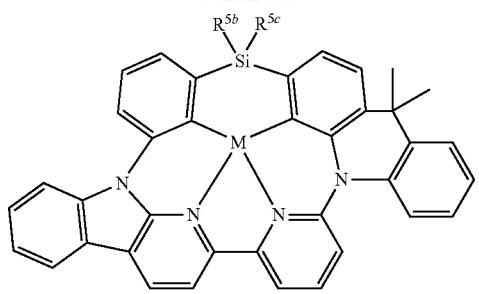
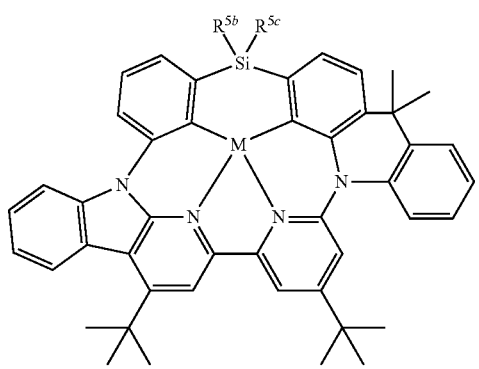
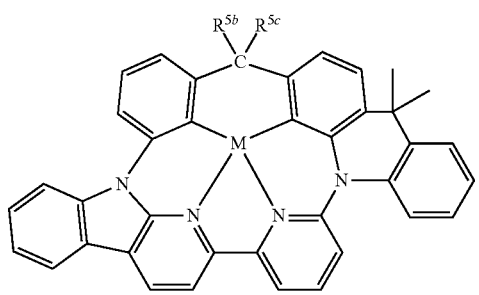
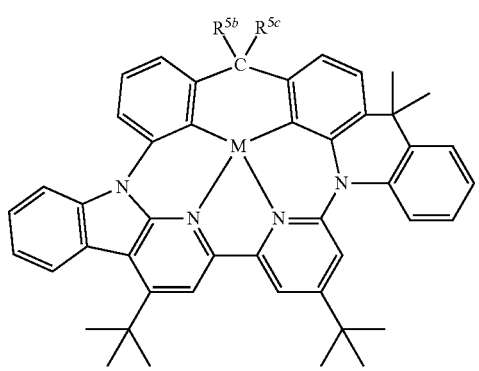
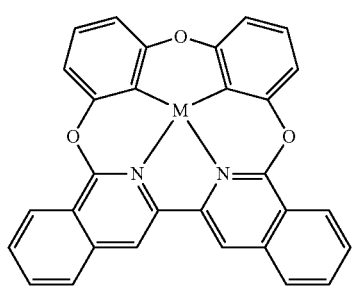

269
-continued
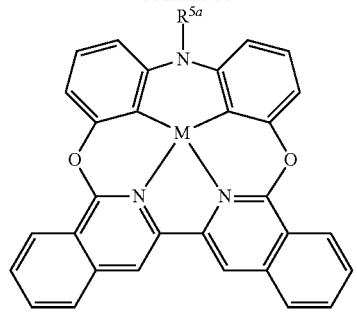
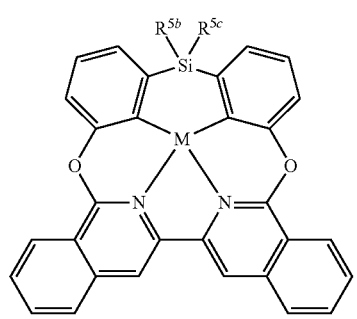
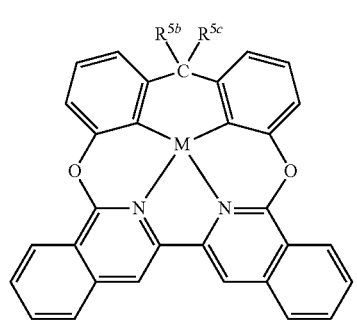
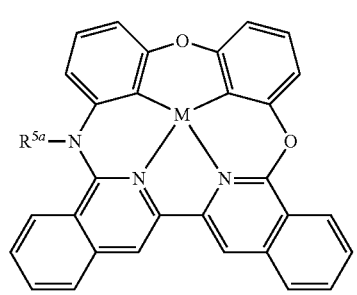
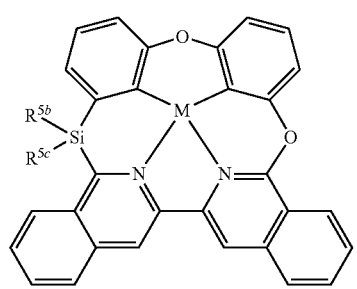
270
-continued
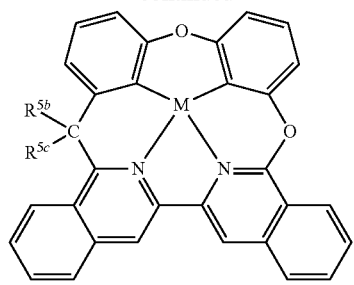
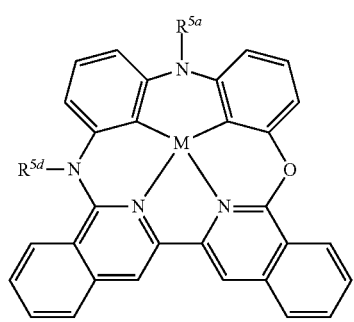
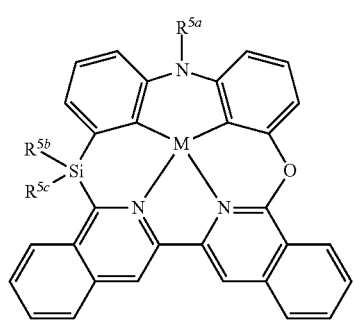
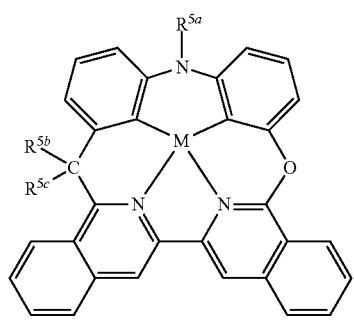
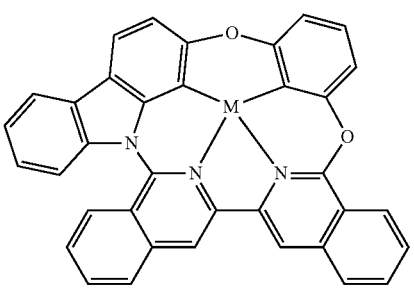

271
-continued
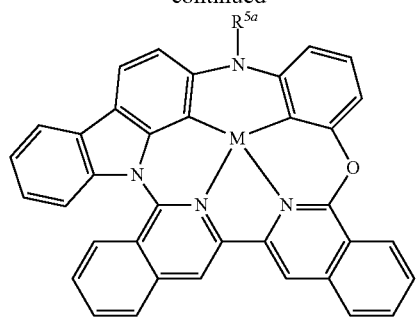
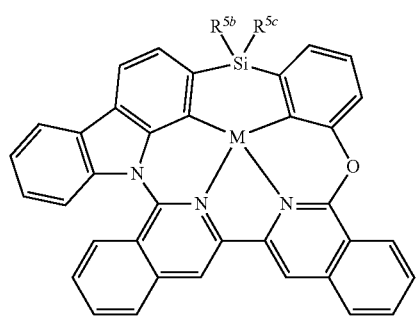
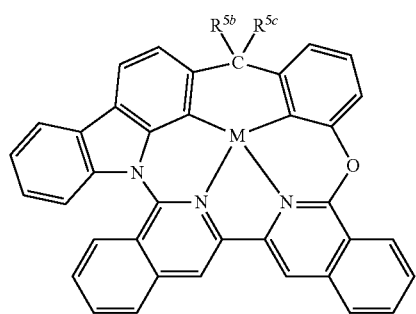
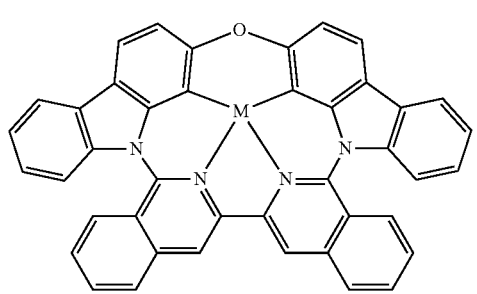
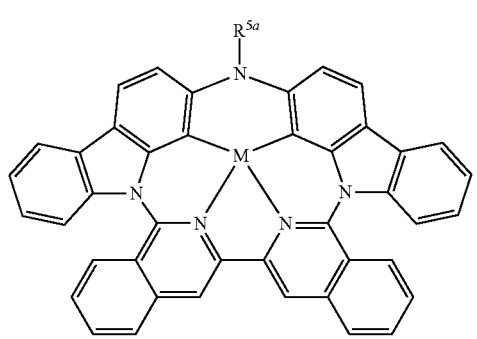
272
-continued
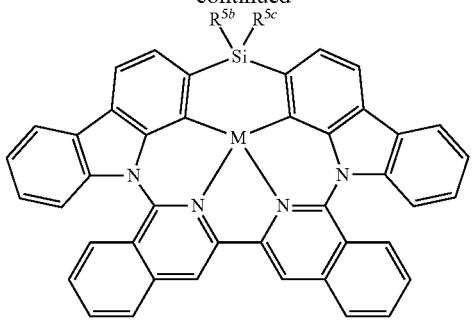
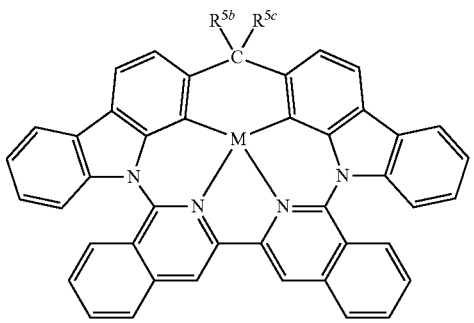
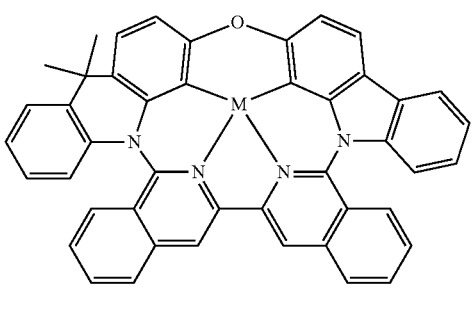
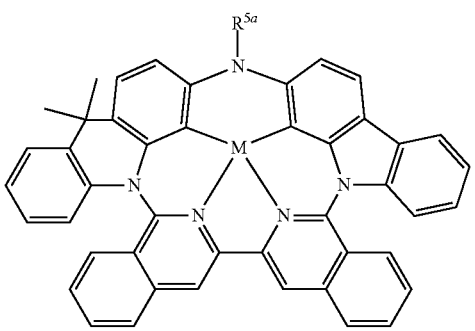
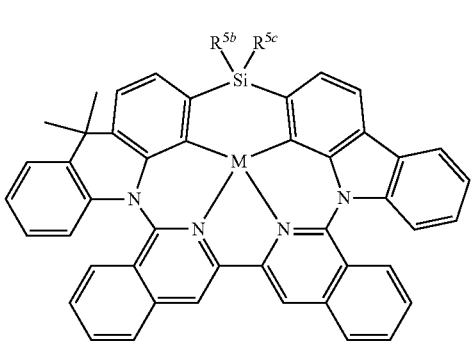

273
-continued
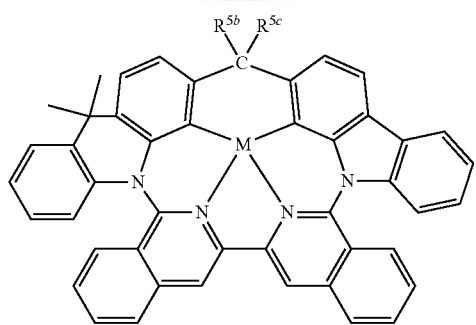
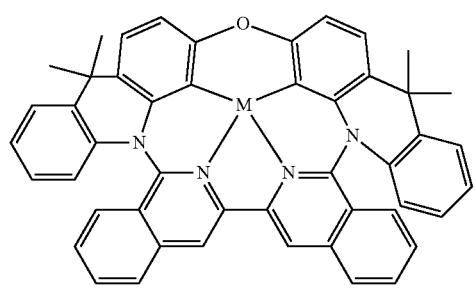
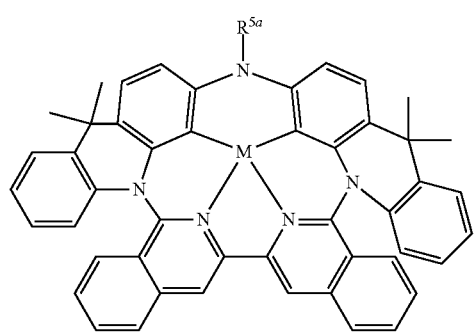
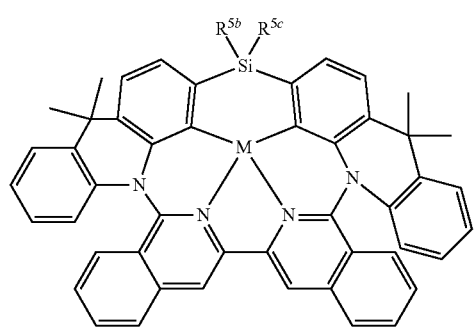
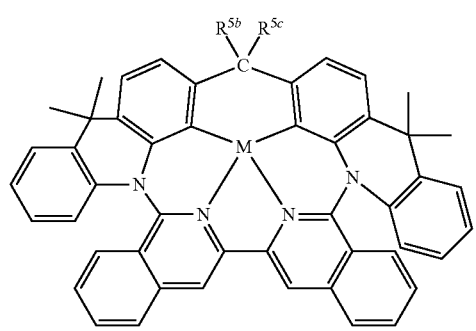
274
-continued
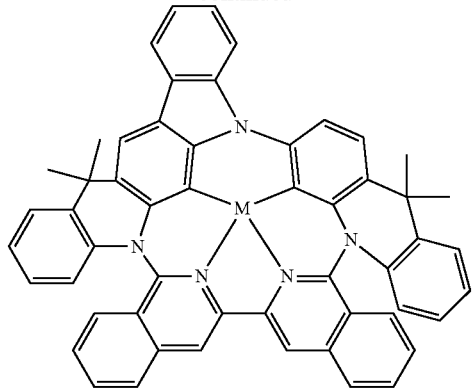
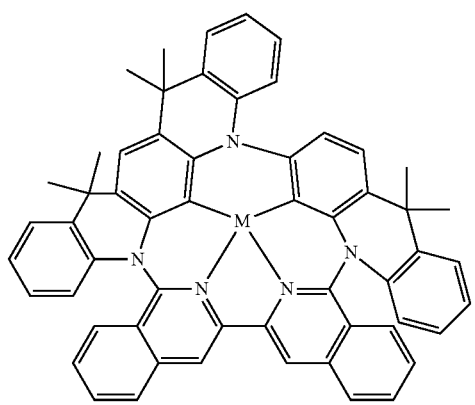
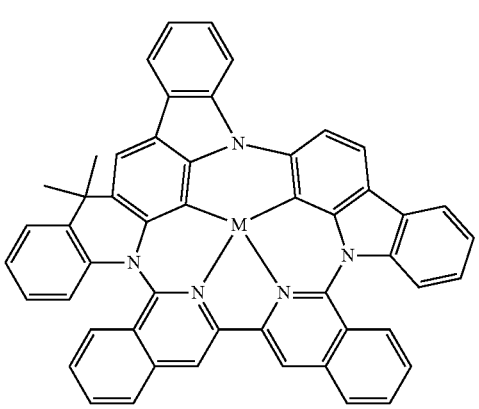
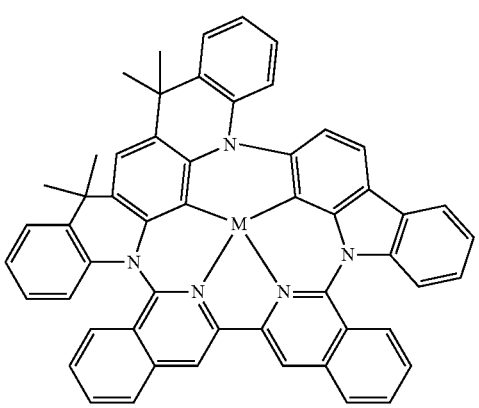

275
-continued
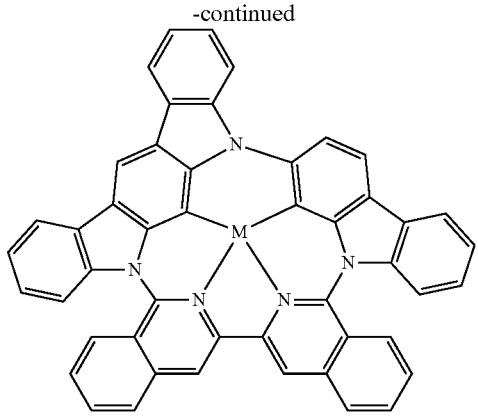
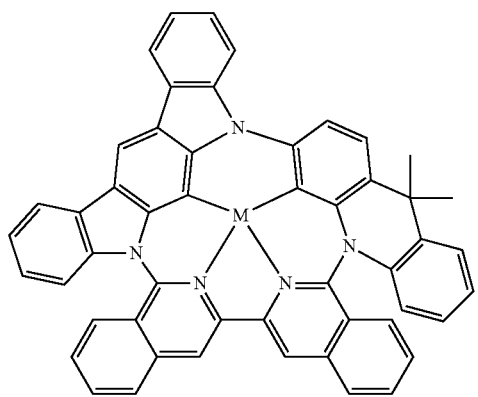
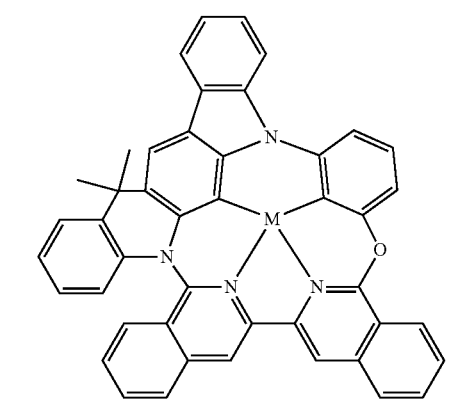
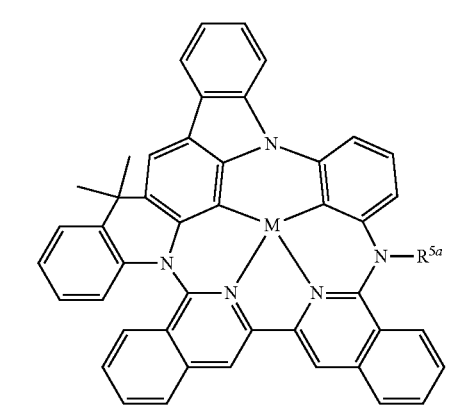
276
-continued
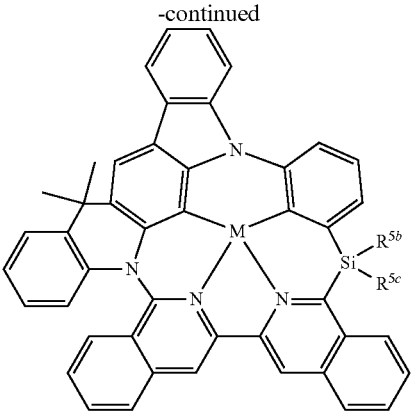
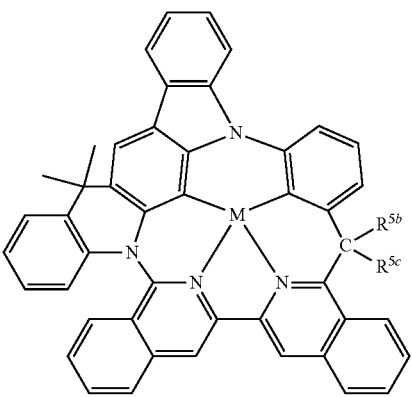
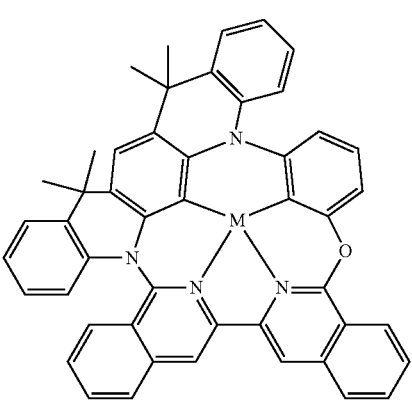
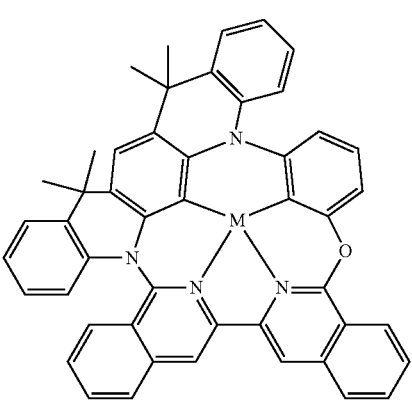

277
-continued
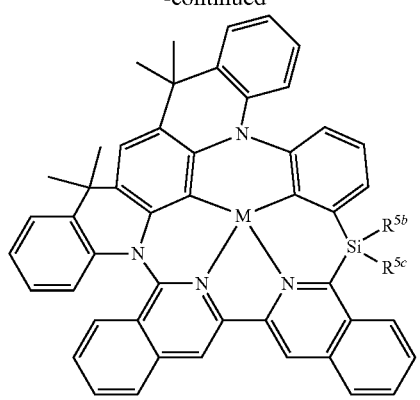
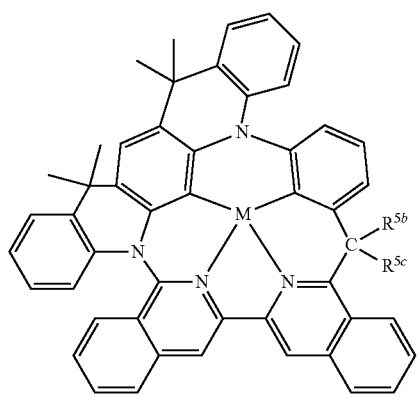
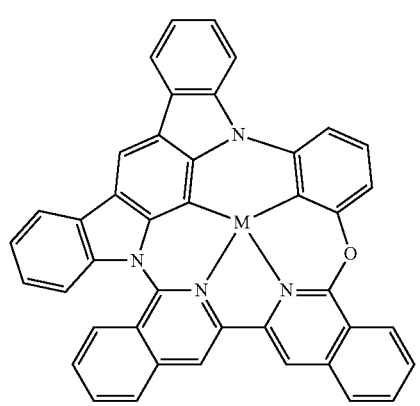
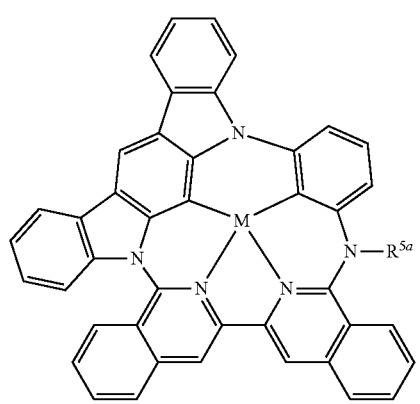
278
-continued
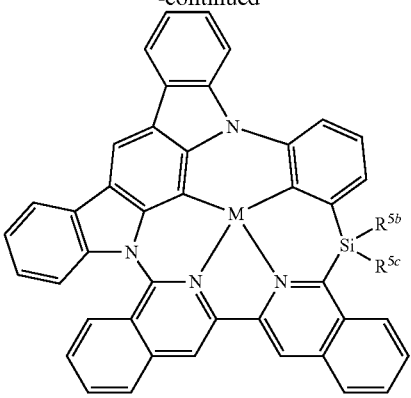
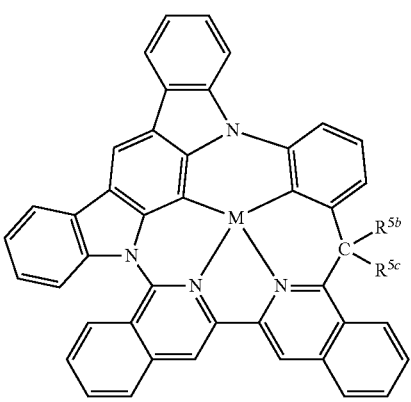
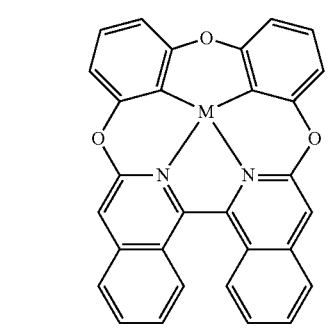
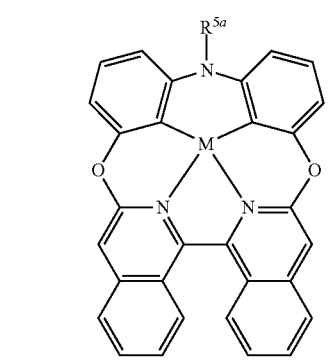

279
-continued
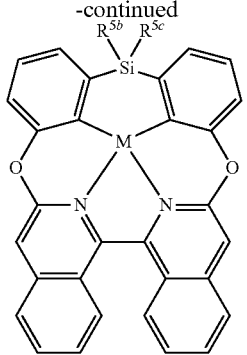
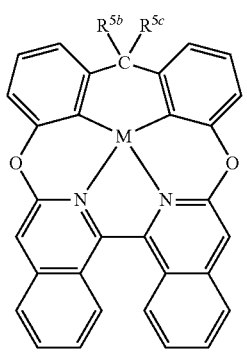
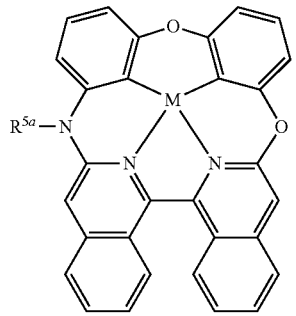
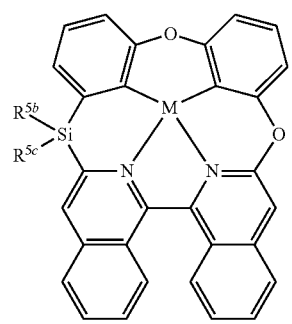
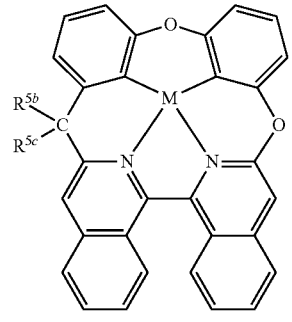
280
-continued
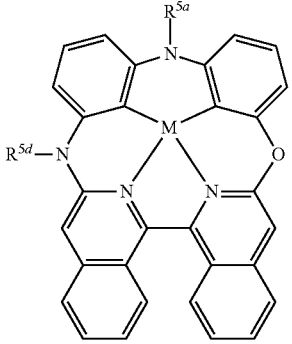
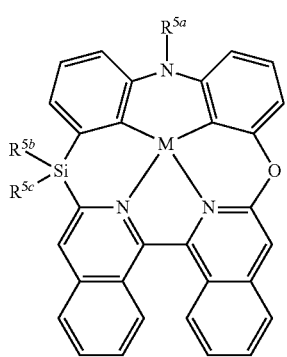
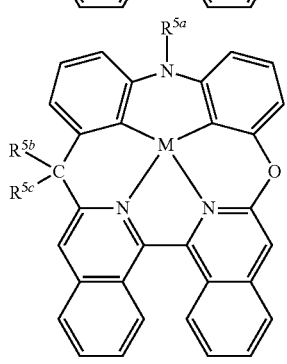
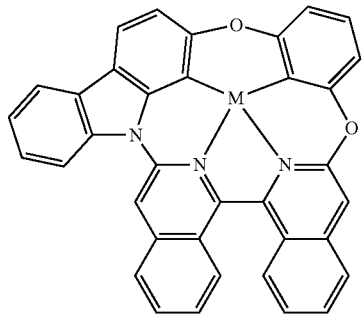
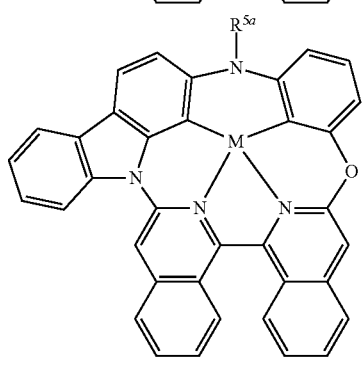

281
-continued
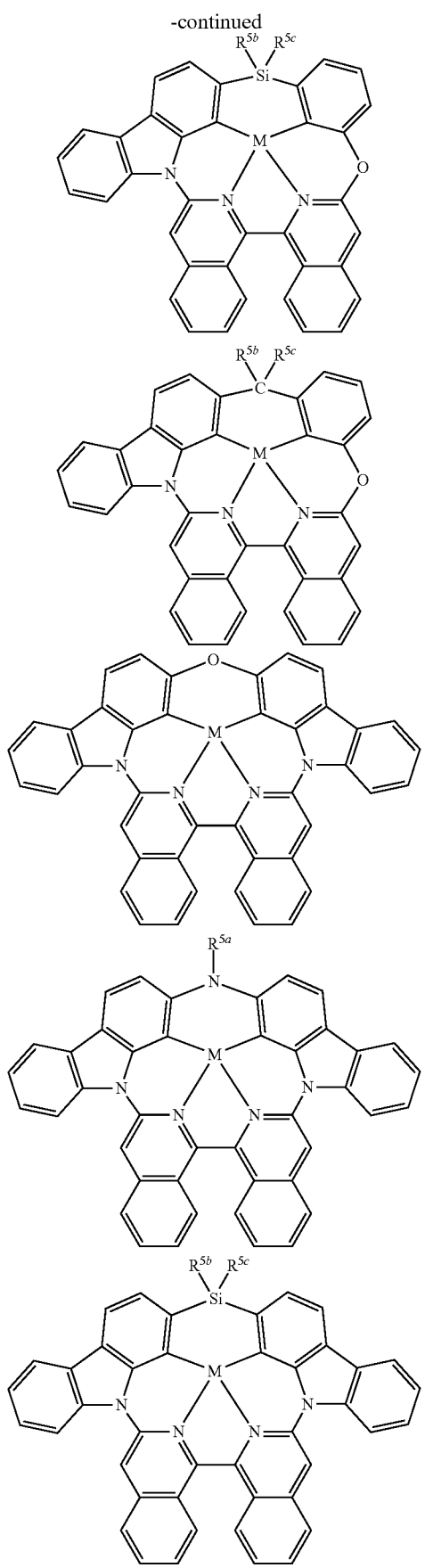
282
-continued
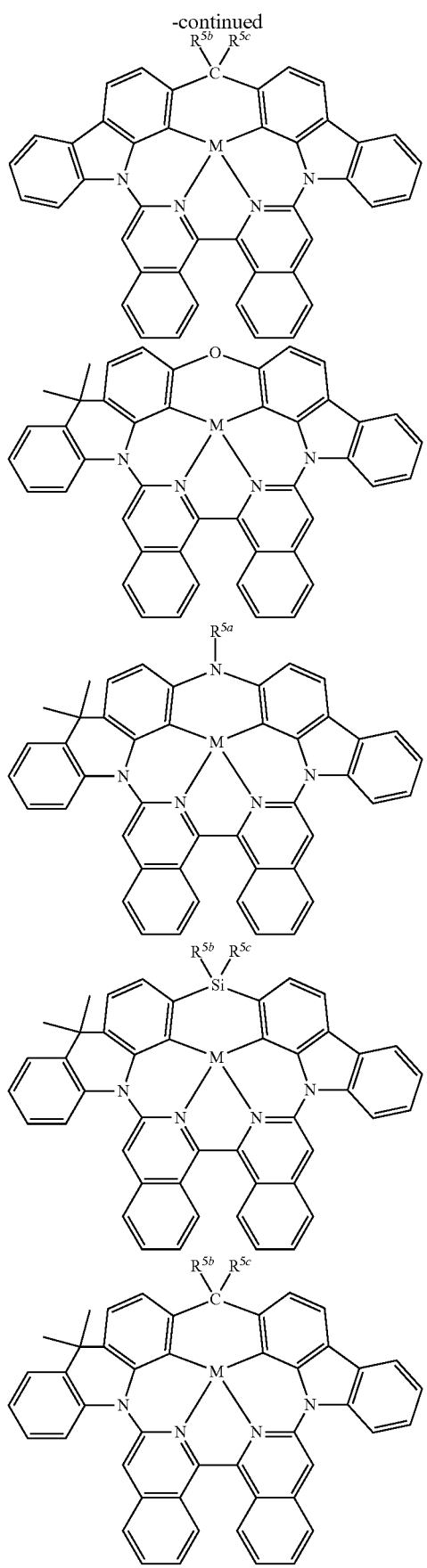

283
-continued
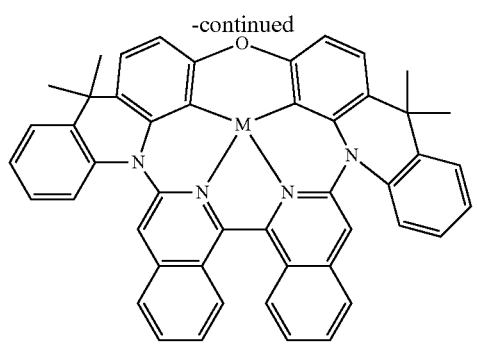
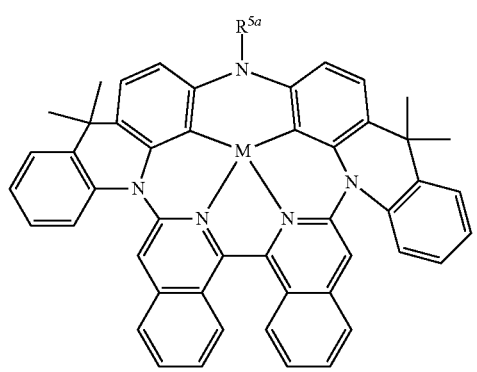
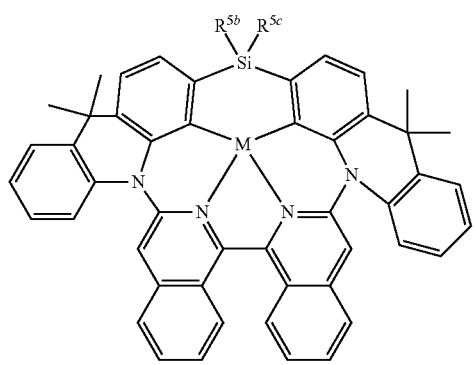
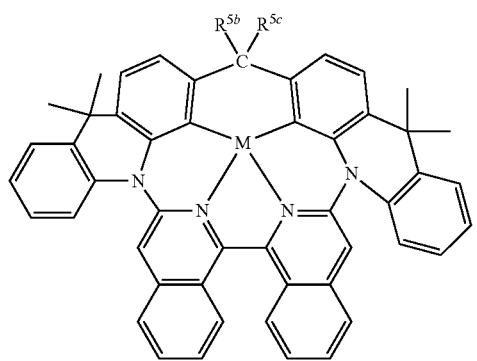
284
-continued
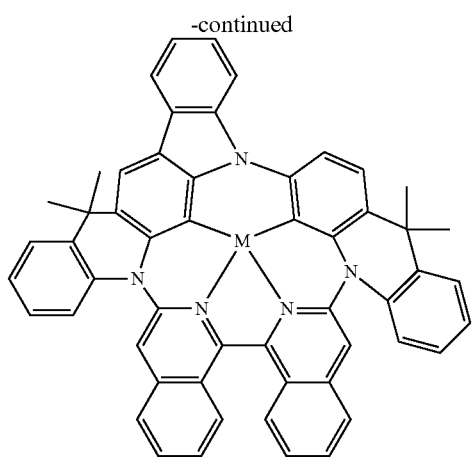
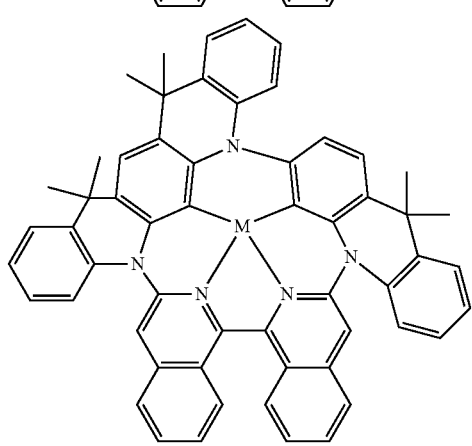
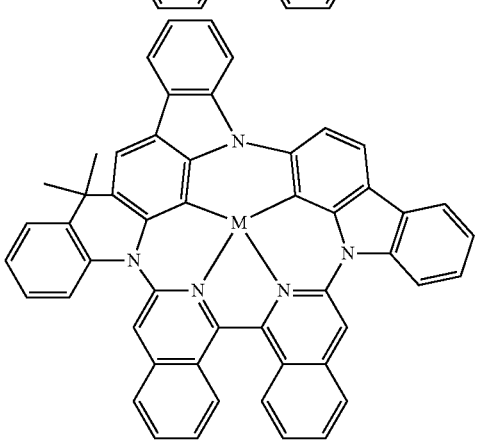
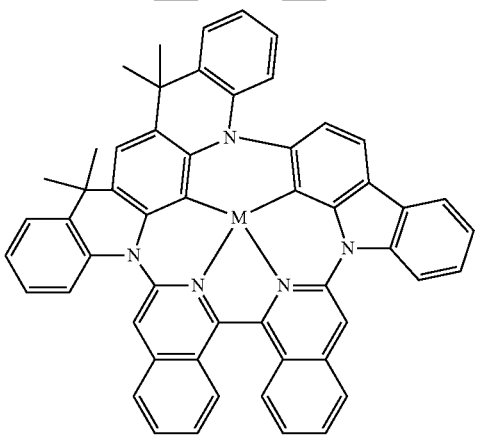

285
-continued
286
-continued
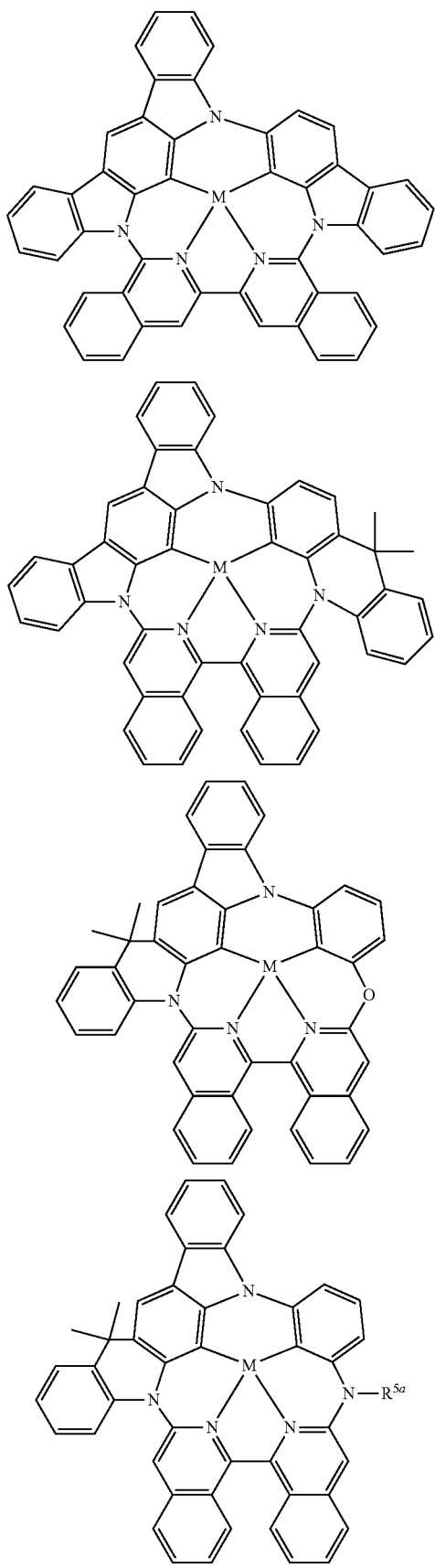
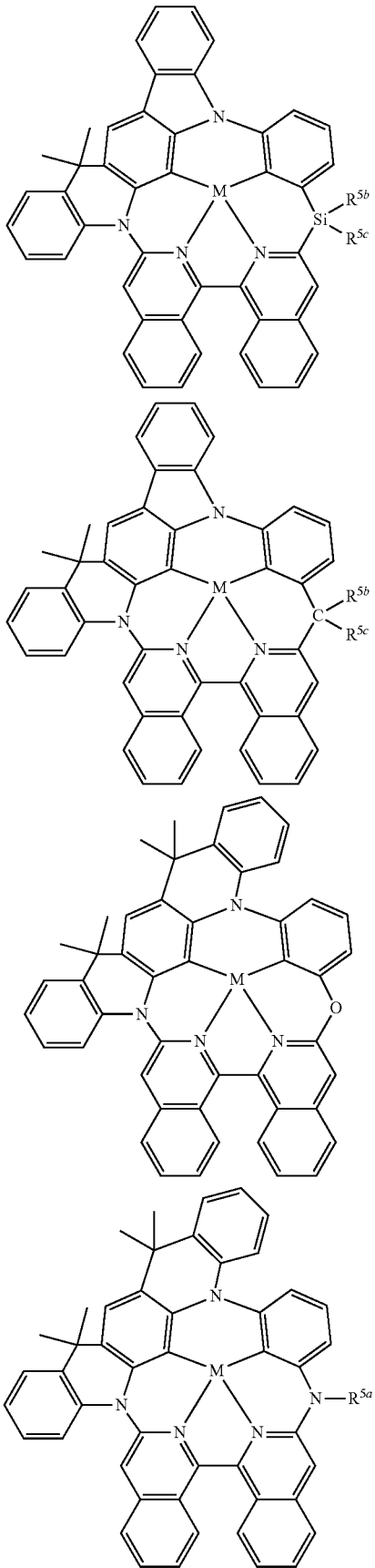

287
-continued
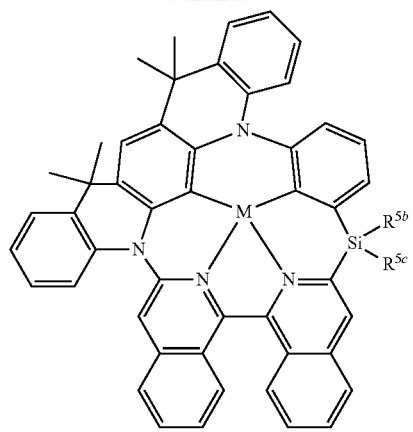
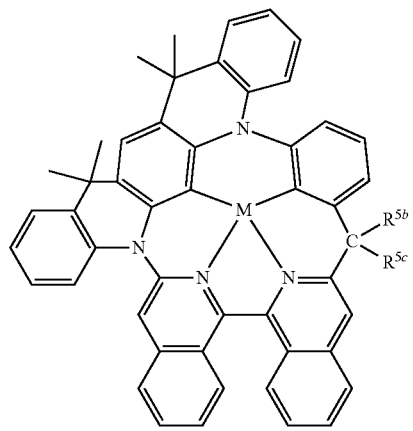
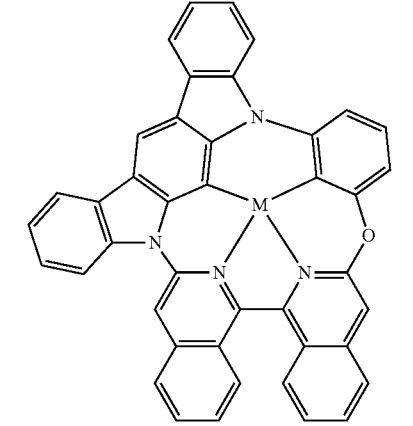
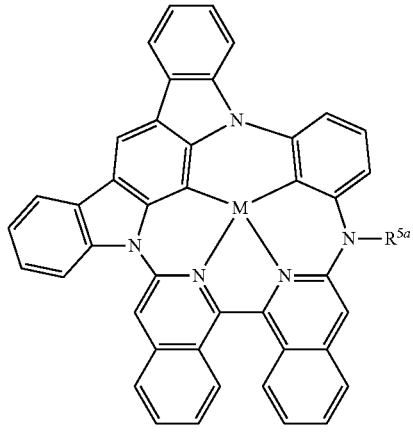
288
-continued
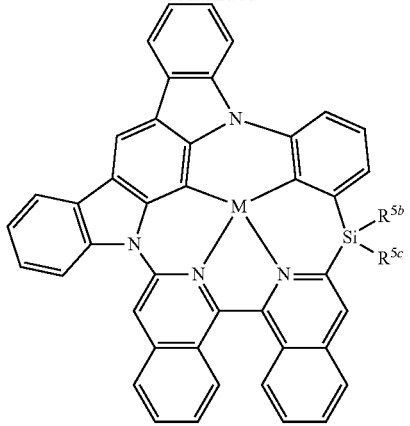
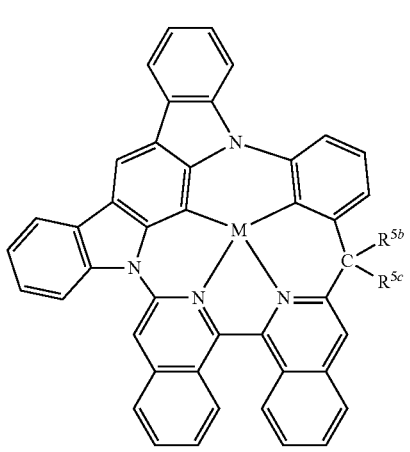
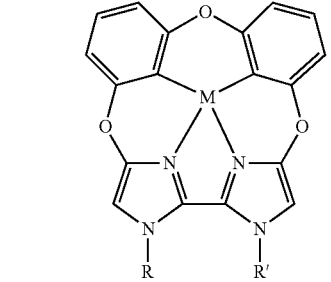
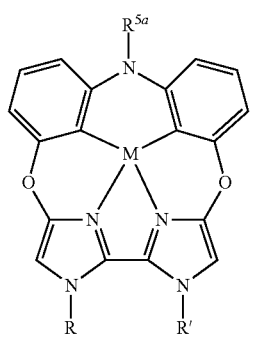

289
-continued
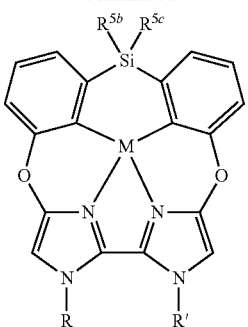
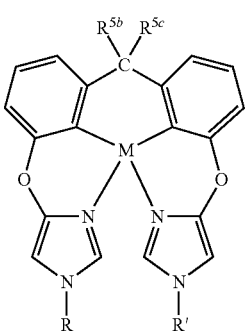
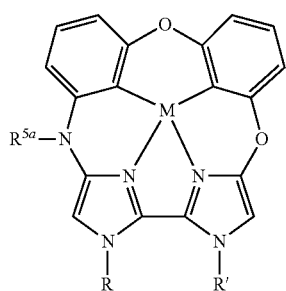
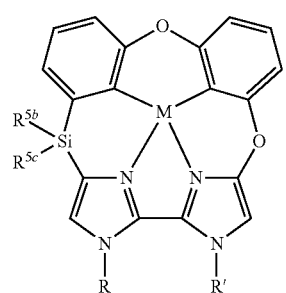
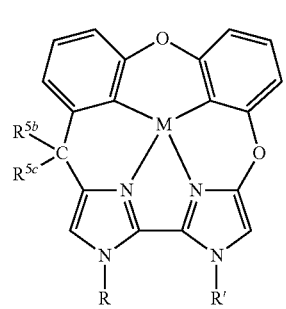
290
-continued
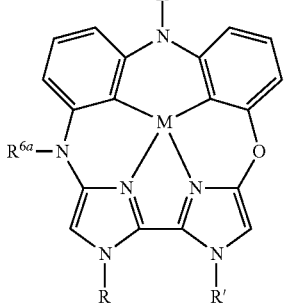
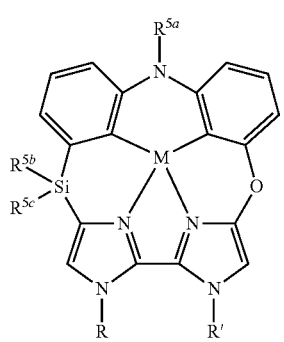
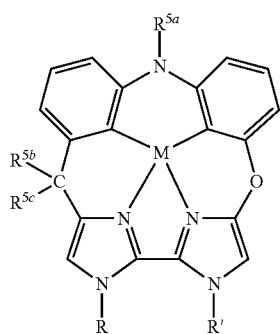
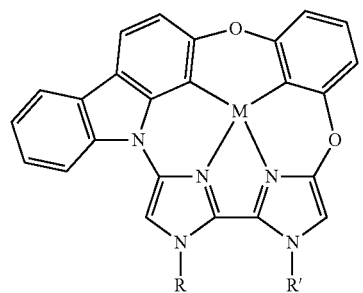
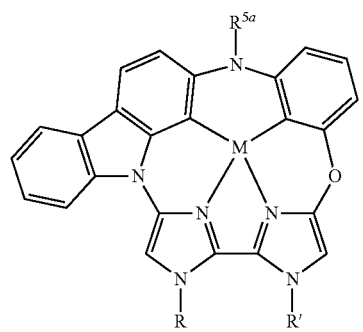

291
-continued
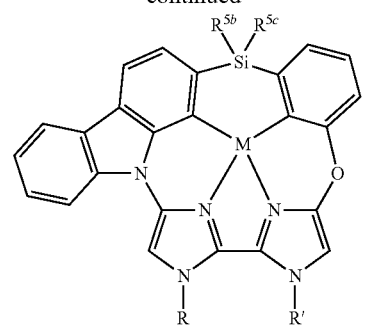
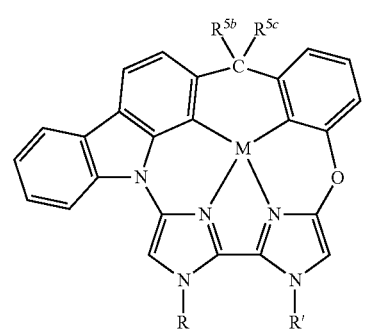
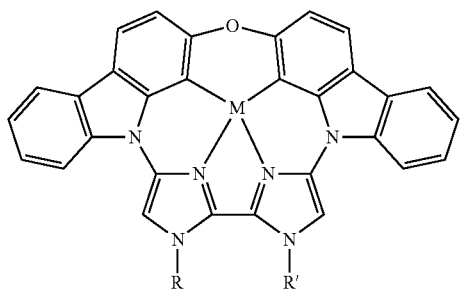
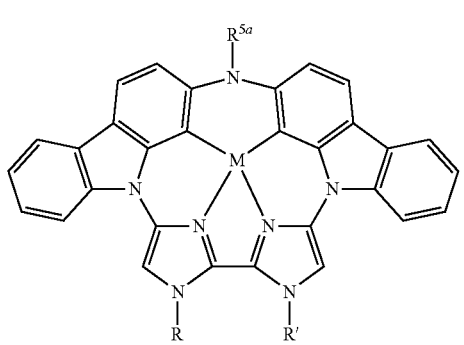
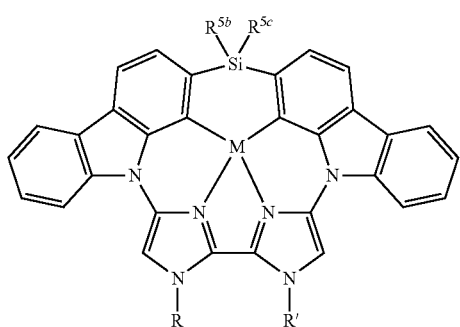
292
-continued
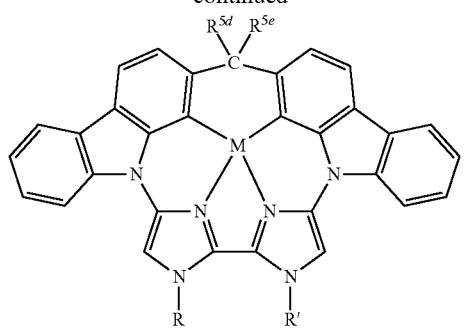
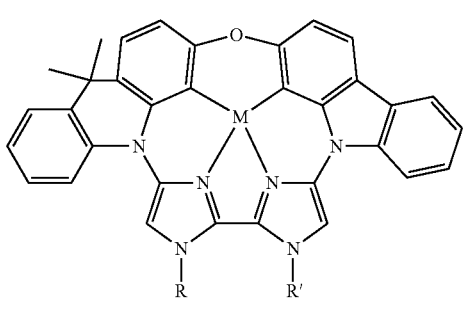
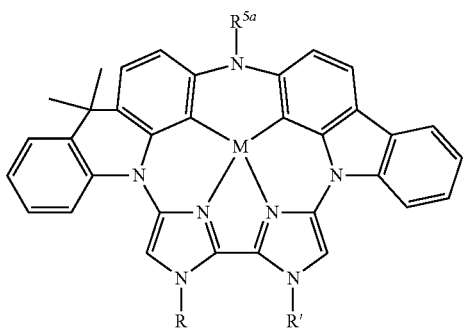
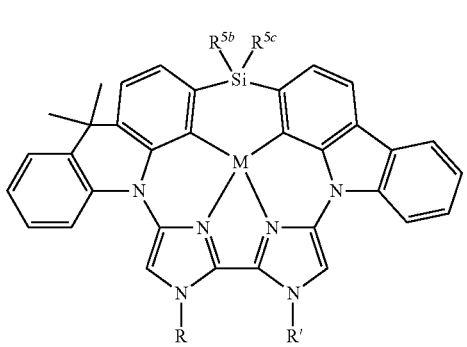
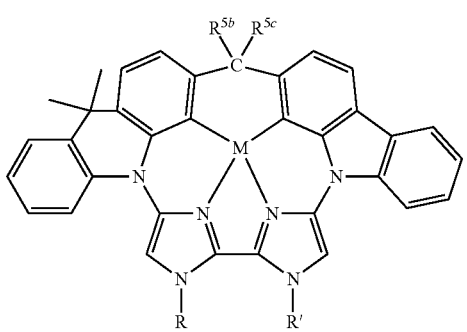

293
-continued
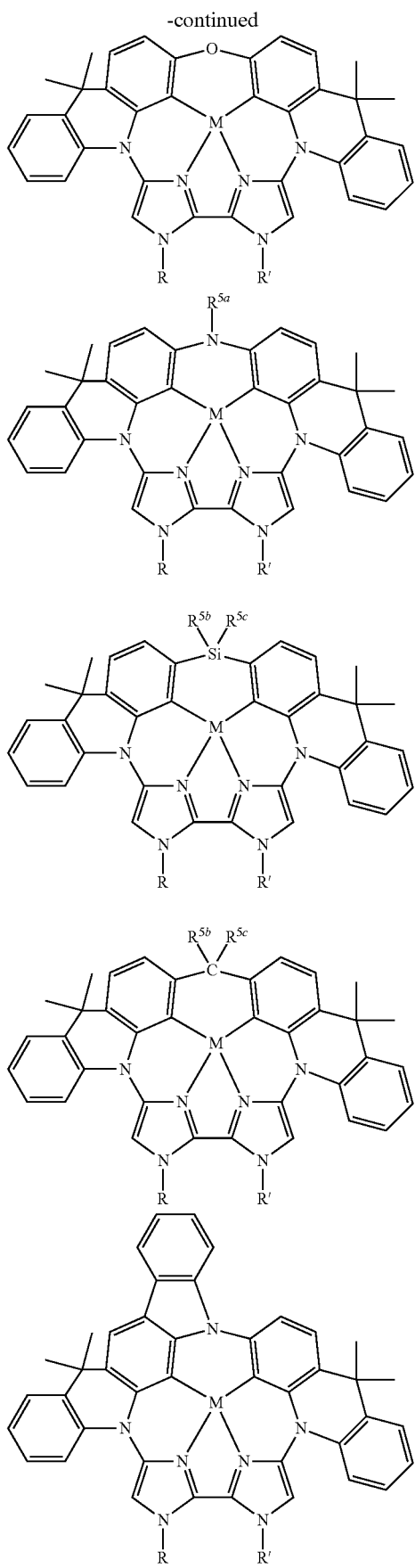
294
-continued
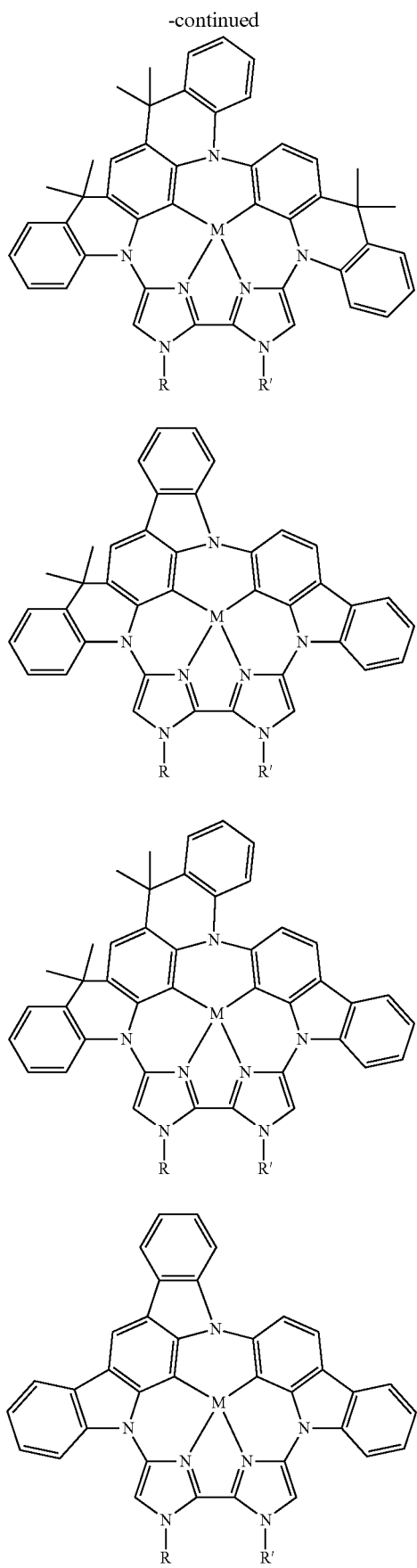

295
-continued
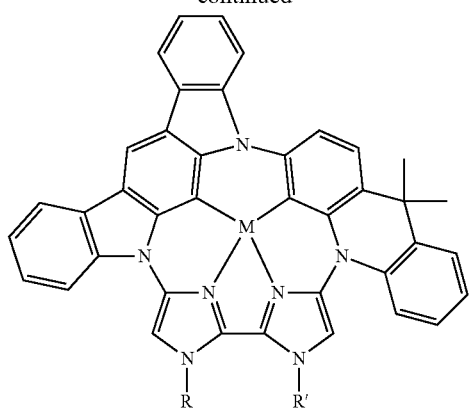
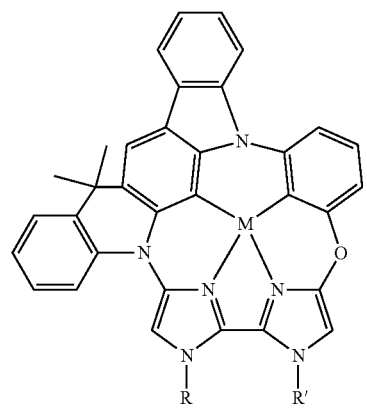
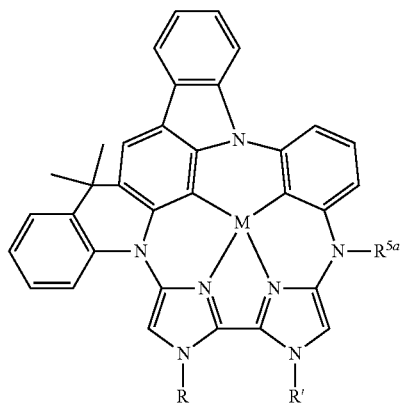
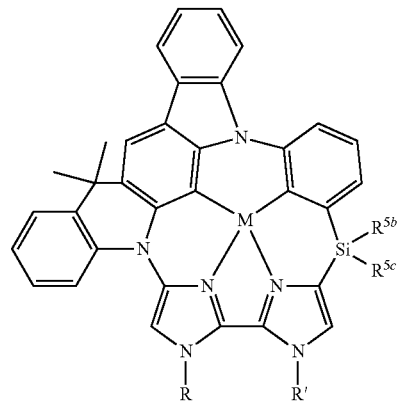
296
-continued
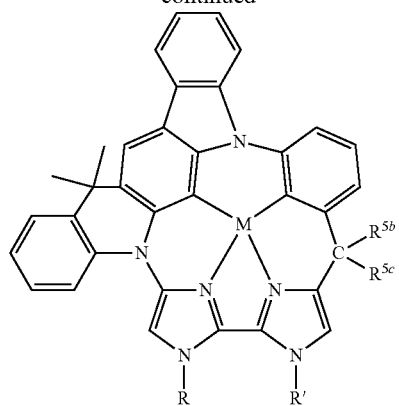
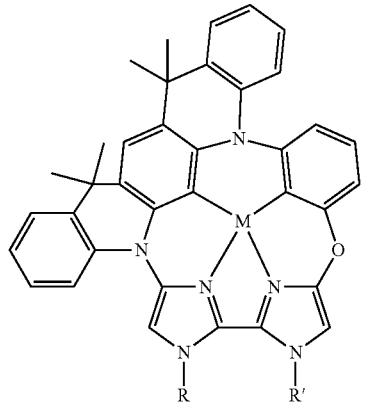
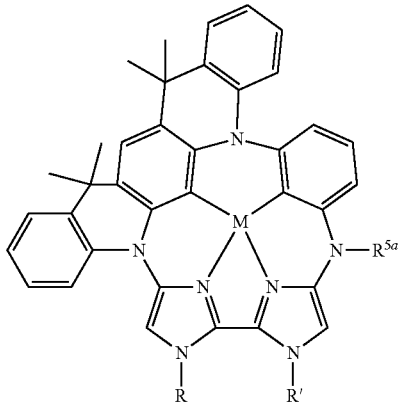
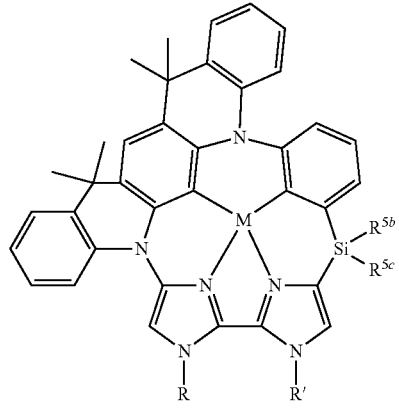

297
-continued
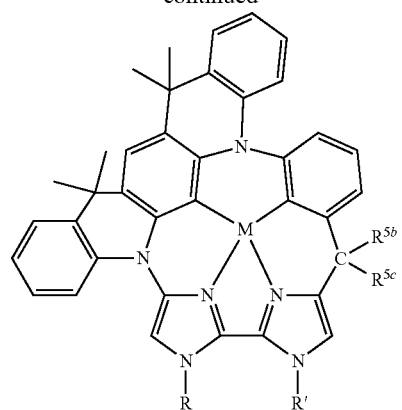
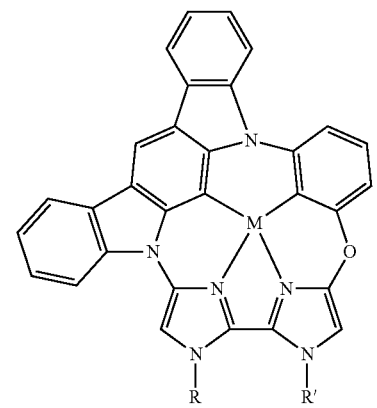
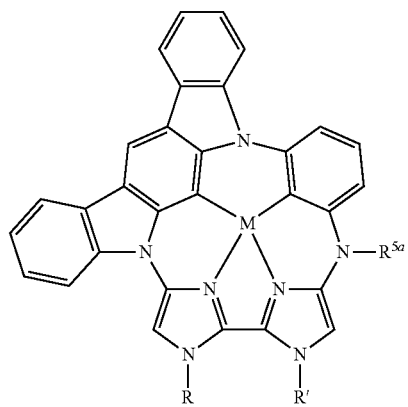
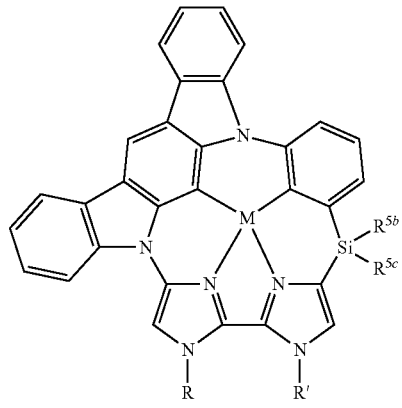
298
-continued
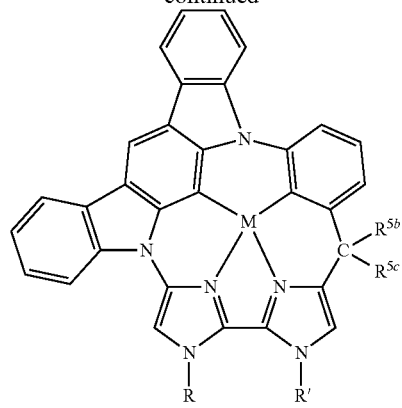
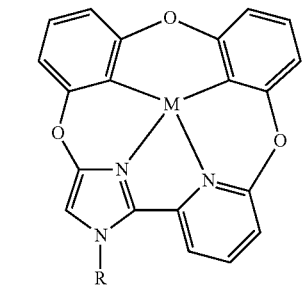
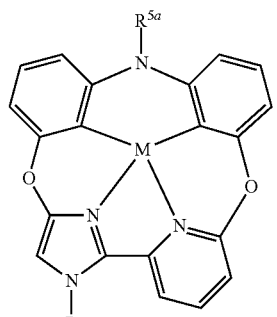
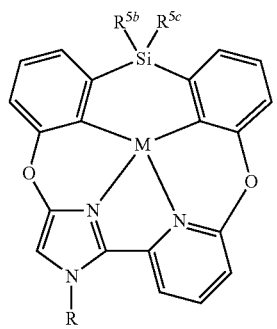
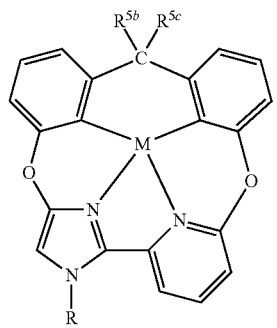

299
-continued
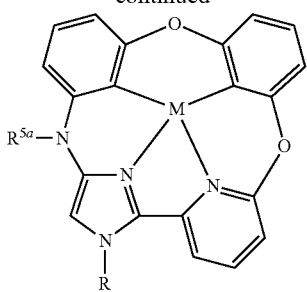
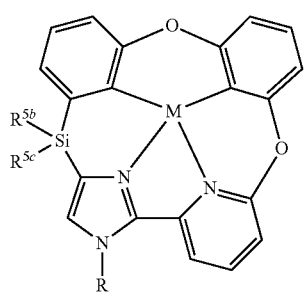
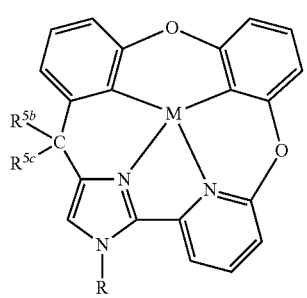
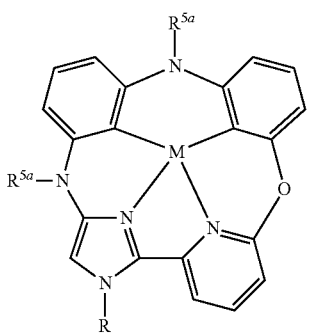
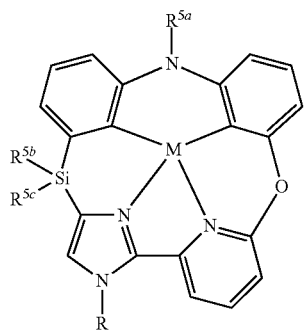
300
-continued
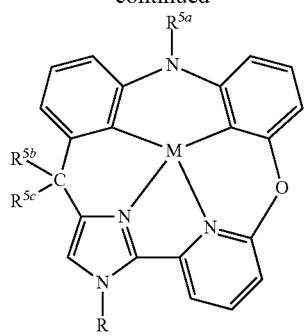
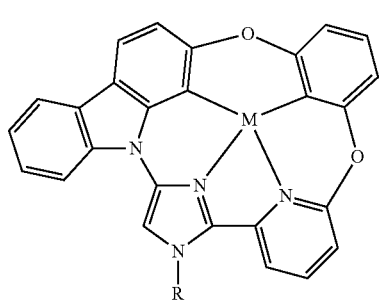
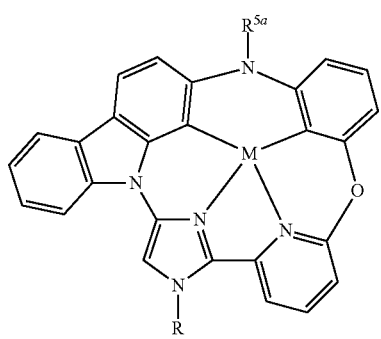
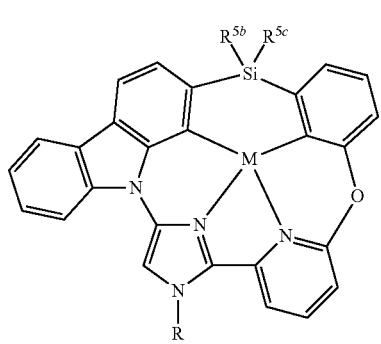
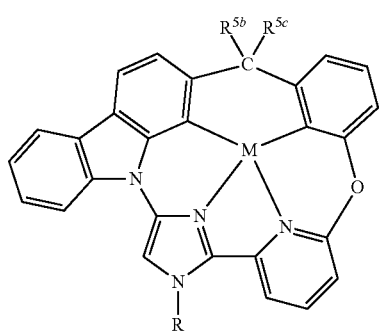

301
-continued
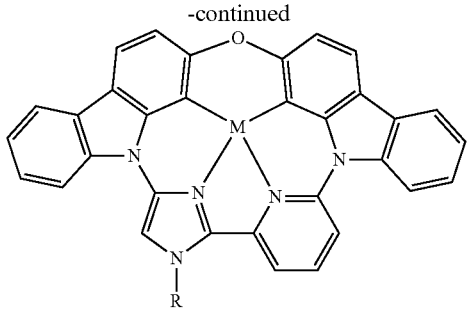
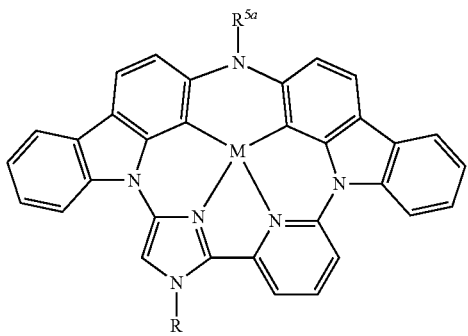
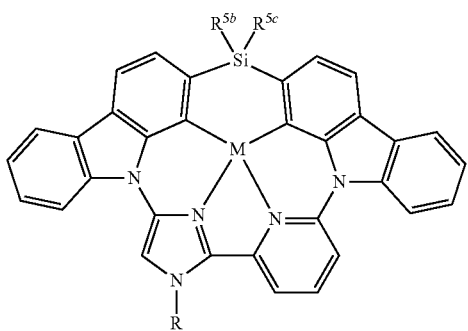
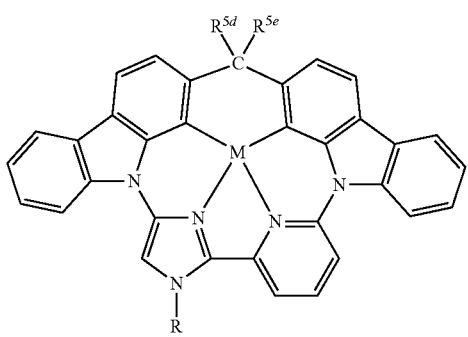
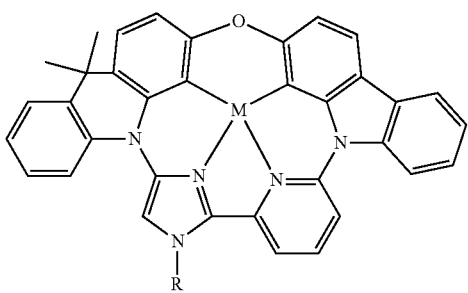
302
-continued
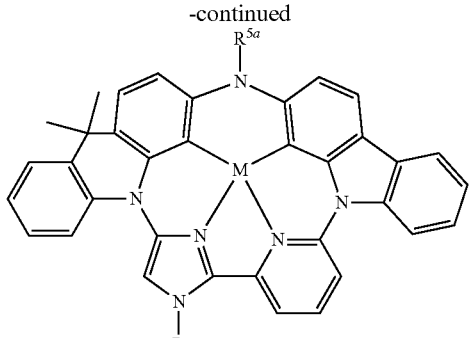
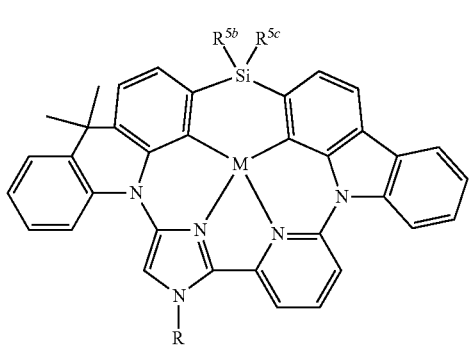
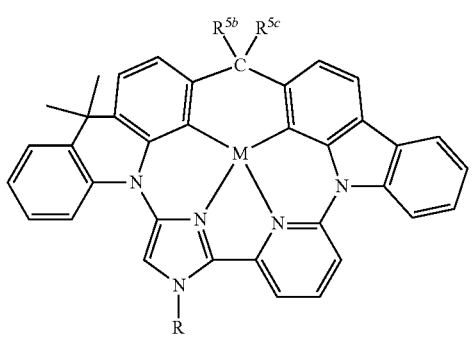
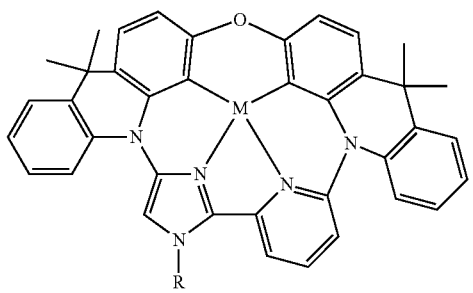
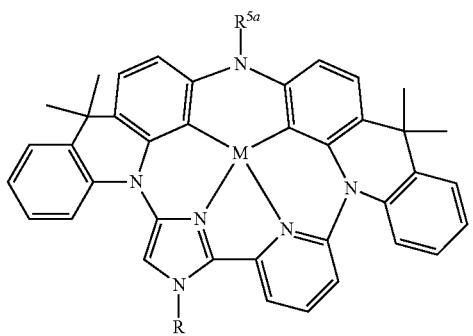

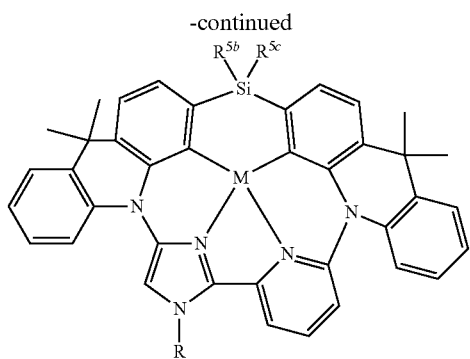
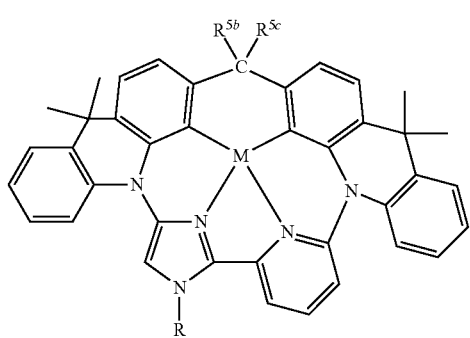
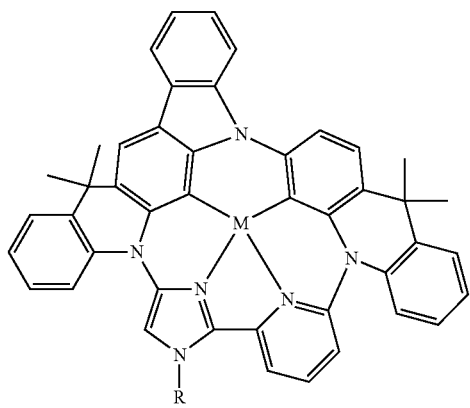
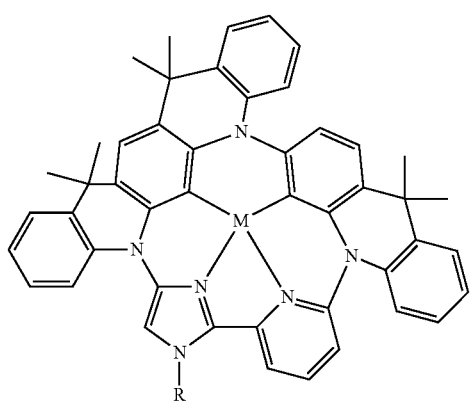
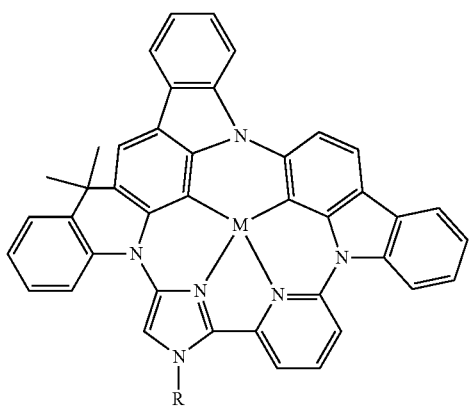
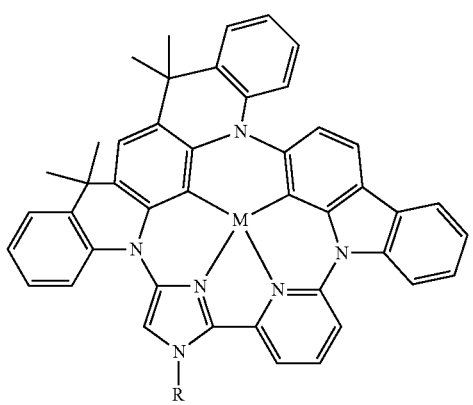
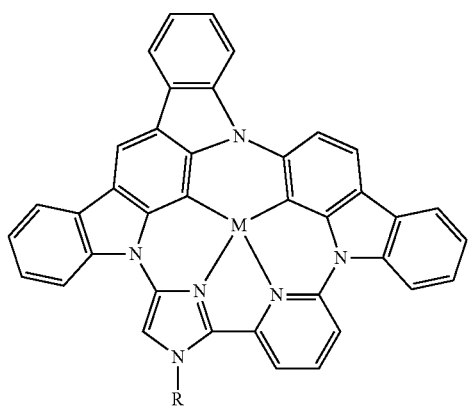
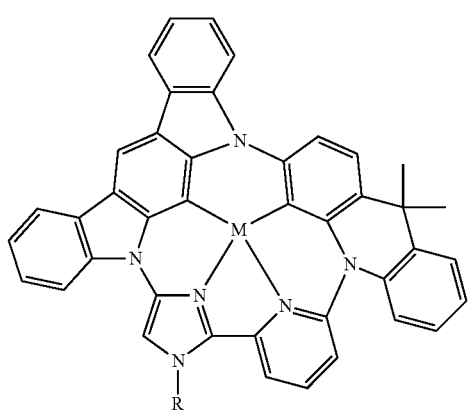

305
-continued
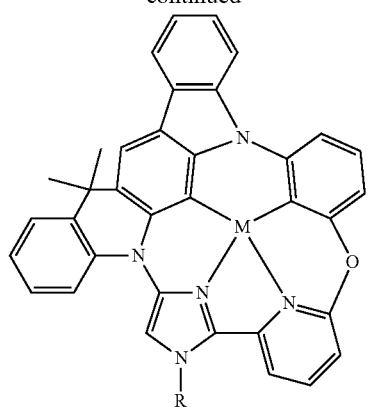
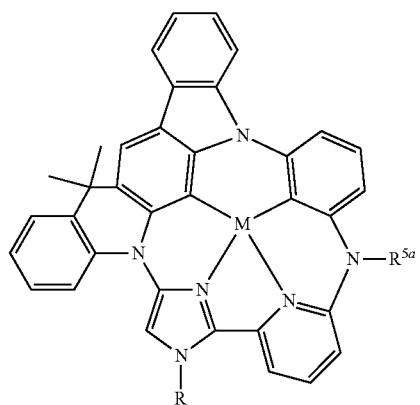
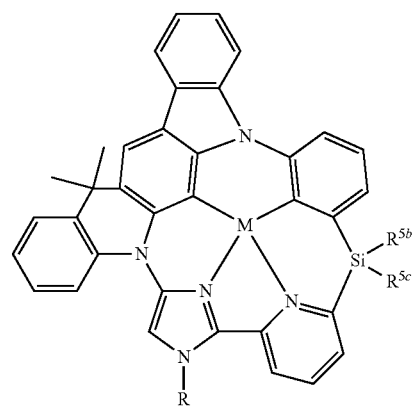
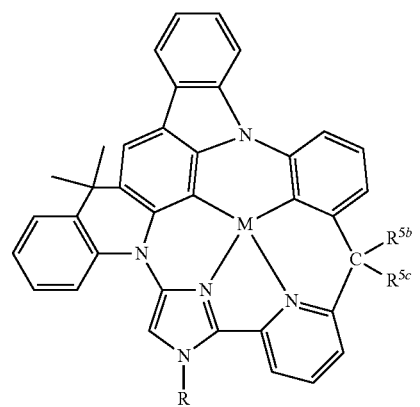
306
-continued
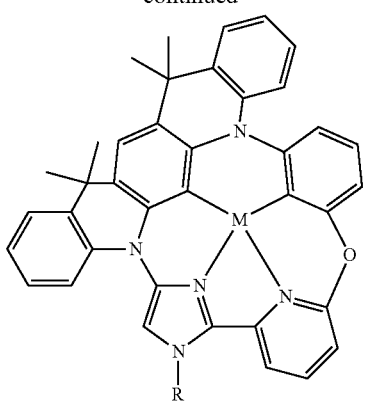
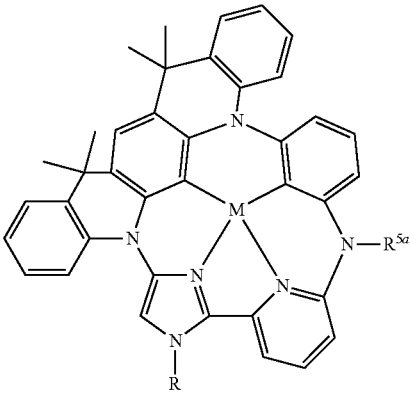
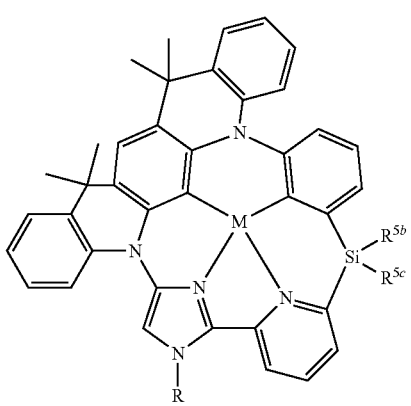
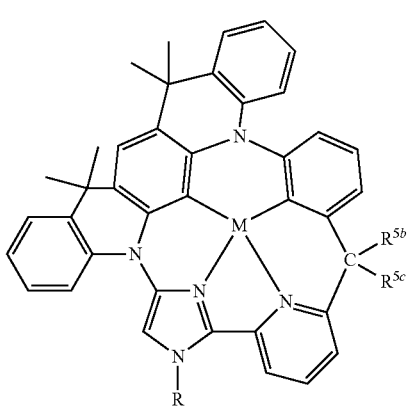

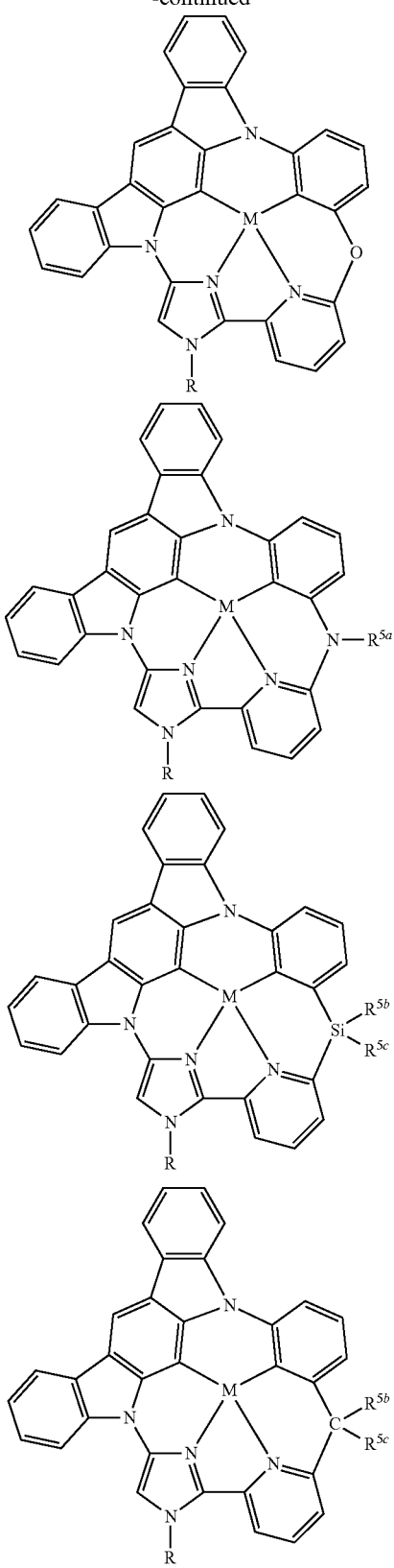

wherein each of the variables in the structures above are as described herein, and R and R' each independently represents hydrogen, halogen, hydroxy, amino, nitro, thiol, substituted or unsubstituted $C_{1-4}$ alkyl, substituted or unsubstituted alkoxy, or substituted or unsubstituted aryl.

It is to be understood that present compounds/complexes, devices, and/or methods are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of compounds of the present disclosure, example methods and materials are now described.

Disclosed are the components to be used to prepare the compositions of this disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C is disclosed as well as a class of molecules D, E, and F and an example of a combination molecule, A-D is disclosed, then even if each is not individually recited each is individually and collectively contemplated meaning combinations A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods described herein.

As referred to herein, a linking atom or group connects two atoms such as, for example, an N atom and a C atom. A linking atom or group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties. The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$", "$A^2$", "$A^3$", "$A^4$" and "$A^5$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound.

Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" or "halo" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —(O)S(O)$_2A^1$, or —(O)S(O)$_2$O$A^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=(O). The term "sulfonyl" is used herein to refer to the sulfo-oxo group represented by the formula —S(O)$_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A'S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

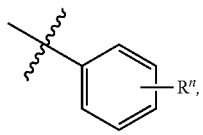

which is understood to be equivalent to a formula:

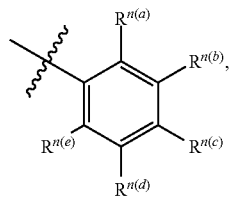

wherein n is typically an integer. That is, R$^n$ is understood to represent five independent substituents, R$^{n(a)}$, R$^{n(b)}$, R$^{n(c)}$, R$^{n(d)}$, R$^{n(e)}$. By "independent substituents," it is meant that each R substituent can be independently defined. For example, if in one instance R$^{n(a)}$ is halogen, then R$^{n(b)}$ is not necessarily halogen in that instance.

Several references to R$^1$, R$^2$, R$^3$, R$^4$, R$^5$, R$^6$, etc. are made in chemical structures and moieties disclosed and described herein. Any description of R$^1$, R$^2$, R$^3$, R$^4$, R$^5$, R$^6$, etc. in the specification is applicable to any structure or moiety reciting R$^1$, R$^2$, R$^3$, R$^4$, R$^5$, R$^6$, etc. respectively.

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include OLEDs, organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Excitons decay from singlet excited states to ground state to yield prompt luminescence, which is fluorescence. Excitons decay from triplet excited states to ground state to generate luminescence, which is phosphorescence. Because the strong spin-orbit coupling of the heavy metal atom enhances intersystem crossing (ISC) very efficiently between singlet and triplet excited state, phosphorescent metal complexes, such as platinum complexes, have demonstrated their potential to harvest both the singlet and triplet excitons to achieve 100% internal quantum efficiency.

Cyclometalated metal complexes of the present disclosure have improved the color purity, enhanced operational stability as well as elimination of the potential intermolecular interaction. The cyclic platinum (II) and palladium (II) complexes described herein are useful for full color displays and lighting applications.

The complexes disclosed herein are suited for use in a wide variety of devices, including, for example, optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

Also disclosed herein are compositions including one or more complexes disclosed herein. The present disclosure provides light emitting device that include one or more complexes or compositions described herein. The light emitting device can be an OLED (e.g., a phosphorescent OLED device). The present disclosure also provides a photovoltaic device comprising one or more complexes or compositions described herein. Further, the present disclosure also provides a luminescent display device comprising one or more complexes or compositions described herein.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4- ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the compounds described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the compounds described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz on Varian Liquid-State NMR instruments in CDCl$_3$ solutions and chemical shifts were referenced to residual protiated solvent. $^1$H NMR spectra were recorded with tetramethylsilane ($\delta$=0.00 ppm) as internal reference. The following abbreviations (or combinations thereof) were used to explain $^1$H NMR multiplicities: s=singlet, d=doublet, t=triplet, q=quartet, p=quintet, m=multiplet, br=broad.

Example 1. Synthesis of PtNON$_C$-dtb

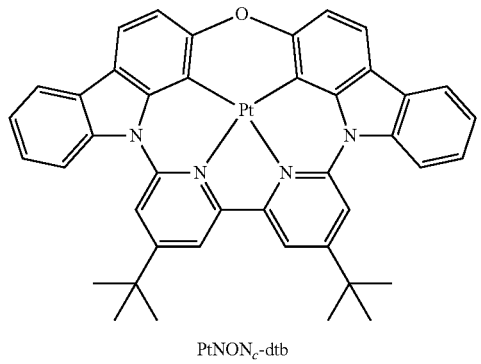

PtNON$_C$-dtb

Step 1: NON-dtb Ligand

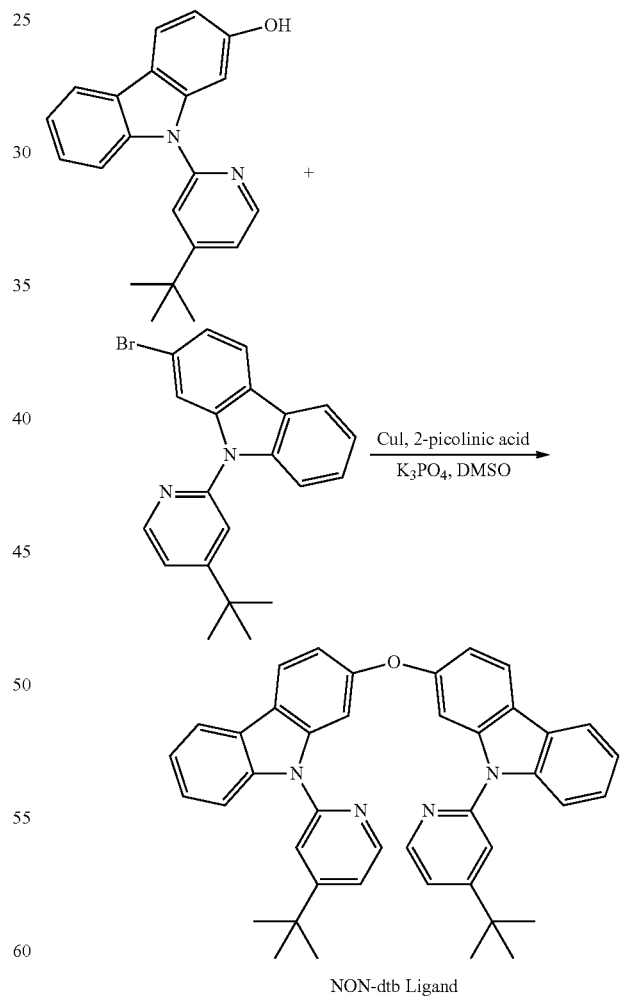

NON-dtb Ligand

To a solution of 9-(4-(tert-butyl)pyridin-2-yl)-9H-carbazol-2-ol (316 mg, 1 mmol) and 2-bromo-9-(4-(tert-butyl)pyridin-2-yl)-9H-carbazole (531 mg, 1.4 mmol) in DMSO (5 mL, 0.2 M) were added CuI (38 mg, 0.2 mmol), 2-picolinic acid (49 mg, 0.4 mmol), K₃PO₄ (424 mg, 2 mmol). The mixture was heated at 100° C. for 2 days. The solvent was then evaporated at reduced pressure. Purification of the residue on column chromatography gave the product (560 mg, 91% yield).

Step 2: PtNON-dtb

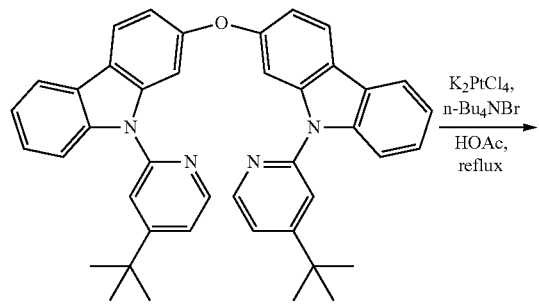

NON-dtb Ligand

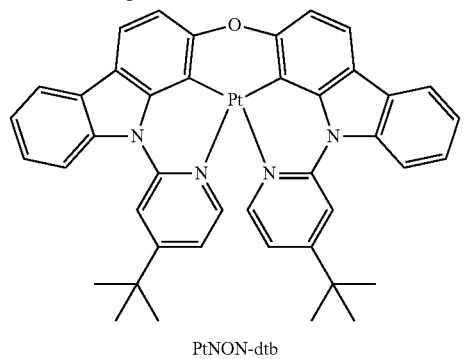

PtNON-dtb

To a solution of NON-dtb ligand (510 mg, 0.83 mmol) in HOAc (41.5 mL, 0.02 M) were added K₂PtCl₄ (362 mg, 0.87 mmol) and n-Bu₄NBr (26 mg, 0.083 mmol). The mixture was heated to reflux and maintained at this temperature for 2 days. The reaction mixture was cooled to room temperature and filtered through a short pad of silica gel. The filtrate was concentrated under reduced pressure. Purification by column chromatography (hexanes:DCM=1:1 to 1:2) gave the PtNON-dtb (540 mg, yield: 80%) as a solid. ¹H NMR (CDCl₃, 400 MHz): δ 8.90 (d, J=6.5 Hz, 2H), 8.19 (d, J=7.6 Hz, 2H), 8.12-8.02 (m, 4H), 7.92 (d, J=8.3 Hz, 2H), 7.52 (m, 2H), 7.45-7.37 (m, 4H), 7.18 (d, J=8.2 Hz, 2H), 1.34 (s, 18H).

Step 3: PtNON-dtb

To a four zone thermal gradient sublimator was added PtNON-dtb (200 mg, 0.9 mmol). The temperature was slowly increased to 300° C. After 3 days, the sublimation gave PtNON$_C$-dtb as an orange solid (20 mg, 10% yield). ¹H NMR (CDCl₃, 400 MHz): δ 8.19 (s, 2H), 8.08-8.00 (m, 2H), 7.93-7.85 (m, 2H), 7.66 (d, J=8.2 Hz, 2H), 7.49-7.41 (m, 4H), 7.40 (s, 2H), 7.01 (d, J=8.2 Hz, 2H), 1.44 (s, 18H); HRMS (APCI+) m/z: [M+H]⁺ Calcd for C₄₂H₃₅N₄OPt 806.2453. Found 806.2449.

Example 2. Synthesis of PtNON'$_C$

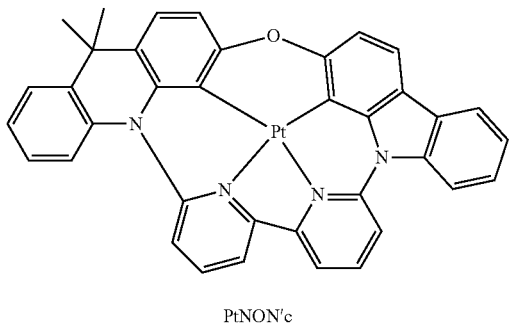

PtNON'c

Step 1: NON' Ligand

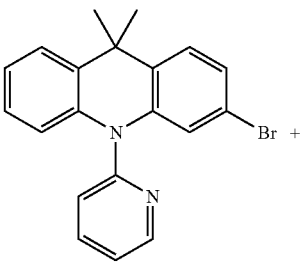

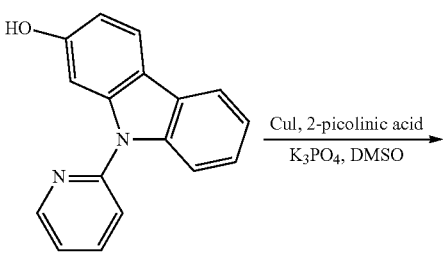

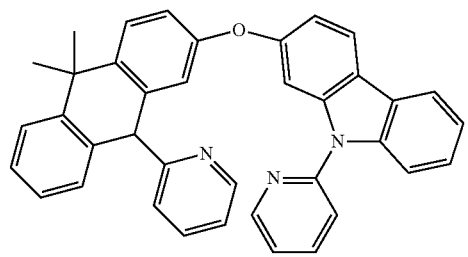

NON' Ligand

To a solution of 3-bromo-9,9-dimethyl-10-(pyridin-2-yl)-9,10-dihydroacridine (438 mg, 1.2 mmol) and 9-(pyridin-2-yl)-9H-carbazol-2-ol (259 mg, 1 mmol) in DMSO (10 mL, 0.1 M) were added CuI (19 mg, 0.1 mmol), 2-picolinic acid (25 mg, 0.2 mmol), K₃PO₄ (318 mg, 1.5 mmol). The mixture was heated at 120° C. for 2 days. The solvent was then evaporated at reduced pressure. Purification of the residue on column chromatography gave the product (410 mg, 75% yield).

Step 2: PtNON'

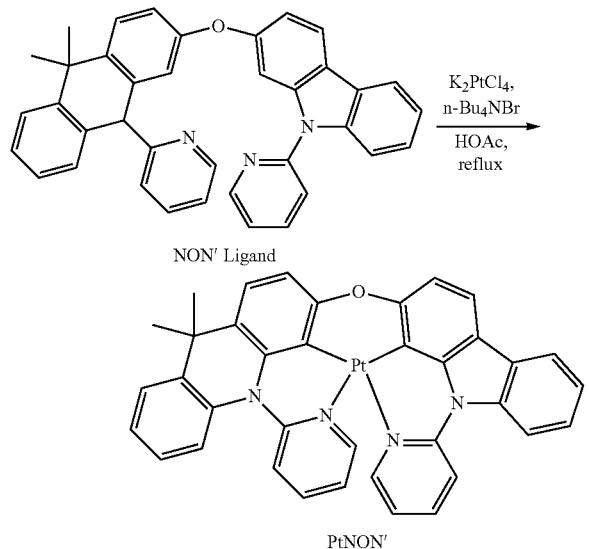

NON' Ligand

PtNON'

To a solution of NON' ligand (330 mg, 0.606 mmol) in HOAc (36 mL, 0.02 M) were added K$_2$PtCl$_4$ (277 mg, 0.667 mmol) and n-Bu$_4$NBr (20 mg, 0.061 mmol). The mixture was stirred at room temperature for 12 hours and heated to reflux and maintained at this temperature for 70 hours. The reaction mixture was cooled to room temperature and filtered through a short pad of silica gel. The filtrate was concentrated under reduced pressure. Purification by column chromatography (hexanes:DCM) gave the PtNON' (205 mg, yield: 77%) as a solid. $^1$H NMR (CDCl$_3$, 400 MHz): δ 8.74 (d, J=5.8 Hz, 1H), 8.70 (d, J=6.0 Hz, 1H), 8.24-8.13 (m, 3H), 8.06 (d, J=8.3 Hz, 1H), 7.99 (t, J=7.9 Hz, 1H), 7.91 (d, J=8.3 Hz, 1H), 7.58 (d, J=7.0 Hz, 1H), 7.51 (d, J=7.5 Hz, 1H), 7.45 (t, J=7.5 Hz, 1H), 7.40 (t, J=7.3 Hz, 1H), 7.35-7.24 (m, 4H), 7.23-7.15 (m, 2H), 7.12 (d, J=8.1 Hz, 2H), 6.92 (d, J=8.3 Hz, 2H).

Step 3: PtNON'c

To a four zone thermal gradient sublimator was added PtNON' (200 mg). The temperature was slowly increased to 300° C. After 3 days, the sublimation gave PtNON'$_C$ as an orange solid (50 mg, 25% yield). $^1$H NMR (CDCl$_3$, 400 MHz): δ 8.64 (m, 2H), 8.60-8.50 (m, 2H), 8.30-8.20 (m, 3H), 8.00 (d, J=8.3 Hz, 1H), 7.62-7.43 (m, 4H), 7.33-7.13 (m, 5H), 7.07 (d, J=8.4 Hz, 1H).

What is claimed is:

1. A complex represented by the following structure:

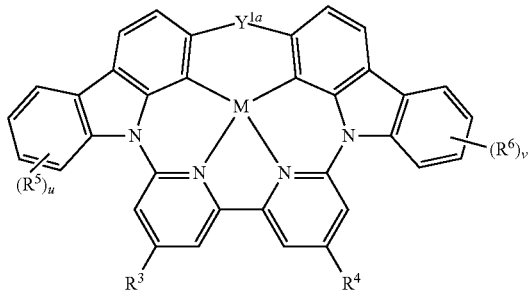

wherein:

M is Pt or Pd;

Y$^{1a}$ represents O, S, S(O), S(O)$_2$, Se, Se(O), Se(O)$_2$, N, NR$^{5a}$, P, PR$^{5a}$, As, AsR$^{5a}$, O=NR$^{5a}$, O=PR$^{5a}$, O=AsR$^{5a}$, B, BR$^{5a}$, SiR$^{5a}$, SiR$^{5b}$R$^{5c}$, CR$^{5a}$, or CR$^{5b}$R$^{5c}$, where R$^{5b}$, R$^{5b}$, and R$^{5c}$ each independently represents hydrogen, substituted or unsubstituted C$_1$-C$_4$ alkyl, or substituted or unsubstituted aryl;

R$^3$ and R$^4$ each independently represents hydrogen, halogen, hydroxy, amino, nitro, thiol, Si(C$_1$-C$_4$ alkyl)$_3$, substituted or unsubstituted C$_1$-C$_4$ alkyl, substituted or unsubstituted alkoxy, substituted or unsubstituted aryl, substituted or unsubstituted cycloalkyl, substituted or unsubstituted heteroaryl, or substituted or unsubstituted heterocycloalkyl;

each R$^5$ and R$^6$ independently represents hydrogen, halogen, hydroxy, amino, nitro, thiol, Si(C$_1$-C$_4$ alkyl)$_3$, substituted or unsubstituted C$_1$-C$_4$ alkyl, substituted or unsubstituted alkoxy, substituted or unsubstituted aryl, substituted or unsubstituted cycloalkyl, substituted or unsubstituted heteroaryl, or substituted or unsubstituted heterocycloalkyl; and each of u and v is an integer, valency permitting.

2. A complex represented by the following structure:

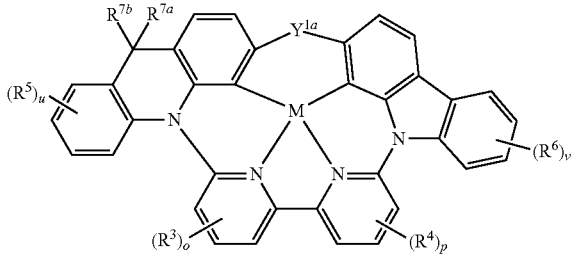

wherein:

M is Pt or Pd;

Y$^{1a}$ represents O, S, S(O), S(O)$_2$, Se, Se(O), Se(O)$_2$, N, NR$^{5a}$, P, PR$^{5a}$, As, AsR$^{5a}$, O=NR$^{5a}$, O=PR$^{5a}$, O=AsR$^{5a}$, B, BR$^{5a}$, SiR$^{5a}$, SiR$^{5b}$R$^{5c}$, CR$^{5a}$, or CR$^{5b}$R$^{5c}$, where R$^{5b}$, R$^{5b}$, and R$^{5c}$ each independently represents hydrogen, substituted or unsubstituted C$_1$-C$_4$ alkyl, or substituted or unsubstituted aryl;

R$^{7a}$ and R$^{7b}$ each independently represents hydrogen, substituted or unsubstituted C$_1$-C$_4$ alkyl, or substituted or unsubstituted aryl;

each R$^3$, R$^4$, R$^5$, and R$^6$ independently represents hydrogen, halogen, hydroxy, amino, nitro, thiol, Si(C$_1$-C$_4$ alkyl)$_3$, substituted or unsubstituted C$_1$-C$_4$ alkyl, substituted or unsubstituted alkoxy, substituted or unsubstituted aryl, substituted or unsubstituted cycloalkyl, substituted or unsubstituted heteroaryl, or substituted or unsubstituted heterocycloalkyl; and each of o, p, u, and v is an integer, valency permitting.

3. The complex of claim 2, represented by the following structure:

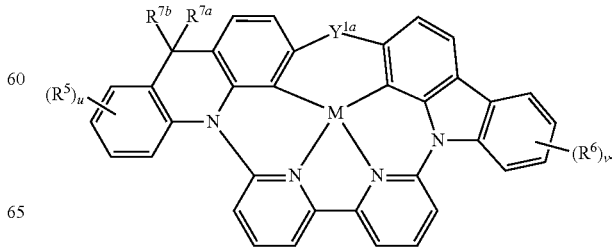

4. A complex represented by the following structure:

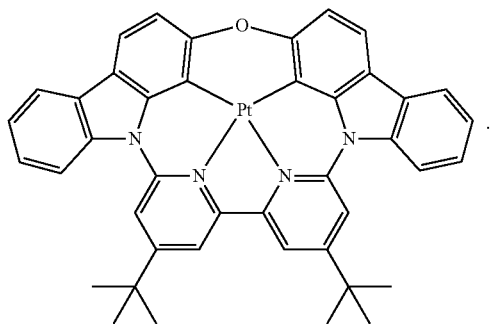

5. The complex of claim 3, represented by the following structure:

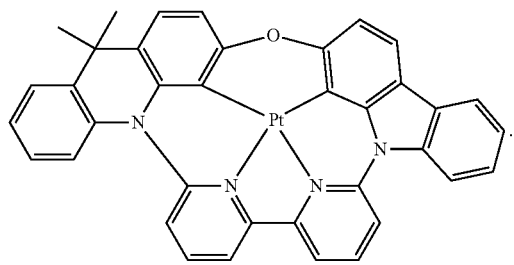

6. A light emitting device comprising the complex of claim 1.

7. An organic light emitting diode comprising the complex of claim 1.

8. An organic light emitting diode comprising the complex of claim 2.

9. A light emitting device comprising the complex of claim 2.

10. A light emitting device comprising the complex of claim 3.

11. A light emitting diode comprising the complex of claim 3.

12. A light emitting device comprising the complex of claim 4.

13. A light emitting diode comprising the complex of claim 4.

14. A light emitting device comprising the complex of claim 5.

15. A light emitting diode comprising the complex of claim 5.

* * * * *